(12) United States Patent
Schachner

(10) Patent No.: US 7,951,373 B2
(45) Date of Patent: May 31, 2011

(54) METHODS USING AGONIST ANTIBODIES TO CNS NEURITE OUTGROWTH MODULATORS

(75) Inventor: Melitta Schachner, Zurich (CH)

(73) Assignee: Melitta Schachner, Hamburg (DE)

( * ) Notice: Subject to any disclaimer, the term of this patent is extended or adjusted under 35 U.S.C. 154(b) by 969 days.

(21) Appl. No.: 10/457,106

(22) Filed: Jun. 9, 2003

(65) Prior Publication Data
US 2004/0022790 A1 Feb. 5, 2004

Related U.S. Application Data

(60) Division of application No. 09/130,158, filed on Aug. 6, 1998, now Pat. No. 6,576,607, which is a continuation-in-part of application No. 09/128,305, filed on Aug. 3, 1998, now abandoned, which is a continuation-in-part of application No. 08/636,514, filed on Apr. 19, 1996, now abandoned, which is a continuation-in-part of application No. 08/483,959, filed on Jun. 7, 1995, now abandoned, which is a continuation-in-part of application No. 08/424,995, filed on Apr. 19, 1995, now abandoned.

(51) Int. Cl.
A61K 39/395 (2006.01)

(52) U.S. Cl. .................................... 424/145.1

(58) Field of Classification Search ................ 424/145.1
See application file for complete search history.

(56) References Cited

U.S. PATENT DOCUMENTS

| | | | |
|---|---|---|---|
| 4,508,715 | A | 4/1985 | Booth et al. |
| 4,955,892 | A | 9/1990 | Danilhoff |
| 5,082,670 | A | 1/1992 | Gage et al. |
| 5,250,414 | A | 10/1993 | Schwab et al. |
| 5,591,432 | A | 1/1997 | Bronson et al. |

FOREIGN PATENT DOCUMENTS

| | | |
|---|---|---|
| WO | WO 90/05191 | 5/1990 |
| WO | WO 93/00427 | 1/1993 |
| WO | WO 95/13291 | 5/1995 |

OTHER PUBLICATIONS

Miura, Masayuki et al (1991) Fedeation of European Biochemical Societies vol. 289, No. 1, 91-95.
Kobayashi, Masaaki et al (1991) Biochimica et Biophysica Acta,1090, 238-240.
Rosenthal, André et al (1991) Nucleic Acids Research vol. 19, No. 19, 5395-5401.
Dong, Ling et al (2003) Molecular and Celullar Neuroscience 22: 234-247.
Aguayo (1985) "Axonal regeneration from injured neurons in the adult mammalian central nervous system." In: Synaptic Plasticity (Cotman, C.W., ed.) New York, The Guilford Press. pp. 457-434.
Appel et al. (1993) J. Neurosci., 13:4764-4775.
Araujo et al., (1993), J. Neurochem. 61:899-910.
Atashi et al. (1992) Neuron 8:831-842.
Bartsch et al. (1989) J.Comp. Neurol 284:451-462.
Bixby et al. (1987) Proc. Nat'l Acad. Sci. U.S.A. 84:2555-2559.
Bixby et al. (1988) J. Cell. Biol. 107:353-362.
Breakfield. (1993), Nature Genetics 3:187-9.
Campbell et al., (1993) Proc. Natl. Acad. Sci. USA 90:10061-65.
Carlstedt et al. (1989) Brain Res. Bull. 22:93-102.
Chang et al. (1987) J. Cell. Biol. 104:355-362.
Davison et al., (1993) Nature Genetics 3:219-33.
Doherty et al. (1992) Curr. Opin. Neurobiol. 2:595-601.
Doherty et al. (1994) Curr. Opin. Neurobiol. 4:49-55.
Doherty et al. (1995) Neuron 14:57-66.
Doyle et al., (1992), J. of Neurochemistry, 59:1570-73.
Eng et al. (1971) Brain Res. 28:351-354.
Fawcett et al. (1990) Annu. Rev. Neurosci 13:43-60.
Fields et al., (1996), Trends in Neuroscience 19:473-80.
Friedmann et al., (1994), Trends in Genetics 10:210-4.
Friedmann et al., (1993). Trends in Biotechnologies, 11:192-97.
Friedman et al (1985) J. Neurosci. 5:1616-25.
Goridis et al., (1985). The EMBO J. 4:631-5.
Horstkorte et al. (1993) J. Cell. Biol. 121:1409-1421 (Abstract).
Hopp et al., (1981) Proc. Natl. Acad. Sci. USA. 78:3824-28.
Hynes (1992) Cell. 69:11-25.
Itoh, K. Et al. (1995) Science 270: 1369-72.
Jackowski. (1995), British J. of Neurosurgery 9:303-17.
Kadmon et al. (1990a) J. Cell. Biol. 110:193-208.
Kadmon et al. (1990b) J. Cell Biol. 110:209-218 (Abstract).
Kalderon (1988) J. Neurosci Res. 21:501-512.
Kappel et al., (1992), Current Opinion: Biotechnology 3:548-53.

(Continued)

Primary Examiner — Robert C Hayes
(74) Attorney, Agent, or Firm — Klauber & Jackson LLC

(57) ABSTRACT

The invention features a method for promoting neural growth in vivo in the mammalian central nervous system by administering a neural cell adhesion molecule which can overcome inhibitory molecular cues found on glial cells and myelin to promote neural growth. Also featured active fragments, cognates, congeners, mimics, analogs, secreting cells and soluble molecules thereof, as well as antibodies thereto, and DNA molecules, vectors and transformed cells capable of expressing them. The neuroprotective of the agents as well as their ability to promote and effect myelination and remyelination are also disclosed, as are the concomitant benefits that these capabilities confer, in the former instance, with regard to reduction of apoptosis and necrosis, and in the latter instance, the treatment of Parkinsonism, Alzheimer's disease and multiple sclerosis. The invention also includes transgenic mouse lines expressing a neural adhesion molecule in differentiated astrocytes, and cells and tissues derived therefrom. The expression of the neural adhesion molecule enhances neurite outgrowth on central nervous system tissue derived from these transgenic mice. The invention also features methods for enhancing neuronal outgrowth of CNS neurons, for enhancing memory and for increasing synaptic efficacy. Also featured are methods of testing drugs which modulate the effects of the neural adhesion molecule, and assay systems suitable for such methods.

3 Claims, 48 Drawing Sheets

OTHER PUBLICATIONS

Kobayahi et al., (1995), Neuroscience Letters 188:191-4.
Lagenaur et al. (1987) Proc. Natl. Acad. Sci. USA 84:7753-7757.
Landry et al. (1990) J. Neurosci. Res. 25:194-203.
Lewis et al. (1984) Proc. Natl. Acad. Sci. 81:2743-2745.
Lieberman. Int. Rev. of Neurobiology. 111:49-124, (1971).
Lindner et al. (1983) Nature 305:427-430.
Luthi et al. (1994) Nature 372:777-9.
Martini (1994) J. Neurocytol. 23:1-28.
Martini et al. (1994a) Glia 10:70-74 (Abstract).
Miller et al. (1985) Develop. Biol. 111:35-41.
Mittal et al., (1994), Molecular and Cellular Neurosciences 5(1):63-77.
Mocchetti et al., (1995) J. of Neurotrauma 12:853-10.
Mohajeri et al. (1996). Eur. J. of Neuroscience 8:1085-97.
Moos et al. (1988) Nature 334:701-703.
Mulligan (1993), Science 240:924-32.
Nieke et al. (1985) Differentiation 30:141-151.
Orkin et al., (1995) Report and Recommendations of the Panel to Assess the NIH Investment in Research on Gene Therapy.
Pollerberg et al. (1985) J. Cell. Biol. 101:1921-1929.
Poltorak et al., (1993), Brain Research 619:255-62.
Proudfoot (1986) Nature 322:562-565.
Rathjen et al. (1984) EMBO J. 3:1-10.
Reik et al. (1987) Nature 328:248-251.
Rose (1995), Behavioural Brain Research 66:73-8.
Rudinger. Peptide Hormones, (Jun. 1976), University Park Press, Baltimore.
Saad et al. (1991) J. Cell. Biol. 115:473-484 (Abstract).
Sapienze et al. (1987) Nature 328:251-254.
Sarid (1991) J. Neurosci. 28:217-228.
Schachner (1990) Seminars in the Neurosciences 2:497-507.
Schachner et al. (1994) Perspectives in Developm. Neurobiol. 2:33-41.
Schuch et al. (1990) Neuron 3:13-20 (Abstract).
Schwab et al. (1993) Ann. Rev. Neurosci. 16:565-595.
Seilheimer et al. (1987) EMBO J. 6:1611-1616.
Seilheimer et al. (1988) J. Cell. Biol. 107:341-351.
Silver et al. (1979) Develop. Biol. 68:175-90.
Silver et al. (1982) J. Comp. Neurol. 210:10-29.
Sloan et al., (1991), Trends in Neuroscience, 14: 341-6.
Smith et al. (1986) J. Comp. Neurol. 251:23-43.
Smith et al. (1990) Dev. Biol. 138:377-390.
Strojek et al., (1988). Genetic Engineering: Principles and Methods 10: 221.
Stuermer et al. (1992) J. Neurobiol. 23:537-550.
Tacke et al. (1987) Neurosci. Lett. 82:89-94.
Toggas et al. (1994) Nature 367:188-193.
von Bohlen and Hallbach et al. (1992) Eur. J. Neurosci. 4:896-909.
Weinstein et al., (1991), The J. of Cell Biology, 112:1205-13.
Williams et al. (1992) J. Cell. Biol. 119:883-892.
Wong et al. (1995) TINS 18:168-72.
Wood et al. (1990) J. Neurosci 10:3635-3645 (Abstract).

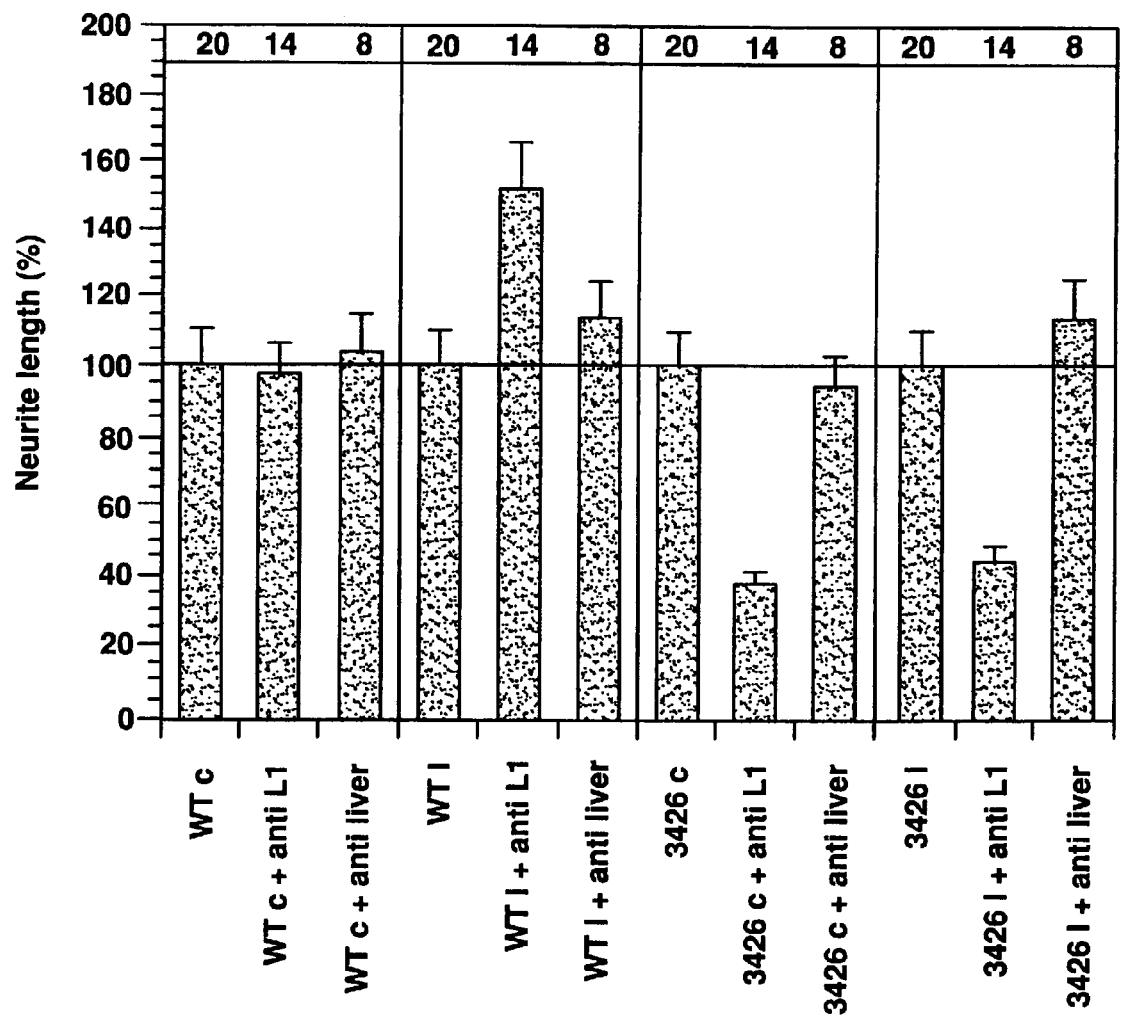

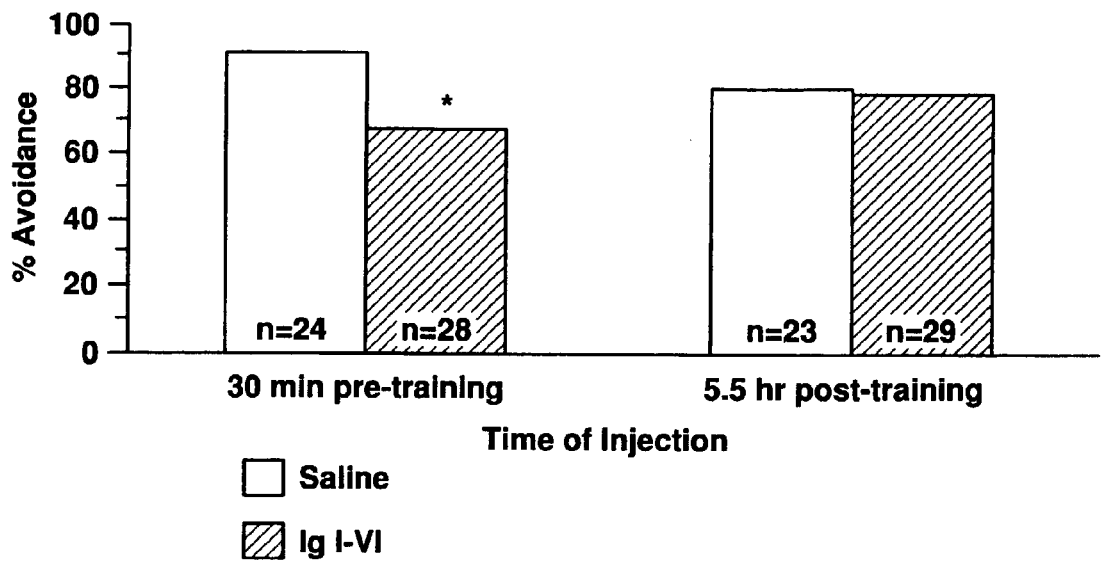
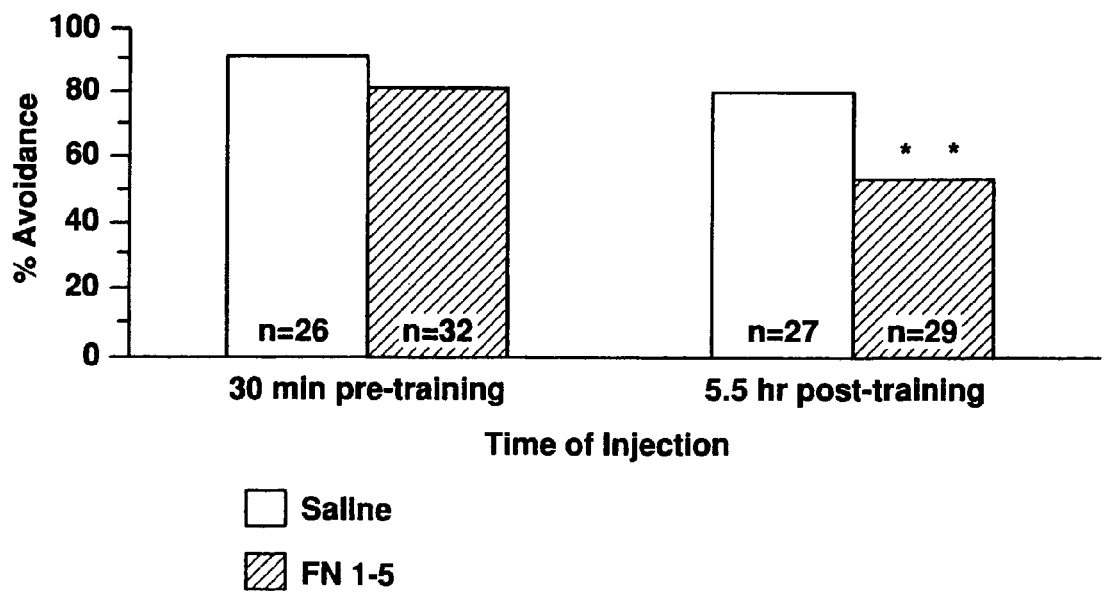

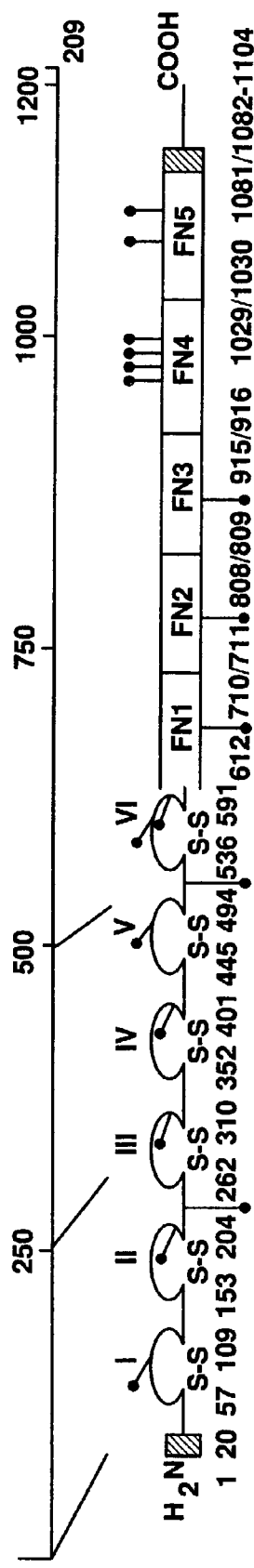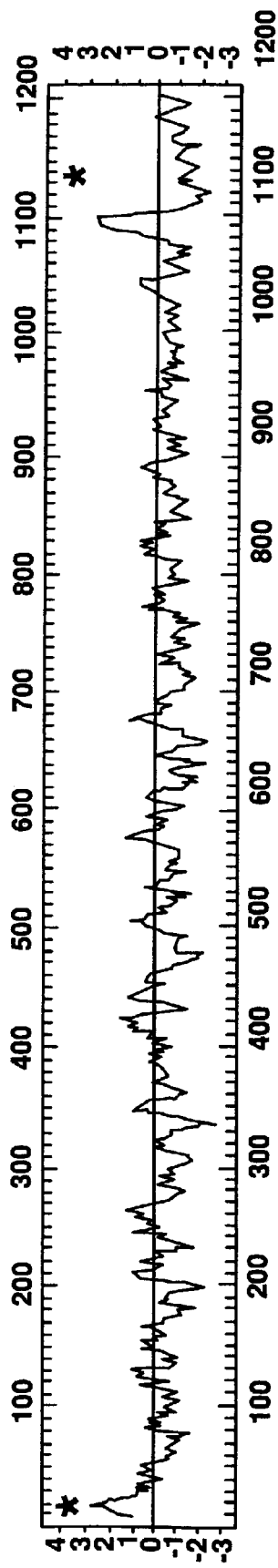
FIG.19A
FIG.19B
FIG.19C

FIG. 20

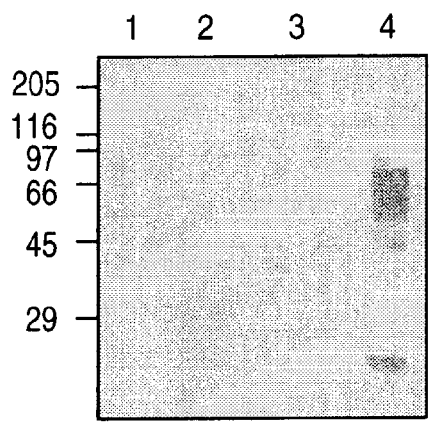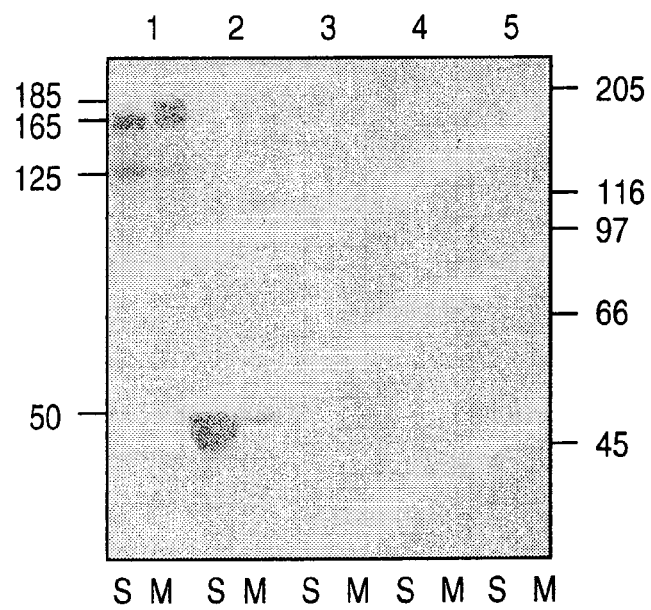

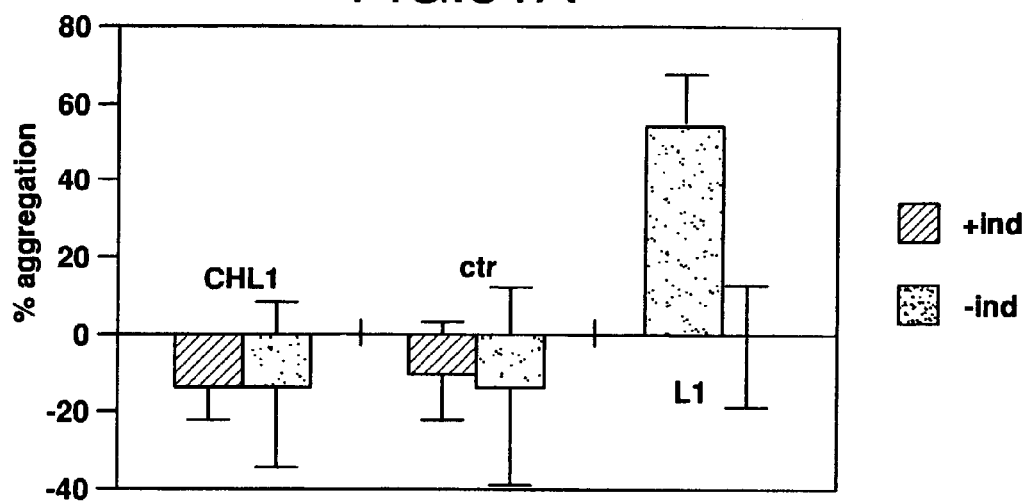
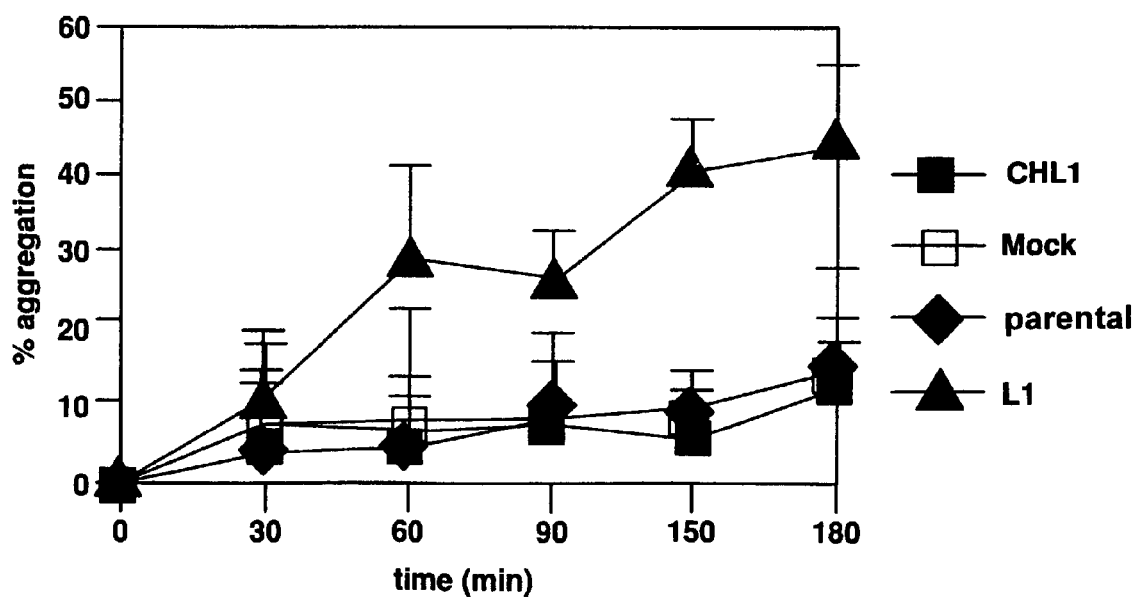

FIG. 34A
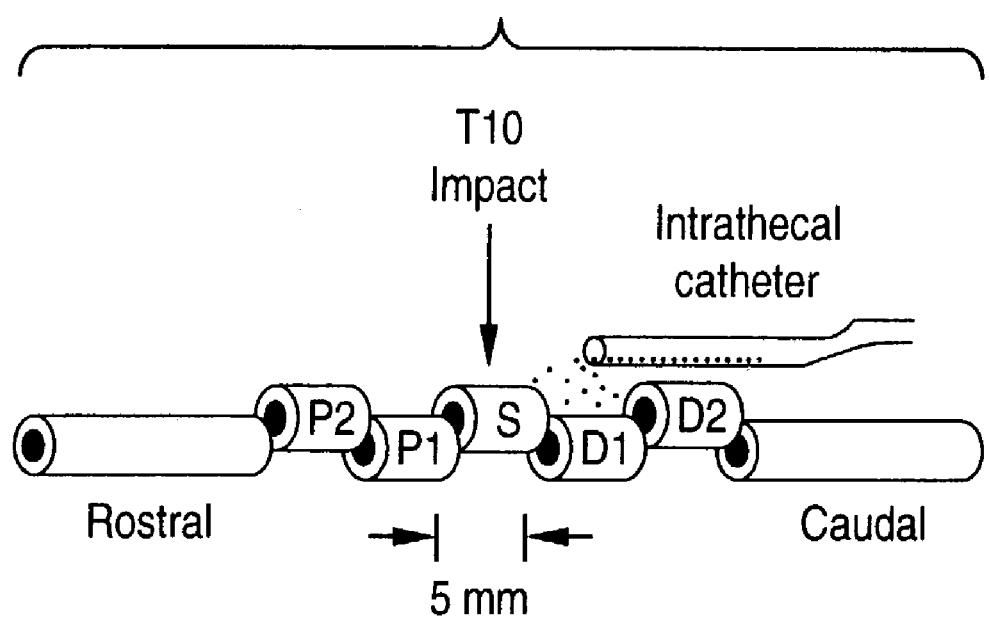
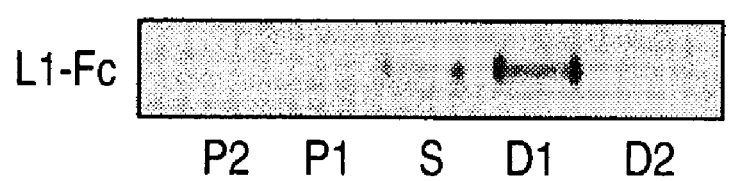
Western blot of spinal extracts

SDS-PAGE

Western Blots

METHODS USING AGONIST ANTIBODIES TO CNS NEURITE OUTGROWTH MODULATORS

CROSS REFERENCE TO RELATED APPLICATIONS

This application is a division of application Ser. No. 09/130,158, filed Aug. 6, 1998, now U.S. Pat. No. 6,576,607 which is in turn, a continuation-in-part of application Ser. No. 09/128,305, filed Aug. 3, 1998, now abandoned which is, in turn, a continuation-in-part of application Ser. No. 08/636,514, filed Apr. 19, 1996, now abandoned which is in turn, a continuation-in-part of application Ser. No. 08/483,959, filed Jun. 7, 1995, now abandoned which is in turn, a continuation-in-part of application Ser. No. 08/424,995, filed Apr. 19, 1995, now abandoned the disclosures of all of which are hereby incorporated by reference in their entireties. Applicants claim the benefits of these Applications under 35 U.S.C. §120.

BACKGROUND OF THE INVENTION

1. Field of the Invention

This invention relates generally to the modulation of neural growth in the central nervous system, and more particularly to methods and associated agents, constructs and compositions for improving CNS neural growth. Specifically, the invention relates to the use of cellular adhesion molecules, and preferably neural cell adhesion molecules such as L1, to foster and improve such neural growth.

2. Description of the Related Art

The ability of neurons to extend neurites is of prime importance in establishing neuronal connections during development. It is also required during regeneration to re-establish connections destroyed as a result of a lesion.

Neurites elongate profusely during development both in the central and peripheral nervous systems of all animal species (Cajal (1928) Degeneration and regeneration in nervous system, Oxford University Press, London). This phenomenon pertains to axons and dendrites. However, in adults, axonal and dendritic regrowth in the central nervous system is increasingly lost with evolutionary progression.

In the peripheral nervous system, after infliction of a lesion, axons of all vertebrate species are able to regrow (Cajal (1928); Martini (1994) *J. Neurocytol.* 23:1-28). However, in mammals, neurite regrowth following damage is limited to neuritic sprouting. Regrowth of neuronal processes is, however, possible in lower vertebrate species (Stuermer et al. (1992) *J. Neurobiol.* 23:537-550). In contrast, in the central nervous system, most, if not all neurons of both higher and lower vertebrate adults possess the potential for neurite regrowth (Aguayo (1985) "Axonal regeneration from injured neurons in the adult mammalian central nervous system," In: Synaptic Plasticity (Cotman, C. W., ed.) New York, The Guilford Press, pp. 457-484.)

Glial cells are the decisive determinants for controlling axon regrowth. Mammalian glial cells are generally permissive for neurite outgrowth in the central nervous system during development (Silver et al. (1982) *J. Comp. Neurol.* 210: 10-29; Miller et al. (1985) *Develop. Biol.* 111:35-41; Pollerberg et al. (1985) *J. Cell. Biol.* 101:1921-1929) and in the adult peripheral nervous system (Fawcett et al. (1990) *Annu. Rev. Neurosci* 13:43-60). Thus, upon infliction of a lesion, glial cells of the adult mammalian peripheral nervous system can revert to some extent to their earlier neurite outgrowth-promoting potential, allowing them to foster regeneration (Kalderon (1988) *J. Neurosci Res.* 21:501-512; Kliot et al. "Induced regeneration of dorsal root fibres into the adult mammalian spinal cord," In: *Current Issues in Neural Regeneration*, New York, pp. 311-328; Carlstedt et al. (1989) *Brain Res. Bull.* 22:93-102). Glial cells of the central nervous system of some lower vertebrates remain permissive for neurite regrowth in adulthood (Stuermer et al. (1992) *J. Neurobiol.* 23:537-550). In contrast, glial cells of the central nervous system of adult mammals are not conducive to neurite regrowth following lesions.

Several recognition molecules which act as molecular cues underlying promotion and/or inhibition of neurite growth have been identified (Martini (1996). Among the neurite outgrowth promoting recognition molecules, the neural cell adhesion molecule L1 plays a prominent role in mediating neurite outgrowth (Schachner (1990) *Seminars in the Neurosciences* 2:497-507). L1-dependent neurite outgrowth is mediated by homophilic interaction. L1 enhances neurite outgrowth on L1 expressing neurites and Schwann cells, and L1 transfected fibroblasts (Bixby et al. (1982) *Proc. Nat'l Acad. Sci. U.S.A.* 84:2555-2559; Chang et al. (1987) *J. Cell. Biol.* 104:355-362; Lagenaur et al. (1987) *Proc. Natl. Acad. Sci. USA* 84:7753-7757; Seilheimer et al. (1988) *J. Cell. Biol.* 107:341-351; Kadmon et al. (1990a) *J. Cell. Biol.* 110:193-208; Williams et al. (1992) *J. Cell. Biol.* 119:883-892). Expression of L1 is enhanced dramatically after cutting or crushing peripheral nerves of adult mice (Nieke et al. (1985) *Differentiation* 30:141-151; Martini et al. (1994a) *Glia* 10:70-74). Within two days L1 accumulates at sites of contact between neurons and Schwann cells being concentrated mainly at the cell surface of Schwann cells but not neurons (Martini et al. (1994a)). Furthermore, the homophilic binding ability of L1 is enhanced by molecular association with the neural cell adhesion molecule N-CAM, allowing binding to occur through homophilic assistance (Kadmon et al. (1990a); Kadmon et al. (1990b) *J. Cell Biol.* 110:209-218 and 110: 193-208; Horstkorte et al. (1993) *J. Cell. Biol.* 121:1409-1421). Besides its neurite outgrowth promoting properties, L1 also participates in cell adhesion (Rathjen et al. (1984) *EMBO J.* 3:1-10; Kadmon et al. (1990b) *J. Cell. Biol.* 110: 209-218; Appel et al. (1993) *J. Neurosci.*, 13:4764-4775), granule cell migration (Lindner et al. (1983) *Nature* 305:427-430) and myelination of axons (Wood et al. (1990) *J. Neurosci* 10:3635-3645).

L1 consists of six immunoglobulin-like domains and five fibronectin type III homologous repeats. L1 acts as a signal transducer, with the recognition process being a first step in a complex series of events leading to changes in steady state levels of intracellular messengers. The latter include inositol phosphates, $Ca^{2+}$, pH and cyclic nucleotides (Schuch et al. (1990) *Neuron* 3:13-20; von Bohlen und Hallbach et al. (1992) *Eur. J. Neurosci.* 4:896-909; Doherty et al. (1992) *Curr. Opin. Neurobiol.* 2:595-601) as well as changes in the activities of protein kinases such as protein kinase C and $pp60^{c-src}$ (Schuch et al. (1990) *Neuron* 3:13-20; Atashi et al. (1992) *Neuron* 8:831-842). L1 is also associated with a casein type II kinase and another unidentified kinase which phosphorylates L1 (Sadoul et al. (1989) *J. Neurochem* 328:251-254). L1-mediated neurite outgrowth is sensitive to the blockage of L type $Ca^{2+}$ channels and to pertussis toxin. These findings indicate the importance of both $Ca^{2+}$ and G proteins in L1-mediated neurite outgrowth (Williams et al. (1992) *J. Cell. Biol.* 119:883-892). L1 is also present on proliferating, immature astrocytes in culture and neurite outgrowth is promoted on these cells far better than on differentiated, L1 immunonegative astrocytes (Saad et al. (1991) *J. Cell. Biol.* 115:473-484). In vivo, however, astrocytes have been found to express L1 at any of the developmental stages examined from embryonic day 13 until adulthood (Bartsch et al. (1989) *J. Comp. Neurol* 284:451-462; and unpublished data).

Given the capability of L1 to promote neurite outgrowth, it is pertinent to investigate whether astrocytic expression of L1 and other members of the immunoglobulin superfamily to which L1 belongs, may overcome potentially inhibitory molecular cues reported to be present on glial cells and myelin in the adult central nervous system (Schachner et al., *Perspectives in Developm. Neurobiol.* in Press; Schwab et al. (1993) *Ann. Rev. Neurosci.* 16:565-595). This is of particular relevance to the development of effective strategies for the treatment of debilitation caused by the malformation of or injury to neural tissues of the CNS, and it is toward such objectives that the present invention is directed.

SUMMARY OF THE INVENTION

In accordance with the present invention, an agent and corresponding methods are disclosed for the modulation of neural growth and particularly, such growth as can be promoted in the compartment of the central nervous system (CNS), and specifically, in myelinated nerve tissue. The agents of the present invention are notable in their ability to promote such neural growth in an environment that has been traditionally viewed as inhibitory to the growth promoting stimulus of known neurite outgrowth factors. Specifically, this inhibitory environment includes inhibitory molecular cues which are present on glial cells and myelin the central nervous system.

The agents of the present invention are broadly selected from a group of cell adhesion molecules, and more preferably neural cell adhesion molecules. Most preferably, the agents of the present invention are selected from the group of molecules belonging to the immunoglobulin superfamily, and particularly to those members that mediate $Ca^{2+}$-independent neuronal cell adhesion, of which L1, N-CAM and myelin-associated glycoprotein are particular members. Other cell adhesion molecules which may also influence CNS neural growth include laminin, fibronectin, N-cadherin, BSP-2 (mouse N-CAM), D-2, 224-1A6-A1, L1-CAM, NILE, Nr-CAM, TAG-1 (axonin-1), Ng-CAM and F3/F11.

In a further aspect of the present invention, the agents of the invention belong to a new family referred to herein as the L1 family of neural recognition molecules. This family includes L1, NgCAM, neurofascin, *Drosophila* neuroglian, zebrafish L1.1 and L1.2, and others. This group of agents all demonstrate the Ig-like domains and FN-like repeats that are characteristic of L1, and in this connection, exhibit a remarkable colinearity, a high degree of N-glycosidically linked carbohydrates, which include the HNK-1 carbohydrate structure, and a pattern of protein fragments comprising a major 185 kD band and smaller bands of 165 and 125 kD.

The agents of the present invention also include fragments including soluble fragments, of cell adhesion molecules and cognate molecules, congeners and mimics thereof which modulate neurite growth in the CNS. In particular, the agents include molecules which contain structural motifs characteristic of extracellular matrix molecules, in particular the fibronectin type III homologous repeats and immunoglobulin-like domains. Preferably, these structural motifs include those structurally similar to fibronectin type III homologous repeats 1-2, and immunoglobulin-like domains I-II, III-IV and V-VI.

The invention extends to methods of promoting and enhancing neural regeneration including neural growth and/or remyelination and/or neuroprotection in vivo, and to the corresponding genetic constructs, such as plasmids, vectors, transgenes, and the like, and to pharmaceutical compositions, all of which may be used to accomplish the objectives of such methods. More specifically, the agents of the present invention may be prepared as vectors or plasmids, and introduced into neural cells located at a site in the CNS where such regeneration or other therapy is needed, for example, by gene therapy techniques, to cause the expression of an agent of the present invention and to thereby promote the requisite neural growth. Another strategy contemplates the formulation of one or more of the appropriate agents in a composition that may likewise be directly delivered to a CNS site, as by parenteral administration. As certain of the agents, such as L1, have demonstrated homophilic binding, the administration of such a composition may serve the purpose of inhibiting rather than promoting neural growth. This effect may be desirable in particular instances where unwanted or uncontrolled growth may occur or is occurring, and therefore the invention extends to this use as well.

Correspondingly, the capability of the agents to engage in homophilic binding renders antagonists to the agents, including antibodies thereto as well as soluble fragments thereof, capable of acting as agonists, and thereby participating in the promotion of neural growth and/or remyelination and/or neuroprotection and regeneration. Thus, the invention extends to the preparation of appropriate constructs and compositions containing the antibodies to the agents, and any soluble fragments, for the therapeutic purposes set forth herein. Also, and as demonstrated later on herein, antibodies to L1 and soluble fragments of L1, for example, may serve as part of a drug discovery assay or the like, to identify further agents that may possess activity and utility both diagnostic and therapeutic, in accordance with the present invention. Particularly, and as illustrated later on herein with reference to the isolation and characterization of CHL1, an L1 analog, antibodies such as polyclonal, monoclonal and chimeric (bispecific) antibodies, including humanized such antibodies, may be used to identify further members of the L1 CAM family, and the invention accordingly extends to such CAM members as are isolated by use of such antibodies.

The invention also covers diagnostic applications, where for example, it is desirable to assess the potential for or actual development of CNS neural growth by the detection and measurement of the presence, amount or activity of one or more of the agents of the invention. Likewise, and as described hereinafter, the invention also extends to assays, including drug discovery and testing assays, that capitalize on the activity of the agents of the present invention in the modulation of CNS neural growth. For example, prospective drugs may be tested for CNS neural growth modulation by means of an assay containing an agent of the invention, or a cell line or culture developed in conjunction herewith may serve as the assay system.

Briefly, the present invention also features transgenic mouse lines expressing a neural adhesion molecule in differentiated astrocytes and glial cells, and cells and tissues derived therefrom. In particular, the neural adhesion molecule is L1. The astroglial L1 expression enhances neurite outgrowth on central nervous system tissue derived from these transgenic mice.

Also as discussed, the invention features methods for enhancing neuronal outgrowth of CNS neurons, for enhancing memory and for increasing synaptic efficacy, as may be measured by stabilization of long term potentiation, and other similarly useful methods. A related aspect of the present invention extends to the neuroprotective effects that are exerted by the present agents including the neural adhesion molecules set forth herein. Among the consequences of such activity is the application of the present agents to the modulation of conditions where neuroprotective activity is relevant, including the reduction of apoptosis and necrosis, and the related effects on neurodegenerative disorders such as Alzheimers and Parkinsons Disease, and multiple sclerosis. Similarly, the agents are capable of increasing neuronal survival as is likewise beneficial in the treatment of the presence or consequences of Alzheimers' disease and Parkinsonism, and are also associated with an increase in remyelination in the central nervous system, and thus would offer an additional strategy for the treatment of conditions where the myelin sheath is destroyed or damaged, such as multiple sclerosis. Accordingly, the present invention includes methods of promoting neuroprotection and/or neuronal survival in a mammal by the administration of an effective amount of the neural adhesion molecules of this invention and/or cells or other constructs that will promote and/or assist in realizing the objectives and benefits of the methods.

Also featured are methods of testing drugs and other manipulations which modulate the effects of the neural adhesion molecule, and assay systems suitable for such methods.

Accordingly, it is a principal object of the present invention to provide a transgenic mammal, the glial cells of which express an exogenous neural adhesion molecule.

A further object of the invention is to provide a cell culture containing the glial cells of the transgenic mammal.

Yet another object of the invention is to provide a cell culture system containing lesioned or unlesioned optic nerves or other parts of the nervous system of the transgenic mammal.

Still a further object of the invention is to provide a method for enhancing neuronal outgrowth of CNS neurons, which includes culturing the neurons on the glial cell culture system.

A further object of the invention is to provide a method for enhancing neuronal outgrowth of CNS neurons, which includes culturing the neurons on the optic nerve or other parts of the nervous system placed in the cell culture system.

A still further object of the invention is to provide a method for enhancing neuronal outgrowth of CNS neurons, which includes the secretion of neural adhesion molecule by implanted cells.

Another object of the invention is to provide a method for enhancing memory, which includes administering to the brain of a mammal, an amount of the cells of the glial cell culture system effective to enhance the memory of the mammal.

Yet another object of the invention is to provide a method for enhancing memory, including administering to the brain of a mammal, an amount of the cells of the optic nerve or other parts of the nervous system placed in the cell culture system effective to enhance the memory of the mammal.

A still further object of the invention is to provide a method for enhancing memory, including delivering to the glial cells of the brain of a mammal, including mammals in need of such memory enhancement, a vector which allows for the expression of a neural adhesion molecule in the glial cells.

A further object of the invention is to provide a method for enhancing memory, which includes the secretion of neural adhesion molecule by implanted cells.

In a yet further object of the present invention a method is provided for the treatment of neurodegenerative conditions such as Alzheimers disease and Parkinson's disease, by the administration of one or more of the present agents.

In a still further object of the present invention a method is provided for the promotion of remyelination and the corresponding treatment of conditions such as multiple sclerosis, by the administration of one or more of the present agents.

Another object of the invention is to provide a method for increasing synaptic efficacy in the CNS of a mammal, including administering to the brain of the mammal, an amount of the cells of the glial cell culture system effective to increase synaptic efficacy in the brain of the mammal.

Yet a further object of the invention is to provide a method for increasing synaptic efficacy in the CNS of a mammal, including administering to the brain of the mammal, an amount of the cells of the optic nerve or other parts of the nervous system placed in the cell culture system effective to increase synaptic efficacy in the brain of the mammal.

A still further object is to provide a method for increasing synaptic efficacy in the CNS of a mammal, which includes delivering to the glial cells of the brain of a mammal in need of such enhancement, a vector which allows for the expression of a neural adhesion molecule in the glial cells.

A further object of the invention is to provide a method for increasing synaptic efficacy, which includes the secretion of neural adhesion molecule by implanted cells.

A still further object of the present invention extends to the treatment of conditions involving a reduction or dysfunction in synaptic efficiency, and includes the treatment of pre-senile and senile dementias.

Another object of the invention is to provide a method of testing the ability of a drug or other entity to modulate the activity of a neural adhesion molecule, which includes adding CNS neurons to the glial cell culture system; adding the drug under test to the cell culture system; measuring the neuronal outgrowth of the CNS neurons; and correlating a difference in the level of neuronal outgrowth of cells in the presence of the drug relative to a control culture to which no drug is added to the ability of the drug to modulate the activity of the neural adhesion molecule.

Another object of the invention is to provide a method of testing the ability of a drug or other entity to modulate the activity of a neural adhesion molecule which includes adding CNS neurons to the optic nerve or other parts of the nervous system cell culture system; adding the drug under test to the cell culture system; measuring the neuronal outgrowth of the CNS neurons; and correlating a difference in the level of neuronal outgrowth of cells in the presence of the drug relative to a control culture to which no drug is added to the ability of the drug to modulate the activity of the neural adhesion molecule.

Yet another object of the invention is to provide an assay system for screening drugs and other agents for ability to modulate the production of a neural adhesion molecule, which includes the glial cell culture system; and CNS neurons added to the cell culture system.

A further object of the invention is to provide an assay system for screening drugs and other agents for ability to modulate the production of a neural adhesion molecule, which includes culturing the glial cell culture system inoculated with a drug or agent; adding CNS neurons to the cell culture system; and examining neuronal outgrowth to determine the effect of the drug thereon.

Yet another object of the invention is to provide an assay system for screening drugs and other agents for ability to modulate the production of a neural adhesion molecule, which includes culturing the optic nerve or other parts of the nervous system in the cell culture system inoculated with a drug or agent; adding CNS neurons to the cell culture system; and examining neuronal outgrowth to determine the effect of the drug thereon.

Another object of the invention is to provide an assay system for screening drugs and other agents for ability to modulate the production of a neural adhesion molecule, which includes inoculating a culture of CNS neurons with a drug or agent; adding a soluble neural adhesion molecule; and examining neuronal outgrowth to determine the effect of the drug thereon.

Other objects and advantages will become apparent to those skilled in the art from a review of the ensuing detailed description taken with reference to the following illustrative drawings.

BRIEF DESCRIPTION OF THE DRAWINGS

FIG. 9 is a graph measuring neurite lengths of cerebellar neurons maintained on cryostat sections of unlesioned (c) and lesioned (l) optic nerves (28 days after the lesion) from wild type (WT) and transgenic animals without and after pre-incubation of sections with affinity purified polyclonal antibodies against L1 (anti L1) and mouse liver membranes (anti liver). Neurite lengths on nerves without pre-incubation with any antibody were taken as 100% and neurite lengths on sections of the same nerves obtained after antibody treatment were expressed in relation to this value. A significant reduction (60%) of neurite length by L1 antibodies was found on cryostat sections from transgenic animals. Numbers on the top represent the total number of nerves measured for each value. Mean values±standard error of the mean are from at least four independent experiments carried out in duplicate.

FIG. 14 comprises two graphs depicting the effect of injections of Ig I-IV and FN fragments at −30 minutes and +5.5 hours on retention of memory for passive avoidance task. All animals were tested at 24 hours post-training. The number of animals in each group is shown in the histograms (*p<0.05; **p<0.005).

FIG. 18A-18B depicts the nucleotide sequence of the 4.43 kb cDNA insert of clone pX#2 and deduced amino acid sequence of mouse CRL1 (SEQ ID NOS: 1-3). The longest open reading frame (bp 296 to by 3922) contains 1209 amino acids terminating with a TGA termination codon (SEQ ID NO:2). The two hydrophobic regions representing the signal peptide (amino acids 1-24) and the transmembrane region (1082-1104) are underlined by a bar. Two arrows indicate the 5' and 3' ends of clone 311 isolated from the 8gt11 library. Potential sites of asparagine-linked glycosylation (Hubbard and Ivatt, 1981) are marked below the amino acid sequence with filled diamonds. The immunoglobulin (Ig)-like domains are numbered with roman numerals from I to VI below the conserved tryptophan. The characteristic cysteines are indicated by circles. The FN-like repeats are numbered F1 to F5 and the characteristic tryptophans (missing in F1; F2; W 732, F3; W 830, F4: W 936, F5; W 1053) and tyrosines/phenylalanines (F1: Y 682, F2: Y 781, F3: F888, F4: Y 989, and missing in F5) are boxed. A bracket highlights the RGD and DGEA sequences (amino acid residues 185-187 and 555-558, respectively). Untranslated sequences are shown numbered in italics. The sequence data are available from EMBL/Genebank/DDBJ under accession number X94310.

FIG. 19 depicts the domain structure, coding region of the bacterially expressed protein fragment, and hydrophobicity plot of mouse CHL1 (a) The diagram sketches the structural features deduced from the primary sequence of CHL1. Numbers refer to the amino acid sequence starting at the translation start site. Ig-like domains I to VI are represented by half circles (amino acid numbers refer to the cysteines forming the disulfide bridges). FN-like repeats 1 to 5 are symbolized by boxes (amino acid numbers refer to the domain boundaries). The potential sites for N-glycosylation are indicated by filled circles. Signal peptide and transmembrane region are denoted by etched boxes. (b) The bar indicates the position of the cDNA encoding the recombinant protein produced in *E. coli* (c) The hydrophobicity plot (Kyte and Doolittle, 1982) of the deduced amino acid sequence shows the characteristic features of an integral membrane protein with the putative hydrophobic signal sequence and transmembrane domain (*). Positive values indicate hydrophobicity. Numbering of the abscissa refers to amino acid position.

FIG. 20 shows the alignment of the intracellular domains of molecules of the L1 family. The sequences of the intracellular domains starting with the first amino acid residue after the putative transmembrane regions are aligned for mouse CRL1 (SEQ ID NO:4), mouse L1 (SEQ ID NO:5), chicken Nr-CAM (SEQ ID NO:6), chicken Ng-CAM (SEQ ID NO:7), chicken neurofascin (SEQ ID NO:8), *Drosophila* neuroglia (SEQ ID NO:9), zebrafish L1.1 (SEQ ID NO:10) and zebrafish L1.2 (SEQ ID NO:11). The numbers refer to the amino acid positions of CHL1 and gray boxes indicate gaps introduced in the CHL1 sequence. Identical amino acids occurring in the majority of sequences are marked by black boxes. The three brackets (I, II and III) refer to highly conserved stretches.

Figure 1:
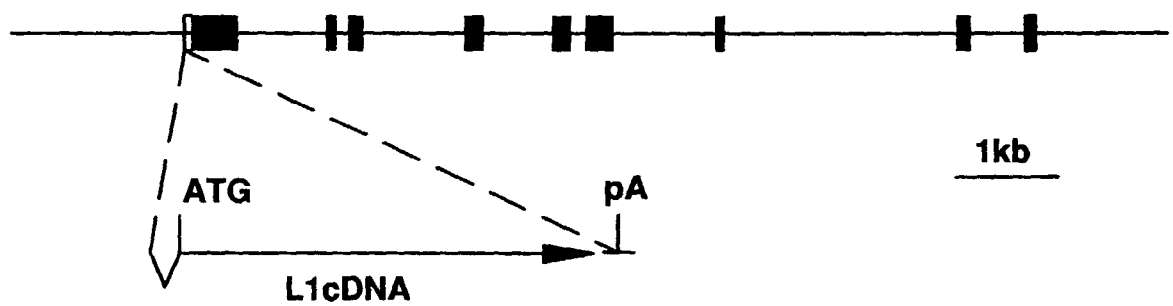
FIG. 1 depicts the map of the GFAP-L1 chimeric transgene. A 4.05 kb mouse L1 cDNA was inserted into exon 1 of a modified GFAP gene using Not I linkers. In this construct, the L1 cDNA is preceded 5' by an SV40 late gene splice (V) and followed 3' by an SV40 polyadenylation signal (pA). The locations of the L1 ATG and the polyadenylation signal are indicated. Exons are shown as boxes.

(b) Total RNA (20 μg) of NGF induced (lane 1) and non-induced (lane 2) PC12 cells, COS-1 cells (lane 3), and total RNA (30 μg) of cerebellum of nine-(lane 4) and six-(lane 5) day-old rats were hybridized with the CHL1 riboprobe. RNA markers are indicated at the left margins.

FIG. 22 demonstrates the specificity of polyclonal antibodies against CHL1 and expression of CHL1 in different tissues. (a) Western blot analysis of brain derived immunopurified L1 (lane 1 (2 μg)), N-CAM (lane 2 (2 μg)). MAG (lane 3 (2 μg)), and recombinant anion exchange chromatography purified CHL1 protein fragment (lane 4 (0.1 μg)) using CHL1 antibodies. (b) Western blot analysis of soluble (S) and insoluble (M) fractions of detergent lysates of crude membranes from brain (lane 1), liver (lane 2), lung (lane 3), kidney (lane 4), and intestine (lane 5) of nine-day-old mice. The numbers at the left (b) refer to the molecular masses of CHL1 immuno-reactive bands of brain (lane 1) and liver (lane 2). Molecular mass standards are indicated in kD at the left (a) and right (b) margins.

FIG. 23 shows the detection of CHL1 on transiently transfected COS-1 cells Monolayer cultures of CHL1-transfected (a) and mock-transfected (c) COS-1 cells were immunostained with polyclonal antibodies against CHL1. (b,d) corresponding phase contrast micrographs for (a.c), respectively, Bar in d=30 μm for a to d.

FIG. 24 depicts the localization of CHL1 and L1 mRNA in sections of mouse retina, optic nerve, and cerebellar cortex by in situ hybridization analysis. In the retina of 7-day-old mice, L1 mRNA is detectable in ganglion cells located in the ganglion cell layer (1 in a) and in amacrine and horizontal cells located in the inner nuclear layer (2 in 1). Other cells types in the retina or glial cells in the optic nerve do not contain detectable levels of L1 transcripts (a). CHL1 mRNA is weekly detectable in ganglion cells and in a few cells located at the inner (i.e. vitread) margin of the inner nuclear layer (b). Glial cells located in proximal (i.e. retina-near) regions of the optic nerve are strongly labeled by the CHL1 antisense cRNA probe whereas glia cells located in more distal regions are only weekly labeled (b). In the cerebellar cortex of two-week-old mice, L1 transcripts are detectable in stellate and basket cells in the molecular layer (mol) and in Golgi and granule cells in the internal granular layer (Igl:d). CHL1 transcripts are distributed in a similar pattern, with the only exception that hardly any labeling is visible in thinner part of the molecular layer (b). Sections hybridized with a CHL1 sense cRNA probe are not labeled (for a 7-day-old retina and optic nerve, see c).

Bar in c=100 μm for a-c: bar in e=150 μmm for d and e.

FIG. 25 illustrates the immunofluorescence microscopic localization of CHL1 in cultures of astrocytes.

Double-immunolabeling of cultured mouse astrocytes was performed with polyclonal antibodies to CHL1 (a,d) and monoclonal antibodies to GFAP (b,e), (c and f) are the corresponding phase contrast micrographs for (a,b and d,e), respectively. Bars in c and F=20 μm for a-c and d-f respectively.

Figure 26:
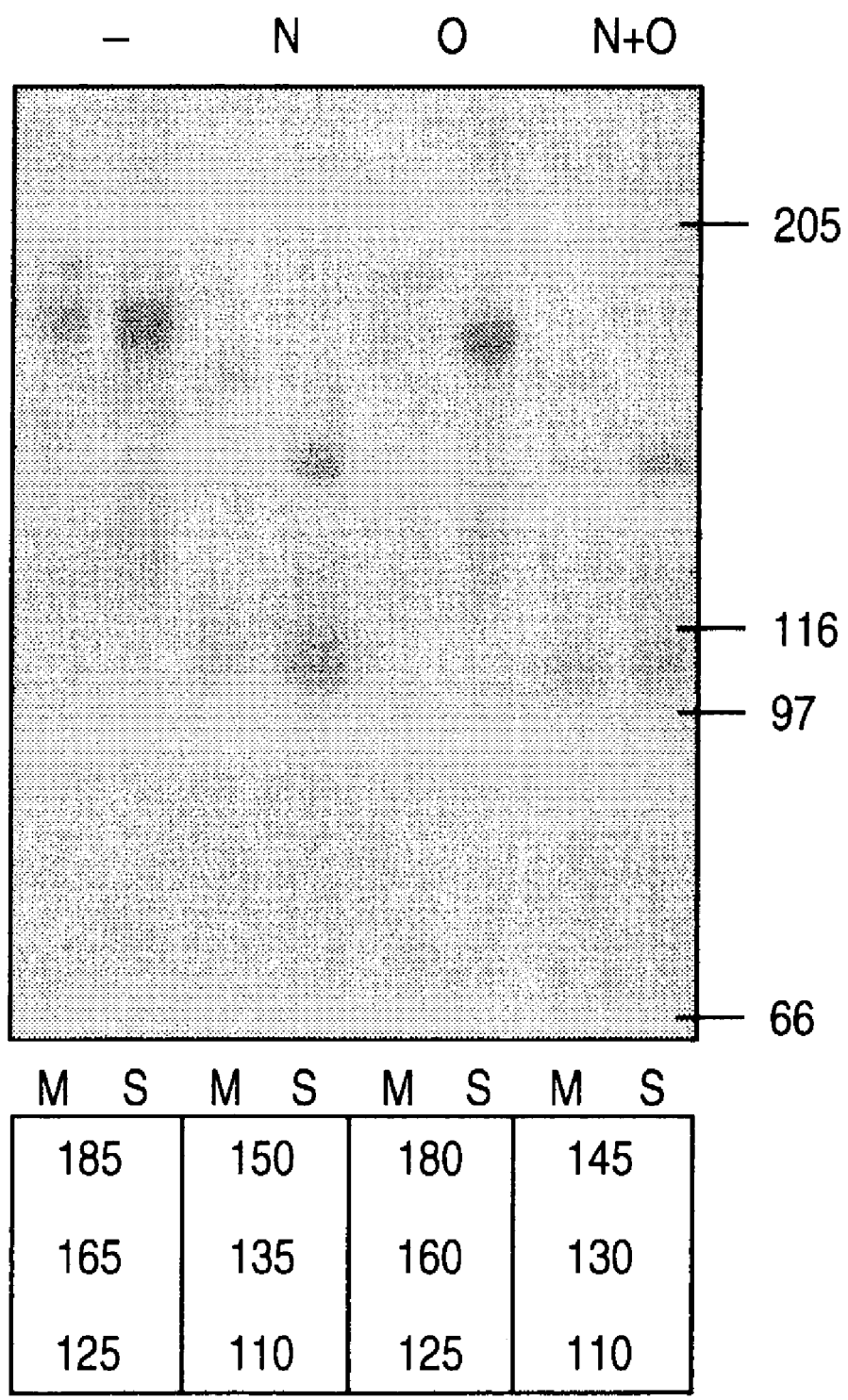

FIG. 26 is a Western blot analysis of deglycosylated CHL1 Soluble (S) and insoluble (M) fractions of detergent lysates of crude membranes from brain of seven-day-old mice were incubated with N-glycosidase F (N). O-glycosidase (O), both enzymes (N+O), or without enzyme (−) and reacted with antibodies against CHL1 in Western blots. Molecular mass standards are indicated in kD at the right margin. The molecular masses of the glycosylated and deglycosylated CHL1 protein components are indicated in kD in the box below.

Figure 27:
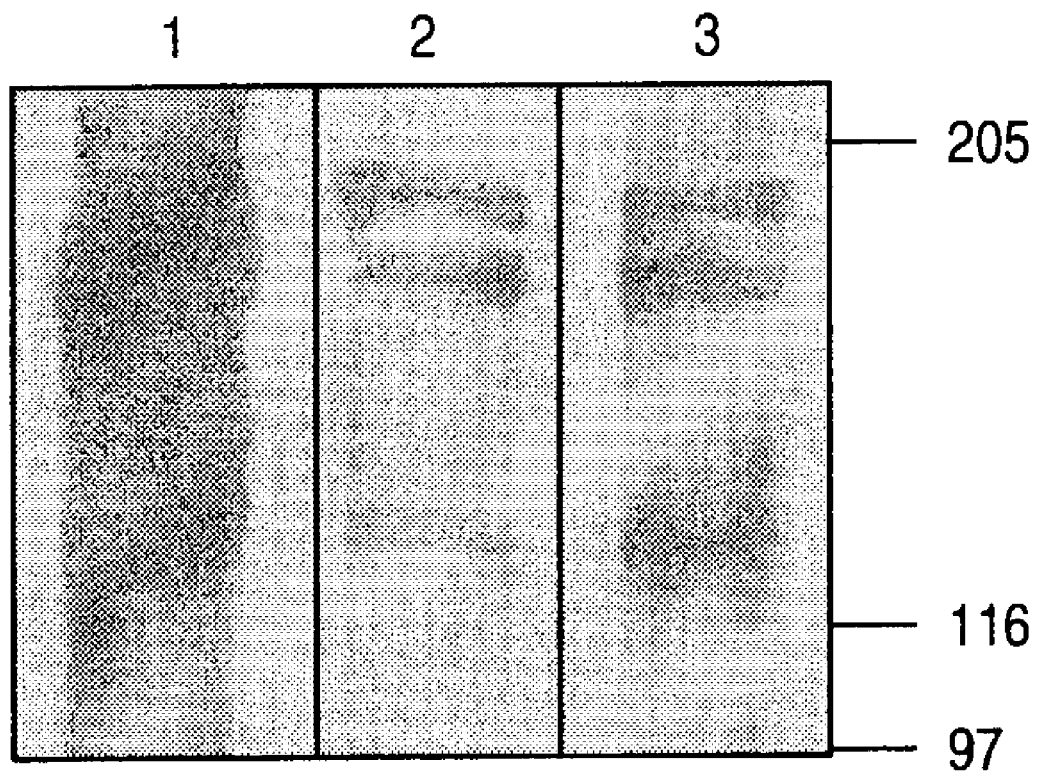

FIG. 27 shows the presence of the HNK-1 carbohydrate in CHL1 immunoprecipates from brain tissue. CHL1 was immunoprecipitated from detergent lysates of whole brain tissue of nine-day-old mouse brain using CHL1 antibodies. Brain lysate (lane 1) and immunoprecipates (lanes 2, 3) were resolved by SDS-PAGE, blotted, and incubated with monoclonal antibody 312 against the HNK-1 epitope (lanes 1, 2) or CHL1 antibodies (lane 3). Molecular mass standards are indicated in kD at the right margin.

Figure 28A:
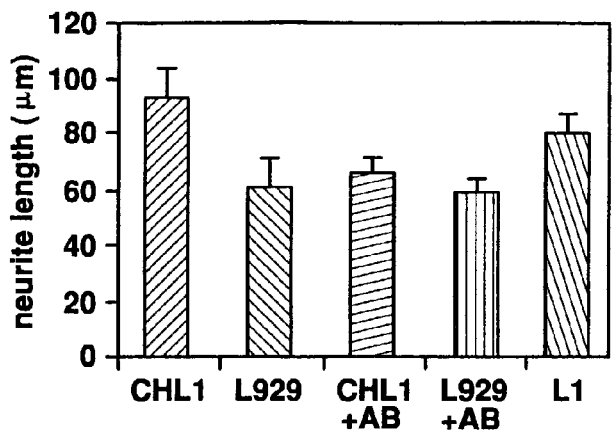
Figure 28B:
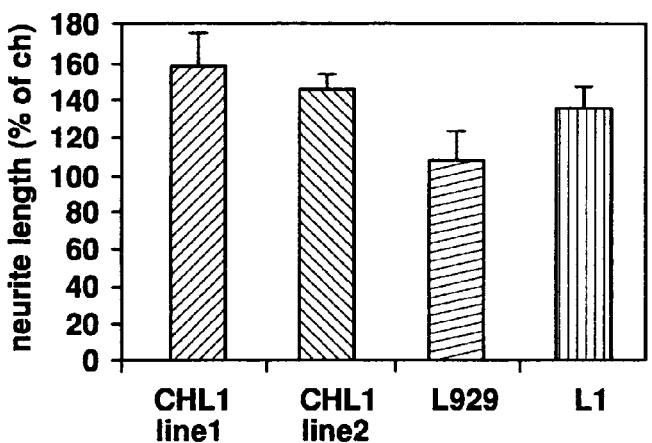
Figure 28C:
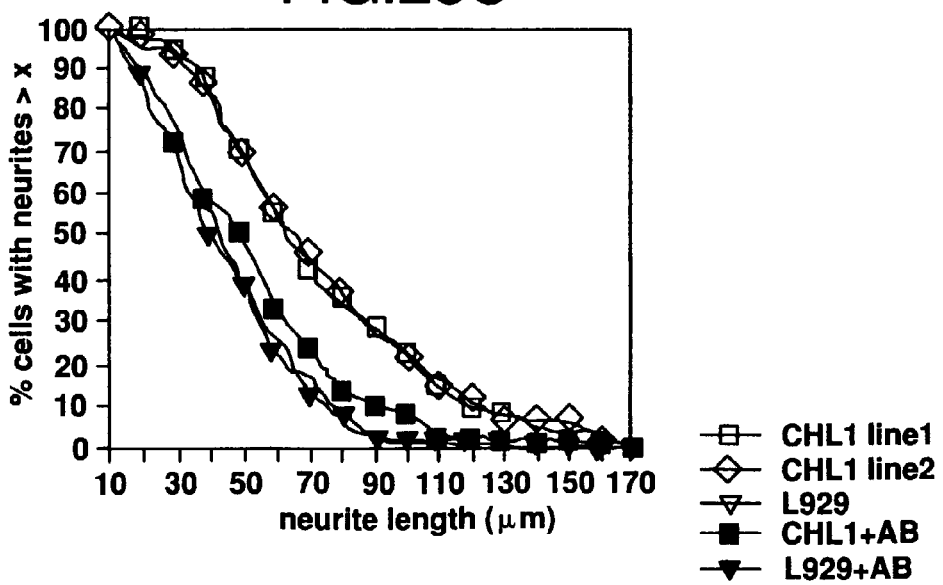

FIGS. 28A, 28B and 28C present data depicting neurite outgrowth of hippocampal neurons in cocultures with L929 transfectants. Hippocampal neurons derived from rats of embryonal day 18 were cultured in subconfluent monolayers of L929 transfectants or parental L929 cells. After 11-12 h of coculture the cells were fixed and labeled with monoclonal antibody 412 (recognizing the HNK-1 carbohydrate epitope) or a polyclonal antibody against NCAM. For measurement of the total neurite length only the longest neurite per each branch was determined due to the highly branched character of the neurons in these cultures.

(A) Neurite outgrowth is promoted by CHL1 and inhibitable by antibodies. Neurons were cocultured with CHL1-transfectants (CHL1) or parental L929 cells (L929) with (+AB) or without polyclonal antibodies against recombinant CHL1 (500 μg/ml of purified IgG, added 45 min after plating) and on L1-transfectants. The mean total neurite length of 4-5 independent experiments is shown. Error bars are standard error of the mean.

(B) Different CHL1 lines promote neurite outgrowth better than L1. Neurons were cultured on two different CHL1-transfectants (CHL1 line 1, CHL1 line 2) with slightly different expression levels, parental L929 cells (L929) and L1 transfectants (L1). Total neurite length is given as percent of L929 cells as a control (ctr). Error bars are standard error of the mean.

(C) Neurite outgrowth promotion affects all length classes of neurites. Cumulative frequency distribution plot of the total neurite length of hippocampal neurons cocultured with CHL1-transfectants (CHL1 line 1 and 2) and parental L929 cells (L929) with (+AB) or without antibody treatment as given in (A). The percentage of neurons with neurites longer than or equal to a certain length×(vertical axis) was plotted as a function of neurite length×(horizontal axis). Values are from one representative experiment.

Figure 29A:
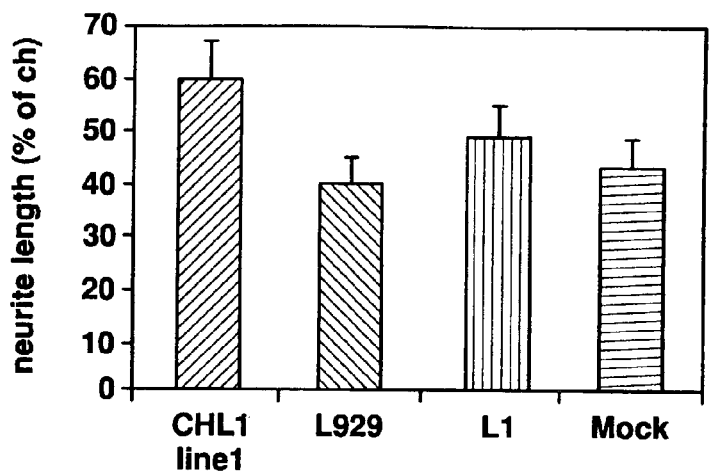
Figure 29B:
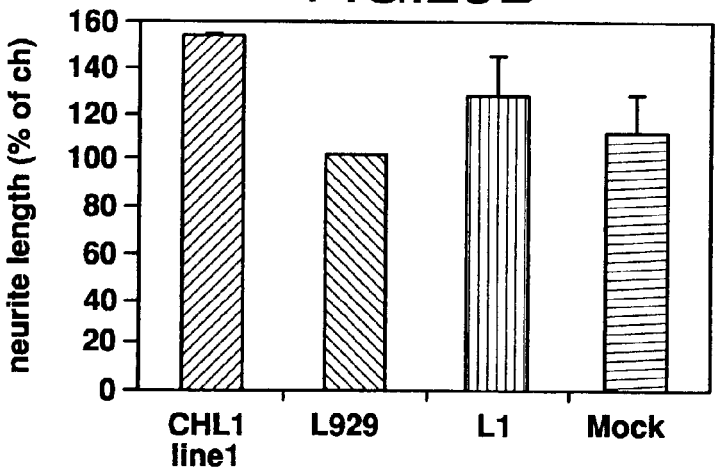
Figure 29C:
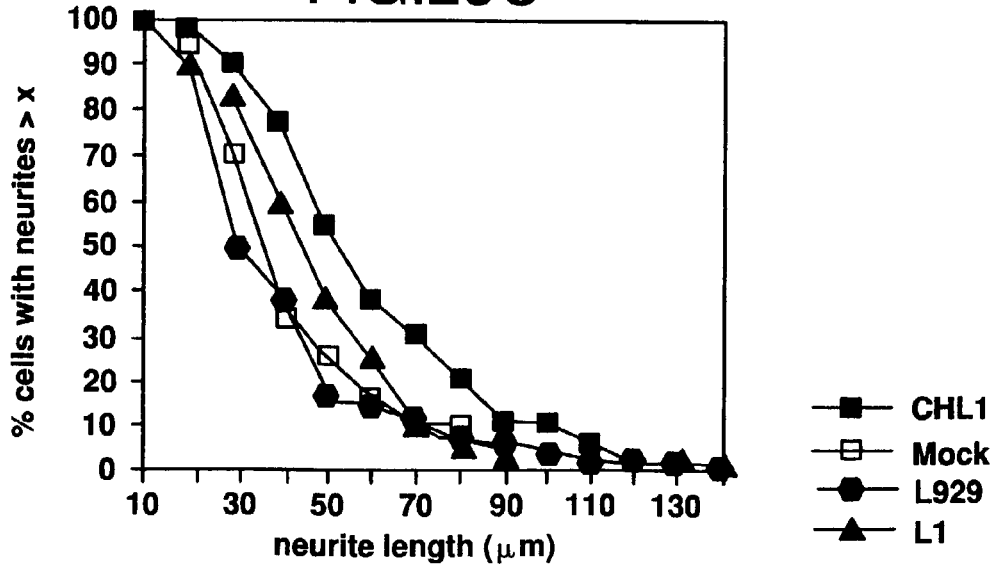

FIGS. 29A, 29B and 29C present data depicting neurite outgrowth of small cerebellar neurons in coculture with L929 transfectants. Cerebellar neurons derived from 6-7 day old mice were cultured for 20 h on CHL1 transfectants (CHL1), CHL1-transfected non-expressing L929 cells (Mock), parental L929, or L1-transfectants (L1). The staining of the cells was performed as already described in FIG. 7.

(A) CHL1 promotes neurite outgrowth of small cerebellar neurons. The mean of total neurite length of three experiments is shown. Error bars are standard error of the mean.

(B) CHL1 promotes neurite outgrowth also of small cerebellar neurons better than L1. The total neurite length is given as percent of L929 cells as a control (ctr). Error bars are standard error of the mean.

(C) Increase of neurite outgrowth of cerebellar neurons by CHL1 affects all size classes of neurites. Cumulative frequency of distribution plot of the total neurite length of the percentage of neurons with neurites longer than or equal to a certain length×(vertical axis) was plotted as a function of neurite length×(horizontal axis). Values from one representative experiment are shown.

Figure 30A:
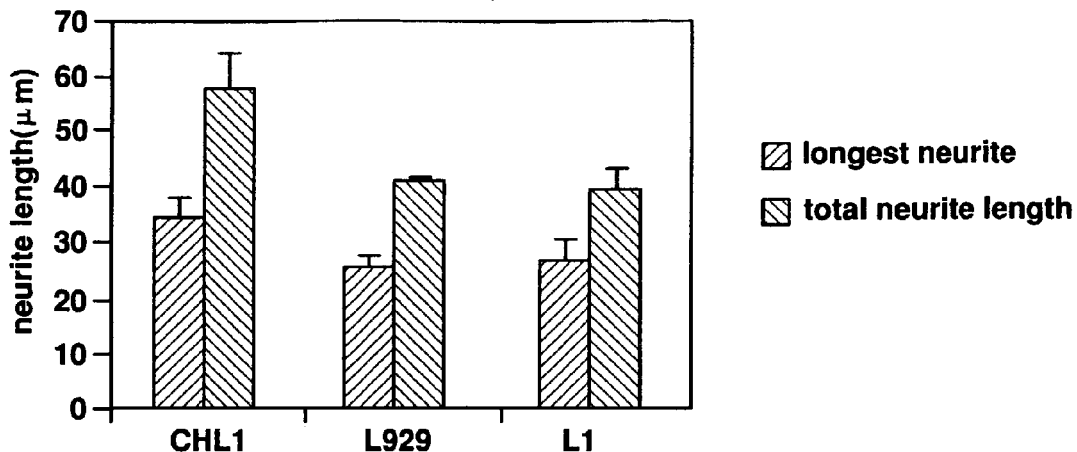
Figure 30B:
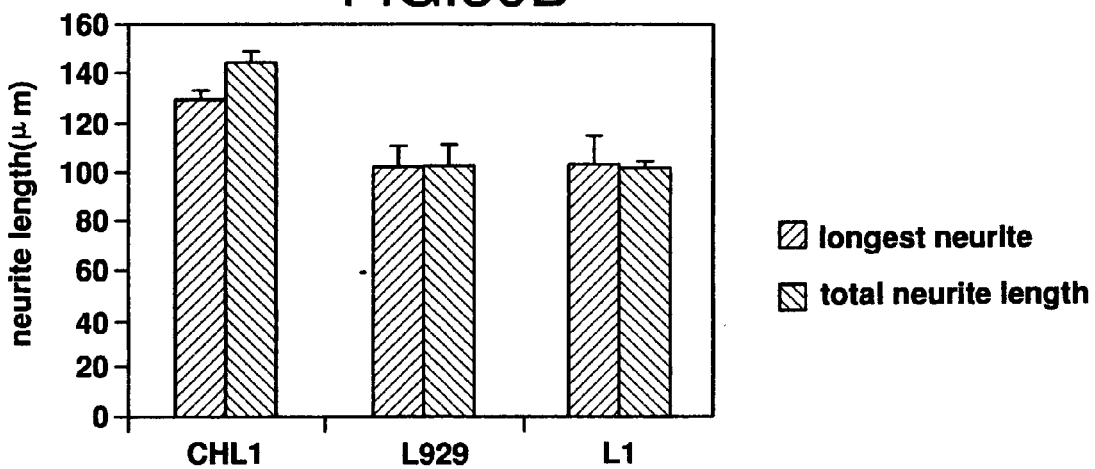
Figure 30C:
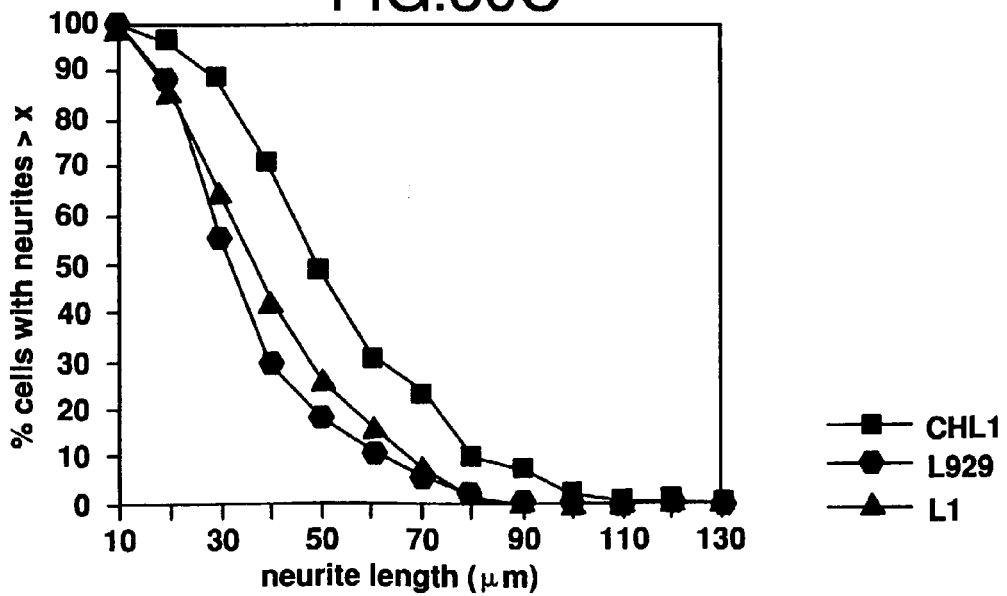

FIGS. 30A, 30B and 30C present data depicting neurite outgrowth of hippocampal neurons treated with soluble CHL1. Hippocampal neurons were cultured on poly-L-lysine coated coverslips for 12 h with addition of supernatants (40 µg/ml of total protein) of crude membrane preparations of CHL1-transfectants (CHL1), parental L929 cells (L929), or L1-transfectants (L1). Staining and measurement of neurite length was performed as already described (FIG. 7).

(A) Soluble CHL1 from L929 transfectants promotes outgrowth of the longest and the sum of all neurites per cell. Absolute length of longest neurite and total neurite length are shown. Values are means of three independent experiments. Error bars are standard error of the mean.

(B) Soluble CHL1 promotes a slight increase of neurite number. Total neurite length in percent of the neurite length of hippocampal neurons treated with supernatants derived from parental L929 cells (ctr) are plotted. Values are means of three independent experiments. Error bars are standard error of the mean.

(C) Also soluble CHL1 affects neurite outgrowths of all length classes of neurites. Cumulative frequency distribution plots of the total neurite length from one representative experiment are shown.

FIGS. 31A and 31B present data illustrating quantitative aggregation analysis and stability of CHL1- and L1-protein in L929 transfectants.

(A) Quantitative analysis of aggregation of S2 cell transfectants. To detect aggregation CHL1-(CHL1) (ctr) and L1-(L1) transfected cells were cultured (at densities of about $3 \times 10^6$ cells/ml) for 18 h in culture medium with (+ind) or without (−ind) induction of transgene expression by $CUSO_4$. Particle number was counted in a hemacytometer at the beginning and at the end of the incubation. The percentage of aggregation was calculated by the index $(1-N/NO) \times 100$. N18 and NO represent the particle numbers at the end or the beginning of the incubation period, respectively. Values are the means of at least four independent experiments. Error bars are standard deviations.

(B) Kinetics of aggregation of L929 transfectants. CHL1-transfected (CHL1), CHL1-transfected non-expressing (Mock), parental L929 (L929), and L1-transfected (L1) cells had been detached from tissue culture by treatment with low concentration of trypsin-EDTA, washed and incubated at 37° C. in polystyrene tubes. An aliquot of each sample was withdrawn every 30 min and the particle number was counted in a hemacytometer. The results are expressed as described in (A). Values shown are the means of at least three independent experiments. Bars are standard deviations.

Figures 32A, 32B:
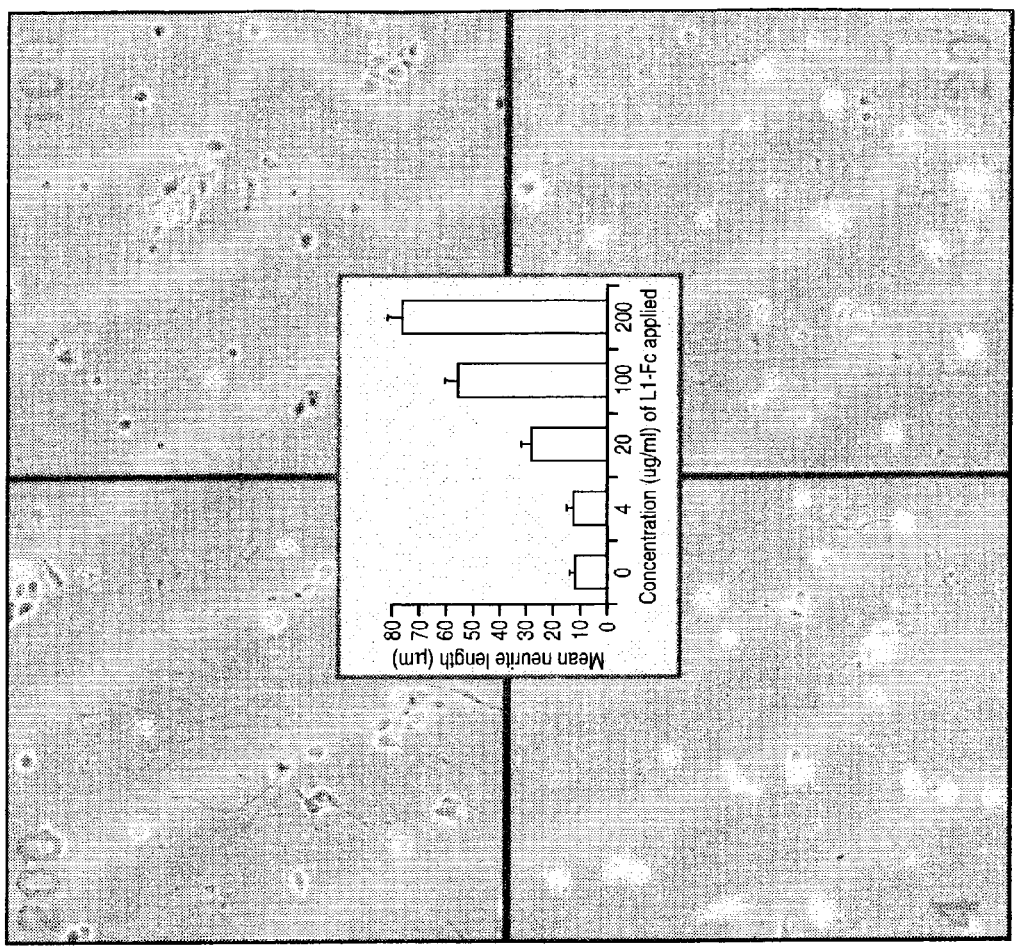

FIGS. 32A and B depict a soluble recombinant form of the cell adhesion molecule L1 and its effect on stimulation of neurite outgrowth. (A) A schematic diagram of the recombinant chimera, which consists of the whole extracellular domain of mouse L1 fused to the human immunoglobulin constant domain (Fc). (B) Substrate-Associated L1-Fc stimulates neurite outgrowth. Dissociated embryonic day 9 chicken dorsal root ganglion cells (DRG) were cultured on L1-Fc adsorbed onto a glass slide pre-coated with 10 µg/ml of polylysine. The cultures were fixed after 16 hrs after which the mean neurite length was determined. The results show absolute values for neurite length against the concentration of the L1-Fc applied in the adsorbing step. For each value, 200-250 neurons were sampled for mean neurite length calculation. Bars show one SEM. Representative pictures are shown for each concentration of L1-Fc applied.

Description of Production of the L1-Fc Chimera

Chinese Hamster Ovary (CHO) cells, secreting the L1-Fc chimera, were generously provided by Dr. Melitta Schachner. The L1-Fc chimera construct consists of the whole extracellular domain of mouse L1 (3387 nucleotides) and human Ig Fc (hinge, CH2-CH3 region, 1487 nucleotides) inserted into the pEE-14 vector. L1-Fc expression was driven by the CMV promoter/enhancer. Selection and amplification was based on expression of glutamine synthetase from a gene on the vector and growth in the presence of 25 µM Methionine Sulfoximine (MSX). The concentration of L1-Fc secreted into the culture supernatant was approximately 1 µg/ml after two days of confluence. The chimeric protein was purified using a protocol developed in collaboration with Drs. Martin Grumet and Takeshi Sakurai. Briefly, L1-Fc is precipitated from medium by the addition of powdered ammonium sulfate to 60% saturation. The precipitate is resuspended in 17.5 mM NaH2PO4, pH 6.3., and dialysed against the same buffer. The dialysate is then loaded onto an anion exchange column, DE52, to enrich the L1-Fc cover co-purifying bovine IgG. The chimera is eluted in 0.15 M KCl+17.5 mM NaH2PO4, pH 6.3. After alkanization to pH 8.0, the eluant is incubated with protein A-Sepharose. The L1-Fc protein is eluted with 100 mM glycine pH3.0; the pH is immediately neutralized by one tenth volume of 1M Tris pH8.0. The final L1-Fc protein is used for assay after dialysis against Phosphate Buffered Saline (PBS) pH 7.5. The native protein is reported to migrate at approximately 400 kDa. Under reducing conditions, the L1-Fc appears as a 200 kDa on Western blot. Protein purity was judged by Coomassie and silver stains.

Figure 33:
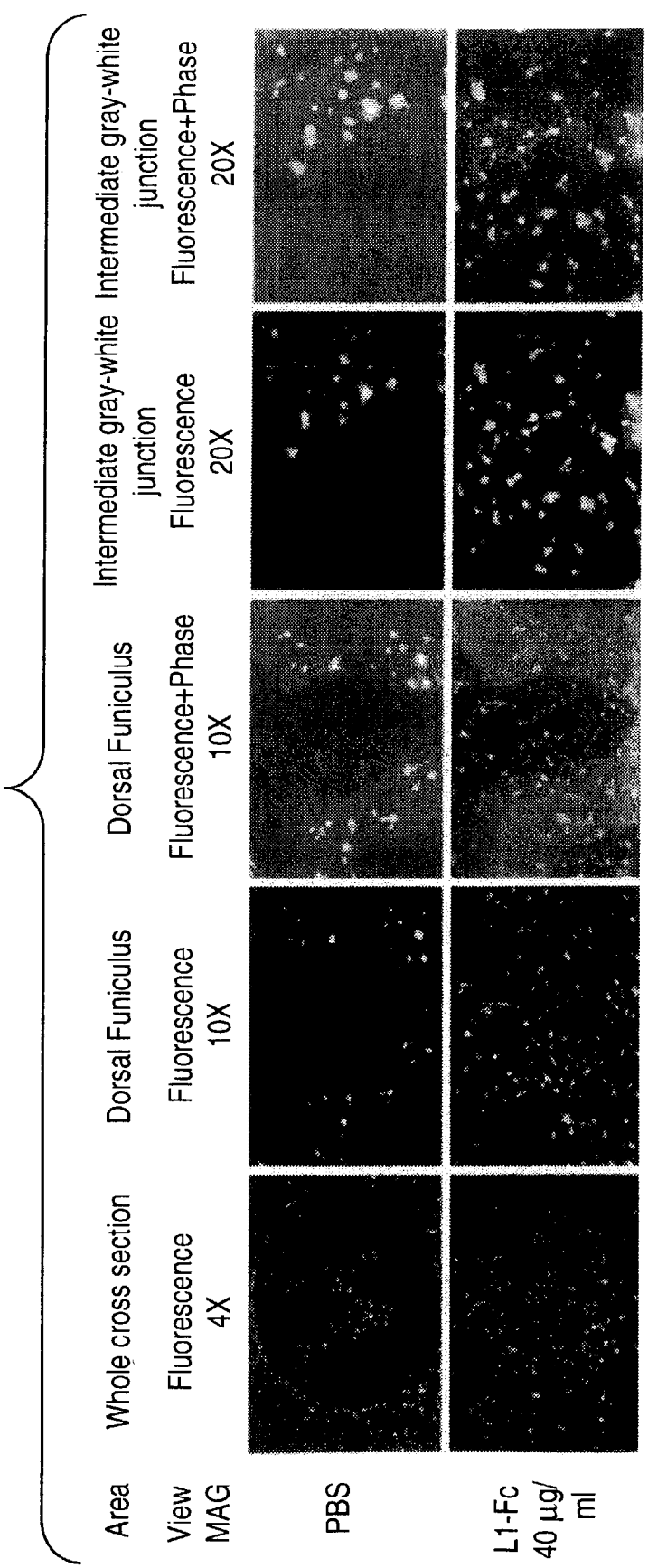

FIG. 33 depicts how L1-Fc can neutralize the inhibition of neurite outgrowth by white matter. Di-I-labeled dissociated embryonic day 8 chicken DRGs were seeded on to 15 µm frozen rat spinal cord cross-sections. In the upper panel, there are five views of a PBS treated spinal cord section. The neurons do not extend long processes and clearly adhere better to the gray matter; they avoid the white matter. In the bottom panel, neurons in the presence of 40 µg/ml of L1-Fc overcome the white matter inhibition, adhere to the section and extend processes.

FIG. 34A illustrates the delivery of L1-Fc to the rat spinal cord. Alzet pumps delivered 150-200 µg/ml of L1-Fc solution through a catheter at the lower lumbosacral area and threaded to 2 mm below the impact site. Western blots of five 5-mm cord segments were done after 2 weeks of L1-Fc application, using antibody against human Fc.

Figure 34B:
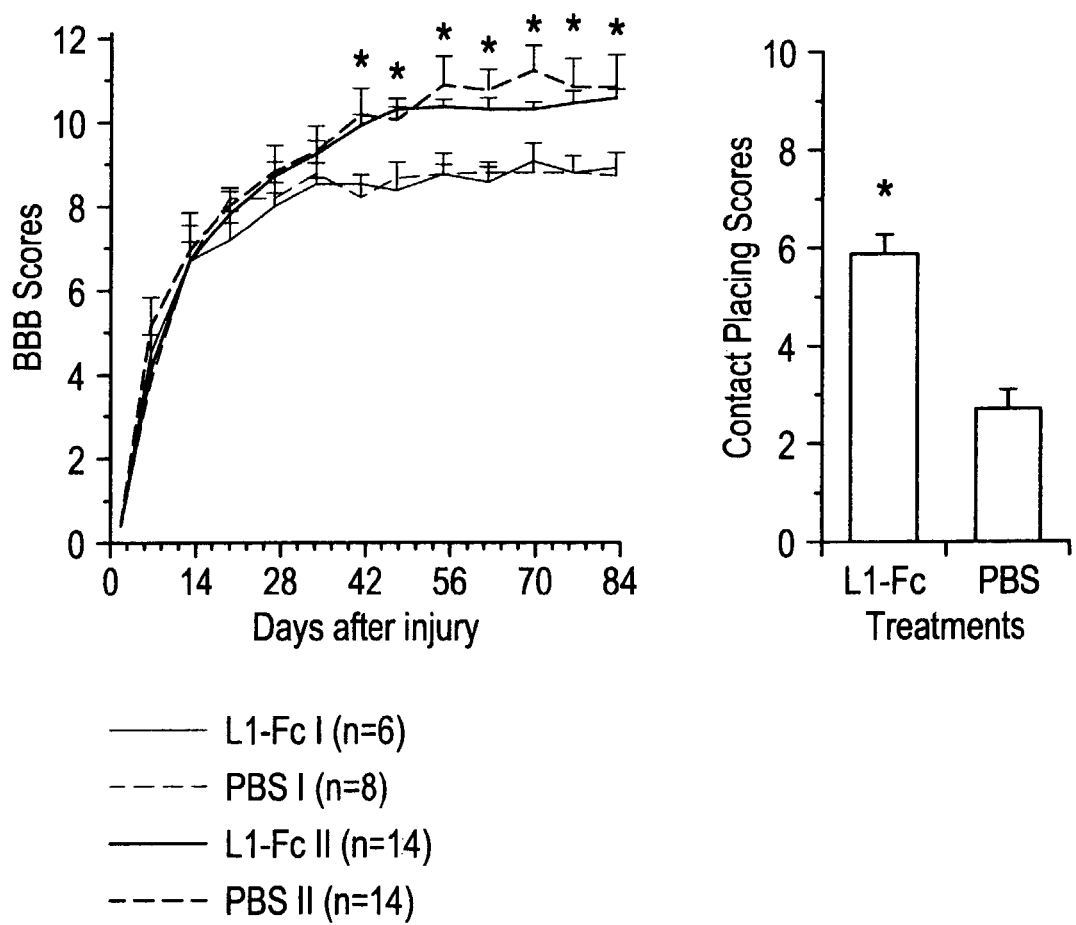

FIG. 34B illustrates the locomotor scores in rats treated with L1-Fc. The left graph shows the recovery of BBB scores over 12 weeks. Two groups of rats received L1-Fc (150 µg/ml n=6, 200 µg/ml n=14) compared with rats that received phosphate buffered saline (PBS). The error bars represent standard errors and asterisks indicate significant differences ($p<0.001$) between L1-Fc and controls. The right graph shows mean contact placing scores. Rats were held upright with hindlimbs dangling and a cotton wisp was used to brush the dorsum of the left and right feet alternatively. A full flexion-extension placing response counted as one while a partial or no response counted as zero. Each rat was tested ten times for a maximum score of 10 per rat. L1-Fc treated rats differed significantly from controls ($p<0.001$).

Figure 35:
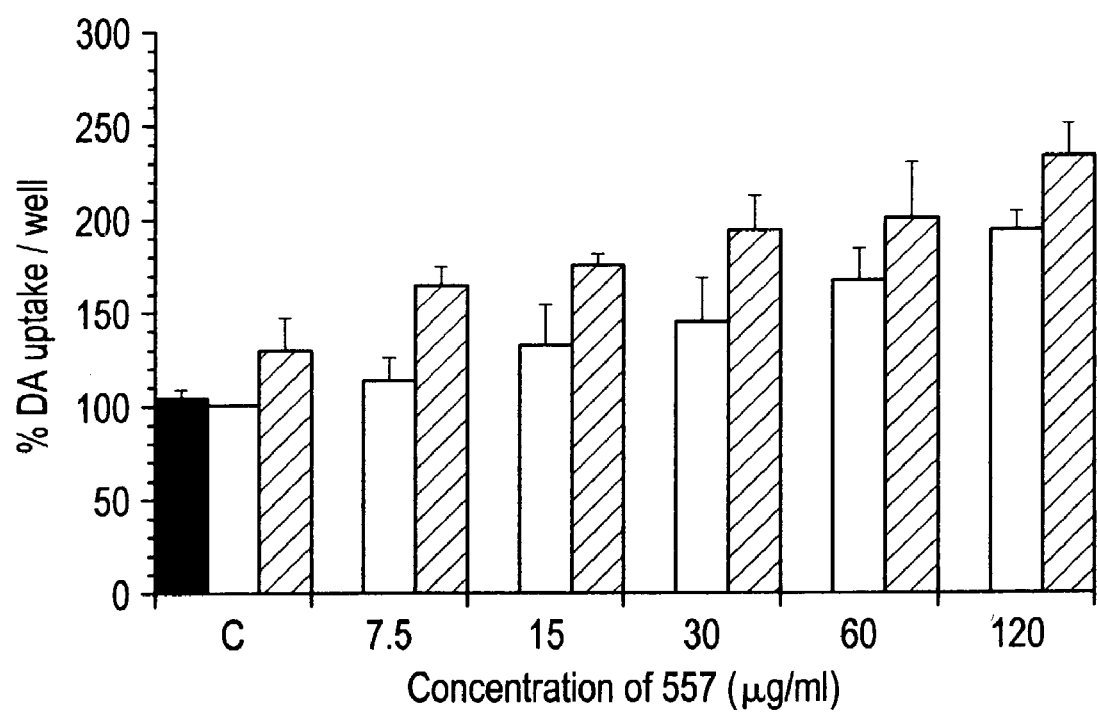

FIG. 35 is a graph depicting the dose dependent increase of tritiated dopamine uptake in 3-day-old primary cultures of embryonic rat ventral mesencephalon. Cultures were treated with 60 µg/ml of antibody 327 (black bar), or the indicated concentrations of antibody 557 without (open bars), and with (stippled bars), 0.5 µM phosphodiesterase type-IV inhibitor NQ-A, on day of plating and [$^3$H] dopamine uptake was assayed 3 days later. Results from 4 independent experiments (each with 4 wells/dose point) are expressed as a percentage±SEM, with untreated controls designated 100%. 100% corresponds to 4298±455, 4637±453, 3055±39, 4528±495 cpm/well in experiments 1, 2, 3 and 4 respectively.

Figure 36A:
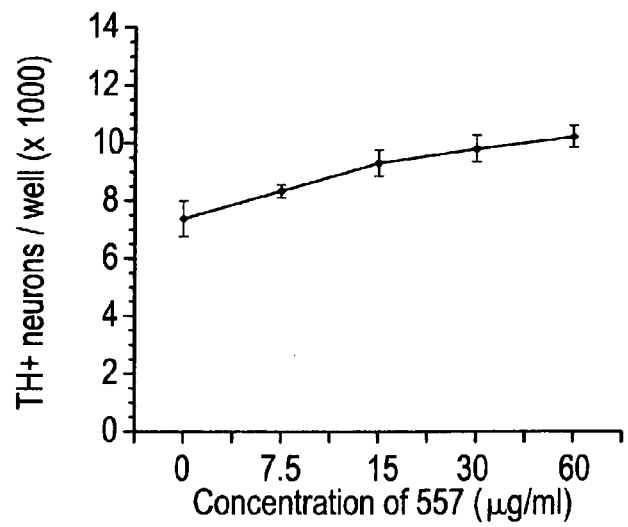
Figure 36B:
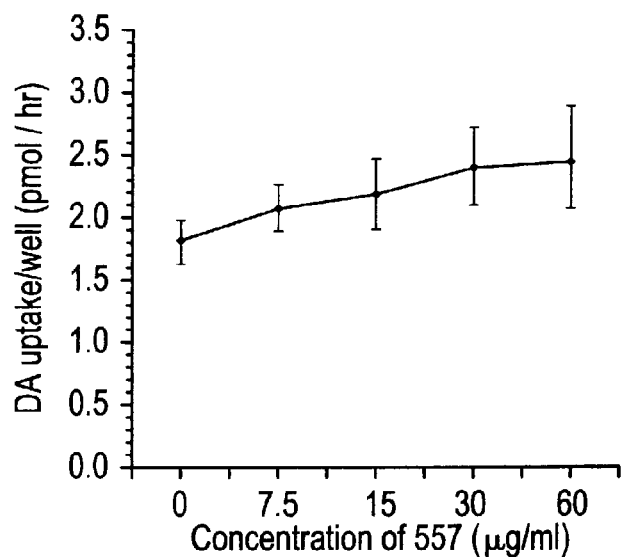
Figure 36C:
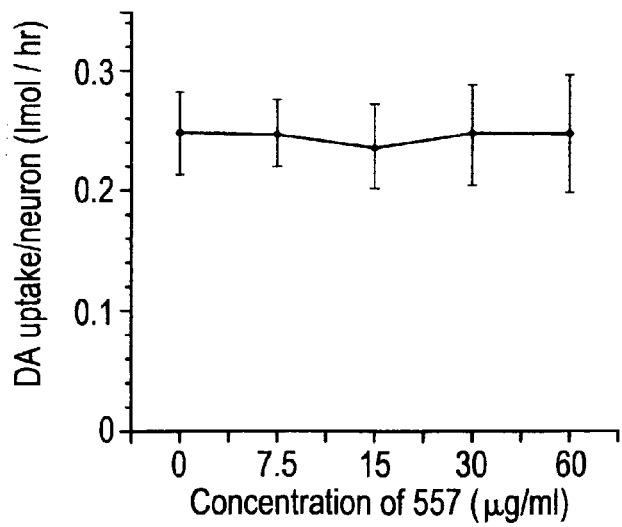

FIGS. 36A-C graphically depict the correlation between dopamine (DA) uptake and survival of dopaminergic neurons in 3-day-old primary cultures of embryonic rat ventral mesencephalon plated in the presence of increasing amounts of anti-L1 antibody, 557. (A) Number of TH+ neurons/well. (B) [$^3$H] dopamine uptake/well. (C) [$^3$H] dopamine uptake per TH+ neuron. This is one representative example of 3 separate experiments, n=1, ±SD (4 wells/dose point).

Figure 37A:
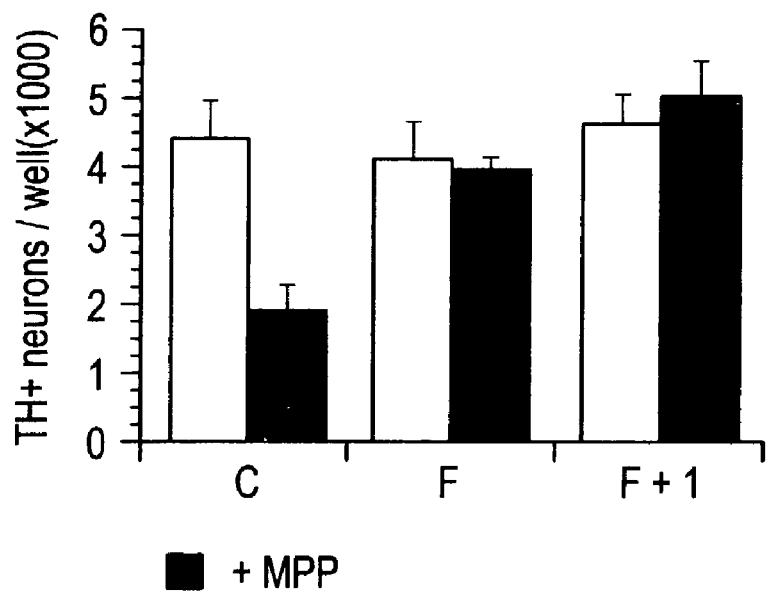
Figure 37B:
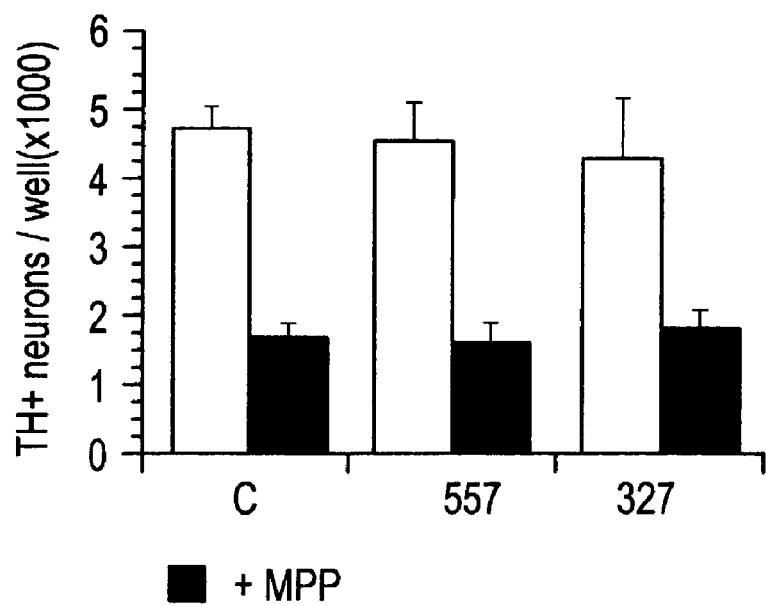

FIGS. 37A and 37B depict the influence of cAMP elevators and antibodies against L1 on survival of dopaminergic neurons in the presence of MPP$^+$ neurotoxin (black bars). 5 day old cultures were treated as indicated with (A) 0.5 µM forskolin alone, or combined with 1 µM phosphodiesterase type-IV inhibitor, NQ-A and (B) antibodies 557 or 327 (120 µM each). On day 6, 1 µM MPP$^+$ was applied and 48 hours later, the cells were stained with a tyrosine hydroxylase antibody and counted. C=untreated control, F=forskolin, F+I=forskolin in combination with PDE-IV inhibitor, NQ-A. Values are given±SD, n=4 wells/point. Experiments were repeated 4-6 times each.

FIG. 38 presents the characterization of L1-Fc and CHL1-Fc by SDS-PAGE and Western blotting.

A. SDS-PAGE analysis of the fusion proteins. L1-Fc (lanes 1 and 2) and CHL1-Fc (lanes 3 and 4) were separated on a 7% SDS-polyacrylamide gel under non-reducing (lanes 1 and 3) or reducing conditions (lanes 2 and 4), and stained with Coomassie blue.

B. A duplicate gel was blotted and probed with antibodies against mouse L1 (lanes 1 and 2) or CHL1 (lanes 3, 4).

FIG. 39 shows that L1-Fc and CHL1-Fc stimulate outgrowth of neurites. Cerebellar granule cells were seeded in X1 medium, with L1-Fc (panel A) or CHL1-Fc (panel B) offered as substrate (black bars) or in soluble form (open bars) at the indicated concentrations. Neurons derived from hippocampus of 18-day-old embryonic rats were cultured in supplemented DME/F12 medium and similarly treated with L1-Fc (panel C) or CHL1-Fc (panel D). The cultures were fixed after 18-20 hr and the mean total neurite length determined as described in the Methods section. Results represent the mean±S.E.M. Asterisks denote significant differences from neurons cultured on PLL alone. *$p<0.001$, $p<0.01$, *$p<0.05$ by Student's t-test.

FIG. 40 shows that cerebellar granule neurons maintained in serum-free medium undergo apoptosis.

A. Cerebellar granule cells maintained in X1 medium for 3 days were examined by phase contrast (a,b) and after staining with Hoechst 33258 (c,d). Apoptotic nuclei with condensed chromatin are indicated by arrowheads in (c,d). B. Phase contrast micrographs of cerebellar granule cells maintained for 5 days in X1 medium alone (a), supplemented with L1-Fc as substrate (b), or with soluble CHL1-Fc.

FIG. 41 demonstrates survival of cerebellar granule cells after different periods of culture with or without L1-Fc or CHL1-Fc (1 µg/ml). Survival was assessed by the MTT assay at the indicated times and was calculated as a parentage of all neurons seeded at time zero. The results of a representative experiment in triplicate are shown. Open symbols, control with PLL coating; closed symbols, with fusion protein. A, L1-Fc coated; B, L1-Fc in soluble form; C, CHL1-Fc coated; D, CHL1-Fc in soluble form. Error bars and asterisks as in FIG. 39.

Figure 42A:
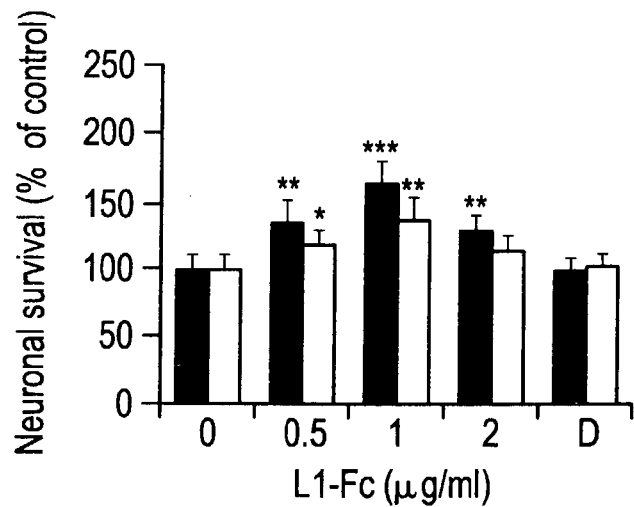
Figure 42B:
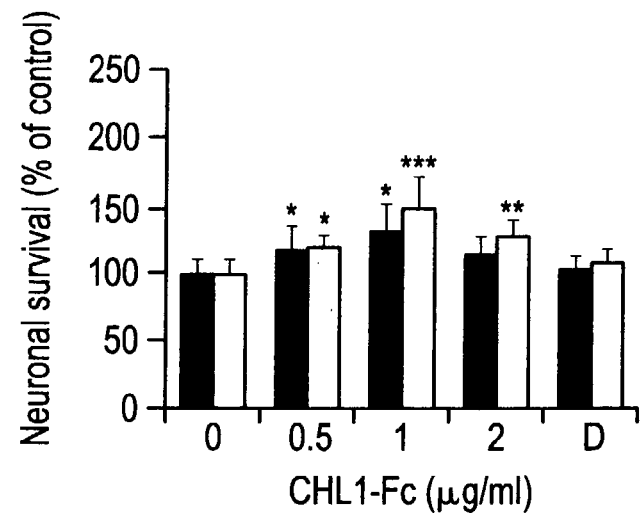

FIG. 42 shows the survival of cerebellar granule cells with different doses of L1-Fc and CHL1-Fc. A, B. Neurons were treated with L1-Fc (panel A) or CHL1-Fc (panel B) at the concentrations indicated (for coating (black bars) or in solution (open bars)). Neuronal survival was determined by the MTT assay after 5 days of culture. The results of representative experiments are shown. D=denatured by boiling for 5 min. The percent survival was defined as 100% in cultures with no fusion protein. C. Survival was also estimated by directly counting the number of viable cells using a double staining procedure ("LIVE/DEAD assay") after 5 days in culture with 1 µg/ml fusion protein. 1, PLL alone; 2, L1-Fc coated; 3, L1-Fc in soluble form; 4, CHL1-Fc coated; 5, CHL1-Fc in soluble form. Error bars and asterisks as in FIG. 39.

Figure 43A:
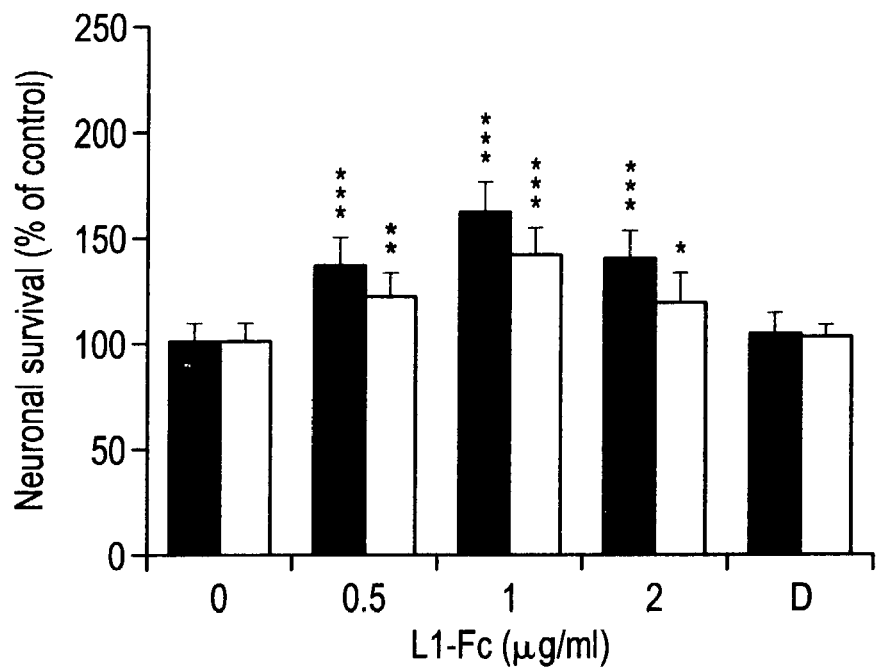
Figure 43B:
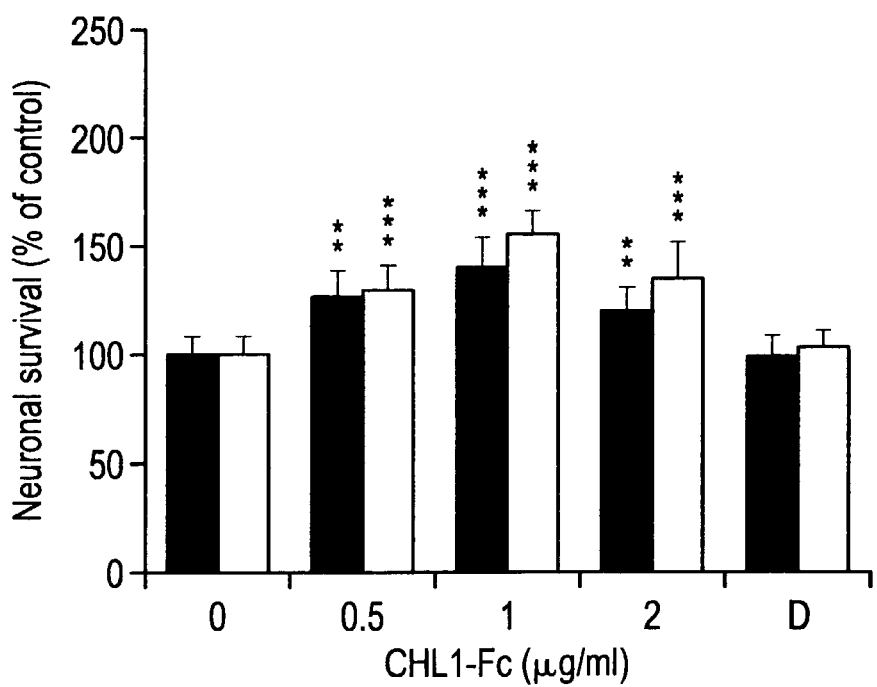

FIG. 43 demonstrates that L1-Fc and CHL1-Fc promote survival of embryonic hippocampal neurons.

A, B. Neurons derived from hippocampus of 18-day-old embryonic rats were treated with L1-Fc (panel A) or CHL1-Fc (panel B) at the concentrations indicated (for coating (black bars) or in solution (open bars)). Neuronal survival was determined by the MTT assay after 5 days in culture, and the percent of survival in the control without fusion protein was defined as 100%. The results of a representative experiment in triplicate are shown. Error bars and asterisks as in FIG. 39.

FIG. 44 shows that L1-Fc fusion protein Increases Sci-2 protein levels in cerebellar granule cells. Cerebellar granule cells were cultured for the indicated times with no additions (lanes 1), or with L1-Fc either coated (lanes 2) or in soluble form (lanes 3) at 1 µg/ml. A, Western blot analysis with polyclonal rabbit antibody against the human Bcl-2 protein, B, Densitometric quantification of Bcl-2 protein levels. The values in control cultures were set to 100%. Means of 3 independent experiments are shown. Error bars and asterisks as in FIG. 39.

Figure 45A:
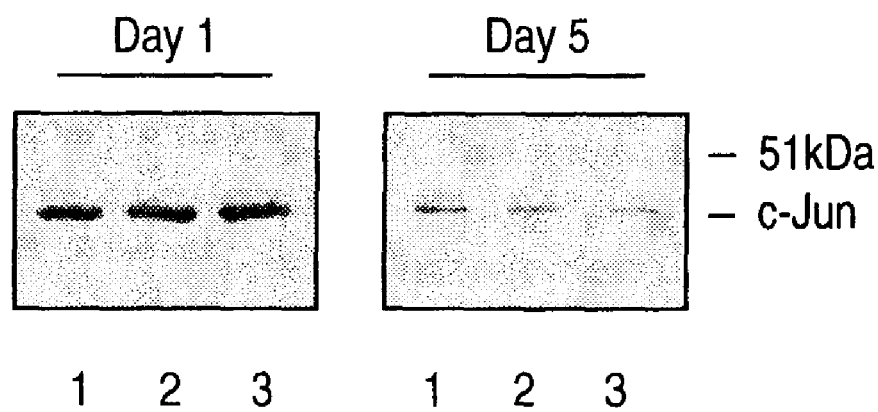
Figure 45B:
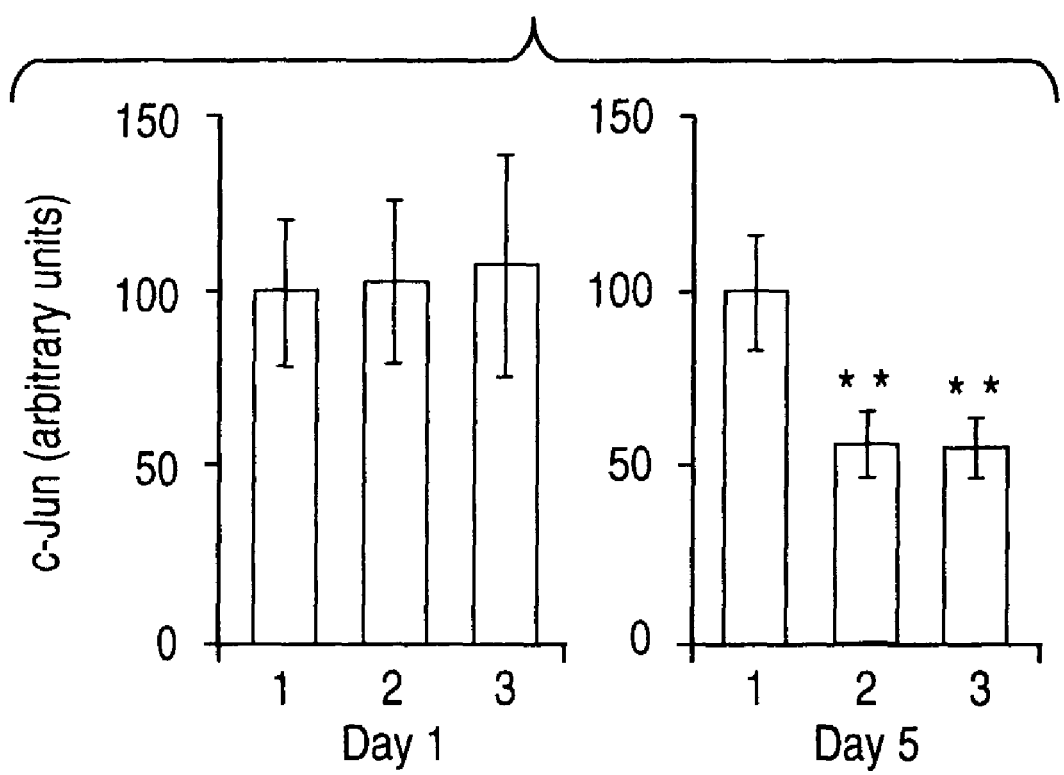

FIG. 45 shows that expression of c-Jun protein is reduced in cerebellar granule cells treated with L1-Fc. Cultures with no additions (lanes 1) or with L1-Fc offered as substrate (lanes 2) or in soluble form (lanes 3) at 1 µg/ml, were harvested at the indicated times.

A. Western blot analysis with affinity-purified rabbit polyclonal antibody against c-Jun.

B. densitometric quantitation of c-jun protein levels. The values in control cultures were set to 100%. Means of 3 independent experiments are shown. Error bars and asterisks as in FIG. 39.

DETAILED DESCRIPTION OF THE PREFERRED EMBODIMENTS OF THE INVENTION

More particularly, the present invention relates to the use of certain agents identified herein as "CNS neural growth modulators" (CNGMs), and particularly to a class of neural cell adhesion molecules as defined herein, to promote neurite outgrowth in the central nervous system (CNS). In general, neurons in the adult central nervous system have been considered incapable of regrowth, due to inhibitory molecular cues present on glial cells. The agents and methods of the present invention can be used to overcome this inhibition and promote CNS neurite outgrowth.

The agents of the invention include and may be selected from any cell adhesion molecule which is capable of modulating or promoting CNS neurite outgrowth, and particularly to molecules belonging to the immunoglobulin superfamily. More particularly, the molecules are selected from the members of the immunoglobulin superfamily which mediate $Ca^{2+}$-independent neuronal cell adhesion, including L1, N-CAM and myelin-associated glycoprotein. The invention also contemplates fragments of these molecules, and analogs, cognates, congeners and mimics of these molecules which have neurite-promoting activity. Particularly preferable structural motifs for these fragments and analogs include domains similar to the fibronectin type III homologous repeats (particularly repeats 1-2) and immunoglobulin-like domains (particularly domains I-II, III-IV and V-VI).

As the agents of the invention, and particularly, the members of the L1 CAM family, exhibit homophilic binding, both the agents and their antagonists, and particularly, their antibodies, may serve as agonists with respect to the receptor for the agents, and may thus be employed in both diagnostic and therapeutic applications in the same manner and for the same purpose as the agents themselves. Thus, L1 acts as a receptor, and its antibody may be employed as an agonist, to promote neurite outgrowth as set forth herein, to assist in neural regeneration particularly in the CNS. This capability is further demonstrated in the ability of the antibodies to L1 to serve in a method for the identification of further members of the L1 CAM family of neural recognition molecules, that will serve as agents herein, and the invention accordingly extends to the molecules that are identified, isolated and characterized by means of such antibodies. As such, therefore, the class of materials identified as CNS neural growth modulators hereinbelow, is considered to include the antibodies to CAMs such as L1 and its analogs, such as CHL1, described later on herein, among its numbers.

The present invention relates in one aspect to the ectopic expression of CNS neural growth modulators (CNGMs) or neural cell adhesion molecules on differentiated astrocytes in vivo. These molecules have been found to enhance neurite outgrowth on monolayer cultures of such astrocytes and cryostat sections of unlesioned and lesioned adult mouse optic nerves, and also in vivo, in optic nerve crush experiments in transgenic animals. The increased neurite outgrowth-promoting capacity is proportional to the level of ectopic CNGM expression. This is demonstrated by comparisons of the distinct transgenic lines of the invention, which express different basal levels of transgenic-encoded CNGM, and by correlations following increased CNGM expression after a lesion of the optic nerve. It should be appreciated that although optic nerves, both lesioned and unlesioned, are suitable for use with the present invention, that any part of the nervous system can likewise be used, including portions of the brain and spinal cord.

Neurite outgrowth is dependent on the levels of CNGM expression by astrocytes, demonstrating the specific effect exerted by CNGM in promoting neurite outgrowth in the transgenic animal. Inhibition of neurite outgrowth by polyclonal CNGM antibodies, but not by antibodies to mouse liver membranes, further supports this specificity, in particular, since both antibodies react well with the cell surfaces of neurons and astrocytes of transgenic animals.

In a preferred embodiment, the CNGM is L1. L1's biological effects can be inhibited by L1 antibodies, which indicates that L1 is homophilically active in a trans configuration at the cell surface of transgenic astrocytes. Furthermore, L1 species-specific antibodies that do not react with chicken dorsal root ganglion neurons inhibit neurite outgrowth of this neuronal cell type on transgenic astrocytes. These findings unequivocally identify L1 as a trans-acting active molecule and show that ectopic expression of L1 by glial cells that normally lack L1 expression significantly enhances neurite outgrowth in vitro.

The transgene-mediated enhancement of neurite outgrowth on glial cells that do not normally express L1 in vivo indicates that glial cells of the adult mammalian central nervous system can be made more conducive to neurite outgrowth. The loss of neurite outgrowth-promoting glia-derived molecules with maturation (Smith et al. (1986) *J. Comp. Neurol.* 251:23-43; Smith et al. (1990) *Dev. Biol.* 138:377-390) therefore appears to be compensated for by expression of a recognition molecule that is normally highly expressed by glial cells in the adult mammalian peripheral nervous system (Niecke et al. (1985); Bixby et al. (1988) *J. Cell. Biol.* 107:353-362; Seilheimer et al. (1988) *J. Cell. Biol.* 107:341-351).

The phenotype of adult astrocytes from the present transgenic lines may be modified towards the more Schwann cell-related capacity of reexpressing L1 after infliction of a lesion. An increase in L1 expression by Schwann cells is likely mediated by neurotrophins upregulated after damage by autocrine mechanisms (Seilheimer et al. (1987) *EMBO J.* 6:1611-1616). Similarly, L1 expression by astrocytes in culture can be upregulated by TGF-β and NGF (Saad et al. (1991)). By generating mice with a GFAP-L1 transgene, the inability of mature astrocytes to respond to neural injury is overcome with an upregulation of the neurite outgrowth promoting molecule L1. The expression of L1 may be particularly beneficial for neurite outgrowth in myelinated tracts of the central nervous system which normally contain several molecules that are neurite outgrowth inhibiting (Schachner et al., *Perspectives in Developm. Neurobiol. in Press*; Schwab et al. (1995) *Ann. Rev. Neurosci.* 16:565-595).

The present invention demonstrates that the inhibitory action of astroglial and oligodendroglial cells may be overcome, at least in part, by the neurite outgrowth promoting properties of the agents defined herein, and as particularly illustrated by the activity of ectopically expressed L1. Expression of L1 by astrocytes seems also to compensate for inhibitory effects exerted by oligodendrocytes. Permissive and non-permissive molecular cues therefore may not have to be localized on the same cell type for neurite outgrowth to occur. Instead, such molecular cues might be partitioned among different cell types. The cellular and molecular manipulation of L1 and other neurite outgrowth promoting molecules may therefore allow enhancement of the regenerative capacity of the adult mammalian central nervous system following injury or disease.

As indicated earlier, the present invention extends to the promotion of neural growth in the CNS, including such growth as is desired to regenerate structures lost due to injury or illness, as well as those structures and tissues exhibiting incomplete or immature formation. The agents of the invention also exhibit a neuroprotective or neuropreservative effect as illustrated later on herein, and for example, could be administered to inhibit or counteract neural degeneration or loss of variable etiology. Likewise, the present agents may be administered to treat such conditions as Alzheimer's disease and Parkinson's disease, where such neurodegenerative effects, among other characteristics, are observed. Also set forth and demonstrated herein is the use of the agents of the invention to enhance memory, the loss of which is a hallmark of Alzheimer's disease.

The invention also extends to the promotion of remyelination in the central nervous system, including the use of the present agents to treat diseases wherein the myelin sheath is damaged or destroyed, such as in multiple sclerosis. Likewise, the invention applies to the concomitant treatment of such conditions where axonal cell death is occurring or may occur, which is also observed in multiple sclerosis. Thus, the methods of the invention contemplate and include this dual objective within their scope.

More particularly, the methods of the invention extend to the inhibition of axonal cell death and the enhancement of myelination and remyelination in the central nervous system by the administration of a therapeutically effective amount of the agents of the present invention. As used herein, the term "therapeutically effective amount" means an amount sufficient to inhibit axonal cell death, or that amount sufficient to enhance myelination and remyelination in the central nervous system. Specific amounts are as set forth herein or as would be within the skill of the clinician having the benefit of the present disclosure.

The invention accordingly extends to constructs and compositions containing or delivering the agents of present invention, whether by the promotion of the expression of certain agents via gene therapy or the like, or by the exogenous administration of the agents where appropriate and beneficial, in pharmaceutical compositions to treat injured or diseased CNS structures. In this latter connection, it is contemplated that certain of the agents are able to exert a growth promoting effect when so administered, although it is recognized that members of the presently identified group, such as L1 and N-CAM appear to bind homophilically and may therefore prove more beneficial when delivered by means of expression. The invention is intended to extend to both routes and protocols where feasible.

It should also be appreciated that the present invention relates to the use of CNGM-secreting cells for the modulation of neural outgrowth, regeneration, neuroprotection and neural survival in the CNS. As such, certain soluble CNGMs and fragments thereof, and cognate molecules thereof are also within the invention.

Therefore, if appearing herein, the following terms shall have the definitions set out below.

The terms "agent", "CNS neural growth modulator", "CNGM", "neural recognition molecule", "recognition factor", "recognition factor protein(s)", "neural adhesion molecule", and any variants not specifically listed, may be used herein interchangeably, and as used throughout the present application and claims refer to proteinaceous material including single or multiple proteins, and extends to those proteins having the amino acid sequence previously described and the profile of activities set forth herein and in the Claims. The foregoing terms also include active fragments of such proteins, cognates, congeners, mimics and analogs, including small molecules that behave similarly to said agents.

Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "CNS neural growth modulator", "CNGM", "neural recognition factor", "recognition factor", "recognition factor protein(s)", and "neural adhesion molecule" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to probes, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

In its general usage apart from reference to the inhibition of axonal cell death and enhancement of myelination and remyelination, defined elsewhere herein, the phrase "therapeutically effective amount" is used herein to mean an amount sufficient to prevent, and preferably reduce by at least about 30 percent, more preferably by at least 50 percent, most preferably by at least 90 percent, a clinically significant change in a particular feature of a given pathology, such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash.

In one aspect, the present invention relates to transgenic animals which express a CNGM or neural recognition molecule, in particular L1, and preferably in astrocytes. These animals have increased capability for neural outgrowth in the central nervous system.

The invention also includes an assay system for the screening of potential drugs effective to modulate neural outgrowth of target mammalian cells by interrupting or potentiating the CNGM's neural recognition activity. By "neural recognition activity" or "neural adhesion activity" is meant any biological effect which is a result of the CNGM's binding to another molecule, including intracellular effects on second messengers. In one instance, the test drug could be administered either to a cellular sample with the ligand that activates the CNS neural growth modulator, or a transgenic animal expressing the CNS neural growth modulator, to determine its effect upon the binding activity of the modulator to any chemical sample, or to the test drug, by comparison with a control. Identifying characteristics of at least one of the present CNS neural growth modulators, in particular L1, is its participation in changes in steady state levels of intracellular messengers, including $Ca^{2+}$, pH, and cyclic nucleotides, as well as changes in the activities of protein kinases such as protein kinase C, pp60$^{c\text{-}src}$, a casein type II kinase and another kinase known to phosphorylate L1.

The assay system could more importantly be adapted to identify drugs or other entities that are capable of binding to the CNGMs or proteins, either in the cytoplasm or in the nucleus, thereby inhibiting or potentiating transcriptional activity. Such assay would be useful in the development of drugs that would be specific to particular cellular activity, such as neural outgrowth or increase in synaptic efficacy, or that would potentiate such activity, in time or in level of activity. For example, such drugs might be used to modulate neural outgrowth in response to injury, or to treat other pathologies, as for example, in treating neurodegenerative diseases such as Parkinson's Disease, ALS, Huntington's Disease and Alzheimer's Disease.

In yet a further embodiment, the invention contemplates agonists and antagonists of the activity of a CNS neural growth modulator. In particular, an agent or molecule that inhibits the ability of neurons to recognize a CNGM such as L1 can be used to block neural outgrowth, where such outgrowth is contraindicated, and as described earlier, a pharmaceutical composition containing such an agent may be administered directly to the target site. In another embodiment, an agonist can be a peptide having the sequence of a portion of an L1 domain particularly that between fibronectin type III homologous repeats 2 and 3, or an antibody to that region. Either of these molecules may potentially be used where a particular CNGM such as L1 has the ability to undergo homophilic binding (i.e., L1 can bind to itself, and therefore both antibodies to L1 and fragments of L1 itself are capable of binding to L1).

One of the diagnostic utilities of the present invention extends to the use of the present CNGMs in assays to screen for protein kinase inhibitors. Because the activity of the CNGMs described herein are phosphorylated, they can and presumably are dephosphorylated by specific phosphatases. Blocking of the specific kinase or phosphatase is therefore an avenue of pharmacological intervention that would modulate the activity of these neural recognition proteins.

The present invention likewise extends to the development of antibodies against the CNGMs, including naturally raised and recombinantly prepared antibodies. For example, the antibodies could be used to screen expression libraries to obtain the gene or genes that encode the CNGMs. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating neural outgrowth.

In particular, antibodies against CNS neural growth modulators can be selected and are included within the scope of the present invention for their particular ability in binding to the protein. Thus, activity of the neural growth modulators or of the specific polypeptides believed to be causally connected thereto may therefore be followed directly by the assay techniques discussed later on, through the use of an appropriately labeled quantity of the neural growth modulator or antibodies or analogs thereof.

Thus, the CNGMs, their analogs, and any antagonists or antibodies that may be raised thereto, are capable of use in connection with various diagnostic techniques, including immunoassays, such as a radioimmunoassay, using for example, an antibody to the CNGM that has been labeled by either radioactive addition, reduction with sodium borohydride, or radioiodination.

In an immunoassay, a control quantity of the antagonists or antibodies thereto, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached. For example, antibodies against the CNGMs may be selected and appropriately employed in the exemplary assay protocol, for the purpose of following protein material as described above.

In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the neural growth modulators, or to identify drugs or other agents that may mimic or block their activity. The system or test kit may comprise a labeled component prepared by one of the radioactive and/or enzymatic techniques discussed herein, coupling a label to the neural growth modulators, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the CNS neural growth modulator(s), its (or their) subunits, or active fragments thereof, or upon agents or other drugs determined to possess the same activity. A first therapeutic method is associated with the promotion of CNS neural growth resulting from the presence and activity of the CNGM, its active fragments, analogs, cognates, congeners or mimics, and comprises administering an agent capable of modulating the production and/or activity of the CNGM, in an amount effective to promote CNS development, regrowth or rehabilitation in the host. Conversely, drugs or other neutralizing binding partners to the CNGM or proteins may be administered to inhibit or prevent undesired neural outgrowth. Also, the modulation of the action of specific kinases and phosphatases involved in the phosphorylation and dephosphorylation of CNGMs or proteins presents a method for modulating the activity of the modulator or protein that would concomitantly potentiate therapies based on CNGM/protein activation.

More specifically, the therapeutic method generally referred to herein could include the method for the treatment of various pathologies or other cellular dysfunctions and derangements by the administration of pharmaceutical compositions that may comprise effective inhibitors or enhancers of the activity of the CNS neural growth modulator or its subunits, or other equally effective drugs developed for instance by a drug screening assay prepared and used in accordance with a further aspect of the present invention. For example, drugs or other binding partners to the CNS neural growth modulator or proteins may be administered to inhibit or potentiate binding and second messenger activity.

As mentioned above, the invention extends to the discovery of a full family of L1 CAMs, and particularly to an analog to L1 known as CHL1. CHL1 comprises an N-terminal signal sequence, six immunoglobulin (Ig)-like domains, and 4.5 fibronectin type III (FN)-like repeats, a transmembrane domain, and a C-terminal, most likely intracellular domain of approximately 100 amino acids. CHL1 is most similar in its extracellular domain to chicken Ng-CAM (about 40% amino acid identity), followed by mouse L1, chicken neurofascin, chicken Nr-CAM, *Drosophila* neuroglian, and zebrafish L1.1 (37 to 28% amino acid identity, respectively), and mouse F3, rat TAG-1, and rat BIG-1 (about 27% amino acid identity). The similarity with other members of the Ig superfamily (e.g. N-CAM, DCC, HLAR, rse) is 16 to 11%. The intracellular domain is most similar to mouse and chicken Nr-CAM, mouse and rat neurofascin (about 50% amino acid identity) followed by chicken neurofascin and Ng-CAM, *Drosophila* neuroglian, and zebrafish L1.1 and L1.2 (about 40% amino acid identity). Besides the high overall homology and conserved modular structure among previously recognized members of the L1 family (mouse/human L1/rat NILE: chicken Ng-CAM; chicken/mouse Nr-CAM; *Drosophila* neuroglian; zebrafish L1.1 and L1.2; chicken/mouse neurofascin/rat ADGP), L1 characteristic criteria were identified with regard to the number of amino acids between positions of conserved amino acid residues defining distances within and between two adjacent Ig-like domains and FN-like repeats. These show a colinearity in the six Ig-like domains and adjacent four FN-like repeats that is remarkably conserved between L1 and molecules containing these modules (designated the L1 family cassette) including the GPI linked forms of the F3 subgroup (mouse F3/chicken F11/human CNTN1; rat BIG-1/ mouse PANG; rat TAG-1/mouse TAX-1/chicken axonin-1). The colorectal cancer molecule (DCC) previously introduced as an N-CAM like molecule conforms to the L1 family cassette. Other structural features of CHL1 shared between members of the L1 family are a high degree of N-glucosidically linked carbohydrates (about 20% of its molecular mass), which include the HNK-1 carbohydrate structure, and a pattern of protein fragments comprising a major 185 kD band and smaller fragments of 100 and 125 kD. As for the outer L1 family members, predominant expression of CHL1 is observed in the nervous system and at later developmental stages.

The following examples are presented in order to more fully illustrate the preferred embodiments of the invention. They should in no way be construed, however, as limiting the broad scope of the invention.

EXAMPLE 1

GFAP-L1 Transgene and Production of Transgenic Mice

Glial fibrillary acidic protein (GFAP, Eng et al. (1971) *Brain Res.* 28:351-354) is expressed predominately by astrocytes at late stages in the development of the mouse central nervous system (Landry et al. (1990) *J. Neurosci. Res.* 25:194-203). Therefore regulatory sequences of the GFAP gene were used to direct the expression of the neural cell adhesion molecule L1 to mature astrocytes of transgenic mice. The GFAP-L1 transgene (FIG. 1) encodes only the neural cell adhesion molecule L1 since the ATG of the GFAP gene was mutated and the L1 coding sequence is followed 3' by a translational stop and a polyadenylation signal (Toggas et al. (1994) *Nature* 367:188-193). This construct was used to establish three different lines of transgenic mice, designated 3418, 3426 and 3427.

The mouse L1 cDNA (Moos et al. (1988) *Nature* 334:701-703) was inserted into exon 1 of the murine glial fibrillary acidic protein (GFAP) gene modified as described previously (Toggas et al. (1994) *Nature* 367:188-193). The 4.05 kb mouse L1 cDNA containing the entire coding sequence of the protein and 250 3' non-translated nucleotides was fused with the modified GFAP-L1 transgene.

The 14.5 kb GFAP-L1 transgene was excised from a modified cloning vector by digestion with Sfi I, followed by electrophoresis and electroelution from an agarose gel. Purified DNA was diluted to a final concentration of 2 μg/ml in $T_5E_{0.1}$ (5 mM Tris-HCl, pH 7.4, 0.1 mM EDTA). Approximately 2 pl of diluted DNA were microinjected into the male pronucleus of fertilized eggs derived from CB6F1 females (superovulated) mated to C57B1/6J males. Eggs surviving the micromanipulation were transferred into oviducts of pseudo-pregnant foster mothers following describes methods (Hogan et al. (1986) *Manipulating Mouse Embryo*, Cold Springs Harbor Laboratory, New York).

EXAMPLE 2

Southern Blot Analysis

Mice were analyzed for the integration of the transgene into the mouse genome by Southern blot analysis of genomic DNA isolated from tail biopsies (Southern (1975) *J. Mol. Biol.* 98:503-517). Transgenic founder mice were mated and pups screened in the same manner to establish transgenic lines. Ten μg samples of DNA were digested with either Bam HI or with Eco RI and Xba I followed by electrophoretic separation on a 0.7% agarose gel and transfer to Hybond N+ membrane (Amersham) under alkaline conditions. A 3.3 kb Eco RI-fragment of the L1 cDNA or a 330 bp Hind III fragment of SV40 late splice and polyadenylation site purified from A1.5 plasmid (Maxwell et al. (1989) *Biotechniques* 7:276-280) were labelled with $^{32}\pi\alpha$-CTP by random priming (Boehringer Mannheim) for use as probes. Prehybridization was performed at 65° C. for one hour in 5×SSPE, 5×Denhardt's solution, 0.5% (w/v) SDS and 0.1 mg/ml sonicated non-homologous DNA. Hybridization was performed overnight. Final stringency wash conditions for all Southern blots were 0.1×SSPE and 0.1% SDS (w/v) at 65° C.

EXAMPLE 3

Northern Blot Analysis

Anaesthetized adult mice (12-weeks-old) were sacrificed by a lethal dose of chloralhydrate and brains were removed and immediately frozen in liquid nitrogen. Total cellular RNA was isolated by pulverizing the tissue in liquid nitrogen. Four molar guanidinium thiocyanate was added to the pulverized tissue. Isolation of total RNA was performed as described (Chomczynski et al. (1987) *Anal. Biochem.* 162:156-159; Pagliusi et al. (1989) *AMOG. J. Neurosci. Res.* 22:113-119). RNA yields were estimated from absorbance at 260 nm. Ten μg of the RNA were fractionated on 1% agarose-formaldehyde gels for Northern blot analysis (Thomas (1980) *Proc. Natl. Acad. Sci. USA* 77:201-205).

Randomly primed L1 cDNA probes were used to simultaneously detect the endogenous L1 mRNA of 6 kb (Tacke et al. (1987) *Neurosci. Lett.* 82:89-94) and the transgene-derived L1 mRNA of 4.2 kb. Densitometric analysis of Northern blots was performed on scanned images (Arcus scanner, Agfa-Gavaert) of the original films using the Image Program (NIH, Research Services Branch, NIMH).

Figure 2:
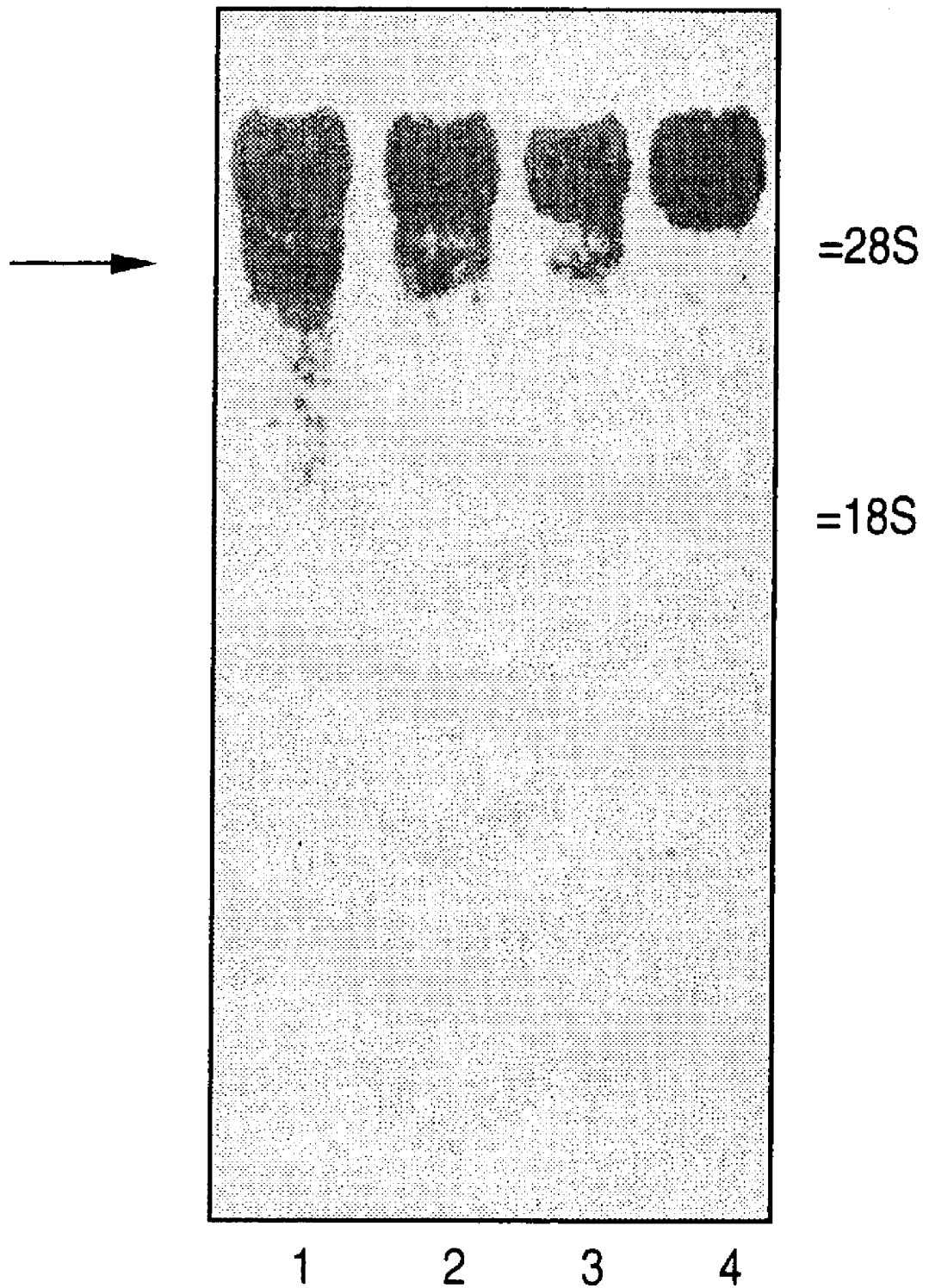
FIG. 2 depicts a Northern blot analysis of brain RNA from different transgenic lines. 10 μg of total RNA of whole adult brain was loaded in each lane and probed with mouse L1 cDNA. Exposure time was 3 days. Lanes 1-3, brains from different transgenic offspring (lane 1: line 3426; lane 2: line 3427; lane 3: line 3418; lane 4, brain from non-transgenic control). Note that the level of transgenic L1 mRNA (arrow) is different in the three transgenic lines, with levels being highest in line 3426, intermediate in line 3427 and lowest in line 3418. The position of 28S and 18S rRNA is shown on the right margin.

Northern blot analysis of total RNA from whole brains of the transgenic animals revealed L1 transcripts of a size (4.2 kb) expected for transgene-derived mRNA (FIG. 2). These transcripts are clearly distinct from the endogenous L1 mRNA which is 6 kb and derived from postmitotic neurons. Densitometric analysis revealed that the levels of transgene-derived L1 mRNA were 34%, 13% and 8% in lines 3426, 3427 and 3418, respectively, as compared to the levels of endogenous L1 mRNA (rated 100%).

EXAMPLE 4

Animals

For cultures on cryostat sections, immunocytochemistry and in situ hybridization experiments, control animals were taken from stocks of age-matched normal C57b1/6J mice or non-transgenic littermates. For isolation of small cerebellar neurons and for preparation of astrocyte cultures six-day-old ICR non-transgenic pups were used. Dorsal root ganglion (DRG) neurons were prepared from eight-day-old chick embryos.

EXAMPLE 5

In Situ Hybridization

To verify that astrocytes of transgenic animals expressed L1 in vivo, optic nerves were analyzed by in situ hybridization. The optic nerve was chosen since it contains only glial cells and is free of neuronal cell bodies. Astrocytes in vivo normally lack expression of L1 at any developmental stage (unpublished data).

For detection of L1 mRNA in cryostat sections of fresh-frozen brain sections, digoxigenin-labelled cRNA was generated by in vitro transcription (Dörries et al. (1993) *Histochemistry* 99:251-262). The sequence encoding the extracellular part of L1 (Moos et al. (1988) was subcloned into the pBluescript KS+ (Stratagene) vector. Anti-sense and sense cRNA probes were generated by transcribing the L1 insert after linearization of the resulting plasmid with Xho I or Xba I, using the T7 and T3 promoters, respectively. For generation of GFAP cRNA probes, a 1.2 kb fragment of GFAP cDNA (Lewis et al. (1984) *Proc. Natl. Acad. Sci.* 81:2743-2745; kindly provided by Dr. N. J. Cowan) encoding the N-terminus of the protein was subcloned into the pBluescript KS+ vector. Anti-sense and sense cRNA probes were generated by transcribing the resulting plasmid, linearized with Eco RI and Xho I, from the T3 and T7 promoters, respectively. To improve tissue penetration, anti-sense and sense probes were sized under alkaline hydrolysis conditions to obtain an average fragment length of about 300 nucleotides. In situ hybridization on sections of optic nerves prepared from adult (12-weeks-old) animals was performed as described by elsewhere (Dörries et al. (1993); Bartsch et al., *J. Neurosci.*, in press).

Figure 3A:
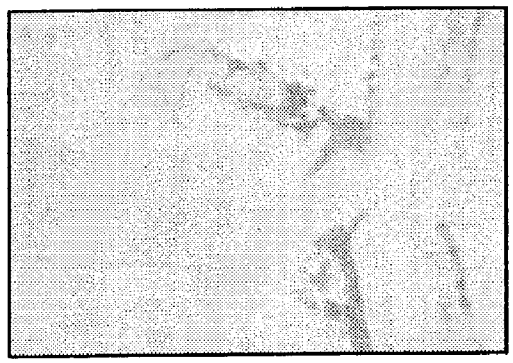
FIG. 3 depicts the localization of L1 mRNA in adult unlesioned (A, C and E) and lesioned (15 days after the lesion, B and D) optic nerves from non-transgenic (A, B and E) and transgenic mice (C and D) of line 3426 by in situ hybridization. In wild type animals, L1 mRNA is detectable only in neuronal cells of the retina but not in the glial cells of the optic nerve (A and B). In transgenic animals, cells containing L1 transcripts are visible in the optic nerve (C and D). The density of L1 positive cells is highest in the unmyelinated proximal part of the nerve. The density of L1 mRNA positive cells in the nerve is slightly increased after a lesion (compare C and D). In the optic nerve, the distribution of cells expressing L1 (C and D) is similar to that of cells expressing GFAP (E). Scale bar in E: 100 μm (for A to E).
Figure 3B:
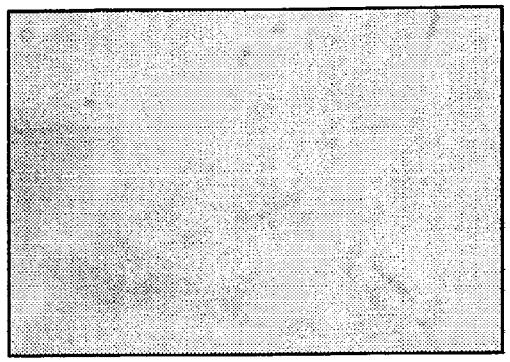
Figure 3C:
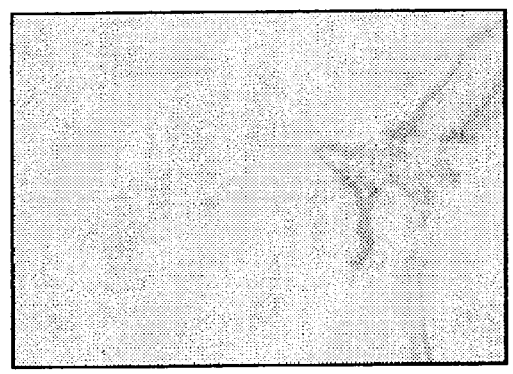

In non-transgenic controls L1 transcripts were detected only in nerve cells of the retina but not in optic nerve, neither before (FIG. 3A) nor after a lesion (FIG. 3B). By contrast, L1 mRNA was expressed by glial cells of the optic nerves from transgenic mice (FIG. 3C). L1 mRNA positive cells were detectable in both the distal myelinated and the proximal unmyelinated parts of the nerve. The intensity of the hybridization signal was higher in the unmyelinated proximal part, when compared to the myelinated distal part of the nerve.

A similar distribution of positive cells and similar differences in labelling intensity between unmyelinated and myelinated regions were observed using a GFAP cRNA probe (compare FIGS. 3C and E). The number of L1 mRNA positive cells in the optic nerve of transgenic animals was, however, always significantly lower than the number of GFAP-positive cells, probably due to the lower sensitivity of the L1 cRNA probe. Alternatively, detectable levels of L1 mRNA might be achieved only in astrocytes with high levels of GFAP expression. Such a threshold effect could be due to the design of the GFAP-L1 transgene which contains only 2 kb of GFAP 5' flanking sequences. In vitro studies suggest that the region between 2 and 6 kb upstream of the transcriptional start site contains sequence elements augmenting expression of GFAP-driven fusion genes in C6 cells (Sarid (1991) *J. Neurosci.* 28:217-228). Finally, the modification of the GFAP exon 1, including the introduction of the large L1 cDNA, might reduce the stability of the chimeric mRNA as compared to GFAP mRNA and alter effects exerted by regulatory GFAP sequences located upstream and downstream of the modified region.

Figure 3D:
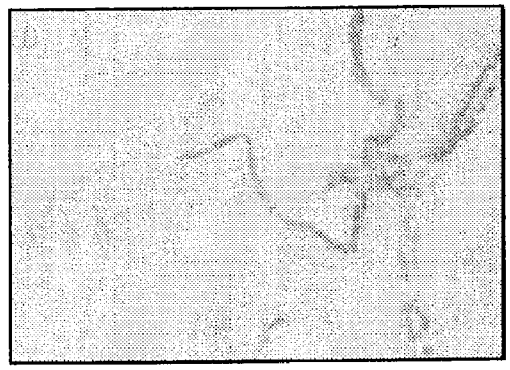
Figure 3E:
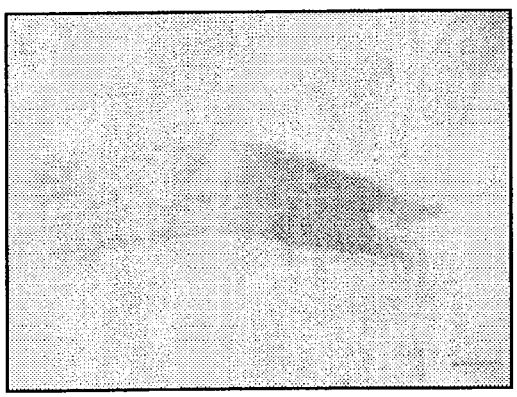

After lesioning the optic nerve, an upregulation of L1 expression was observed in transgenic (FIG. 3D) but not in nontransgenic (FIG. 3B) optic nerves. The number of cells which expressed L1 and the intensity of the L1 hybridization signal were similar in different individuals of the same transgenic line but varied across different transgenic lines. Consistent with the results obtained by Northern blot analysis (see above), L1 mRNA positive cells were most abundant in line 3426 followed by line 3427 and, finally, line 3418. This variability in the level of transgene expression in different lines could be related to a number of factors, in particular, effects caused by the neighboring host chromatin regions flanking the different transgene integration sites (Proudfoot (1986) *Nature* 322:562-565; Reik et al. (1987) *Nature* 328:248-251; Sapienze et al. (1987) *Nature* 328:251-254).

EXAMPLE 6

Antibodies

Production of polyclonal rabbit antibodies against mouse L1 and purification on an L1 immunoaffinity column (Rathjen et al. (1984); Martini et al. (1988) and polyclonal antibodies against mouse liver membrane (Lindner et al. (1983); Pollerberg et al. (1985) have been described. A mouse monoclonal antibody against GFAP was purchased (Boehringer Mannheim).

For Western blot analysis, polyclonal and monoclonal antibodies were visualized by horseradish peroxidase conjugated goat anti-mouse or rabbit antibodies (Dianova, Hamburg, Germany). For immunocytochemistry, primary antibodies were detected using fluorescein isothiocyanate- or tetramethylrhodamine isothiocyanate-conjugated goat anti-rabbit and goat anti-mouse antibodies (Dianova). Digoxigenin-labelled cRNA probes for in situ hybridization were visualized by alkaline phosphatase-conjugated Fab fragments to digoxigenin (Boehringer Mannheim).

EXAMPLE 7

Maintenance of Neurons on Cryostat Sections

To analyze whether optic nerves from transgenic animals are more conducive to neurite outgrowth than optic nerves from wild type animals, cerebellar neurons were maintained on cryostat sections of lesioned and contralateral unlesioned optic nerves (FIG. 7).

Optic nerves of 6 to 16-week-old mice were prepared as described by Bartsch et al. (1989) *J. Comp. Neurol.* 284:451-462. In brief, lesioned and unlesioned optic nerves were embedded and frozen in serum-free, hormonally defined medium (Fischer (1986b) *Neurosci. Lett.* 28:325-329) using liquid nitrogen. Tissue sections (14 μm thick) were cut longitudinally on a Frigocut 270-cryostat (Jung-Reichardt), mounted onto poly-L-lysine-coated (Sigma, 0.001% in water) sterile glass coverslips and air-dried for 2-3 hours in a sterile chamber. After washing the sections for 5 minutes with medium, Percoll gradient-purified small cerebellar neurons (Keilhauer et al. (1985) *Nature* 316:728-730) from six-day-old ICR mice ($6 \times 10^4$ cells in 100 μl medium) were applied to each coverslip. Cells were maintained in an incubator at 37° C. with a humidified atmosphere of 5% $CO_2$ and 95% air.

Neurite outgrowth was also measured in the presence of antibodies. Sections were pre-incubated with polyclonal L1 antibodies or polyclonal antibodies against mouse liver membranes (100 μg/ml, dialyzed extensively against and diluted in culture medium) for 1 hour at 37° C. After removal of antibodies, sections were washed carefully with culture medium (5 times, each for 5 minutes at room temperature) and Percoll gradient purified small cerebellar neurons were added. After 2 days, cryostat cultures were fixed in 4% paraformaldehyde in PBS for 30 minutes at room temperature and the neurite lengths were measured. To avoid "edge effects" in the measurements, we did not evaluate the sections which were situated in the outer rim comprising 20% of the coverslips. Using a semi-automatic computer image analysis program (IBAS, Kontron, Zeiss) the lengths of all neurites which had grown on these sections were measured and the average neurite length per neuronal cell body calculated. For each experiment and optic nerve (lesioned or unlesioned), the average length of neurites grown on nerves of transgenic animals was related to the corresponding values of control animals. Twelve independent experiments were performed with lesioned and contralateral unlesioned nerves using at least two transgenic animals.

Figure 8:
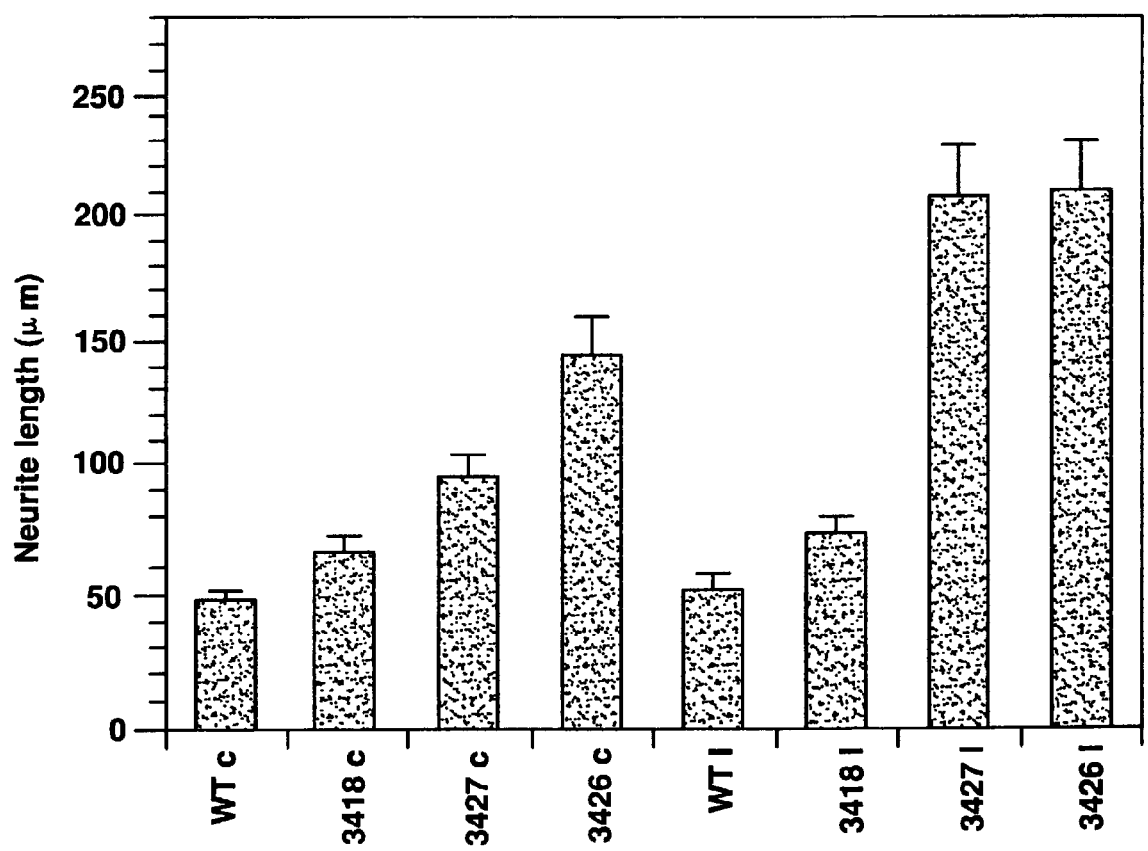
FIG. 8 depicts and compares neurite lengths of cerebellar neurons maintained on cryostat sections of unlesioned (c) and lesioned (l) optic nerves (28 days after the lesion) from wild type (WT) and transgenic animals (lines 3426, 3427 and 3418). Note that the length of neurites on sections from transgenic animals is greater than on sections from wild type animals. In transgenic lines neurites are always longer on lesioned than on unlesioned nerves, whereas neurite lengths on unlesioned and lesioned nerves of wild type animals do not show a significant difference. Note that the neurite length correlates positively with the levels of L1 expression in different transgenic lines (see also Western blot data). Mean values±standard error of the mean from one representative experiment (out of 12) are shown.

For transgenic animals, an increase in neurite length was observed on lesioned compared with unlesioned nerves. In contrast, neurite lengths on lesioned and unlesioned optic nerves of wild type animals were not significantly different (FIG. 8). Neurites of neurons cultured on unlesioned optic nerves from transgenic animals were consistently longer than neurites of neurons cultured on unlesioned nerves from wild type animals. A maximal increase in neurite length of about 300% was observed when using sections from line 3426. Similarly, neurite length on lesioned nerves of transgenic lines was increased up to 400% when compared with lesioned nerves from wild type animals.

The neurite outgrowth promoting activity of transgenic optic nerves correlated positively with the level of L1 expression (FIG. 8). Unlesioned optic nerves of line 3426, which express the highest levels of L1 protein were more potent in increasing neurite outgrowth than those of lines 3427 and 3418 expressing, by comparison, lower levels of L1 (in decreasing order). On lesioned optic nerves of lines 3426 and 3427 (28 days after the lesion), neurite outgrowth was four times higher than on lesioned optic nerves of wild type animals. The finding that the increase in neurite outgrowth in lesioned optic nerves was similar for the lines 3426 and 3427 (although line 3426 shows 25% increase in L1 protein expression after lesion as compared with line 3427) could indicate that the level of L1 protein in line 3427 already suffices for maximal induction of neurite outgrowth from small cerebellar neurons.

Pre-incubation of unlesioned optic nerves from wild type animals with polyclonal antibodies to L1 or mouse liver membranes did not significantly affect neurite lengths (FIG. 9). In contrast, neurite lengths were reduced by more than 50% when cryostat sections of unlesioned or lesioned optic nerves from the transgenic line 3426 were pre-incubated with L1 antibodies (FIG. 9). Antibodies to liver membranes, which strongly bind to optic nerves and small cerebellar neurons (data not shown), did not show similar inhibitory effects. Interestingly, pre-incubation of lesioned optic nerves from wild type animals with L1 antibodies induced an increase in neurite outgrowth compared with lesioned nerves from wild type animals without a prior antibody pre-incubation. Antibodies to mouse liver membranes did not show a significant increase under the same conditions, indicating that addition of cell surface reactive antibodies per se does not disturb neurite outgrowth.

EXAMPLE 8

Maintenance of Neurons on Monolayer Cultures of Astrocytes

To prepare astrocyte monolayers, forebrains from six-day-old mice were cleaned free of non-neuronal tissue and dissociated as described elsewhere (Schnitzer et al. (1981) *J. Neuroimmunol.* 1:429-456; Fischer et al. (1982a) *Neurosci. Lett.* 29:297-302; Keilhauer et al. (1985). Cells were maintained on poly-L-lysine-coated (Sigma, 0.001% in water) cell culture flasks in BME medium (Gibco) containing 10% horse serum and 2 mM glutamine for 14 to 21 days. Contaminating oligodendrocytes and neurons were removed by shaking the flasks at every medium change and by subculturing the cells at intervals of four days. Immunostaining for GFAP after 14 days of maintenance showed that more than 90% of the cells were astrocytes. After 14 days in culture, the cells were trypsinized and maintained as monolayers for five days on poly-L-lysine-coated glass coverslips. Percoll gradient purified small cerebellar neurons (Schnitzer et al. (1981)) from six-day-old mice and dorsal root ganglion (DRG) (Seilheimer et al. (1988) *J. Cell. Biol.* 107:341-351) neurons from eight-day-old chick embryos were then added onto the astrocyte monolayers. After 6 hours of co-culture for cerebellar and 12 hours for DRG neurons, the co-cultures were fixed with 2% paraformaldehyde in PBS and neurite lengths were analyzed as described in Example 7.

Figure 10A:
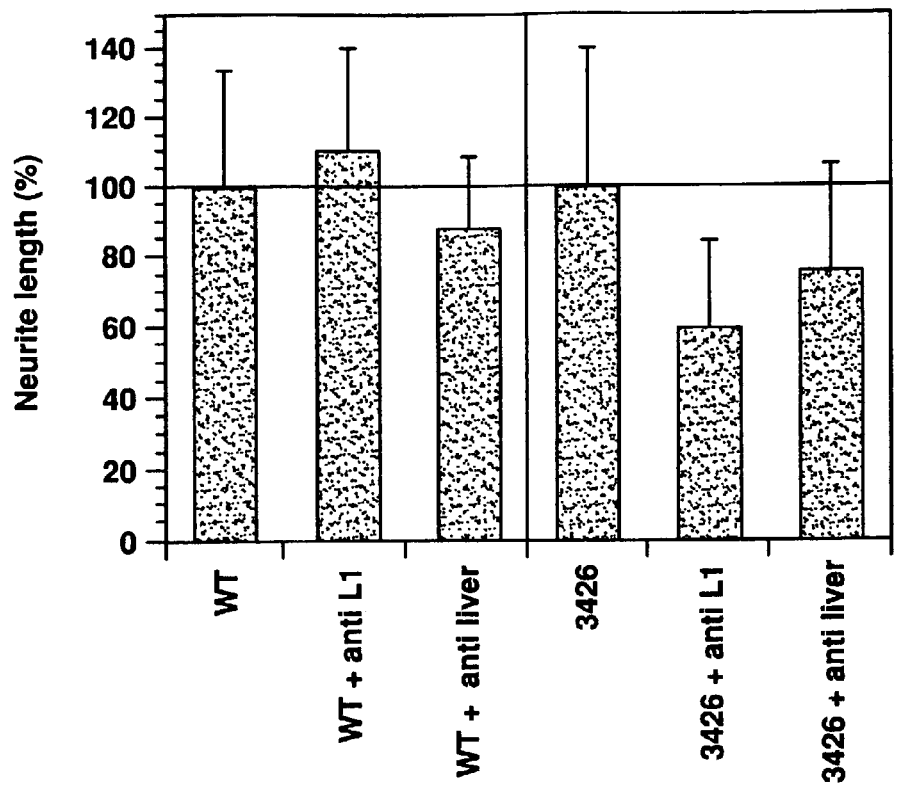
FIG. 10 depicts and compares neurite lengths of mouse cerebellar (A) or chick DRG (B) neurons on astrocytic monolayers prepared from wild type (WT) and transgenic animals (line 3426) in the absence of antibodies and after pre-incubation of sections with affinity purified polyclonal antibodies against L2 (anti L1) and mouse liver membranes (anti liver). The neurite length on astrocytes without pre-incubation with any antibody was taken as 100% and the neurite lengths on astrocyte monolayers obtained after antibody treatment are expressed in relation to this value. A significant reduction (about 40%) of neurite length is only visible on transgenic astrocytes after preincubation of the monolayers with L1 antibodies. Mean values±standard deviation are from at least 100 neurons from two independent experiments carried out in quadruplicate. * indicates means that were significantly different (p<0.05, Mann-Whitney U test) from the control (wild type or transgenic astrocytes without any antibody treatment).
Figure 10B:
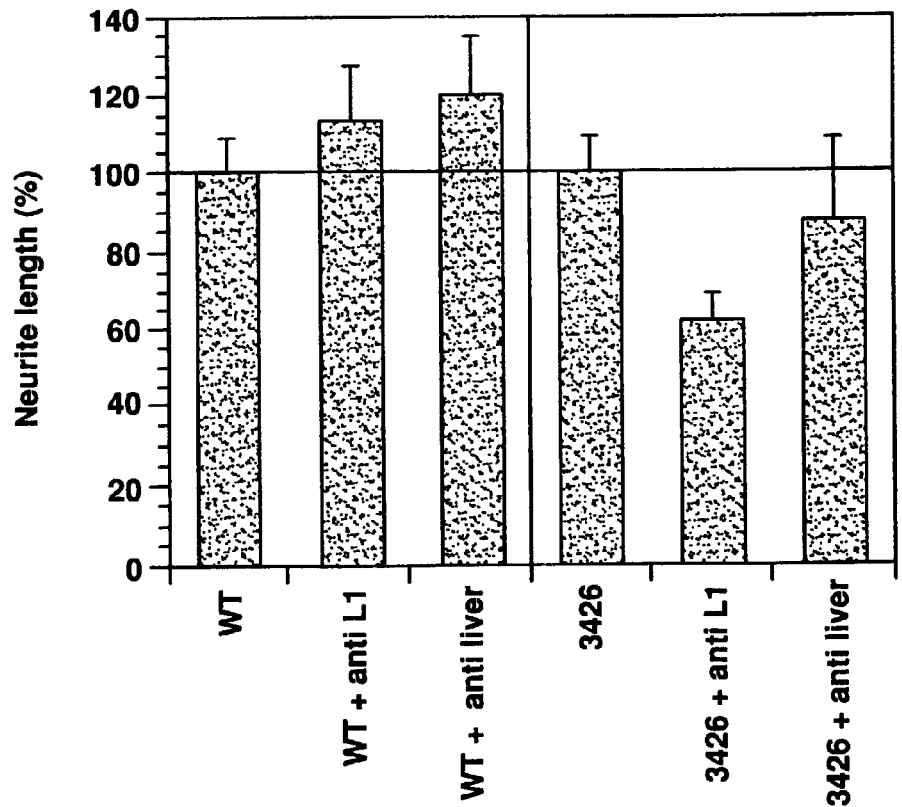

Neurite outgrowth from mouse small cerebellar or chick dorsal root ganglion (DRG) neurons was also studied in monolayer cultures of astrocytes derived from transgenic (line 3426) or non-transgenic controls (FIG. 10, Table 1).

TABLE 1

Neurite lengths of cerebellar and dorsal root ganglion (DRG) neurons maintained on astrocytic monolayers prepared from wild type mice (WT) and the transgenic line 3426.

|  | Cerebellar neurons | DRG neurons |
| --- | --- | --- |
| WT | 65 ± 34 mm | 90 ± 10 mm |
| WT + anti L1 | 72 ± 30 mm | 105 ± 14 mm |
| WT + anti liver | 57 ± 24 mm | 107 ± 12 mm |
| 3426 | 75 ± 41 mm | 137 ± 10 mm |
| 3426 + anti L1 | 45 ± 25 mm | 88 ± 8 mm |
| 3426 + anti liver | 58 ± 31 mm | 124 ± 15 mm |

Neurite lengths on astrocytes without pre-incubation with any antibody or after treatment with polyclonal antibodies against L1 (anti L1) or antibodies against mouse liver membranes (anti liver) are shown. Mean values ± standard deviation are from at least 100 neurons from two independent experiments carried out in quadruplicate.

Neurite length of cerebellar or DRG neurons on transgenic astrocytes was approximately 15% or 50% higher, respectively, when compared with neurite length using wild type astrocytes (Table 1). Anti-liver membrane antibodies did not affect neurite length on astrocyte monolayers from wild type or transgenic animals (FIG. 10, Table 1). Pre-incubation of astrocyte monolayers with L1 antibodies did not significantly affect neurite length on cells from wild type animals. In contrast, it reduced neurite length of cerebellar or DRG neurons grown on cells from transgenic animals by approximately 40%. It is noteworthy in this context that the polyclonal antibodies directed against mouse L1 used in this study do not react with neurons from chicken (Martini et al., 1994a; data not shown). By immunofluorescence analysis it could be shown, however, that these antibodies bind as efficiently as L1 antibodies to astrocytes from transgenic animals as well as to mouse small cerebellar neurons (data not shown).

EXAMPLE 9

Immunofluorescence and Aurion-GP Immunogold Microscopy

L1 and GFAP immunostaining of fresh-frozen cross- or longitudinally sectioned optic nerves or astrocytic monolayers of wild type and transgenic animals were performed as described (Bartsch et al. (1989)). For double-labelling, we first incubated astrocytes as live cells with L1 antibodies (2 µg/ml in 1% BSA in PBS) at 4° C. for 30 minutes. After permeabilizing the cells with 70% methanol at −20° C. for 10 minutes, cells were incubated with GFAP antibody for 30 minutes at 4° C.

For quantification of neurite lengths in cryostat culture experiments, the Aurion immuno R-Gent silver enhanced staining was used according to the manufacturer's instructions (Aurion, Immuno Gold Reagents & Accessories Custom Labelling, Wageningen, The Netherlands) with minor modifications. In brief, cultures were fixed in 4% paraformaldehyde in PBS for 10 minutes at room temperature, incubated in 50 mM glycine in PBS for 10 minutes and then treated for 15 minutes in blocking buffer (BB, 0.5% BSA in PBS). After 3 washes in BB, each for 5 minutes, cells were incubated with L1 antibodies diluted in BB (2 µg/ml) for 30 minutes at room temperature. Subsequently, cultures were washed 3 times in BB each for 5 minutes and secondary antibody diluted 1:20 in BB was added for 1 hour at room temperature. After 3 washes with distilled water, cultures were fixed in 2% glutaraldehyde in PBS for 10 minutes at room temperature and washed 3 times with distilled water. A 1:1 mixture of enhancer and developer was then added at room temperature. After the appearance of the reaction product, coverslips were washed 3 times with distilled water and embedded in glycerol.

Figure 4A:
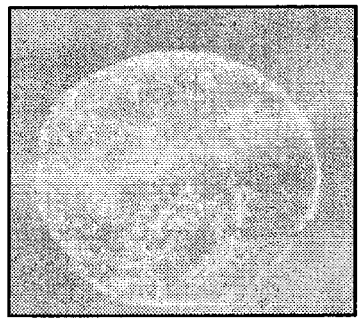
FIG. 4 depicts the double immunofluorescence microscopic localization of L1 (A and B) and GFAP (C) in unlesioned (A and C) and lesioned (28 days after the lesion, B) optic nerves from adult transgenic (line 3426, A and B) and wild type (C) animals. L1 immunoreactivity in optic nerves from transgenic animals is significantly increased after a lesion (compare A and B). The pattern of L1 immunoreactivity in lesioned transgenic nerves is similar to the pattern of GFAP immunostaining in unlesioned wild type nerves. L1 positive unmyelinated retinal cell ganglion axons are present in unlesioned wild type nerve (A). Scale bar in C: 50 μm (For A to C).
Figure 4B:
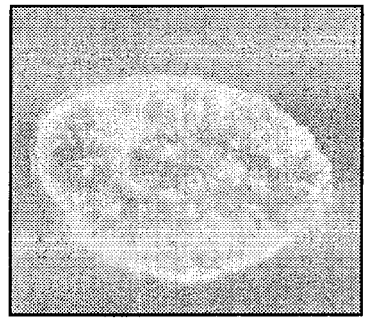
Figure 4C:
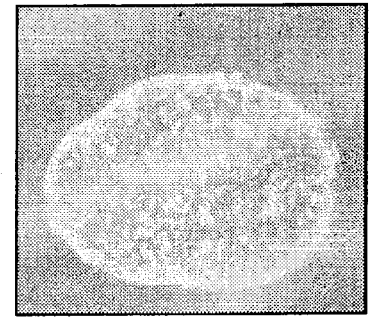

In optic nerves of non-transgenic mice, L1 immunoreactivity was restricted to unmyelinated retinal ganglion cell axons (Bartsch et al. (1989)). In unlesioned optic nerves from transgenic animals, weak L1 immunoreactivity was also found in association with cell bodies and radially oriented cell processes (FIG. 4A). The intensity of this L1 immunoreactivity in transgenic optic nerves increased significantly after a lesion (FIG. 4B) and was similar in distribution to the GFAP immunoreactivity found in unlesioned (FIG. 4C) or lesioned (not shown) wild type nerves.

Figure 5A:
FIG. 5 depicts the double immunofluorescence microscopic localization of L1 (A and D) and GFAP (B and E) in cultured astrocytes from transgenic animals of line 3426 (A, B and C) and wild type animals (D, E and F). Note that only the cells from transgenic animals express L1, whereas astrocytes from wild type animals are L1 negative. Scale bar in F: 30 μm (for A to F).
Figure 5B:
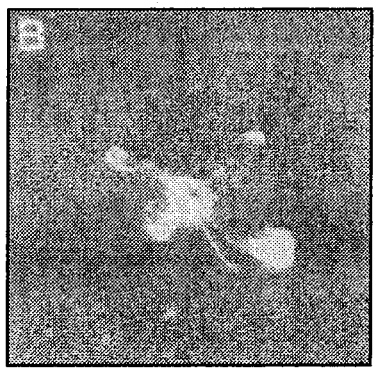
Figure 5C:
Figure 5D:
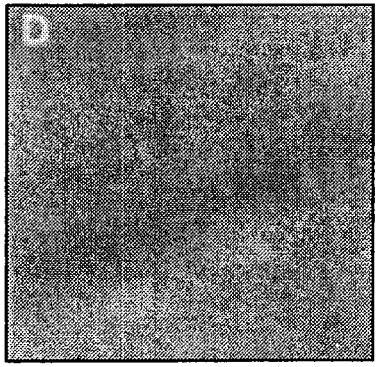
Figure 5E:
Figure 5F:
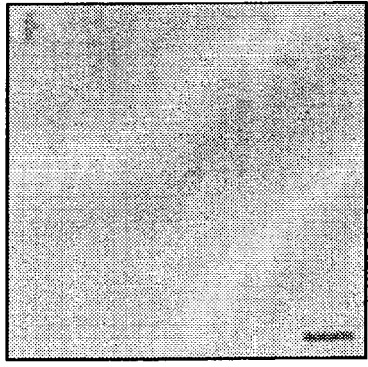

L1 expression was additionally analyzed in cultures of astrocytes prepared from forebrain of six-day-old transgenic animals. No L1 immunoreactivity was detectable on astrocytes from wild type animals (FIG. 5D). In contrast, L1 positive cells were present in cultures from transgenic animals (FIG. 5A). As demonstrated by double-immunostaining, the same cells also proved positive for GFAP (FIGS. 5B and E) indicating that the cells expressing L1 are indeed astrocytes. Since L1 immunostaining was performed on living cells, it seems likely that in the transgenic animals L1 is also exposed on the cell surface of astrocytes in vivo.

EXAMPLE 10

Western Blot Analysis

Figure 6:
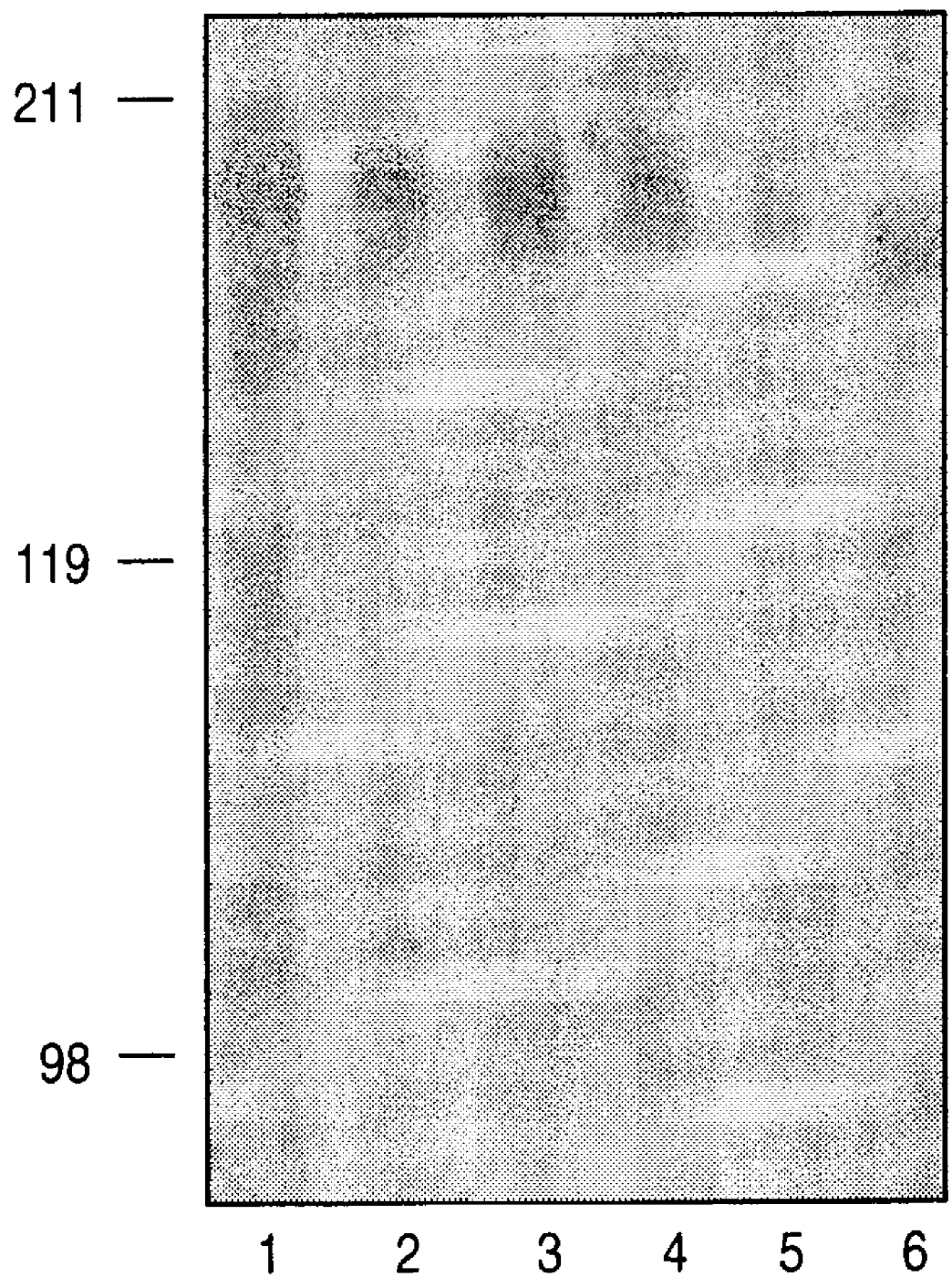
FIG. 6 shows (A) Western blot analysis of lesioned (15 days after the lesion) and unlesioned optic nerves from transgenic and wild type animals. 25 μg of total protein of lesioned (lanes 1, 3 and 5) or unlesioned nerves (lanes 2, 4, and 6) was loaded and detected using affinity purified polyclonal antibodies against L1. Protein extracts were made from mice of transgenic lines 3426 (lanes 1 and 2), 3427 (lanes 3 and 4) and from wild type animals (lanes 5 and 6). There is an increase in L1 expression in transgenic animals compared to non-transgenic controls. Following optic nerve lesion, an up-regulation of L1 occurred in transgenic animals, whereas the amount of L1 in wild type animals decreased. Apparent molecular weights (in kD) are shown on the left margin.
Figure 7A:
FIG. 7 depicts examples of neurite outgrowth from mouse cerebellar neurons cultured on cryostat sections of optic nerves from wild type (A and B) and transgenic (C and D) animals (line 3426). A and C represent unlesioned optic nerves, B and D represent lesioned optic nerves. Scale bar in D: 50 μm (for A to D).
Figure 7B:
Figure 7C:
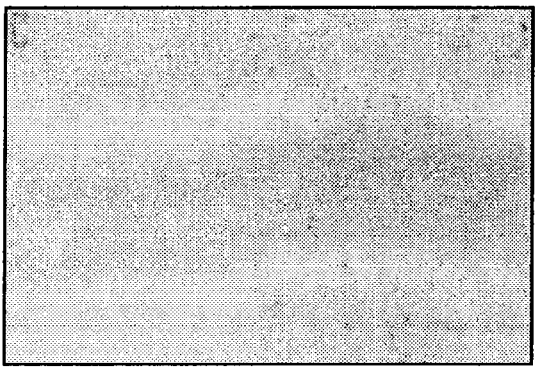
Figure 7D:

To further quantitate the amount of L1 expression in GFAP-L1 transgenic mice, detergent extracts of homogenates of unlesioned and lesioned (15 days after the lesion) optic nerves from wild type and transgenic adult mice were analyzed on Western blots (FIG. 6).

Lesioned (15 days after the lesion) and contralateral unlesioned optic nerves from 8-week-old animals were cleaned free of non-neuronal tissues and then frozen in liquid nitrogen. Care was taken that only myelinated distal but not L1 immunoreactive unmyelinated or partly myelinated proximal regions of the nerves were used. Nerves were frozen and thawed ten times before sonication with a Branson B15 sonicator at 4° C. for 5 minutes. The tissues were then homogenized with a Dounce homogenizer in homogenization buffer (1% Triton X-100, 2 M urea, 5 mM benzamidine, 0.1 mM iodoacetamide, 1 mM phenylmethanesulfonyl fluoride, 5 mM Na-p-tosyl-L-lysinechloro-methyl ketone in PBS). Homogenates were cleared by centrifugation at 16,000 g at 4° C. for 15 minutes. Supernatants were treated with methanol/chloroform to precipitate proteins as described by Wessel et al. (1984). The protein content was determined in the supernatant (Pierce). After SDS-PAGE on 7% slab gels under reducing conditions, proteins (25 µg) were analyzed by Western blotting using polyclonal L1 antibodies (0.4 µg/ml). Horseradish peroxidase-conjugated secondary antibody (2 µg/ml) was detected by the ECL Western blotting detection kit (Amersham). Densitometric analysis of immunoblots was performed on scanned images (Arcus scanner, Agfa-Gavaert) of the original films using the Image Program (NIH, Research Services Branch, NIMH).

Densitometric analysis of the immunoblots demonstrated that L1 expression in unlesioned optic nerves of transgenic animals was about 40% and 13% (lines 3426 and 3427, respectively) higher than in unlesioned optic nerves of wild type animals. L1 expression in lesioned transgenic nerves was 310% and 200% (lines 3426 and 3427, respectively) higher as compared with lesioned nerves of wild type animals. A comparison between lesioned and contralateral unlesioned optic nerves from wild type animals revealed a decrease in L1 protein expression of about 40% on the lesioned side. In contrast, the amount of L1 protein in lesioned nerves of lines 3427 and 3426 increased by approximately 30% when compared with the unlesioned contralateral side. The expression level of L1 in line 3426 was approximately 35% and 25% higher than in the line 3427 for unlesioned and lesioned optic nerves, respectively.

EXAMPLE 11

Figure 11:
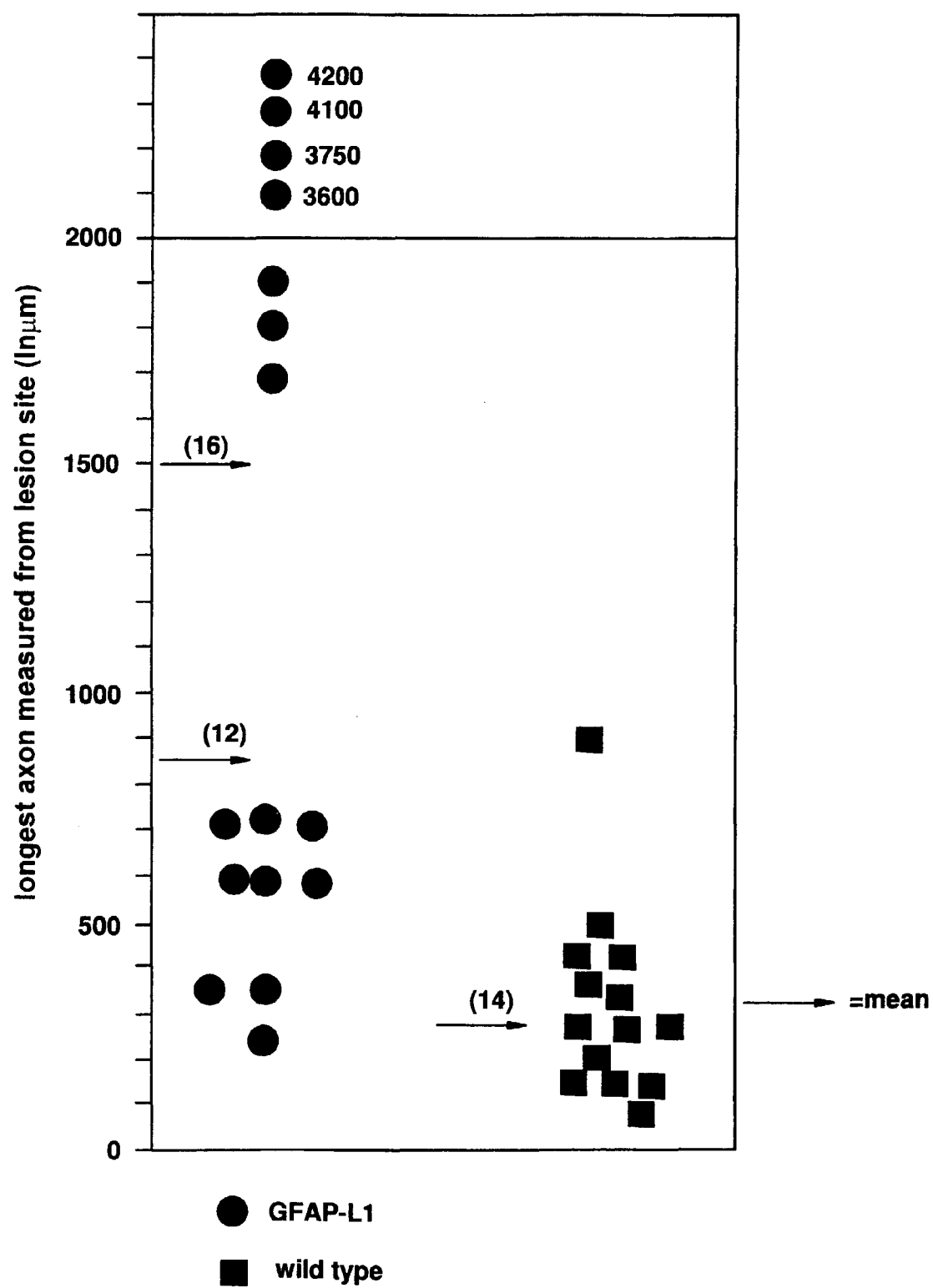
FIG. 11 demonstrates the in vivo regrowth of axons in the optic nerve (0-2000 μm). Axons from 6-8 week old GFAP-L1 transgenic mice and wild type mice were crushed intraorbitally and, after 14 days, traced with a fluorescein-labeled biotin ester to mark retinal ganglion cell axons by anterograde labeling. Each point represents one animal.
Figure 12:
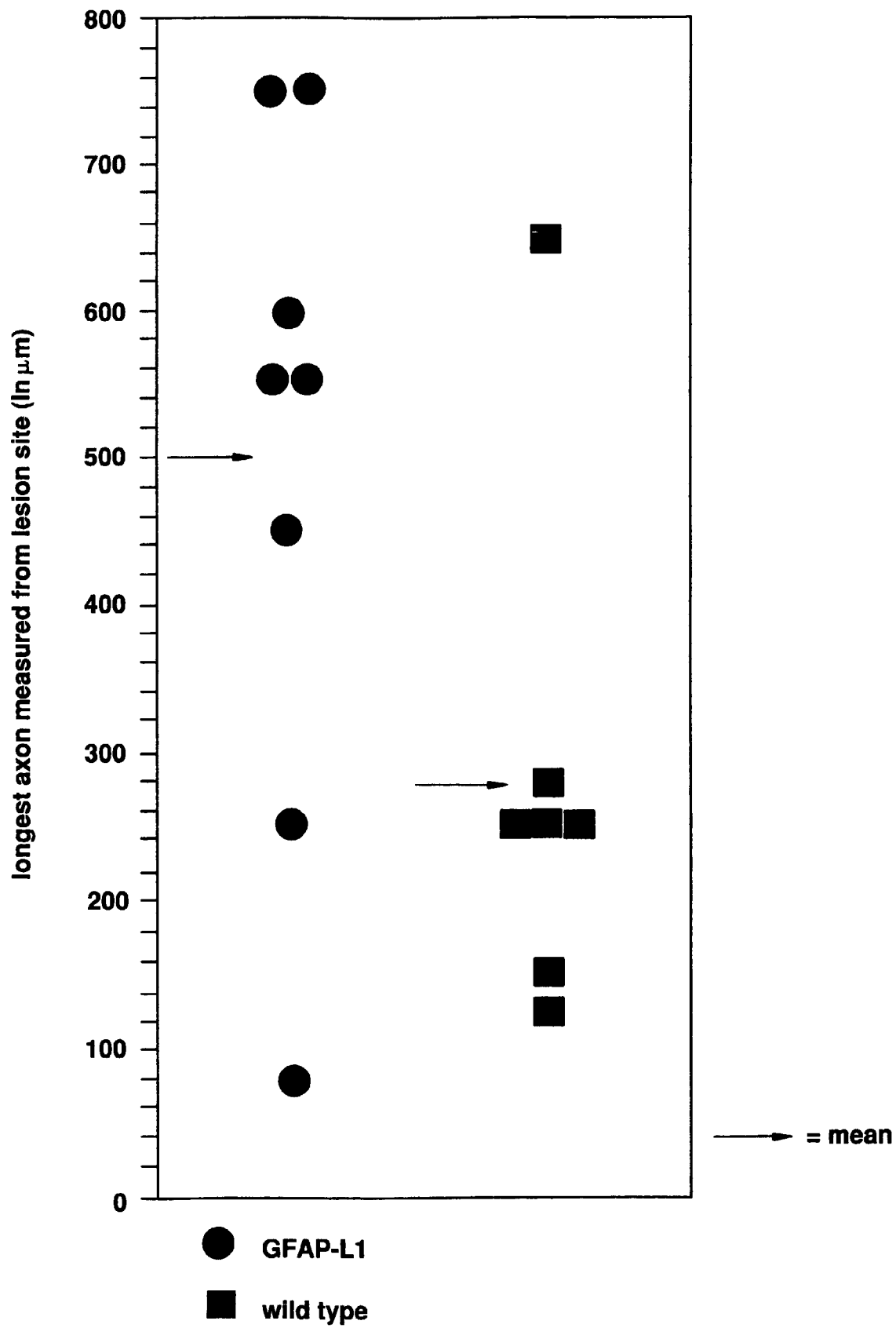
FIG. 12 depicts in vivo regrowth of axons in the optic nerve (0-800 µm). 6-8 week old GFAP-L1 transgenic mice and wild type mice were crushed intraorbitally and, after 14 days, traced with a fluorescein-labeled biotin ester to mark retinal ganglion cell axons by anterograde labeling. Each point represents one animal.

In Vivo Regrowth of Axons in the Optic Nerve 6-8 week old GFAP-L1 transgenic mice and wild type mice were crushed intraorbitally and, after 14 days, traced with a fluorescein-labeled biotin ester to mark retinal ganglion cell axons by anterograde labeling. Results are shown in FIGS. 11 and 12. Each point represents one animal.

EXAMPLE 12

Identification of the Border Between Fibronectin Type III Homologous Repeats 2 and 3 of the Neural Cell Adhesion Molecule L1 as a Neurite Outgrowth Promoting and Signal Transducing Domain To determine the domains of neural cell adhesion molecule L1 involved in neurite outgrowth, monoclonal antibodies against L1 were generated and their effects on eleven antibodies were coated as substrate, only antibody 557.B6, which recognizes an epitope represented by a synthetic peptide comprising amino acids 818 to 832 at the border between the fibronectin type III homologous repeats 2 and 3, was as potent as L1 in promoting neurite outgrowth, increasing intracellular levels of $Ca^{2+}$ and stimulating the turnover of inositol phosphates. These findings suggest that neurite outgrowth and changes in these second messengers are correlated. Such a correlation was confirmed by the ability of $Ca^{2+}$-channel antagonists and pertussis toxin to inhibit neurite outgrowth on L1 and antibody 557.B6. These observations indicate for the first time a distinct site on cell surface-bound L1 as a prominent signal transducing domain through which the recognition events appear to be funneled to trigger neurite outgrowth, increase turnover of inositol phosphates and elevate intracellular levels of $Ca^{2+}$.

EXAMPLE 13

L2/HNK-1 Immunoreactivity in Reinnervated Peripheral Nerve

Preferential Expression of Previously Motor Axon-Associated Schwann Cells

The carbohydrate epitope L2/HNK-1 (hereafter designated L2) is expressed in the adult mouse by myelinating Schwann cells of ventral roots and muscle nerves, but rarely by those of dorsal roots or cutaneous nerves. Since substrate-coated L2 glycolipids promote outgrowth of cultured motor but not sensory neurons, L2 may thus influence the preferential reinnervation of muscle nerves by regenerating motor axons in vivo.

Therefore, the influence of regenerating axons on L2 expression by reinnervated Schwann cells was analyzed by directing motor or sensory axons into the muscle and cutaneous branches of femoral nerves of eight-week-old mice. Regenerating axons from cutaneous branches did not lead to immunocytochemically detectable L2 expression in muscle or cutaneous nerve branches. Axons regenerating from muscle branches led to a weak L2 expression by few Schwann cells of the cutaneous branch, but provoked a strong L2 expression by many Schwann cells of the muscle branch. Myelinating Schwann cells previously associated with motor axons thus differed from previously sensory axon-associated myelinating Schwann cells in their ability to express L2 when contacted by motor axons. This upregulation of L2 expression during critical stages of reinnervation may provide motor axons regenerating into the appropriate, muscle pathways with an advantage over those regenerating into the inappropriate, sensory pathways.

EXAMPLE 14

L1 in Consolidation of Memory

A. Passive Avoidance Tasks in the Chick

Training day-old chicks on a one trial passive avoidance task, in which they learn to suppress their tendency to peck at a small bright bead if it is coated in the bitter-tasting methylanthranilate, results in a time-dependant cellular and molecular cascade culminating in the remodelling of pre- and post-synaptic elements in two discrete regions of the forebrain, the intermediate medial hyperstriatum ventrale (IMHV) and Lobus parolfactorius (LOP) (Rose (1991) *Trends In Neurosciences* 14:390-397). The cascade involves two distinct waves of glycoprotein synthesis, as evidenced by enhanced fucose incorporation, occurring in both IMHV and LPO at varying times following training. Both waves are necessary for long-term (that is, 24 hours plus) memory retention for the avoidance tasks, in which amnesia is evidenced by chicks, which would otherwise avoid the previously bitter bead, pecking at a dry bead on test.

Given the role of L1 in mediating cell-cell contact, the present study was undertaken in order to determine if L1 is amongst the learning-associated glycoproteins participating in either or both waves of glycoprotein synthesis, and is necessary for memory formation. If so, antibodies to L1 administered at an appropriate time relative to training should prevent the synaptic remodelling necessary for long term memory and therefore produce amnesia for the task. Similarly, if the extracellular domains of the L1 molecule play a part in the recognition and adhesion processes which are required for synaptic remodelling and stabilization, exogenously applied extracellular domain fragments which will bind homophilically to the endogenous molecule might disrupt this process.

Antibodies and Fragments

Polyclonal antibodies were prepared in rabbits by immunization with immuno-affinity purified L1 (Ng-CAM, 8D9) following an established immunization procedure (Rathjen et al. (1984)). L1 was isolated from one-day old chicken brains using an 8D9 monoclonal antibody (Lagenaur and Lemmon (1987) *Proc. Nat'l. Acad. Sci. USA* 84:77533-7757) column again using established procedures (Rathjen et al. (1984)). Antibodies were isolated from the serum obtained after the third immunization using Protein G Sepharose (Pharmacia LKB) according to the manufacturer's instructions. Recombinantly expressed fusion proteins in *E. coli* representing the six immunoglobulin-like (Ig-I-VI) and five fibronectin type III homologous repeats (FN1-5) were prepared as described by Appel et al (1993).

Sodium Dodecyl Sulfate Polyacrylamide Gel Electrophoresis (SDS-PAGE) and Immunoblots of Chick Subcellular Fractions Fifty µg of protein from brain homogenate, from crude membranes, from a soluble fraction (Burchuladze et al. (1990) *Brain Res.* 535:131-138) and from postsynaptic densities (Murakami et al. (1986) *J. Neurochem.* 46:340-348), all from day-old chicken brains were separated by SDS-PAGE under reducing conditions on a 5-15% polyacrylamide gradient gel (Laemmli (1970) *Nature* 227:146-148), whereafter they were transferred to nitrocellulose according to the method of (Burnette (1981) *Anal. Biochem.* 112:195-203). After overnight incubation with L1 antibodies at a dilution of 1:1,000 in Tris-buffered saline, pH 7.2, containing 5% defatted milk powder, immunoreactive bands were detected according to previously described methods (Scholey et al. (1993) *Neurosciences* 55:499-509).

Training and Testing Procedures

Day-old Ross chunky chicks of both sexes, hatched in incubators were place in pairs in small pens, pretrained to peck at small (2.5 mm) white beads and then trained on a larger (4 mm) chrome bead coated with methylanthranilate as described by Lossner and Rose ((1983) *J. Neurosciences* 41:1357:1363). Birds which pecked the bitter bead evinced a stereotyped disgust response, shaking their heads vigorously and backing away from the bead. Twenty four hours following training, each animal was tested by the presentation of a dry chrome bead identical to the one used in training. Retention of passive avoidance learning was indicated in animals avoiding the test bead. In each replication of this protocol, 24-36 chicks were trained and tested. More than 80% of trained, uninjected chicks normally avoid the bead on test under these conditions, though there is sometimes a slight reduction in avoidance in saline injected birds. By contrast, birds which are trained on a water-coated bead peck the dry bead avidly on test, and their avoidance score is rarely above 5-10%. All training and testing was routinely carried out by an experimenter blind as to the prior treatment of the animals.

Injections

Figure 13:
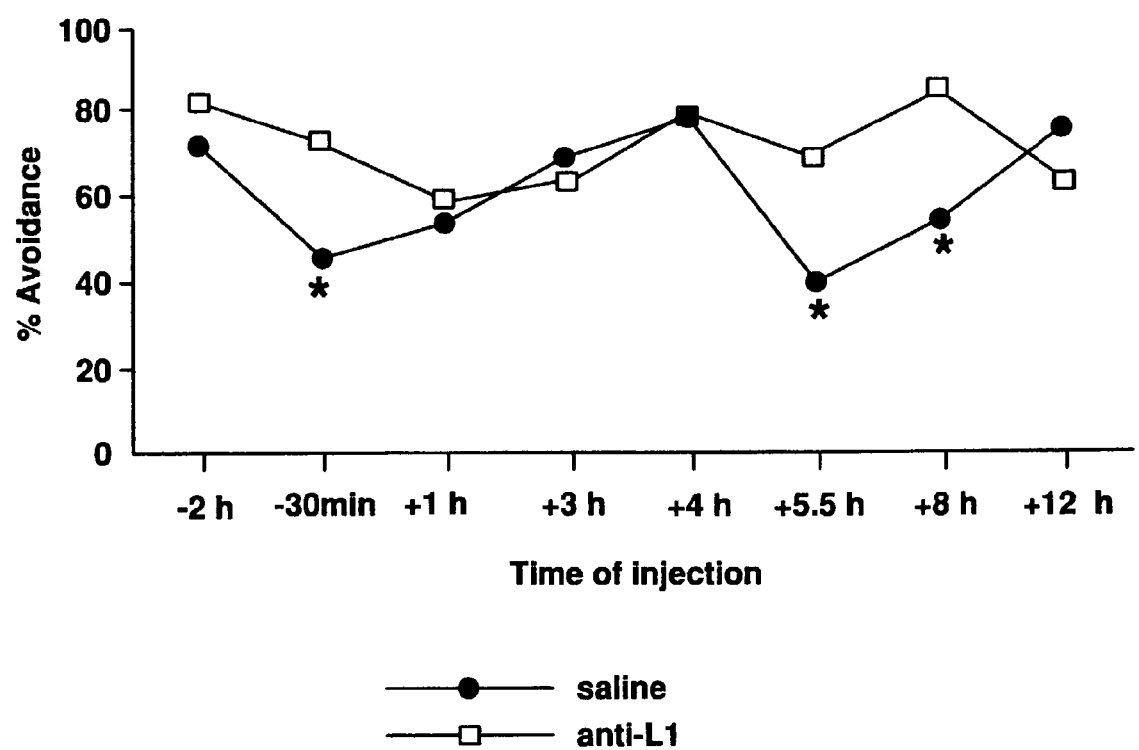
FIG. 13 shows the effect of the injection of chicken L1 antibodies into the IMHV on percent avoidance (retention of memory) on a one-trial passive avoidance task. Each point represents a group of birds who received injections of L1 antibodies (anti-L1) (closed circles) or saline (open squares) at the time relative to training indicated. All animals were tested at 24 hours post-training (*, p<0.05 between saline and antibody groups, $\chi^2$).
Figure 15A:
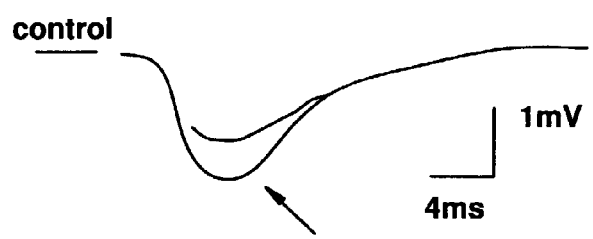
FIG. 15 comprises a series of graphs showing the influence of antibodies against L1 (anti-L1) on LTP in pyramidal neurons in the CA1 region of rat hippocampal slices. A, Averaged (n=4) EPSP's recorded before and 50 minutes after (arrow) TBS at the control site not injected with antibodies. B, Averaged (n=4) EPSPs recorded before and 50 min. after TBS (arrow) in the presence of rabbit polyclonal antibodies against mouse L1 (Rathjen et al. (1984)). C, Time-course of the EPSP initial slope before and after TBS in the presence of L1 antibodies (IgG fraction, 6.2 mg/ml ○) or polyclonal antibodies to the immunoglobulin-like domains I-VI recombinantly expressed in CHO cells (Hynes (1992) *Cell.* 69:11-25) (antiserum containing approximately 1 mg/ml of specific antibodies, ▼) and the following controls: (1) Control LTP (no antibodies, □), (2) in the presence of the IgG fraction of the polyclonal antibodies to mouse liver membranes (3.5 mg/ml, ●), which react strongly with rat hippocampal slices (Lindner et al. (1983) *Nature* 305:427-430), (3) in the presence of rabbit non-immune serum, and (4) in the presence of L1 antibodies without induction of LTP by TBS (6.2 mg/ml, ○; see also E, F). Results are expressed as means±S.E.M. of the EPSP initial slope in percent of the baseline values recorded during the 20 min. before TBS (n=5) slices from at least 3 animals; values for LTP's in the presence of L1 antibodies differ from the control LTP at p<0.001 for the antibodies against L1, and at p<0.01 for the antibodies to the immunoglobulin-like domains I-VI). D, Concentration-dependence of the reduction in LTP by the IgG fraction of polyclonal antibodies against L1 (6.2 mg/ml; ○); 2 mg/ml, ●; 0.6 mg/ml, ▲; 0.06 mg/ml, □; p<0.0001). As a control, the results from polyclonal antibodies against liver membranes are shown (3.5 mg/ml, ■). E, Averaged (n=4) EPSP's recorded before and 60 min. after (arrow) the application of polyclonal antibodies against L1 in the absence of TBS. F, Averaged (n=4) intracellular excitatory postsynaptic currents (EPSP) recorded before and 30 min. after (arrow) the application of polyclonal antibodies against L1 in the absence of TBS.
Figure 15B:
Figure 15C:
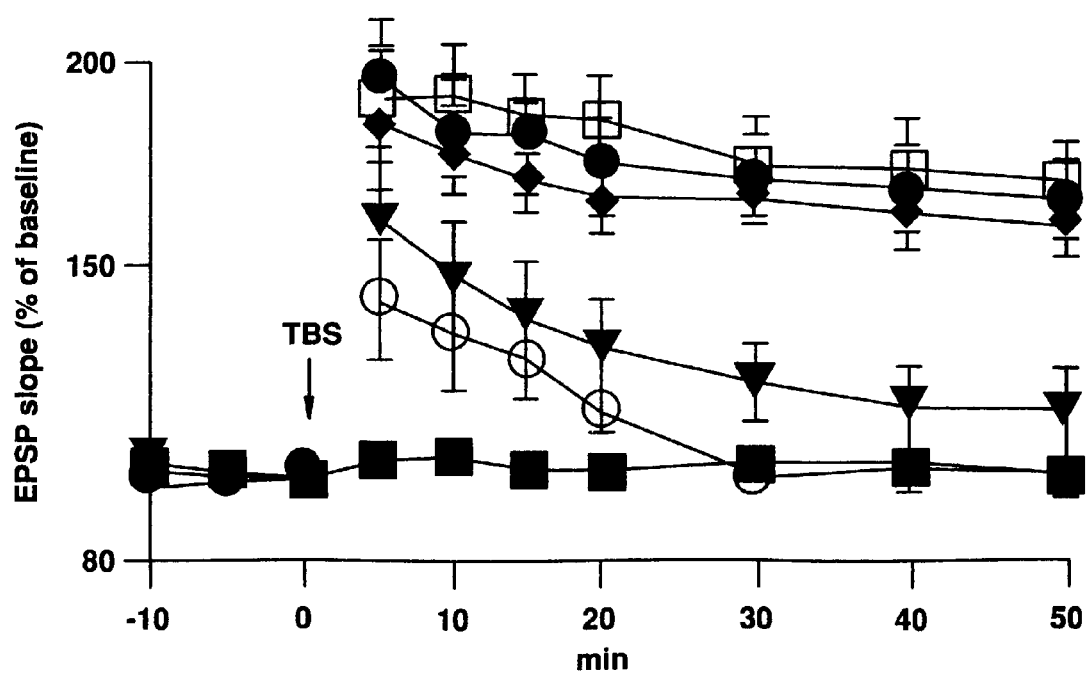
Figure 15D:
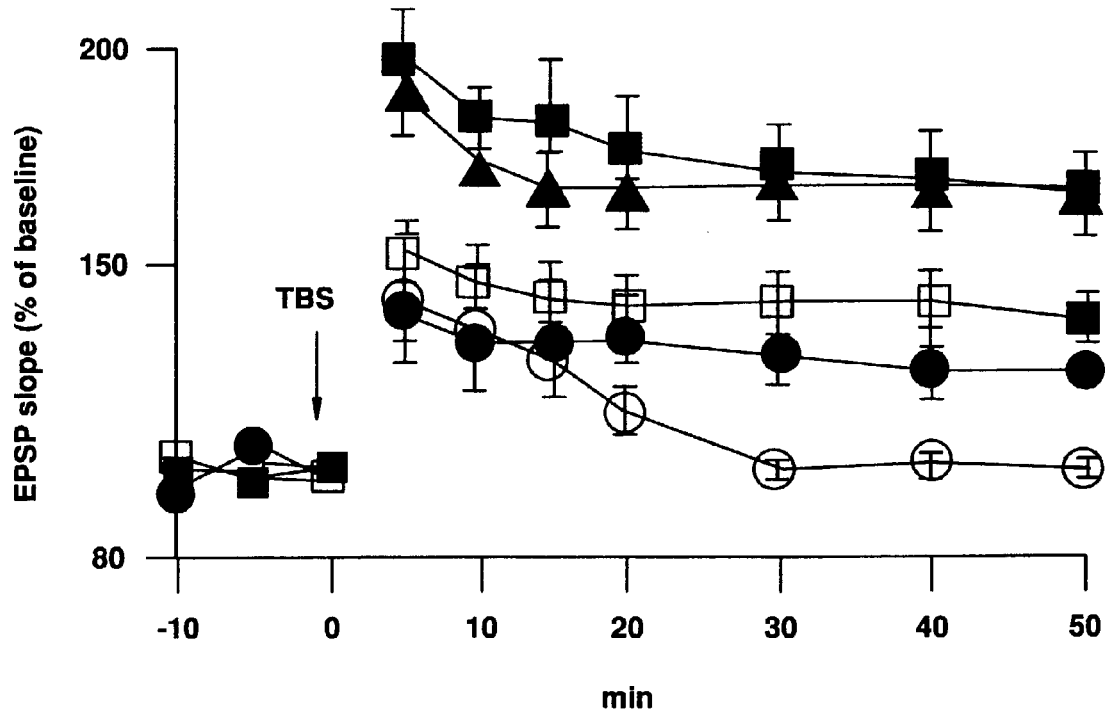
Figure 15E:
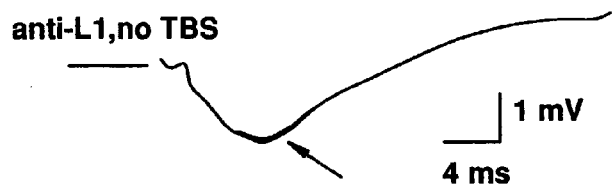
Figure 15F:
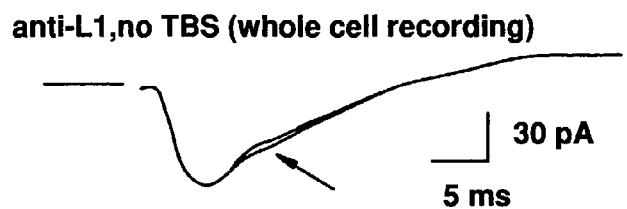

L1 antibodies, FN1-5 and Ig I-VI fragments were dialyzed overnight against 0.9% saline and the concentration adjusted to 1 mg/ml for L1 and 250 µg/ml for the fragments. Chicks received bilateral intracranial injections into the intermediate medial hyperstriatum ventrale (IMHV) of 10 µl L1 antibodies per hemisphere; control animals received similar injections of saline. Accurate delivery into the IMHV was received by the use of a specially designed head holder and sleeved Hamilton syringe (Davis et al. (1982) *Pharm. Biochem. Behav.* 17:893-896). Chicks receiving this injection volume of either saline or antibodies prior to training or testing showed no overt behavioral effects, pecking the bead accurately during training. The large extracellular volume of the brain of the newly hatched chick means that injections of this size are well-tolerated, and can be achieved without leakage. A previous report has demonstrated (Scholey et al. (1993)) that there is a slow diffusion of antibody from the injection site in the hours following injection. The accuracy of placement of the injection was routinely monitored by visual inspection of the brains post-mortem. In each replication of the experiment, a balanced group of saline and antibody or fragment-injected chicks were employed. In the L1 experiment, groups of chicks were injected with saline or antibody at one of eight time points relative to training; 2 hours or 30 minutes pre-training, or +1 hour, +3 hours, +4 hours, +5.5 hours, +8 hours or +12 hours post-training. On the basis of previous observations, it was predicted that any effects would be observed in birds injected at either 30 minutes prior or 5.5 hours post-training, and the numbers of replications at these time points were accordingly greater (N=17, 28, 17, 19, 18, 21, 19 and 18 respectively for antibody injections). L1 fragments FN1-5 and Ig I-IV were injected at either −30 minutes or +5.5 hours and retention tested at 24 hours. Retention in groups of saline and L1-antibody or L1-fragment-injected chicks was compared statistically by $\chi^2$. Results are shown in FIGS. 13 and 14.

EXAMPLE 15

Involvement of L1 and NCAM in Long Term Potentiation

Transverse hippocampal slices (400 µm) from halothane-anaesthetized male Wistar rats (180-220 g) were prepared using standard techniques. Slices were maintained in an interface chamber and initially allowed to recover for 45 min. in a hyperosmolar (320 mOsm/kg) artificial cerebrospinal fluid (ACSF) at room temperature. The bath temperature was then raised to 30° C. and the medium was changed to a normotonic ACSF (307 mOsm/kg) containing (in mM): NaCl, 124.0; KCl, 2.5; $MgSO_{24}$, 2.0: $CaCl_2$, 2.5; $KH_2PO_4$, 1.25; $NaHCO_3$, 26.0; glucose, 10; sucrose, 4; bubbled with $O_2$/5% $CO_2$ (pH 7.4); perfusion rate: 0.75 ml/min. The Schaffer collateral/commissural fibers were stimulated by twisted platinum-iridium wires (50 µm diameter) placed in the stratum radiatum of the CA1 region. Test stimuli consisted in monophasic impulses of 100 µs duration every 30 seconds and the stimulus strength was adjusted to obtain 30% of the maximal EPSP amplitude (maximal EPSP without superimposed population spike). EPSP's were recorded from the CA1 stratum radiatum by means of 2 glass micropipettes (2 M NaCl, 1-5 MΩ) positioned about 300 µM apart from the stimulation electrode on each side.

After stable recording for at least 15 minutes, antibodies or protein fragments were ejected onto the CA1 dendritic field in the vicinity (50-75 µm) of one recording electrode (the one carefully adjusted at 30%) by using a modified microinjection system (Nanoliter injector, WPI) continuously delivering 5 nl every 10 seconds up to the end of the experiment unless otherwise indicated. A wash-out of the antibodies with subsequent induction of LTP was not possible for evident reasons, but it was verified whether LTP could be induced within each slice by recording from the second electrode where no antibodies were applied. Although the tip of the ejection micropipette did not penetrate the slice, a small reduction in the EPSP amplitude was sometimes observed when the ejection was started. This volume artifact was independent of the nature of the ejected material. Proteins were dialyzed against 20 mM PBS at pH 7.4 unless otherwise indicated and concentrations referred to the pipette concentration.

Twenty minutes after initiating the microejection, LTP was induced with a theta burst stimulation (TBS) paradigm consisting of three trains spaced by 4 seconds; each train consisted of ten high frequency bursts of 5 pulses at 100 Hz and the bursts were separated by 200 ms (Reichardt et al. (1991) *Annu. Rev Neurosci.* 14:531-570). Duration of the stimulation pulses was doubled during TBS. Induction of LTP could be totally prevented by perfusion of 10 µM D(−)-2-amino-5-phosphonopentanoic acid (D-AP5; Tocris). Whole cell recordings were obtained from CA1 neurons using the "blind" patch clamp method with an EPC-9 patch clamp amplifier. The bath temperature was 30° C. Patch electrodes were pulled from 1.5 mm OD borosilicate glass and had resistances between 3 and 8 MΩ. The pipettes were neither fire polished nor coated. The electrodes were routinely filed with a solution containing (in mM): potassium gluconate, 129; KCl, 5; $MgCl_2$, 1; $CaCl_2$, 1; N-(1-hydroxyethyl)-piperazine-N'-(2-ethanesulphonic acid) (HEPES), 5; 1,2-bis(2-aminophenoxy)ethane-N,N,N',N'-tetraacetic acid (BAPTA), 5; Na-ATP, 10 and Na-GTP, 0.3, with pH adjusted to 7.3 using KOH. Series resistance was not compensated. Responses were sampled as an average of three to four signals, either printed out for visual analysis, or stored on disk for further analysis. Statistical evaluations were performed by analysis of variances with planned comparisons and contrast analysis; time was considered as a dependent variable with one level of repeated measures. Anti-L1 (Rathjen et al. (1984)), anti-Ig I-VI (Hynes et al. (1992)) and anti-liver membranes antibodies (Linder (et al. (1983)) were produced as previously described. Results are shown in FIG. 15.

Figure 16A:
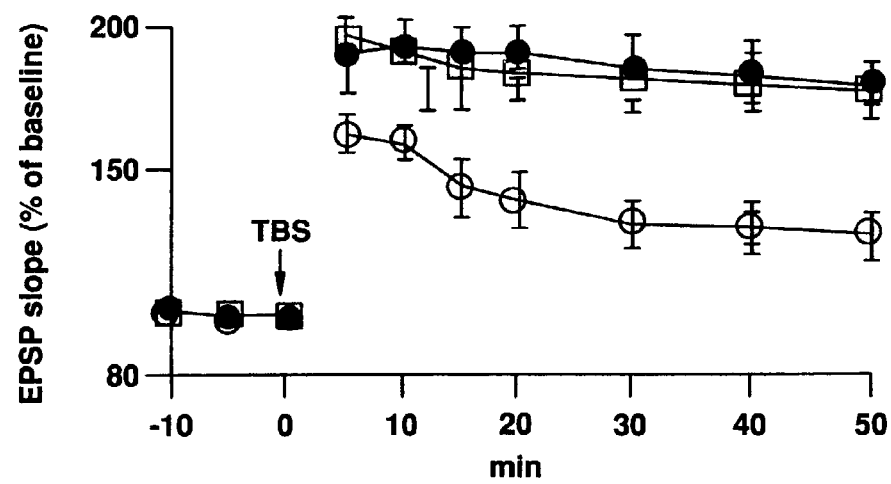
FIG. 16 demonstrates the influence of the immunoglobulin-like domains I-VI, polyclonal NCAM antibodies and oligomannosidic glycopeptides on LTP. A, time-course of the EPSP initial slope before and after TBS in the presence of the immunoglobulin (Ig)-like domains I-VI (216 µg/ml; 3.2 mM; in 20 mM Tris/HCl pH 7.6, ○; p<0.01) and the fibronectin (FN) type III homologous repeats I-V (225 µg/ml; 3.8 mM; in 20 mM Tris/HCl pH 7.6, ■) of L1, compared to control LTP (20 mM Tris/HCl, pH 7.6, □). B, Time-course of the EPSP initial slope before and after TBS in the presence of antibodies to NCAM (IgG fraction, 3.9 mg/ml, ▲), an antiserum against axonin-1 (●), and the following controls: (1) a non-immune rabbit serum (▲), (2) an IgG fraction of non-immune rabbit serum (3.0 mg/ml, ♦), and (3) in the presence of NCAM antibodies (3.9 mg/ml, □; p<0.06) without induction of LTP by TBS. C, time-course of the EPSP initial slope before and after TBS in the presence of oligomannosidic glycopeptides (○), control glycopeptides (●) derived from asialofetuin (both at 100 µM), and in the absence of glycopeptides (□). Results are expressed as means±S.E.M. of the EPSP initial slope in percent of the baseline values recorded during the 20 min. before TBS (n=5 or 6 slices from at least 3 animals).
Figure 16B:
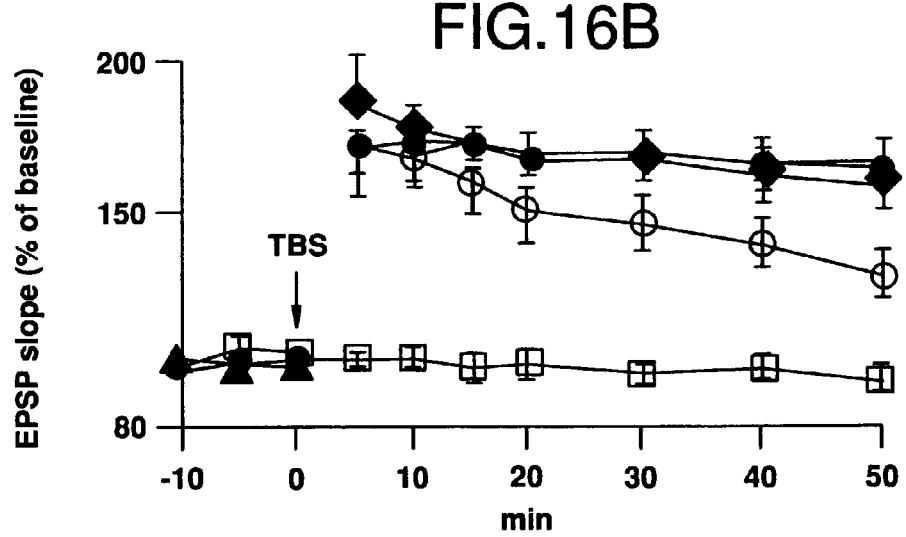
Figure 16C:
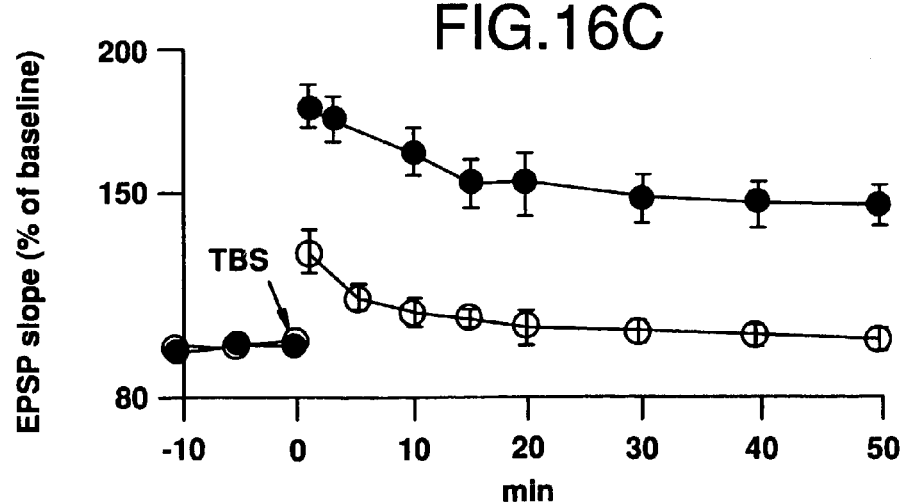
Figure 17A:
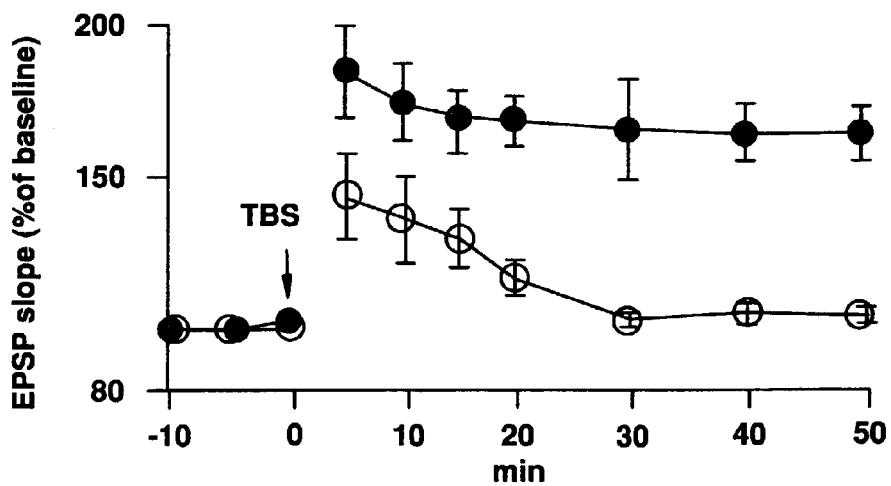
FIG. 17 graphically depicts the influence of L1 antibodies and oligomannosidic carbohydrates on previously established LTP and on NMDA receptor-mediated synaptic transmission. A, Time-course of the EPSP initial slope before and after TBS in the presence of L1 antibodies applied either throughout the experiment (6.2 mg/ml; ○) or starting 10 minutes after TBS (6.2 mg/ml; ●). B, time-course of the EPSP initial slope before and after TBS in the presence of oligomannosidic carbohydrates applied either throughout the experiment (100 µM; ○) or starting 20 minutes after TBS (100 µM; ●). C, Averaged (n=4) NMDA receptor-dependent EPSP's recorded in the presence of CNQX (30 µM) before and after 30 minutes (arrow) application of L1 antibodies. D, Averaged (n=4) NMDA receptor-dependent EPSP's recorded in the presence of CNQX (10 µM) before and after (arrow) 60 minutes of application of oligomannosidic carbohydrates. Results in A and B are expressed as means±S.E.M. of the EPSP initial slope in percent of the baseline values recorded during the 20 min. before TBS (n=5 slices from at least 3 animals).
Figure 17B:
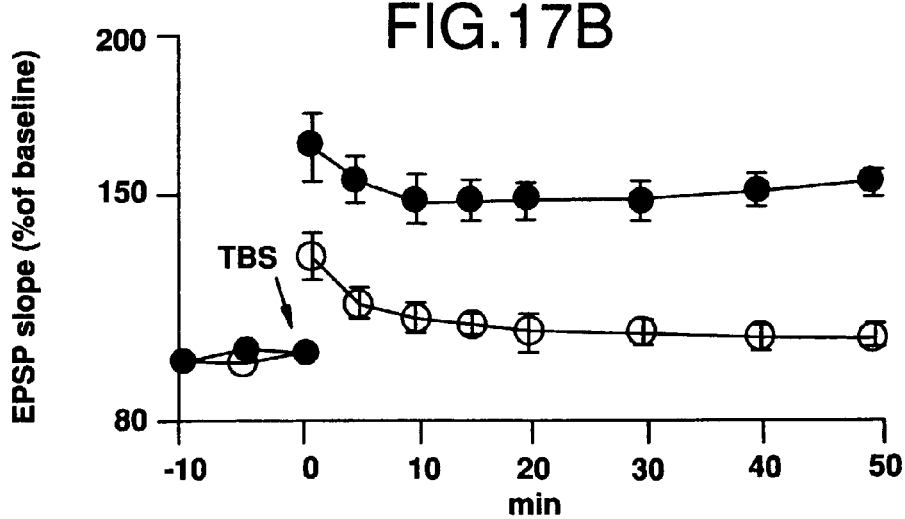
Figure 17C:
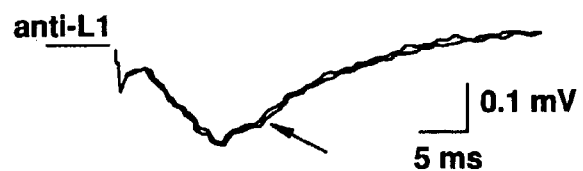
Figure 17D:
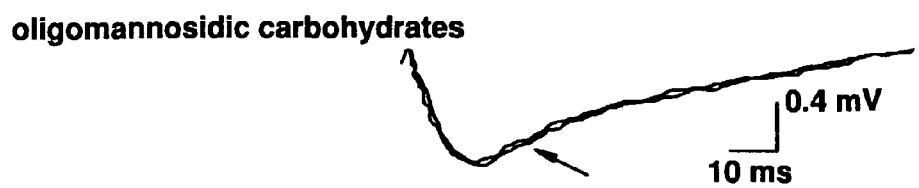

Ig-like domains I-VI and FN type III homologous repeats I-V of L1 were expressed in bacteria and purified as described (Hynes et al. (1992)). Antibodies to NCAM and axonin-1 were produced as described (Larson et al. (1986) *Science* 232:985-988; Bailey et al. (1992) *Science* 256:645-649). Production of oligomannosidic glycopeptides from ribonuclease B and control glycopeptides from asialofetuin have been described (Larson et al. (1986)). Results are shown in FIG. 16.

NMDA receptor-mediated EPSP's were isolated by applying 30 µM of the non-NMDA blocker 6-cyano-7-nitroquinoxaline-2,3-dione (CNQX; Tocris) starting 20 minutes prior to the application of antibodies or glycopeptides. At the end of each experiment, it was verified that D(−)-2-amino-5-phosphonopentanoic acid (D-AP5; 30 µM; Tocris) completely suppressed these responses. Results are shown in FIG. 17.

EXAMPLE 16

L1 Exerts Neuropreservative Effect

An experiment was performed to further elucidate the activity of L1 with CNS nerve tissue. Specifically, aliquot samples of mouse mesencephalon cells were plated and cultured on four separate plates having media prepared as follows: the first control plate was coated with poly-L-lysine alone; a second plate was coated with poly-L-lysine and L1; a third control plate was coated with poly-L-lysine and laminin; and a fourth plate was coated with poly-L-lysine, laminin and L1. All plates received aliquot amounts of cells and were incubated under identical conditions. After 7 days, the plates were all stained for the presence of dopamine and thereafter observed. The plates that were coated with L1 exhibited a growth of 200% to 400% greater than the controls. The plates coated with laminin exhibited greater neurite outgrowth, but not more cells than those coated with L1. The results demonstrate and suggest that L1 exerts a profound neuropreservative effect, as cell viability measured by numbers of cells grown was dramatically increased over controls.

EXAMPLE 17

Soluble L1 (L1-Fc) is Functionally Active and is a Potent Agent in Neuronal Survival Soluble L1 was made in COS cells as a recombinant L1-Fc fusion protein by the procedure described in *Neuron* 14:57-66, 1995. The recombinant protein was purified by Protein A affinity chromatography, and was used either as a substrate coated onto plastic or as a soluble molecule added to the culture medium at approximately 1-10 μg/ml. Neurite outgrowth and survival of mesencephalic neurons from day 17 rat embryos were examined in culture after 7 days in vitro maintenance. Dopaminergic neurons were recognized by immunostaining for dopamine-β-hydroxylase (DBH) and quantified using IBAS morphometric equipment. Cultures with added soluble L1-Fc were maintained on poly-DL-omithine (PORN) and substrate-coated L1-Fc was added on top of previously coated PORN (under conditions described in Appel et al, *J. Neuroscience* 13:4764-4775, 1993). NCAM-Fc was used as a control.

TABLE 2

Survival and neurite outgrowth of DBH neurons after 7 days in vitro

|  | number of neurons[+] | length of neurites[++] |
|---|---|---|
| substrate-coated L1 | 129 ± 20 | 179 ± 40 |
| soluble L1 | 98 ± 7 | 135 ± 27 |
| PORN only (control) | 14 ± 2 | 37 ± 9 |

Mean values are from at least three independent experiments ± SEM
[+]The numbers are from a unit field
[++]The lengths of all neurites (total neurite length) per neuron was determined (in μm)

Recognition among neural cells is an important prerequisite for the development of a functioning nervous system. Recognition molecules are expressed at the cell surface, where they mediate interaction between neighboring cells, like cadherins, or between the cell surface and the extracellular matrix, like integrins (Takeichi, 1991; Ruoslahti, 1988; Hynes, 1992). The most prominent family of recognition molecules comprises immunoglobulin (Ig)-like domains. The Ig-like domains reflect a common ancestry of immunoglobins and cell adhesion molecules, both of which are involved in specific recognition events (Edelman, 1970). In the nervous system the Ig superfamily comprises by now more than two dozen distinct molecules. Some Ig-like domain containing molecules have multiple functions within the extracellular domain: Receptors for cytokines and neurotrophins have high affinity receptive functions as well as recognition properties (Tannahill et al., 1995; Pulido et al., 1992). The three-dimensional structure of Ig-like domains is similar to FN-like repeats (Main et al., 1992; Leahy et al., 1992), which are also structural motifs in several extracellular matrix molecules, such as fibronectin, members of the tenascin family, and others (Williams and Barclay, 1988; Baron et al., 1992; Erickson, 1993). Neural recognition molecules of the Ig superfamily have characteristic temporal, spatial, and cell-type specific expression patterns (for reviews, see Edelman, 1988; Schachner, 1991, 1994; Rathjen and Josseli, 1991; Rutie-hauser, 1993). Recognition molecules of this family are functionally overlapping in that all promote cell adhesion and neurite outgrowth. Some recognition molecules are strongly homophilic, i.e. self binding partners, whereas others are predominantly heterophilic, i.e. they bind to non-self partners which often comprise other members of the Ig superfamily or extracellular matrix molecules (Brümmendorf and Rathjen, 1993, 1994). Present knowledge of the functional properties of the individual Ig-like domains and/or FN-like repeats of neural recognition molecules indicate both distinct, and overlapping functional properties in recognition, neurite outgrowth, and repulsion (Gennarini et al., 1991; Frel et al., 1992; Taylor et al., 1993; Appel et al., 1993, 1995; Pesheva et al., 1993; Feisenfeld et al., 1994; Hoim et al., 1995).

Among neural recognition molecules of the Ig superfamily, the family of molecules related to the neural recognition molecule L1 shows striking similarity in function and structure. They are potent neurite outgrowth promoters and are expressed relatively late during development, mostly at the state when axogenesis occurs. They are predominantly expressed by neurons, although some members of the L1 family are also present on neurite outgrowth promoting glial cells (Martini and Schachner, 1986; Bixby et al., 1988; Seilheimer and Schachner, 1988).

EXAMPLES 18-25

In the experiments that follow, another member of the L1 family is identified and characterized, that is designated a close homolog of L1 (CHL1). It contains six Ig-like domains and FN-like repeats, of which four are highly homologous to the FN-like repeats of other L1 family members. The partial FN-like repeat localizes to the membrane-adjacent region of the molecule, which is the most variable region among L1 related molecules. Other features of CHL1 shared with members of the L1 family are its predominant and developmentally late expression in the nervous system, and its high level of N-glycosylation, including expression of the HNK-1 carbohydrate.

EXAMPLE 18

Sequencing of CHL-1 and Comparison to L1

Material and Methods
Animals
ICR mice and Wistar rats were used for tissue preparations.
Antibodies
Polyclonal antibodies directed against the recombinantly expressed extracellular part of CHL1 (amino acids 499-1063 (FIGS. 18 and 19)) and L1 (amino acids 126-1981 (Appel et al., 1993)) were raised in rabbits as described (Rathjen and Schachner, 1984). To raise antibodies against CHL1 200 μg of purified peptide was injected into rabbits followed by four additional injections of 100 μg in intervals of three weeks. L1 antibodies were concentrated from serum by ammonium sulfate precipitation (13.5 mg/ml). Monoclonal rat antibody 412 was used to identify the HNK-1 carbohydrate epitope (Kruse et al., 1984). Monoclonal antibodies against glial fibrillary acidic protein (GFAP) were obtained from Boehringer (Mannheim). The monoclonal antibodies to the O1 antigen(s) has been described (Sommer and Schachner, 1981).
Purification of Neural Adhesion Molecules
L1, N-CAM, and MAG were immunoaffinity purified from detergent extracts of crude membrane fractions from adult mouse brain using monoclonal antibody columns (Rathjen and Schachner, 1984; Falssner et al., 1985; Poltorak et al., 1987).

cDNA Libraries and Screening

Preparation of the λgt11 library derived from poly(A)+ RNA of brains from 8-day-old mice and screening of this library with immunoaffinity purified polyclonal L1 antibodies were performed as described (Tacke et al., 1987). To obtain longer cDNA clones, a new DNA library was constructed: RNA was purified from brains of 6 to 14-day-old mice by the guanidinium thiocyanate/acid phenol method (Chomezynski and Sacchi, 1987). Poly(A)+ RNA was enriched by two subsequent passages over an oligo(dT)-cellulose column (Sambrook et al., 1989). Eight micrograms of poly(A)+ RNA were used for synthesis of oligo(dT)-primed double-stranded cDNA using a cDNA synthesis kit (Amersham). The cDNA was size-selected and ligated into the plasmid pXMD1 with DraIII-adaptors containing a SalI site (Kluxen et al., 1992). For propagation and amplification of the library, E. coli strain TOP10 (Invitrogen, Netherlands) was used. For screening, aliquots were directly plated onto Nylon membranes (BIODYNE™ Pall) with a density of about $2 \times 10^4$ bacteria/filter (138 cm²). Replica filters were incubated overnight at 37° C. Subsequently, the bacteria were lysed (0.5M NaOH; 1.5M NaCl), filters were neutralized (3M NaCl; 0.5M Tris-HCl pH 8.0), washed in a 2×SSC, air-dried, and baked for 2 hr. at 80° C. The Nylon membranes were prehybridized, hybridized with a 1 kb fragment (HincII/KpnI) of CHL1 (derived from the λgt11 library) redioiabelled by random-priming (Boehringer Mannheim) according to the manufacturer's protocol, washed under high-stringency conditions at 42° C., and then exposed to X-ray film as described elsewhere (Sambrook et al., 1989). Six positive clones were further characterized by restriction mapping and sequencing according to standard protocols (Sambrook et al., 1989). One clone (pX#2) containing a 4.43 kb CHL1 insert was used for further analysis.

DNA Sequencing and Sequence Analysis

Nucleotide sequences were determined by the dideoxy-chain-termination method (Sanger et al., 1977) using double-stranded DNA as a template for T7 DNA polymerase (Pharmacia) and synthetic oligonucleotides as primers. cDNA sequences were assembled and analyzed with the DNASTAR program (DNASTAR, Inc., London). Unless otherwise indicated, amino acid sequences were aligned by the Jolun Hein method (Hein, 1990) (gap penalty=11, gap length penalty=5, K tuple=2).

Comparison of Protein Sequences

To calculate a similarity index (%) for comparison of the distances between conserved amino acid residues, several distinct proteins containing six Ig-like domains and at least four FN-like repeats were aligned at conserved amino acid residues in the Ig-like domains (cysteines which refer to S-S bridges) and in the FN-like repeats (tryptophan and tyrosine/phenylalanine). The number of amino acid residues between these conserved positions was determined. This is referred to as the consensus distance. The mean value of the distances, i.e. the consensus distance and standard deviation (SD) among L1 family members were calculated. SD values were rounded up to the next integer. The distance for each protein was compared to the mean distance and considered as match if the distance value equaled the mean value±the SD (=consensus distance). The number of matches to the 19 consensus distances was calculated for each individual protein (similarity index number of matches/19×100). For example: In the CHL1 protein 16 distance values match to the consensus distances, while three of all criteria did not match. This leads to a similarity index of 16/19 or 84% for CHL1.

EXAMPLE 19

Cell Culture and Expression of CHL1 and L1 in COS-1 Cells

The 4.43 kb insert of clone pX#2 was ligated into SalI digested pXMD 1 (Kluxen et al., 1992, Kluxen and Lobbert, 1993). A subfragment (EcoRI (plasmid polylinker)/PvuII bp 4048) of the mouse L1 cDNA (Moos et al., 1988) was treated with T4 DNA polymerase and ligated into pXMD1.

COS-1 cells were maintained in DMEM (0.1% glucose) supplemented with 10% (v/v) fetal calf serum at 37° C. in a humidified atmosphere with 5% $CO_2$. DEAE dextran-mediated DNA transfection was performed as described (Kluxen et al., 1992) with some modifications. Briefly, the cells were seeded at about 10,000 cells/cm². One day later, after two washes with DMEM (0.45% glucose), the medium was replaced by transfection solution composed of DMEM supplemented with 10% (v/v) Nu-serum (Becton Dickinson, Switzerland), 0.4 mg/ml (w/v) DEAE-dextran (Pharmacia), 50 μM chloroquine, and 1.25 μg/ml DNA (4 ml per 10 cm dish). The cells were incubated 4 hr at 37° C. and 5% $CO_2$. Then the medium was removed and the cells were incubated for 2 min in phosphate-buffered saline (pH 7.3) containing 10% dimethylsulfoxide (v/v). After two washes with DMEM (0.45% glucose), DMEM supplemented with 10% (v/v) fetal calf serum and 20 μg/ml gentamycin was added and the cells were incubated in this medium. 24 hr later cells were detached by incubation with 0.01% trypsin and 0.0004% EDTA in Hanks' balanced salt solution (HBSS) for 5 min at 37° C., replated for immunocytochemistry at a density of about 20,000 cells/cm² in 24-well plates (Falcon) containing poly-L-lysine coated glass coverslips (11 mm in diameter), and incubated for an additional 24 hr. For Western blot analysis the cells were replated on tissue culture dishes and incubated for an additional 48 hr.

PC12 cells were maintained in DMEM with 10% (v/v) fetal calf serum and 5% (v/v) horse serum on collagen coated tissue culture dishes. For induction of the cells with nerve growth factor (NGF) the medium was removed from monolayers at about 50% confluency and replaced with medium of reduced serum content (5% horse serum) supplemented with 100 ng/ml 7s-NGF (Sigma, Switzerland). After two days of incubation the cells were detached by incubation with 0.1% trypsin and 0.04% EDTA, collected and subjected to RNA extraction.

Primary cultures of astrocytes were prepared according to McCarthy and De Vellis (1980) with modifications (Guénard et al. 1994) and used for immunostaining after one to two weeks in vitro. Primary cultures of oligodendrocytes were prepared as described by Laeng et al. (1994) and maintained in vitro for 12 days.

EXAMPLE 20

Production of Antisense RNA

The 4.43 kb insert of clone pX#2 was ligated into SalI digested pBS II SK. (Stratagene) followed by deletion of an ApaI (vector)/AvrII (bp 3330 (FIG. 18)) fragment to obtain the cDNA fragment of CHL1 encoding the extracellular part of the protein (see FIGS. 18 and 19). A similar construct for L1 was prepared by ligation of an EcoRI (plasmid polylinker)/EcoNI (bp 3304) fragment of the L1 cDNA (Moos et al., 1988) treated with T4 DNA ploymerase and ligated into SmaI digested pBS II SK-. The plasmids were digested with XbaI and used for synthesis of $^{32}$P-labeled antisense RNA with T7 RNA polymerase as described (Melton et al., 1984).

Northern Blot Analysis

Poly (A)$^+$ mRNA was prepared from different tissues of neonatal and 9-day-old mice using the Oligotex™ Direct mRNA-Method (QIAGEN Inc., Düsseldorf, Germany) following the manufacturer's instructions. Poly (A)$^+$ mRNA and RNA marker (RNA ladder, GIBCO/BRL) were subjected to electrophoresis on a 0.8% formaldehyde/agarose gel and subsequently transferred to Hybond-N membrane (Amersham) by capillary transfer (Southern, 1975) in 20×SSC. After UV crosslinking (UV-Stratalinker® 1800, Stratagene, La Jolla, Calif.), the amount of RNA transferred and bound to the membrane was controlled by methylene blue staining (Sambrook et al., 1989). Following prehybridization for 2 hr at 65° C., the membrane was hybridized overnight using CHL1- and L1-specific $^{32}$P-labeled antisense RNA probes in hybridization buffer (5×SSC, 2.5×Denhart's solution, 50 mM Na$_2$PO$_4$ (pH 6.5), 0.1% SDS, 1 mM EDTA, 2 μg/ml salmon sperm DNA, 50% formamide) at 65° C. The filter was then washed three times at 65° C. in 0.1×SSC, 0.1% SDS for 1 hr and exposed to X-ray film.

EXAMPLE 21

Expression and Purification of Recombinant CHL1 Protein in E. coli

A 1.7-kb cDNA-fragment of CHL1 (MscI; bp 1791 (which originates from the vector cloning site and the 5' end of the λgt11 derived CHL1 clone) and BsmAI; bp 3494) encoding the 6th Ig-like domain (IgV1) and FN-like repeats 1.4.5 (see FIGS. 18 and 19b) was subcloned into the unique BamHI restriction site of the pET-vector (Studier and Moffatt, 1986). The correct sequence of the plasmid was confirmed by sequencing. E. coli strain BL21 (DE3) was transformed with this plasmid. Expression and purification by anion exchange chromatography of the recombinant protein were performed according to Appel et al. (1993). SDS-PAGE and Coomassie staining showed a major band at the expected molecular weight (70 kD) which contained at least 80% of the total protein (not shown).

Tissue Fractions

Detergent lysales of whole tissue were prepared by homogenization of tissues in 40 mM Tris-HCl (pH 7.4), 150 mM NaCl, 5 mM EDTA, 5mM EGTA, 1 mM phenylmethysulfonylfluoride (PMSF), 1% Triton X-100 and maintained at 4° C. for 3 hr under constant stirring. The soluble fraction was separated from insoluble material by centrifugation at 100,000 g.

For preparation of detergent lysates of membrane fractions, tissues were homogenized in 1 mM NaHCO$_2$ (pH 7.9), 0.2 mM CaCl$_2$, 0.2 mM MgCl$_2$, 1 mM spermidine, 5 μg/ml aprotinin, 10 μg/ml soybean trypsin inhibitor, 1 mM PMSF, and 0.5 iodoacetamide at 4° C. Membrane and soluble fractions were then separated and the membrane pellet was resuspended in solubilization buffer (20 mM Tris-HCl (pH 7.9), 0.15 M NaCl, 1 mM EDTA, 1 mM EGTA, 0.5% Triton X-100, 5 μg/ml Aprotinin, 10 μg/ml soybean trypsin inhibitor, 1 mM PMSF, and 0.5 mM iodoacetamide).

Transiently transfected COS-1 cells were washed twice with HBSS and incubated with 1 mM EDTA in HBSS for 10 min at 37° C. The cells were then detached with a fire polished Pasteur pipette and collected by centrifugation at 200 g for 10 min at 4° C. The cells were lysed in 20 mM Tris-HCl (pH 7.4), 150 mM NaCl, 1 mM EDTA, 1 mM EGTA, 1 mM iodoacetamide, 1 mM PMSF, and 1% MP-40 and the supernatant was cleared by centrifugation (13000 g). Protein determinations were performed as described by Bradford (1976).

Western Blot Analysis

Proteins were separated by SDS-PAGE (Laemmil, 1970) on 8% or 10% slab gels under reducing conditions and transferred to nitrocellulose filters (0.45 μm, BA 85; Schleicher & Schuell, Dassel, Germany) for immunodetection according to Faissner et al. (1985), using CHL1 antiserum (diluted 1:500, 1:10000 for ECL), L1 polyclonal antibodies (diluted 1:1000, 1:15000 for ECL), or monoclonal antibody 412 (diluted 1:1000, 1:10000 for ECL) and alkaline phosphatase-coupled secondary anti-rabbit or anti-rat IgG. Bound antibodies were either detected by the enhanced chemiluminescence (ECL) method according to the manufacturer's instructions using ECL Western blotting detection reagents (Amersham) and X-ray films, or by using BCIP and NBT as chromogenic substrates.

EXAMPLE 22

Enzyme-Linked Immunosorbent Assay

The enzyme-linked immunosorbent assay (ELISA) was performed as described by Husmann et al. (1992) with the exception that proteins were coated at concentrations of 100 ng/ml. CHL1 antiserum was used in several dilutions between 1:250 to 1:2×10$_6$.

Deglycosylation of CHL1

Detergent lysates of brain tissue homogenate (200 μl. 6 mg/ml protein concentration) from seven-day-old mice were separated into a soluble fraction and insoluble material by centrifugation (see Tissue fractions) and incubated with 0.5 units N-glycosidase F or 2.5 units O-glycosidase, or both enzymes at these concentrations according to the manufacturer's instructions (Boehringer Mannheim, Germany). The lysates were resolved by SDS-PAGE on 10% gels. The proteins were transferred to nitrocellulose and incubated with CHL1 antiserum (1:500 diluted) directed against the recombinant CHL1 protein fragment (see FIG. 18).

Immunoprecipitation

The soluble fraction of detergent lysates of brain tissue homogenate (300 μl. 5 mg/ml protein concentration) from nine-day-old mice (see Tissue fractions) was incubated with 10 μl. CHL1 antiserum or polyclonal antibodies against L1 overnight at 5° C. in 5 ml buffer (20 mM Tris-HCl (pH 7.4), 150 mM NaCl, 5 mM EDTA) containing 1% NP40 and 30 μl of G-Sepharose (Pharmacia/LKB). After sequentially washing the buffers containing 0.1% NP40, 0.05% SDS, and then 20 mM Tris-HCl (pH 7.4), the Sepharose beads were boiled for 10 min in 5× sample buffer (250 mM Tris-HCl (pH 6.6), 10% SDS, 50% glycerol, 0.5% bromophenol blue, 25% B-mercaptoethanol) and the supernatant was resolved by SDS-PAGE on 10% gels. The proteins were transferred to nitrocellulose and detected with polyclonal antibodies against L1, CHL1 antiserum, or monoclonal antibody 412 by Western blot analysis.

Indirect Immunofluorescence

For cell surface staining (Schnitzer and Schachner, 1981) CHL1-, and mock (vector only)-transfected COS-1 cells plated on coverslips were incubated for 30 min at room temperature with primary antibody (CHL1 antiserum (1:100 diluted) or L1 polyclonal antibodies (1:200 diluted)) in DMEM containing 10% fetal calf serum, 10 mM Hepes (pH 7.3), and 0.02% NaN$_3$, and then with secondary antibody.

After innunostaining, the cells were fixed with 4% paraformaldehyde in phosphate buffered saline (pH 7.3) and mounted in Moviol (Hoechst) containing 2.5% potassium iodide. For double-immunofluorescence staining of astrocytes and oligodendrocoytes, incubation of primary antibodies to cell surface antigens was performed as described for transfected COS-1 cells. Subsequently, incubation of cells with primary antibodies against intercellular antigens was performed after permeabilizing the cells with methanol at −20° C.

EXAMPLE 23

In Situ Hybridization

To generate digoxigenin-labelled antisense cRNA probes of equal size from corresponding parts of CHL1 and L1 the same constructs as for Northern blot analysis were used. Sense probes were generated from similar constructs with the inserts in opposite direction. All the cRNA probes were generated using T7 RNA polymerase followed by an alkaline treatment to obtain an average fragment length of 250 nucleotides. In situ hybridization was performed as described (Bartsch et al., 1992; Dorries et al., 1994).

Results and Discussion

Identification of CHL1 cDNA

Screening of a λgt11 expression library for cDNA clones encoding the cell adhesion molecule L1 with polyclonal antibodies raised against brain-derived immunopurified L1 (Tacke et al. 1987) identified the clone 311. It contained a partial cDNA homologous to L1 (34.1% according to Lipman and Pearson (1985)) and an open reading frame of 2112 base pairs (bp) coding for 704 amino acids including the cytoplasmic part. To isolate full length cDNA clones, a DNA fragment of this clone was used for screening a different cDNA library. Six independent clones were isolated. Two clones contained 4.2 and 4.4 kb inserts comprising the entire coding region of a close homolog of L1 (CHL1). The clone containing the 4.4 kb insert was further investigated.

DNA and Deduced Amino Acid Sequences and Structural Features

Figure 18A:
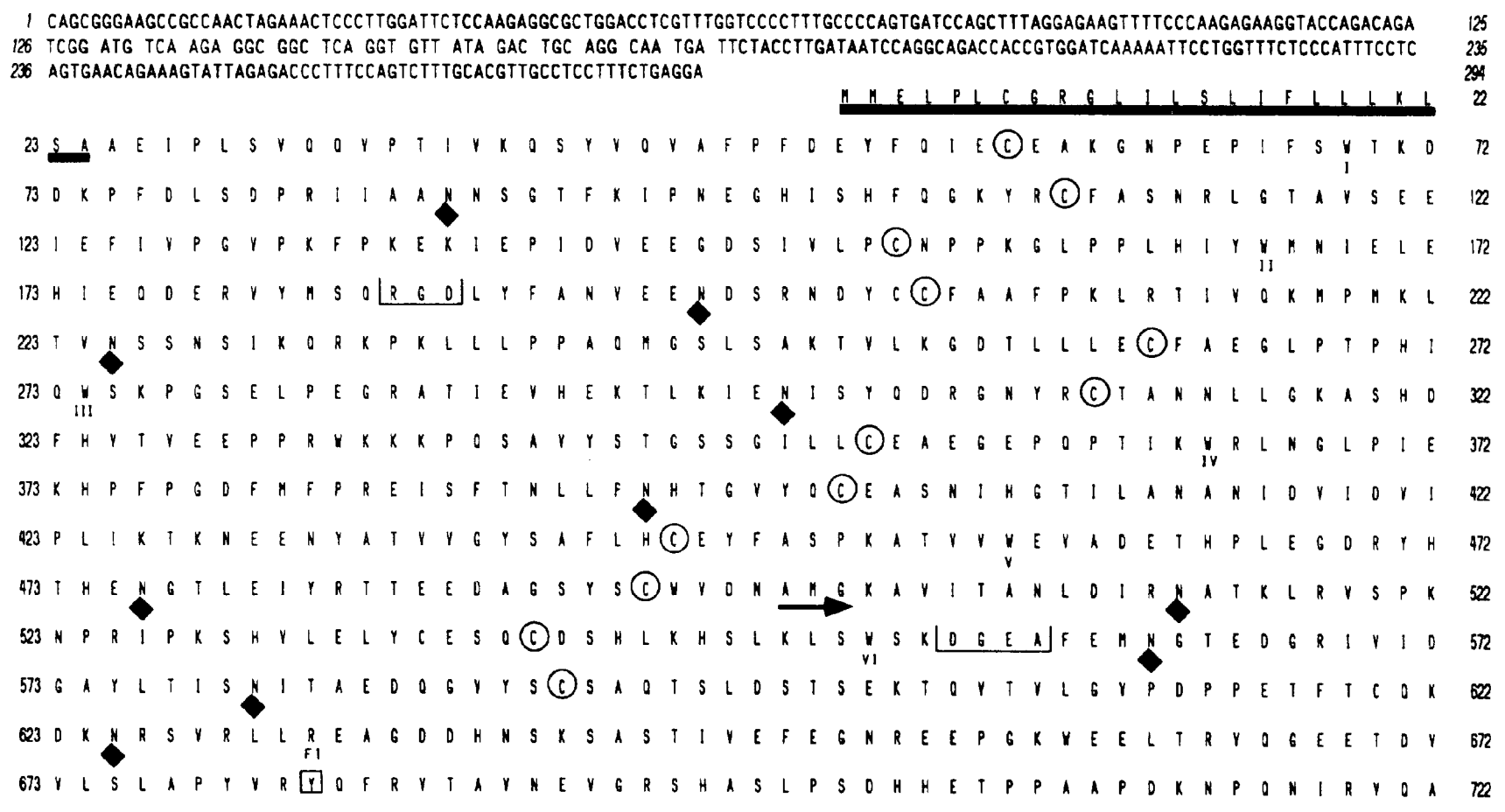
Figure 18B:
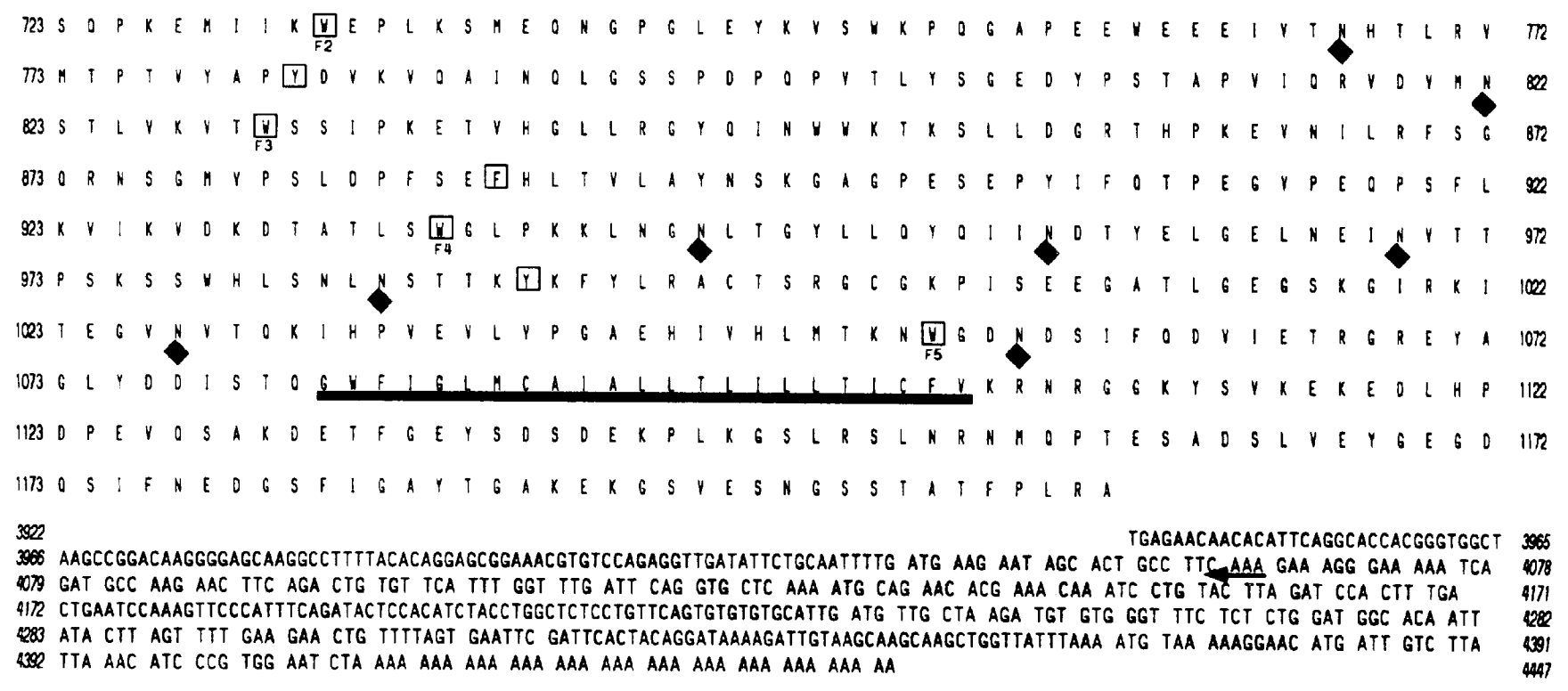

The 4.4 kb insert encodes a 5' untranslated region of 295 bp, an open reading frame of 3627 bp, and a 3' untranslated region of 518 bp (FIG. 18). Although there is an oligo(A) tract at its 3' terminus, a clear consensus polyadenylation signal upstream of this sequence is missing. The flanking sequences of the AUG start codon (position 296, FIG. 18) do not conform to the optimal consensus sequence for initiation of translation (Kozak, 1987). However, this AUG is taken as the start codon for translation based on two lines of evidence. It is preceded upstream by stop codons in all three reading frames and is followed by a potential signal sequence with a cleavage site predicted after residues 24 or 25 (scores of 8.65 and 6.40, respectively, according to the algorithm of von Heijne (1986)) (FIG. 18).

Translation of the open reading frame yields a protein of 1209 amino acids with a calculated molecular mass of 134.9 kD and features characteristic of an integral membrane glycoprotein. The putative extracellular domain is composed of 1081 amino acids, with 18 potential sites for N-glycosylation (FIGS. 18 and 19*a*) and more than 60 potential O-glycosylation consensus sites (not shown) (Pisano et al., 1993), followed by a transmembrane domain of 23 amino acids, as judged by hydropathy analysis according to Kyte and Doolittle (1982) (FIG. 19*c*). This domain is flanked at its N-terminal end by a polar residue and at its C-terminal end by a basic amino acid, consistent with a stop transfer signal (FIG. 18). The intracellular region is composed of 105 amino acid residues.

The extracellular region contains the two major structural motifs of repeated domains that are characteristic of the L1 family: a 685 amino acid stretch with homology to Ig-like domains and a 472 amino acid stretch with homology to FN-like repeats (FIGS. 1 and 2*a*). All of the six Ig-like domains contain the characteristic pair of cysteine residues located at 47-54 amino acids apart from each other (FIG. 19). A conserved proline (except in the sixth Ig-like domain) at the end of β-strand B in conjunction with a C2-type cluster of conserved amino acids around the second cysteine residue in each domain (DXGXYXCXAXN) assign the Ig-like domains to the C2-set (Williams and Barclay, 1988). Between the Ig-like domains and the membrane spanning region are four domains that are homologous to the FN-like repeats in fibronectin (Kornblihtt et al., 1985). Each of these domains of approximately 100 amino acids contains the highly conserved tryptophan (except for the first FN-like repeat) and tyrosine/phenylalanine residues in the N- and C-terminal regions, respectively. Interestingly, the fifth FN-like repeat is, in contrast to the other members of the L1 family, only a rudimentary one-half FN-like repeat (FIG. 18). Whether this half FN-like repeat represents one of several alternatively spliced forms, one of which contains a full FN-like repeat, remains to be determined by other methods than Northern blot analysis. It is noteworthy in this context that no evidence for alternative splicing was found by restriction analysis of the six independently isolated clones (not shown). Alternative splicing of the fifth FN-like domain was observed for Nr-CAM/BRAVO, where cDNA isoforms were isolated lacking the fifth FN-like repeat (Grumet et al., 1991; Kayyem et al., 1992.) The absence of the fifth FN-like domain in chicken neurofascin (Volkmer et al., 1992) is most probably also due to alternative splicing, since its rat homolog, the ankyrin-binding glycoprotein (ABGP) (Davis et al., 1993), contains a fifth FN-like domain. Thus, CHL1 adds a new structural feature to the L1 family; only four and one-half FN-like repeats are expressed (FIG. 19).

Another structural feature of CHL1 is the presence of an RGD sequence (amino acids 185-187) in the second Ig-like domain (FIG. 18). This tripeptide has originally been identified as a cell attachment site within the tenth type III domain of fibronectin (Pierschbacher and Rusolahti, 1984) and contributes to integrin binding (for review see Rusolahti and Pierschbacher, 1987). Three dimensional structure analysis of FN-like repeats showed that the RGD motif is localized between the β-strands F and G (Main et al., 1992). This motif is also found in other members of the L1 family. In the third FN-like repeats of chicken Ng-CAM (Burgoon et al., 1991) and the species homologs chicken neurofascin and rat ABGP, the RGD sequence is found at the same position, between the β-strands F and G. RGD motifs are also found in L1 (two in L1 mouse and rat (NILE), and one in human L1 (Moos et al., 1988; Hlavin and Lemmon, 1991; Prince et al., 1991). All L1 RGD sequences are found in the sixth Ig-like domain, but in a different amino acid environment than RGDs in the FN-like modules of fibronectin. As in L1, the tripeptide in CHL1 is localized on the β-strand E of the second Ig-like domain. Whether the RGD sequences in these proteins are functionally active is currently not known. It is noteworthy in this context that neurite extension induced by TAG-1 (Furley et al., 1990), a member of the F3/F11 family (Brümmendorf and Rathjen, 1993, 1994) that contains a RGD motif in the second FN-like domain depends on B, integrin and L1 (Felsenfeld et al., 1994). This observation raises the possibility of a direct physical interaction between the second FN-like repeat of TAG-1 and $\beta_1$ integrin.

CHL1 also contains a DGEA sequence (amino acids 555-558) in the β-strand C of the sixth Ig-like domain (FIG. 18). This sequence is not found in other members of the L1 family. The DGEA sequence has also been implicated in $\alpha_2\beta_1$, integrin recognition of type I collagen containing this motif (Staatz et al., 1991).

Structural Similarity of CHL1 with Other Recognition Molecules of the Ig Superfamily A comparison of the amino acid sequence of CHL1 with the translated EMBL gene sequence database showed that CHL1 is 87.2% identical to a 109 amino acid long stretch and 79.6 identical to a 93 amino acid long stretch previously identified in human brain (accession number HS2431 and HSXT02610 (Adams et al., 1992, 1993)). Thus, there appears to be a highly conserved CHL1 molecule in human. The sequences of mouse, human, and rat L1/NILE, chicken Ng-CAM, chicken Nr-CAM, zebrafish L1.1 (Tongiorgi et al., 1995), chicken neurofascin/rat ABGP, *Drosophila* neuroglian (Bieber et al., 1989), mouse F3/chicken F1/human CNTN1 (Gennarini et al., 1989; Ranscht, 1988; Brümmendorf et al., 1989; Berglund and Ranscht, 1994), rat TAG-1/chicken axonin-1/human TAX-1 (Furley et al., 1990; Hasler et al., 1993; Tsiotra et al., 1993), and rat BIG-1/mouse PANG (Yoshihara et al., 1994; Connelly et al., 1994) taken from the translated EMBL gene sequence database were compared with CHL1. The comparison is displayed in Table 3, below.

TABLE 3

Comparison of sequence similarities of the extracellular parts of CHL1 and other L1 related molecules

| | CHL1 (m) | L1 (m) | ngCAM (c) | NrCAM (c) | neurofascin (c) | L1.1 (zf) | neuroglian (d) | F3 (m) | TAG-1 | BIG-1 (r) |
|---|---|---|---|---|---|---|---|---|---|---|
| L1 (m) | 37 | | | | | | | | | |
| NgCAM (c) | 39 | 37 | | | | | | | | |
| NrCAM (c) | 33 | 43 | 35 | | | | | | | |
| neurofascin (c) | 36 | 36 | 47 | 33 | | | | | | |
| L1.1 (zf) | 28 | 28 | 30 | 26 | 30 | | | | | |
| neuroglian (d) | 33 | 36 | 36 | 34 | 34 | 28 | | | | |
| F3 (m) | 27 | 28 | 27 | 26 | 27 | 26 | 24 | | | |
| TAG-1 (r) | 27 | 27 | 26 | 25 | 25 | 25 | 24 | 51 | | |
| BIG-1 (r) | 27 | 29 | 27 | 27 | 25 | 27 | 24 | 44 | 43 | |
| DCC (h) | 14 | 14 | 14 | 15 | 14 | 16 | 14 | 16 | 15 | 15 |
| Axl (m) | 11 | 12 | 11 | 12 | 12 | 11 | 11 | 13 | 12 | 11 |
| HLAR (h) | 15 | 15 | 13 | 14 | 13 | 14 | 11 | 13 | 14 | 14 |
| NCAM (m) | 16 | 15 | 17 | 16 | 15 | 16 | 15 | 15 | 15 | 15 |

The extracellular regions of the members of the L1 family were compared with each other and with other neural cell adhesion molecules of the Ig superfamily. Values indicate the percentage of amino acid identity after alignment according to Hein (1990). The species are indicated in brackets: c = chicken, d = Drosophila, h = human, m = mouse, r = rat, and zf = zebrafish.

TABLE 4

Comparison of sequence similarities of the intracellular parts of L1 related molecules

| | CHL1 (m) | L1 (m, r, h) | NrCAM (m) | NrCAM (c) | NgCAM (c) | ABGP (r) | neurofascin (m) | neurofascin (c) | neuroglian (d) | L1.1 (zf) | L1.2 (zf) |
|---|---|---|---|---|---|---|---|---|---|---|---|
| L1 (m, r, h) | 57 | | | | | | | | | | |
| NrCAM (m) | 64 | 55 | | | | | | | | | |
| NrCAM (c) | 62 | 56 | 99 | | | | | | | | |
| NgCAM (c) | 43 | 61 | 48 | 43 | | | | | | | |
| ABGP (r) | 59 | 54 | 64 | 64 | 38 | | | | | | |
| neurofascin (m) | 62 | 56 | 64 | 65 | 43 | 100 | | | | | |
| neurofascin (c) | 54 | 58 | 58 | 60 | 40 | 87 | 86 | | | | |
| neuroglian (d) | 39 | 34 | 41 | 40 | 34 | 40 | 43 | 37 | | | |
| L1.1 (zf) | 43 | 61 | 46 | 45 | 50 | 45 | 48 | 47 | 36 | | |
| L1.2 (zf) | 36 | 54 | 39 | 38 | 37 | 37 | 40 | 39 | 22 | 44 | |
| DCC (h) | 14 | 12 | 15 | 13 | 18 | 12 | 13 | 12 | 11 | 12 | 9 |
| fasciclin III (d) | 21 | 17 | 20 | 18 | 19 | 16 | 20 | 17 | 15 | 17 | 15 |
| MAGp72 (r) | 8 | 10 | 11 | 11 | 10 | 10 | 10 | 11 | 11 | 10 | 8 |
| NCAM180 (m) | 7 | 7 | 7 | 7 | 13 | 5 | 5 | 5 | 5 | 13 | 9 |
| Po (m) | 11 | 6 | 12 | 13 | 6 | 15 | 15 | 15 | 28 | 7 | 3 |

The intracellular regions of the members of the L1 family (including species homologs) were compared with each other and with other neural cell adhesion molecules of the Ig superfamily. Values indicate the percentage of amino acid identity after alignment according to Hem (1990). The species are indicated in brackets: c = chicken; d = Drosphila, h = human, m = mouse, r = rat, and zf = zebrafish. Mouse, rat, and human L1 are identical. Mouse NrCAM and neurofascin are partial sequences of 91 and 86 amino acid residues, respectively.

TABLE 5

Structural relationships between members of the L1 family
and other members of the Ig superfamily containing C2 domains

| CAMs | Ig1 | 1-2 | Ig2 | 2-3 | Ig3 | 3-4 | Ig4 | 4-5 | Ig5 | 5-6 | Ig6 |
|---|---|---|---|---|---|---|---|---|---|---|---|
| L1 | 56 | 44 | 51 | 55 | 48 | 42 | 50 | 44 | 49 | 42 | 52 |
| CHL1 | 52 | 44 | 51 | 58 | 48 | 42 | 49 | 44 | 49 | 42 | 55 |
| NgCAM | 51 | 44 | 51 | 55 | 46 | 42 | 49 | 44 | 49 | 42 | 49 |
| NrCAM | 55 | 44 | 51 | 55 | 48 | 42 | 50 | 44 | 49 | 42 | 49 |
| ABGP | 55 | 44 | 51 | 55 | 48 | 42 | 50 | 44 | 49 | 42 | 49 |
| L1.1 | ? | 45 | 51 | 56 | 48 | 42 | 50 | 44 | 49 | 40 | 53 |
| neuroglian | 52 | 44 | 65* | 48* | 49 | 43 | 50 | 43 | 47 | 42 | 52 |
| TAG-1 | 50 | 44 | 52 | 54 | 45 | 42 | 47 | 45 | 48 | 42 | 57 |
| BIG-1 | 50 | 44 | 52 | 53 | 48 | 42 | 47 | 45 | 48 | 42 | 56 |
| F3 | 49 | 44 | 53 | 52 | 47 | 42 | 39* | 45 | 48 | 42 | 59 |
| Average | 52 | 44 | 51 | 55 | 48 | 42 | 49 | 44 | 49 | 42 | 53 |
| SD | 2.5 | 0.3 | 0.7 | 1.7 | 1.2 | 0.3 | 1.3 | 0.6 | 0.7 | 0.6 | 3.6 |
| DCC | 56 | 44 | 51 | 49 | 49 | 42 | 48 | | | | |
| HLAR | 53 | 49 | 51 | 46 | 45 | | | | | | |
| rse | 53 | 43 | 43 | | | | | | | | |
| NCAM | 55 | 43 | 50 | 46 | 53 | 42 | 56 | 41 | 53 | | |
| MAG | 58 | 59 | 58 | 44 | 44 | 42 | 45 | 40 | 56 | | |
| neuromusculin | 55 | 45 | 63 | 48 | 54 | 47 | 58 | 45 | 46 | 45 | 72 |
| fibronectin (III) | | | | | | | | | | | |

| CAMs | Ig6-FN1 | FN1 | FN1-FN2 | FN2 | FN2-FN3 | FN3 | FN3-FN4 | FN4 | Similarity index |
|---|---|---|---|---|---|---|---|---|---|
| L1 | 44 | 50 | 50 | 49 | 49 | 58 | 47 | 51 | 84% |
| CHL1 | 41 | ? | ? | 49 | 49 | 58 | 48 | 53 | 84% |
| NgCAM | 40 | 50 | 50 | 57* | 49 | 77* | ? | ? | 74% |
| NrCAM | 51* | 50 | 50 | 50 | 49 | 58 | 48 | 52 | 95% |
| ABGP | 56* | 50 | 50 | 50 | 49 | 58 | 48 | 51 | 95% |
| L1.1 | 41 | 50 | 50 | 50 | 49 | 62 | 47 | 52 | 74% |
| neuroglian | 40 | 50 | 50 | 52 | 51 | 53 | ? | 54 | 68% |
| TAG-1 | 41 | 53 | 50 | 53 | 49 | 51 | 48 | ? | 74% |
| BIG-1 | 41 | 53 | 50 | 53 | 49 | 52 | 48 | 47 | 84% |
| F3 | 41 | 53 | 50 | 53 | 49 | 48* | 48 | 47 | 63% |
| Average | 41 | 51 | 50 | 51 | 49 | 56 | 48 | 51 | |
| SD | 1.2 | 1.4 | 0.0 | 1.7 | 0.6 | 3.8 | 0.5 | 2.6 | |
| DCC | | 49 | 50 | 46 | 49 | 51 | 51 | 51 | 50% |
| HLAR | | 46 | 49 | 50 | 48 | 46 | 49 | 53 | 42% |
| rse | | 49 | 48 | 49 | | | | | 33% |
| NCAM | | 35 | 56 | 41 | | | | | 25% |
| MAG | | | | | | | | | 11% |
| neuromusculin | | | | | | | | | 13% |
| fibronectin (III) | | 45 | 42 | 46 | 48 | 44 | 47 | 44 | 14% |

The table shows the number of residues between conserved amino acids within the Ig-like domains (cysteines involved in the S-S bridges: Ig1, Ig2, Ig3, Ig4, Ig5, and Ig6), FN-like repeats (tryptophan of the second β-strand and tyrosine/phenylalanine of the sixth β-strand: FN1, FN2, FN3, and FN6), and between these domains (1-2, 2-3, 3-4, 4-5, and 5-6; FN1-FN2, FN2-FN3, and FN3-FN4). The distance between the conserved amino acids of the second cysteine of the sixth Ig-like domain and the first tryptophane of the first FN-like repeat (Ig6-FN1) reflects the distance between the Ig-like domains and FN-like repeats. Th average and standard deviation (SD) of the individual distances for the L1 related molecules are indicated, DCC, HLAR, rse, NCAM, MAG, neuromusculin, and fibronectin (III) are given as a control. Similarity index is given at the right margin. ? = no conserved amino acid, * = not used for average and SD calculations.

CHL1 is most similar to chicken Ng-CAM (37% amino acid identity in the extracellular domain, Table 3) and mouse Nr-CAM (64% amino acid identity in the intracellular domain, Table 4). However, the degree of identity, particularly in the extracellular part, is not sufficient to consider these proteins as species homologs. Recently, a partial cDNA clone of mouse Nr-CAM (Moscoso and Sanes, 1995) was identified. Mouse Nr-CAM is nearly identical (99%) to chicken NR-CAM (see Table 4). Therefore, CHL1 is not likely the Nr-CAM homolog in the mouse. CHL1 is the fourth member of the L1 family in the mouse with L1, Nr-CAM, neurofascin (Moscoso and Sanes, 1995), and CHL1, with a highly conserved species homolog in human (Adams et al., 1992, 1993).

Considering the similarity of the intracellular sequences of chicken and mouse Nr-CAM and of chicken and mouse neurofascin (99% and 87%, respectively, Table 4), it is highly unlikely that mouse L1 and chicken Ng-CAM are species homologs, since they show only 01% sequence identity in the intracellular domain (Table 4). Rather, the existence of Ng-CAM as the fifth member of the L1 family in the mouse with a highly conserved intracellular domain is to be expected. Interestingly, mouse L1 upon heterophilic interaction with chicken Ng-CAM promotes neurite outgrowth (Lemmon et al., 1989), suggesting that members of the L1 family may interact with each other.

Figure 20:
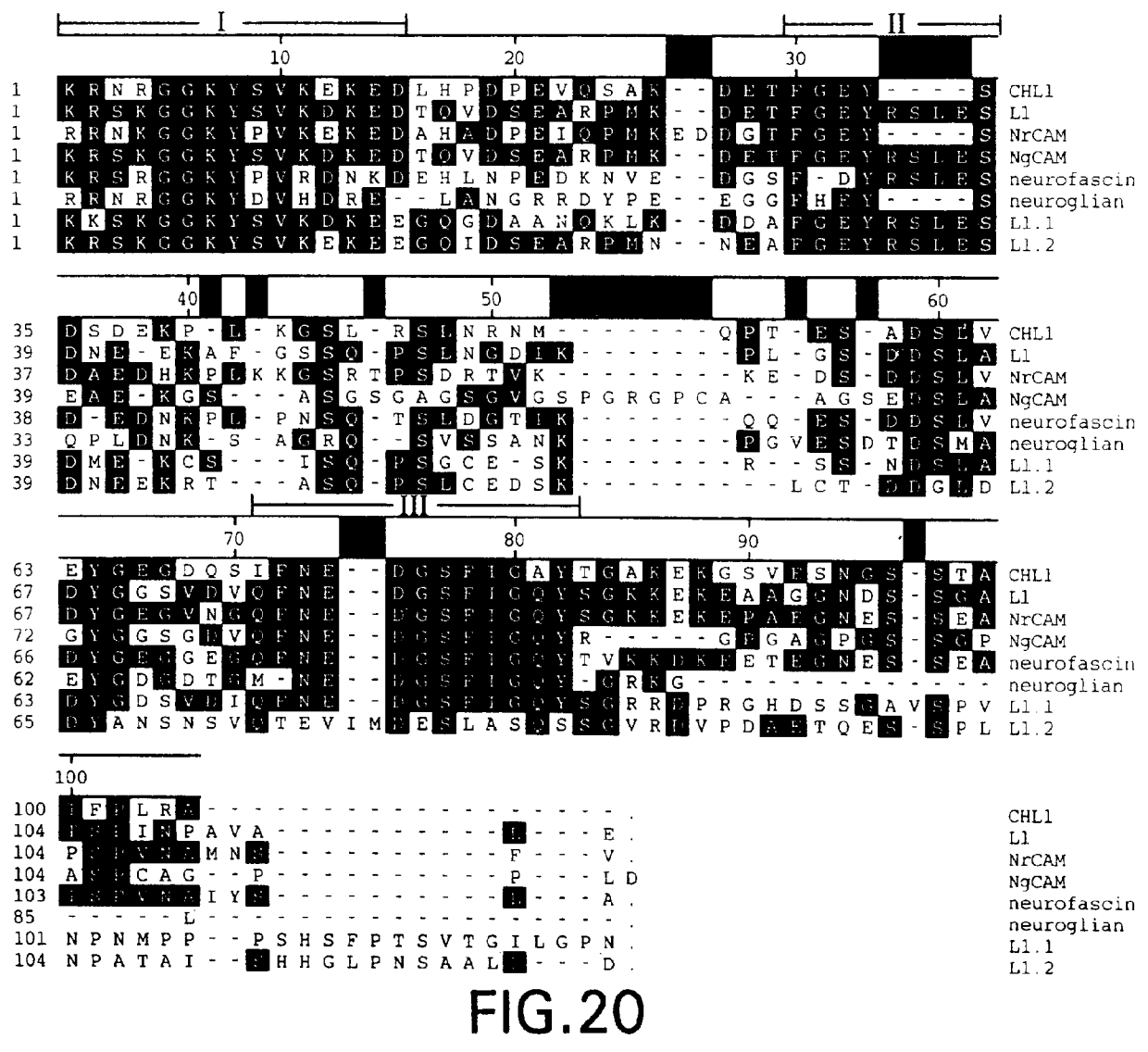

Besides the similarities in the overall structure of L1 family members (Table 3 and Table 5), the most highly conserved regions can be identified in the cytoplasmic domain (FIG. 20). This striking homology is evident for members of the L1 family in all species so far identified which contain an intracellular domain: L1, CHL1, Nr-CAM, Ng-CAM, neurofascin, neuroglian, and zebrafish L1.1 and also for the partial sequences of zebrafish L1.2 (Tongiorgi et al., 1995) and mouse Nr-CAM and neurofascin (Moscoso and Sanes, 1995) (Table 4). Within this region two stretches, one located close to and partially within the plasma membrane-spanning segment and the other at its C-terminal end (I, III in FIG. 20), are nearly identical. Another amino acid stretch conserved in L1, Ng-CAM, Nr-CAM, neurofascin, L1.1 and L1.2 but not in CHL1 (Table 4) contains a RSLE motif (II in FIG. 3) that originates by alternative splicing and is expressed only in neurons (Grumet et al., 1991; Miura et al., 1991; Volkmer et al., 1992). Since the intracellular region is most highly conserved between these proteins, all members of the L1 family may use the same signal transduction pathway to activate neurite extension. It has been demonstrated that the cytoplasmic domains of ABGP, L1, and Nr-CAM can interact with ankyrin linking cell recognition to the cytoskeletal scaffold (Davis et al., 1993, Davis and Bennett, 1994).

EXAMPLE 24

Identification of Structural Requirements in the Extracellular Domain to Classify Members of the L1 Family To further study the general criteria for membership in the L1 family, we investigated the position of highly conserved amino acids in the Ig-like domains (cysteines which refer to the S-S bridges) and FN-like repeats (tryptophan, tyrosine/phenylalanine) for several members of the Ig superfamily (Table 5). Molecules containing six Ig-like domains and at least four FN-like repeats (L1 family and the GPI linked F3/F11 subgroup (Brümmendorf and Rathjen, 1993)) reveal a very constant number of amino acids separating these conserved amino acids. Five different distance parameters were considered:
1) the number of amino acids separating the conserved cysteines which form the cysteine (S-S) bridges of each Ig-like domain (Table 5, columns Ig1, Ig2, Ig4, Ig5, and Ig6);
2) the number of amino acids between the second cysteine of one Ig-like domain and the first cysteine of the next Ig-like domain reflecting the distance between two adjacent Ig-like domains (Table 5, columns 1-2, 2-3, 3-4, 4-5, and 5-6);
3) the number of amino acids between the last conserved cysteine of the sixth Ig-like domain and the conserved tryptophan of the first FN-like repeat reflecting the distance between the Ig-like domain-module and the FN-like repeat-module (Table 5, columns Ig6-FN1):
4) the number of amino acids between the conserved tryptophan, tyrosine/phenylalanine of each individual FN-like repeat (Table 5, columns FN1, FN2, FN3, and FN4):
5) the number of amino acids between the tyrosine/phenylalanine of one FN-like repeat and the tryptophan of the next FN-like repeat reflecting the distance between two adjacent FN-like repeats (Table 5, columns FN1-FN2, FN2-FN3, and FN3-FN4).

To obtain highly stringent conditions for comparison of the L1-like molecules, we did not consider a few values clearly deviating from the average, most probably due to alternative splicing, for the calculation of the average distances and standard deviations (neuroglian: Ig2, 2-3: Nr-CAM and ABGP: Ig6-FN1; F3: Ig4, FN3; Ng-CAM; FN2, FN3 (Table 5, marked with an *)). Whereas the number of amino acids between the S-S bridges for the first and sixth Ig-like domain (Ig1; standard deviation (SD)=3: Ig6: SD=4) and the number of amino acids between the conserved tryptophan, tyrosine/phenylalanine of FN-like repeats three and four (FN3: SD-4; FN4: SD=3) are slightly variable, all other distance parameters remain remarkably constant for the different molecules (FN1-FN2: SD=0; FN2 and 2-3: SD=2 (Table 5)). Based on these criteria we calculated a similarity index (see Material and Methods) for several Ig-like molecules in relation to the average values listed in Table 5. For L1, CHL1, Ng-CAM, Nr-Cam, ABGP, L1.1, TAG-1 and BIG-1 a similarity index of 74-95% was obtained (Table 5). For *Drosophila* neuroglian a slightly lower value was determined (66%), most probably reflecting the evolutionary distance between vertebrates and insects. F3 and its species homologs are loss conserved, particularly in their Ig-like domains, but still show a similarity index of 63%. However, some conserved amino acid stretches underlying the strongly conserved colinearity (e.g. FxVxAx-NxxG(8x)S(4x)TxxAxPxxxP at the end of the first FN-like repeat or NxxGxGPxS between the last two β-strands of the third FN-like repeat (not shown) support the notion that F3 belongs to the L1 family. Interestingly, the number of amino acids between adjacent domains (Ig-like domains or FN-like repeats) is even more conserved among these molecules, indicating that the distance between the individual domains is an important structural feature, i.e. critical for functioning of neural recognition molecules (Table 5, columns 1-2, 2-3, 3-4, 4-5, 5-6, FN1-FN2, FN2-FN3, and FN3-FN4). Thus, this high conservation of the order (colinearity) and spacing may be used to define More generally the extracellular domain of the L1 family members. With the criteria just defined, these contain a module of six Ig-like domains at the N-terminus followed by four FN-like repeats. We would like to call this structural feature the L1 family cassette.

Thus, all members of the L1 family share the characteristic features of the L1 family cassette and, additionally, highly conserved amino acids. These results suggest that these molecules derive from a common ancestral L1-like molecule containing the L1 family cassette, which might have spread its function potential via gene duplication to accommodate the evolving demands for diversifying cell interactions in more complex nervous systems. The general L1 family may thus be subdivided into the "classical" L1 family members (L1, CHL1, Ng-CAM, Nr-CAM, neurofascin, neuroglian, L1.1) which contain a variable fifth FN-like repeat, a transmembrane domain, and a highly conserved intracellular domain, and the F3/F11 subgroup (F3/F11/CNTN1, BIG-1/PANG, and TAG-1/Axonin-1/TAX-1), the common feature of which is the linkage by GPI to the membrane and for which a variable fifth FN-like repeat has so far not been identified. The extracellular domains of both subgroups contain the L1 family cassette.

Other members of the Ig-superfamily, e.g. N-CAM (Cunningham et al., 1987, Barthels et al., 1987), MAG (Arquint et al., 1987; Lai et al., 1987; Salzor et al., 1987), neuromusculin (Kanla et al., 1993), and rse (Mark et al., 1994) or fibronectin (Komblihtt et al., 1985) which contain Ig-like domains and/or FN-like repeats, show clearly distinct distance parameters, indicating that they are much less related to each other and to the members of the L1 family (Table 5). Interestingly, the human leukocyte common antigen-related gene (HLAR) (Streull et al., 1988) and the tumor suppressor gene product (DCC) deleted in colorectal cancer (Fearon et al., 1990) are closely related to the L1 family according to the distance parameters (42% and 50% similarity index, respectively). Inspection of conserved amino acids reveals that DCC is indeed related more closely to the L1 family than to N-CAM as previously suggested by Fearon et al. (1990) and Pierceall et al. (1994), although it seems to have lost the fifth and sixth Ig-like domain. Recent studies show that DCC is expressed predominantly in brain and that neurite outgrowth of rat PC12 cells is stimulated on a substrate of DCC-transfected fibroblasts expressing the protein on its cell surface (Pierceall et al., 1994). Although HLAR also shows a relatively high similarity index its relationship to the L1 family is not so obvious.

EXAMPLE 25

Tissue Distribution of CHL1 mRNA and Protein

Figure 21A:
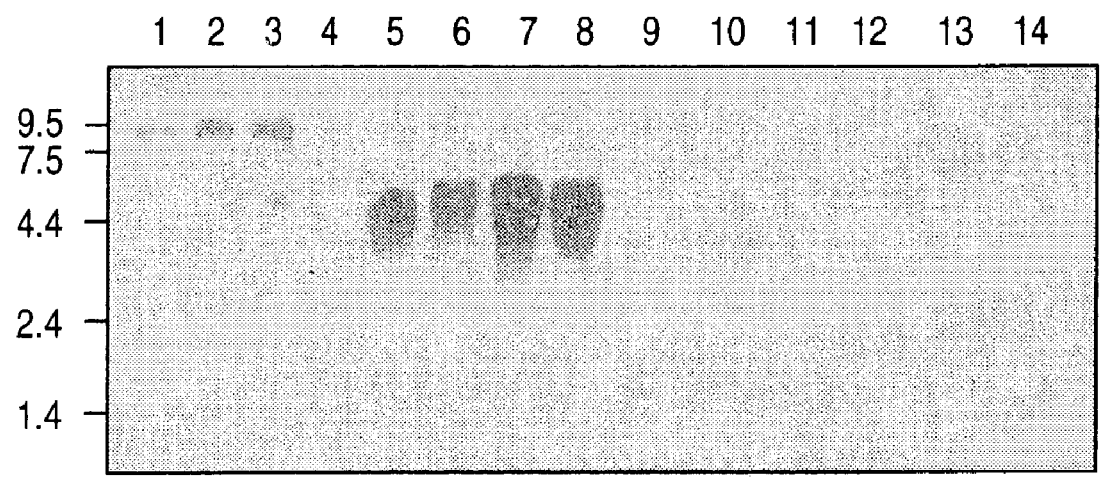
FIG. 21 is a Northern blot analysis of CHL1 and L1 mRNA in different tissues of mouse and rat (a) Poly (A) RNA (2 μg) from brain minus cerebellum (lanes 1, 5), spinal cord (lanes 3, 7), and dorsal root ganglia (lanes 4, 8) and total RNA (10 μg) from cerebellum (lanes 2, 8) of nine-day-old mice were hybridized with CHL1 (lanes 1 to 4) or L1 (lanes 5 to 8) riboprobes. Poly (A)* RNA (1 μg) from kidney (lane 9), spleen (lane 10), liver (lane 11), and thymus (lane 12) and poly (A)* RNA (0.5 μg) from intestine (lane 13) and lung (lane 14) of nine-day-old mice were hybridized with the CHL1 riboprobe.
Figure 21B:
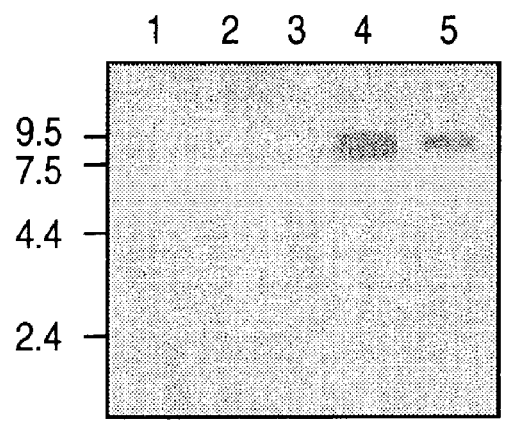

To investigate whether CHL1 shares the predominant expression in the nervous system with other members of the L1 family, we analyzed the expression of CHL1 in various tissues at the mRNA and protein levels. In Northern blot analysis the CHL1 riboprobe hybridized with a predominant mRNA band of approximately 8 kb (FIG. 21) which is significantly larger than the size of the mRNA detected with L1 probes (approximately 6 kb) (Tacke et al., 1987). The smaller and weaker RNA band (FIG. 21a, lane 3) is most probably due to the cross-hybridization with ribosomal RNA. The 8 kb RNA was detected in cerebellum, brain minus cerebella, and spinal cord but not in dorsal root ganglia (DRG) (FIG. 21a). In contrast, the L1 riboprobe showed a strong signal with RNA from DRG (FIG. 21a). CHL1 mRNA was also detectable in nine-day-old rat cerebellum and six-day-old rat spinal cord but not in rat PC12 cells maintained with and without NFG or in COS-1 cells (FIG. 21b). In all other tissues analyzed (thymus, lung, liver, intestine, spleen, and kidney) no signal was detectable (FIG. 21a).

To identify the CHL1 protein, antibodies to a bacterially expressed fragment of the CHL1 protein were generated. Excluding regions of high homology to other known L1 family members, e.g. transmembrane spanning or intracellular regions, a 1.7 kD cDNA fragment representing part of the sixth Ig-like domain and the four, FN-like repeats (FIGS. 18 and 19b) was cloned into the pET expression vector. Expression of the resulting protein fragment led to a 70 kD band detected by Coomassle blue staining after SDS-PAGE which was purified by anion exchange chromatography. Western blot analysis (FIG. 22a) and ELISA (not shown) showed that the antisera from two rabbits reacted with the CHL1 protein fragment but not with purified L1, N-CAM, or MAG. Some reaction with bacterial proteins copurified with the CHL1 peptide or degradation products of the CHL1 fragment was observed (FIG. 22a, lane 4).

To further examine the specificity of the antibodies and to determine whether they recognize the native cell surface expressed CHL1, transiently transfected COS-1 cells were examined with the antibodies. Immunocytochemistry revealed cell surface expression of CHL1 on CHL1-transfected cells, but not on cells mock-transfected with the vector (FIG. 23). These results also demonstrate that the putative signal sequence is functional and that the open reading frame is correct.

Although the first CHL1 cDNA clone was isolated from an expression library by screening with immunoaffinity purified polyclonal antibodies against brain derived L1, reaction of a different preparation of L1 antibodies against the recombinantly expressed Ig-like domains of L1 with CHL1-transfected cells was not observed (not shown). Also CHL1 antibodies directed against the extracellular part of the molecule (FIG. 19) did not react with L1-transfected cells (not shown). It is therefore likely that the L1 polyclonal antibodies used for screening the expression library were reactive with the C-terminal, intracellular part of CHL1 which is most homologous between CHL1 and L1.

Figure 23A:
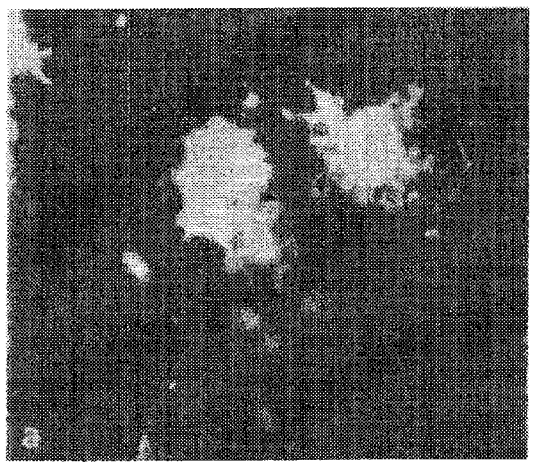
Figure 23B:
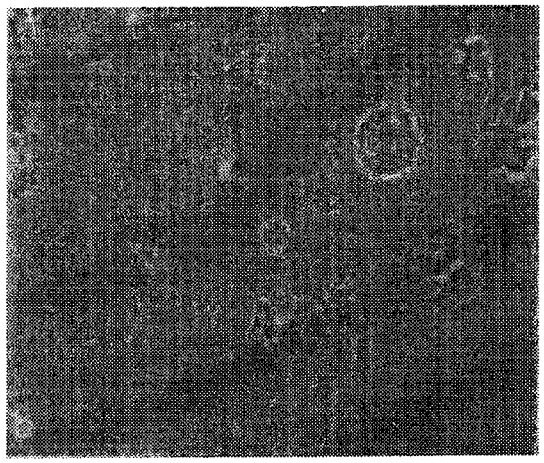
Figure 23C:
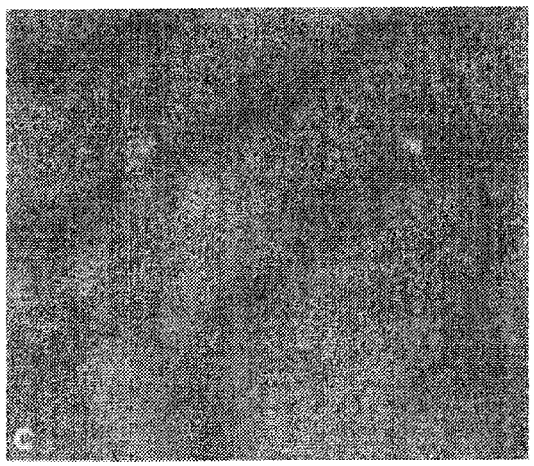
Figure 23D:
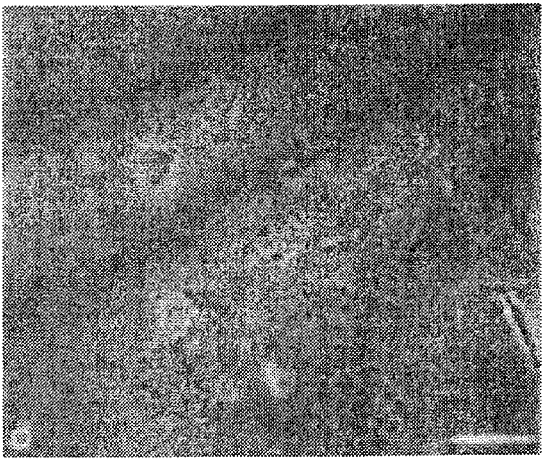

The CHL1 antisera were used to identify immunoreactive proteins in several tissues (brain, liver, lung, kidney, and intestine from nine-day old mice. FIG. 23b). Crude membrane fractions, soluble and insoluble in 0.5% Triton X-100, were analyzed by Western blotting. Polyclonal antibodies against L1 were used as a control. The CHL1 antibodies recognized three distinct bands of 185, 165, and 125 kD in the insoluble and soluble fractions of brain membranes. The 185 kD band was only weakly detectable in the soluble fraction and the 125 kD band was less prominent in the insoluble fraction (FIG. 23b, lane 1 and 2), indicating that the 185 kD band is probably the membrane bound form of CHL1, whereas the 125 and 165 kD forms are probably proteolytically cleaved fragments. A similar pattern of immunoreactive bands was observed after Western blot analysis of CHL1 transfected COS cells and total brain tissue (not shown). A similar pattern of bands has been observed for L1 (Faissner et al., 1985: Sadoul et al., 1988), Ng-CAM (Grumet et al., 1984), and NrCAM (Kayyem et al., 1992). However, a dibasic consensus sequence for proteolytic cleavage in the third FN-like domain (L1: "SKR": Ng-CAM: "SRR": Nr-CAM: "SRR": Nr-CAM: "SRRSKR") is not present in CHL1. Like the other members of the L1 family, CHL1 was found to be expressed only at later stages of development. It was not detectable in brain before embryonic day 15 by Western blot analysis (not shown). A 50 kD immunoreactive band was detected in the detergent soluble fraction of whole liver tissue. This band is most probably due to some cross-reactivity of the CHL1 antibodies with a CHL1-related protein, since no CHL1-specific mRNA was seen in liver by Northern blot analysis (FIG. 22a). No CHL1 immunoreactivity could be detected in the other tissues that were tested (FIG. 23b).

Figure 24A:
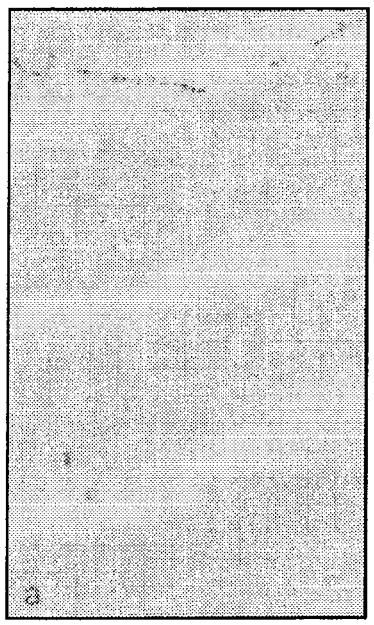
Figure 24B:
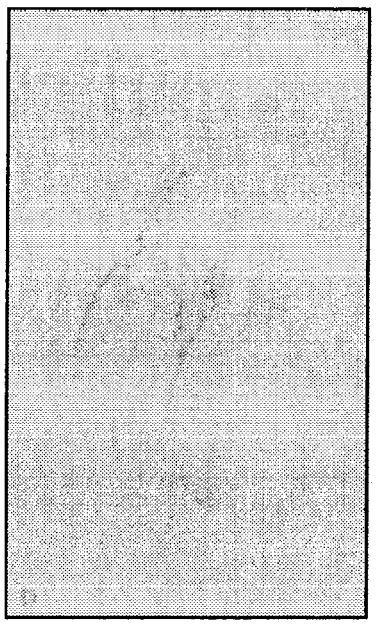
Figure 24C:
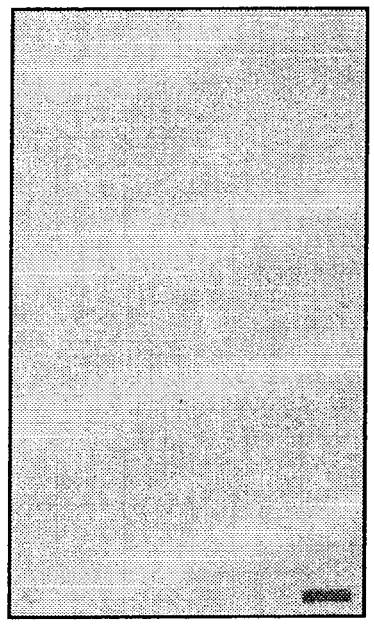

In the CNS, members of the L1 family are predominantly expressed by neurons. Therefore, we were interested if CHL1 shares this pattern of expression with L1. In situ hybridization experiments were performed to identify the cells synthesizing CHL1 and L1 in the retina, optic nerve, and cerebellar cortex of young postnatal mice. In the retina of 7-day-old mice, L1 (FIG. 24a) and CHL1 mRNA (FIG. 24b) are expressed by ganglion cells. L1 transcripts were additionally detectable in amacrine and horizontal cells located in the inner nuclear layer (FIG. 24a). CHL1 mRNA, in contrast, was only occasionally detectable in a few cells located at the inner (i.e. vitread) margin of the inter nuclear layer (FIG. 24b). Glial cells in the optic nerve did not contain detectable levels of L1 transcripts (FIG. 24a). In striking contrast, CHL1 mRNA was strongly expressed by glial cells located in proximal (i.e. retina-near) regions of the optic nerve (FIG. 24b) and low levels of CHL1 expression were visible in glial cells located in more distal regions of the nerve (FIG. 24b).

Figure 24D:
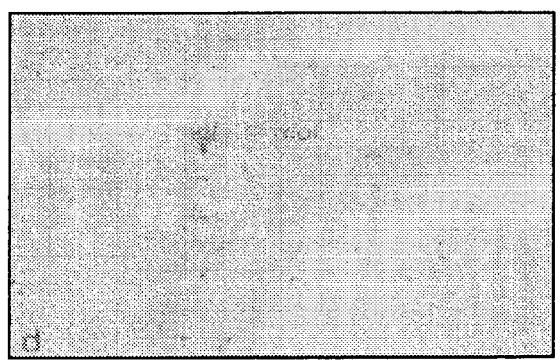
Figure 24E:
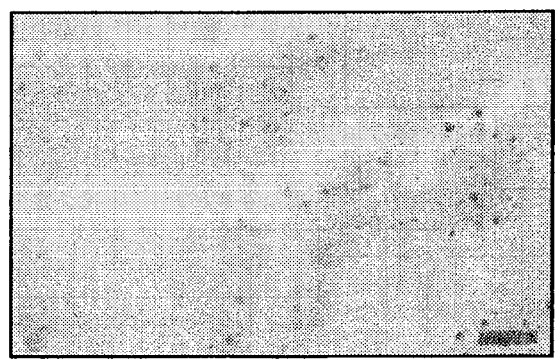
Figure 25A:
Figure 25B:
Figure 25C:
Figure 25D:
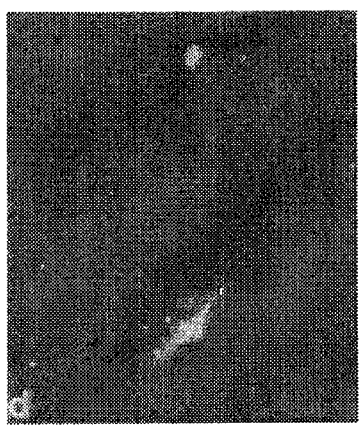
Figure 25E:
Figure 25F:

In the cerebellar cortex of two-week-old mice, L1 mRNA was detectable in stellate and basket cells located in the molecular layer and in Golgi and granule cells located in the internal granular layer (FIG. 24d). The same cells types were labeled when sections were hybridized with the CHL1 antisense cRNA probe (FIG. 24e), with the exception that CHL1 transcripts were hardly detectable in cells located in the inner part of the molecular layer (compare FIGS. 24d and e). As a negative control, sections were hybridized with the corresponding sense cRNA probes and no labeling of cells was detectable (for a retina and optic nerve hybridized with a CHL1 sense cRNA probe, see FIG. 24c). In order to address whether glial cells express CHL1 in vitro, cultures of purified astrocytes or oligodendrocytes were prepared from the forebrain of young postnatal mice or rats. The same polyclonal CHL1 antibodies which specifically detected CHL1 at the cell surface of transfected COS-1 cells were used. Astrocytes and oligodendrocytes were identified with antibodies to GFAP or with antibodies to the O1 antigen, respectively. Astrocyte cultures contained some cells which were double-labeled by polyclonal CHL1 (FIG. 25a, d) and monoclonal GFAP (FIG. 25b, e) antibodies. Analysis of oligodendrocyte cultures, however, revealed no co-localization of CHL1 and the O1 antigen, indicating that mature oligodendrocytes in vitro do not express detectable levels of CHL1. The combined observations indicate that CHL1 and L1 show overlapping but also distinct patterns of expression. Most strikingly CHL1, but not L1, is expressed by certain glial cells of the nervous system in vivo, suggesting that different members of the L1 family perform different functions.

Analysis of Glycosylation and Detection of the HNK-1 Carbohydrate by the CHL1 Glycoprotein Since the observed molecular weight of CHL1 (185 kD) is considerably larger than the calculated molecular mass (134.9 kD), the carbohydrate contribution to the molecular mass and the type of carbohydrate modification was analyzed. The detergent soluble and insoluble fractions from crude brain membranes of seven-day-old mice were subjected to enzymatic deglycosylation. After N-glycosidase F (PNGasoF) treatment the molecular mass of all CHL1 immunoreactive proteins was reduced (FIG. 26): The 185 kD band shifted to 150 kD, the 165 kD band to 135 kD, and the 125 kD band to 110 kD. Treatment with O-glycosidase, an enzyme known to cleave serine/threonine linked galactosyl β(1-3)N-acetylgalactosaminyl disaccharides (Glasgow et al., 1977) resulted in a slightly increased mobility: The 185 and 165 kD bands shifted to about 180 and 160 kD, respectively, whereas the 125 kD band did not shift. These observations indicate that most of the carbohydrate molecular mass is due to N-linked carbohydrates. Treatment with both enzymes together (FIG. 26) led to a larger shift than seen with treatment with individual enzymes from 185 to 145 kD, suggesting that not all glycosylation sites, most probably the O-glycosylation sites were cleaved by O-glycosidase alone. The results show that CHL1 contains approximately 30% of its molecular mass as N-glycosidically linked carbohydrates.

Several neural cell adhesion molecules carry the HNK1-carbohydrate, such as L1 (Kruse et al., 1984), TAG-1 (Dodd et al., 1988), Nr-CAM (Grumet et al., 1991), F3 (Gennarini et al., 1989), N-CAM (Kruse et al., 1984), the myelin associated glycoprotein MAG (McGarry et al., 1983; Kruse et al., 1984), and $P_o$ (Bollenson and Schachner, 1987). Therefore, we analyzed whether CHL1 carries the HNK-1 carbohydrate. CHL1 was immunoprecipitated from detergent lysates of whole brain tissue from nine-day-old mice with CHL1 antibodies. As control, L1 was similarly immunoprecipitated with polyclonal antibodies from the same brain extract. Western blot analysis with monoclonal antibody 412 directed against the HNK-1 carbohydrate epitope showed that both immunoprecipitates contained bands which were recognized by the monoclonal antibody 412 at molecular masses expected for CHL1 (FIG. 27) or L1 (not shown). Since the HNK-1 carbohydrate is involved in cell-to-cell adhesion and binds to laminin (Keilhauer et al., 1985; Künemund et al., 1988; Hall et al., 1993, 1995), CHL1, like the other members of the L1 family, may interact with laminin via the HNK-1 carbohydrate.

Further Characterization of CHL1

In addition to the studies conducted and reviewed above, further experiments were conducted with CHL1 to define its role in neurite outgrowth and the parameters of its action. Thus and as depicted and described earlier with reference to FIGS. 28A-C, hippocampal neurons were co-cultured with L929 transfectants and L929 parental cells. Particularly, hippocampal neurons derived from rats of embryonal day 18 were cultured in subconfluent monolayers of L929-transfectants or parental L929 cells. After 11-12 h of coculture the cells were fixed and labeled with monoclonal antibody 412 (recognizing the HNK-1 carbohydrate epitope) or a polyclonal antibody against NCAM. For measurement of the total neurite length only the longest neurite per each branch was determined due to the highly branched character of the neurons in these cultures. The results of the experiments are given below with letter reference to the respective Figures within FIG. 28.

(A) Neurite outgrowth is promoted by CHL1 and inhibitable by antibodies. Neurons were cocultured with CHL1-transfectants (CHL1) or parental L929 cells (L929) with (+AB) or without polyclonal antibodies against recombinant CHL1 (500 µg/ml of purified IgG, added 45 min after plating) and on L1-transfectants. The mean total neurite length of 4-5 independent experiments is shown. Error bars are standard error of the mean.

(B) Different CHL1 lines promote neurite outgrowth better than L1. Neurons were cultured on two different CHL1-transfectants (CHL1 line 1, CHL1 line 2) with slightly different expression levels, parental L929 cells (L929) and L1 transfectants (L1). Total neurite length is given as percent of L929 cells as a control (ctr). Error bars are standard error of the mean.

(C) Neurite outgrowth promotion affects all length classes of neurites. Cumulative frequency distribution plot of the total neurite length of hippocampal neurons cocultured with CHL1-transfectants (CHL1 line 1 and 2) and parental L929 cells (L929) with (+AB) or without antibody treatment as given in (A).

CHL1 activity was also tested with cerebellar neurons as set forth with reference to FIG. 29. Thus, cerebellar neurons derived from 6-7 day old mice were cultured for 20 h on CHL1-transfectants (CHL1), CHL1-transfected non-expressing L929 cells (Mock), parental L929, or L1-transfectants (L1). The results are likewise set forth in paragraphs that correspond in designation to the sub-figures within FIG. 29.

(A) CHL1 promotes neurite outgrowth of small cerebellar neurons. The mean of total neurite length of three experiments is shown. Error bars are standard error of the mean.

(B) CHL1 promotes neurite outgrowth also of small cerebellar neurons better than L1. The total neurite length is given as percent of L929 cells as a control (ctr). Error bars are standard error of the mean.

(C) Increase of neurite outgrowth of cerebellar neurons by CHL1 affects all size classes of neurites. Cumulative frequency of distribution plot of the total neurite length of the percentage of neurons with neurites longer than or equal to a certain length×(vertical axis) was plotted as a function of neurite length×(horizontal axis).

In a study the results of which are presented in FIGS. 30A-C, soluble CHL1 was cocultured with hippocampal neurons and a comparison was conducted with L1 and parental L929 cells. Specifically, hippocampal neurons were cultured on poly-L-lysine coated coverslips for 12 h with addition of supernatants (40 µg/ml of total protein) of crude membrane preparations of CHL1-transfectants (CHL1), parental L929 cells (L929), or L1-transfectants (L1). The results are set forth below in the same manner as with reference to FIGS. 28 and 29, above.

(A) Soluble CHL1 from L929 transfectants promotes outgrowth of the longest and the sum of all neurites per cell. Absolute length of longest neurite nad total neurite length are shown. Values are means of three independent experiments. Error bars are standard error of the mean.

(B) Soluble CHL1 promotes a slight increase of neurite number. Total neurite length in percent of the neurite length of hippocampal neurons treated with supernatants derived from parental L929 cells (ctr) are plotted. Values are means of three independent experiments. Error bars are standard error of the mean.

(C) Also soluble CHL1 affects neurite outgrowths of all length classes of neurites. Cumulative frequency distribution plots of the total neurite length from one representative experiment are shown.

The general observation is that soluble CHL1 exhibits an improved growth-promoting effect on a broad range of neuronal populations.

In FIGS. 31A and B, the stability of CHL1 was measured in relation to L1 in L929 transfectants. Thus, both quantitative aggregation analysis and stability of CHL1- and L1-protein were measured in L929 transfectants. The results and observations are set forth below.

(A) Quantitative analysis of aggregation of S2 cell transfectants. To detect aggregation CHL1-(CHL1) (ctr) and L1-(L1) transfected cells were cultured (at densities of about $3 \times 10^6$ cells/ml) for 18 h in culture medium with (+ind) or without (−ind) induction of transgene expression by $CuSO_4$. Particle number was counted in a hemacytometer at the beginning and at the end of the incubation. The percentage of aggregation was calculated by the index (1−N/NO)×100. N18 and NO represent the particle numbers at the end or the beginning of the incubation period, respectively. Values are the means of at least four independent experiments. Error bars are standard deviations.

(B) Kinetics of aggregation of L929-transfectants. CHL1-transfected (CHL1), CHL1-transfected non-expressing (Mock), parental L929 (L929), and L1-transfected (L1) cells had been detached from tissue culture by treatment with low concentration of trypsin-EDTA, washed and incubated at 37° C. in polystyrene tubes. An aliquot of each sample was withdrawn every 30 min and the particle number was counted in a hemacytometer. The results are expressed as described in (A). Values shown are the means of at least three independent experiments. Bars are standard deviations.

The above data demonstrate that CHL1 operates as an adhesion molecule and thereby shares this profile of activity with L1, and supports the view that both molecules promote neurite outgrowth in both their substrate-bound and soluble forms.

Conclusions

The above experiments have added CHL1 as another member of the L1 family of neural recognition molecules found in such diverse species as human, rat, mouse, chicken, zebrafish, and *Drosophila*, thus constituting a phylogenetically conserved family of molecules all of which are expressed late in development at the onset of axogenesis by neurons and subsets of neurons. The fact that many L1 related molecules exist points to nature's requirement for structurally similar, but functionally most likely distinct neurite outgrowth promoting molecules, and to the evolution of the L1 family as a group of molecules that may determine the fine-tuning of axonal pathfinding.

EXAMPLE 26

In Vivo Confirmation of Neuroregenerative Effects of L1

In the following series of experiments, certain studies were undertaken to confirm the findings presented earlier herein that the present invention has utility for the treatment of neurologically impaired, and especially, spinal cord injured, patients. Particularly, the following experiments were conducted using L1 cellular adhesion molecules (CAMs) in the treatment of injured rat spinal cords. While L1 has long been speculated to play a role in regeneration, its usefulness in such therapy has been unclear, as L1 is a homophilic molecule that acts as both an agonist and a receptor, and activates intracellular messengers that stimulate axonal growth. Studies have also shown that myelinated tissues of the CNS possess potent inhibitors of neurite growth, so that any agent which would serve to stimulate regeneration must also possess some mechanism by which these inhibitors can be overcome.

A soluble chimeric form of the L1 glycoprotein stimulates neurite outgrowth. Doherty et al. (Doherty P, Williams E, Walsh F S (1995) *Neuron* 14: 57-66) recently found that L1 coupled with human immunoglobulin Fc will form a soluble L1-Fc dimer which can stimulate neurite growth. In the present and in earlier filed applications, and a post-filing publication (Mohajeri M H, Bartsch U, van der Puttan H, Sanzig G, Mucke L, et al. (1995) "Ectopic expression of the neural cell adhesion molecule L1 by astrocytes improves neurite outgrowth in vitro" *European Journal of Neuroscience* in press) applicant has shown that optic nerves taken from transgenic mice possessing L1 gene linked to the GFAP promoter can support axonal growth in vitro. Other studies indicate that central myelinated tissues possess potent inhibitors of neurite growth. It has been indicated that L1 not only stimulates growth but also has the ability to neutralize neurite growth inhibitors.

The following studies involved three phases, briefly summarized as follows:

A. A quantity of mouse L1 coupled to human Fc was made. To assess the ability of mouse-human chimera L1-Fc to stimulate neurite growth, poly-lysine coated tissue culture plates were briefly exposed to increasing concentrations of the L1-Fc, seeded chick dorsal root sensory ganglia onto this surface, and then measured neuron survival and neurite length at 16 hours. This was to confirm that an active form of L1-Fc was present, and to compare this activity with the that reported by Doherty, et al. supra who used a human L1-Fc dimer.

B. To assess the ability of L1-Fc to neutralize neurite growth inhibitors, frozen coronal sections of adult rat spinal cord were placed in culture tissues and plated dissociated dorsal root sensory ganglia neurons on top of the sections. The neurons adhered to gray matter or poly-lysine surface of the culture plates but not to white matter. Within 24 hours, the neurons had grown to confluence and were extending neurites everywhere except white matter. By contrast, in the presence of L1-Fc in the supernatant, large numbers of neurons not only adhered to but also extended neurites for long distances on spinal white matter.

C. Exogenous L1 was applied to the spinal cords of rats after injury. Twelve rats were injured with a 10 gram rod dropped 25.0 mm onto the T9-10 spinal cord. In half of the rats, a solution of L1-Fc (150 µg/ml 0.5 µliter/hour) was infused intrathecally below the injury site with an Alzet pump for 2 weeks. The rats were evaluated weekly for locomotor recovery for a period of 12 weeks and applied BDA (biotinylated dextran amine) tracer to the motor cortex to label corticospinal tract. The study showed a significant improvement of locomotor scores at 3 months and histological evidence of BDA labelled axons coursing several mm beyond the injury site. The methods and results of these three studies are described more fully below.

Materials and Methods

The three experiments relied on the following methods: the NYU impactor model of rat spinal cord injury, an in vitro assay of neurite growth inhibition on spinal white matter, the production of L1-Fc, the application of L1-Fc to the spinal cord of rats after injury, the assessment of locomotor recovery, and BDA tracing of regenerating corticospinal tracts. Each of these will be described briefly in sequence.

Production and Purification of L1-Fc

The L1-Fc gene was transfected into a stable cell line of CHO (Chinese hamster ovary) cells that had been transfected with the L1-Fc gene driven by a CMV promoter/enhancer that included the gene for glutamine synthetase.

Specifically, the CHO cells secreting L1-Fc were provided by Dr. Melitta Schachner. The L1-Fc chimera construct consists of the whole extracellular domain of mouse L1 (3387 nucleotides) and human Ig Fc (hinge, $CH_2$-$CH_3$ region, 1487 nucleotides) inserted into the pEE-14 vector. L1-Fc expression was driven by the CMV promoter/enhancer. Selection and amplification was based on expression of glutamine synthetase from a gene on the vector and growth in the presence of 25 μM methionine sulfoximine (MSX). The concentration of L1-Fc secreted into the culture supernatant was approximately 1 μg/ml after two days of confluence. The chimeric protein was purified using a protocol developed in collaboration with Drs. Martin Grumet and Takeshi Sakurai. Briefly, L1-Fc is precipitated from medium by the addition of powdered ammonium sulfate to 60% saturation. The precipitate is resuspended 17.5 mM $NaH_2PO_4$, pH 6.3, and dialysed against the same buffer. The dialysate is then loaded onto an anion exchange column, DE52, to enrich the L1-Fc over co-purifying bovine IgG. The chimera is eluted in 0.15 M KCl+17.5 mM $NaH_2PO_4$, pH 6.3. After alkanization to pH 8.0, the eluant is incubated with protein A-Sepharose. The L1-Fc protein is eluted with 100 mM glycine pH 3.0; the pH is immediately neutralized by one tenth volume of 1 M Tris pH 8.0. The final L1-Fc protein is used for assay after dialysis against Phosphate Buffered Saline (PBS) pH 7.5. The native protein is reported to migrate at ~400 kDa. Under reducing conditions, the L1-Fc appears as a 200 kDa on Western blot. Protein purity was judged by Coomassie and silver stains.

The cells were grown anchored either to flat culture bottles or microspheres, in the absence of glutamine and the presence of methionine sulfoximine (MSX), which suppressed non-producer cells. The cells grown initially to confluence in high serum media and then low-serum media until the cells were spent. The supernatant from the two batches were purified separately. The structure of L1 is shown in FIG. 32A attached hereto.

Supernatant from batch cultures were purified by initial precipitation with ammonium sulfate, dialyzed, suspended at pH 6.3, bound with an anion-exchange column to enrich for L1-Fc, alkalinized to pH 8.0, incubated with protein A-sepharose, eluted with 100 mM glycine at pH 3.0, neutralized with TRIS, and dialyzed. Western blot analysis, using antibodies against the human Fc, showed that the protein migrated at ~200 kD and approximately 95% pure by Coomassie and silver stains. This solution was dialyzed to concentrations of approximately 200 μg/ml for the in vitro and in vivo experiments. The solutions were detergent free.

In Vitro Assessment of L1-Fc Activity

To assess the activity of L1-Fc and its ability to stimulate neuronal growth, tissue culture plates were exposed first to poly-lysine (10 μg/ml) and then to various concentrations of L1-Fc for short periods of time. The L1-Fc solution was poured out of the culture plate. Dissociated chick (7 day) embryonic dorsal root ganglion neurons were seeded on top. At 16 hours after seeding, the cultures were fixed with formaldehyde (4%) and inspected by phase contrast light microscopy. Neurite lengths were measured from video images, using NIH Image.

To assess the ability of L1-Fc to neutralize white matter growth inhibitors, frozen coronal sections (15 μm) of thoracic spinal cord from adult Long-Evan's hooded rats were placed onto poly-lysine coated culture wells. Dissociated embryonic (8-day) chick sensory ganglion cells were first incubated with the lipid-soluble fluorescent vital dye DiI and seeded on the sections. At 24 hours, the cultures were fixed with formaldehyde (4%) and observed with epifluorescent and phase-contrast microscopy. Neuron distribution on white matter, gray matter, and poly-lysine coated culture dishes were compared.

All culture media were standardized across experiments for fetal calf serum content and concentrations. Spinal cord sections were from adjacent cord. Density of dissociated cells, incubation conditions were likewise uniform across experiments, culture dish volume and surface areas were the same in all the experiments. Likewise, viewing and light conditions were carefully matched.

The Spinal Cord Injury Model

The NYU Impactor and rat contusion models of spinal cord injury have been extensively described. [Kwo S, Young W, DeCrescito V (1989) Journal of Neurotrauma 6: 13-24; Huang P, Young W (1994). Journal of Neurotrauma 11: 547-62; Basso M, Beattie M, Bresnahan J, Anderson D K, Faden A, et al. (1996) Journal of Neurotrauma in press; Constantini S, Young W (1994) Journal of Neurosurgery 80: 97-111]. Rats were anesthetized with an intraperitoneal dose of pentobarbital (40 mg/kg female, 60 mg/kg male), suspended with clamps placed on the T8 and T11 dorsal processes, and injured at one hour after induction of anesthesia. The impactor drops a 10 g rod a distance of 12.5, 25.0, or 50.0 mm onto the dorsal surface of T9-10 spinal cord, exposed by laminectomy. Two digital optical potentiometers measured the trajectory of the falling rod and vertebral movement with a precision of ±20 μm and ±20 μsec. Cord compression rate (Cr) was calculated from the distance of cord compression divided by time required for compression. Cr correlates linearly with 24-hour lesion volumes (r<0.900), as well as 6-week locomotor scores and spared white matter (WM).

The rats received daily Kefling® (15 mg/kg b.i.d. subcutaneous) for one week after injury and then Baytril® (5 mg/kg b.i.d. subcutaneous) for 10 days for recurrent urinary tract infections. Because the rats were receiving a foreign protein (mouse L1 and human Fc), both the L1-Fc and saline-treated rats received cyclosporin (10 mg/kg/day i.p.) for the two week period of intrathecal drug administration. All rats had twice daily bladder compression until they recovered voiding. The rats were assessed weekly for locomotor recovery, using the Basso-Beattie-Bresnahan (BBB) scale developed at Ohio State University. At 11 weeks after injury, the rats received injections of BDA (Biotinylated dextran amine) into their motor cortex to label their corticospinal tracts. At 12 weeks, the rats were anesthetized with pentobarbital and perfused with formaldehyde (4%) solution through the heart.

Locomotor Scoring

The BBB score is a 21-point scale representing 21 stages of locomotor recovery after spinal cord injury. The scale is based on unique combinations of scored behaviors, ranked according to time of appearance after injury. Behaviors that appeared last or in the least severely contused rats had higher scores than behaviors appeared early on or in more severely injured rats. The score can be divided into three parts: from 0-8, the scores emphasize voluntary movements of hindlimb joints; from 8-14, the scores represent standing and stepping with progressively better forelimb-hindlimb coordination; from 15-21, the scores indicate greater strength and better foot placement and balance. Each score represented a unique combination of behaviors, providing a non-ambiguous ordinal scale. The scale is described in Table 6.

Every week, the rats were placed in a standard open field (a plastic tub with walls) and observed by two trained investigators from two sides for 4 minutes. Characteristics of locomotion were checked of on scoring sheet and the final score represents the consensus opinion of the two observers. Detailed inter-rater reliability analyses indicate that experienced observers can achieve a standard deviation of less than 1 point on the scale. All scoring was done by people who were not aware of the treatments received by individual rats. Treatments were masked through the analysis except for an interim analysis at 6 weeks to perform a "futility" test to determine whether there was sufficient difference among treatment groups to continue the trial.

TABLE 6

| BBB OFT scores | Comments |
| --- | --- |
| 0 No observable hindlimb (HL) movement | None |
| 1 Slight movement on one or two HL joints | Slight ≦50% of joint range |
| 2 Extensive movement of one HL joint and slight movement of the other joint | Extensive ≧50% of joint range |
| 3 Extensive movement of two HL joints | Two joints = usually hip & knee |
| 4 Slight movement of three HL joints | Three joints = hip, knee & ankle |
| 5 Slight movement of two HL joints & extensive movement of third HL joint | |
| 6 Extensive movement of two joints HL joints & slight movement of third HL joint | Third joint = usually the ankle |
| 7 Extensive movement of all three HL joints | |
| 8 Sweeping with no weight support or Plantar placement with no weight support | Sweeping = rhythmic 3 joint movement |
| 9 Plantar placement with weight support OR Dorsal stepping with weight support | Weight support = HL extensor contraction with elevation of hindquarters in stance |
| 10 Occasional weight supported steps with no forelimb-hindlimb (FL-HL) coordination | Occasional = >5% & ≦50% Steps = plantar steps with weight support |
| 11 Frequent to consistent steps (FCS) with no coordination | Frequent = 51-94% of the time |
| 12 FCS with occasional coordination | 6-50% bouts of locomotion |
| 13 FCS with frequent coordination | 51-95% bouts of locomotion coordinated |
| 14 Consistent coordinated steps (CCS) & paw rotated on placement & liftoff OR Frequent steps, consistent coordination With occasional dorsal steps | Rotated = internal or external rotation |
| 15 CCS & no or occasional toe clearance & parallel paw position on initial placement | Parallel = paw placement to body Toe clearance = steps without toe drag |
| 16 CCS & frequent toe clearance | Frequent toe clearance ≧50% no toe drag |
| 17 CCS & parallel paw on placement and liftoff | |
| 18 CCS & consistent toe clearance | Consistent toe clearance 4 toe drags |
| 19 CCS & parallel paw on placement and liftoff Tail down part or all the time | Tail down = touches ground when walking |
| 20 CCS & parallel paw on placement and liftoff Tail consistently up, trunk unstable | Trunk instability = lateral weight shifts, waddling, lurching |
| 21 CCS, consistent toe clearance, parallel paws, tail consistent up, consistent trunk stability | Consistent trunk stability no lurching |

Histological Assessment of Injured Spinal Cords

The spinal cords were removed and immersed in 4% formaldehyde for several days. A 1-mm section at the contusion center is removed and embedded in plastic for analysis of spared white matter. The cord sections were stained with toluidine blue to show axons and myelin. White matter sparing was estimated from the cross-sectional areas of spinal cord that contained myelinated axons. Percent (WM) white matter sparing was calculated by dividing the area of WM sparing by the total cross-sectional area.

The proximal and distal pieces of cord were passed through 50% and 75% sucrose solutions, and frozen at −5° C. The proximal cords were horizontally frozen-sectioned at 40 μm thickness to show the labelled corticospinal tract. This distal cords were coronally frozen-sectioned and every fifth section was reacted with DAB and nickel (0.25 mg/ml diaminobenzidine+0.04% nickel) to stain labelled corticospinal tract. The sections were observed with a dark-field condenser.

Statistical Analyses

To assess the significance of neurite length differences for each concentration of L1-Fc solutions used to coat poly-lysine substrate, analysis of variance (ANOVA) was done with a commercial program (Statview 4.2, Abacus Concepts, Berkeley), using L1-Fc concentrations as the main factor and neurite length as the dependent variable. Post hoc analyses were then used to compare individual pairs of groups, based on the Bonferroni-Dunn test, corrected for multiple comparisons. Probability values of less than 0.05 were considered significant.

In the L1-Fc neutralization of white matter inhibitor experiments, the differences between treatment groups were so striking that statistical analyses were not necessary. In all experiments, no neurons were observed growing on white matter in the absence of L1-Fc in the solution. By contrast, all L1-Fc incubated cultures showed many hundreds of neurons growing on white matter. Each of these experiments was replicated at least 8 times. The differences are clearly statistically significant since there was no overlap in the data from the two treatment groups.

To determine whether the spinal cord L1 concentrations differed before and after injury, repeated ANOVA measures were used where the dependent variable was L1 concentration values measured in proximal, injury, and distal segments and the main factor was Injury (25 mm weight drop versus controlled uninjured). Since this was a qualitative study, designed to assess whether L1 was present in injured cord, further statistical analyses were not carried out once it was clear that injury upregulates L1.

To assess the significance of locomotor recovery among treatment or injury, repeated ANOVA measures were used, where the repeated measures represented the weekly locomotor scores. The mean locomotor score represented the average of all the scores collected over the 12 week period. In the case of the experiment comparing L1-Fc and saline treatment, the main factor was treatment and the dependent measure was the repeated weekly locomotor scores. Although analysis of co-variance (ANCOVA) could be used to correct for differences in cord compression rates, the data was statistically highly significant without the need for such correction.

Results

Four sets of experiments were carried out: Effect of substrate associated L1-Fc on neurite outgrowth in vitro, effect of soluble L1-Fc on neurite growth on poly-lysine, gray matter, and white matter, and effect of L1-Fc on injured spinal cords. Each will be described in sequence.

Stimulation of Neurite Outgrowth by L1-Fc Coated Onto Poly-Lysine Surfaces

Dissociated chick (embryo day 9) dorsal root ganglion cells were seeded onto poly-lysine coated (10 μg/ml) tissue culture dishes exposed for 10 minutes to L1-Fc solutions of varying concentrations. The cultures were fixed at 16 hours after initiation of culture. As FIG. 32B shows, the neurons showed relatively little neurite (~10 μm) extension when plated on poly-lysine or 4 μg/ml L1-Fc exposed poly-lysine. Neurite length is significantly longer at 20 μg/ml, even longer at 100-200 µg/ml. The photographs in the background show typical examples of neurons and neurites at each of the concentration levels.

Several findings are noteworthy. First, at low concentrations (4 µg/ml of L1), the cells clearly appear unhealthy. The cell bodies are bright and swollen. In contrast, there were more and healthier-appearing cells in the 200 µg/ml cultures, suggesting that L1 not only promotes neurite growth but may also enhance neuronal attachment and survival on polylysine. Second, even at 200 µg/ml, the dose-response curve clearly has not yet reached a plateau, suggesting that even higher concentrations of L1 may be beneficial. The concentrations refer to L1-Fc solution used to coat the poly-lysine and not the concentration bound to the poly-lysine.

Stimulation of Neurite Adhesion and Growth on Spinal White and Gray Matter

Dissociated chick (embryo day 8) dorsal root ganglion cells were labelled with the fluorescent lipid-soluble dye Di-I, seeded onto 15 µm thick frozen coronal sections of adult rat thoracic spinal cord, and grown for 24 hours in small tissue culture wells under and observed under a epifluorescent light microscope. Dorsal root ganglion cells normally avoid white matter but will adhere to and extend neurites on gray matter. FIG. 33 shows neuronal distribution on spinal cord sections with and without L1-Fc. The top left picture (4×) shows a Di-I labelled cells surrounding the section and growing on the butterfly shaped gray matter in the center of the cord but not on white matter. Cells completely eschew dorsal column white matter. Phase-contrast backlighting shows no cells are growing on white matter or extending from gray to white matter.

In sections incubated with 40 µg/ml L1-Fc containing culture media, however, the seeded neurons adhered, grew and extended neurites freely on both gray and white matter. Inspection at higher magnification showed many neurites growing long distances across gray-white matter interfaces in the dorsal, lateral, and ventral spinal cord regions. Cell densities were slightly higher on the tissue cultures than on poly-lysine surfaces. Finally, sections incubated in L1-Fc had more surviving neurons, often growing in clumps and neurites that extended over longer distances than the tissue cultures that did not have added L1-Fc. The chick-human chimera L1-Fc clearly has neurite growth promoting activity and effectively neutralizes white matter neuron growth inhibitor.

Intrathecal Administration of L1-Fc to Lumbosacral Spinal Cord after Injury.

Two series of experiments were carried out. In the first series, 6 rats received 150 µg/ml L1-Fc and 8 rats received PBS vehicle solution. In the second 14 rats received 200 µg/ml of L1-Fc and 14 received vehicle solution. FIG. 34A illustrates the delivery system for intrathecal administration of Lc-Fc to the rat spinal cord. Western blot analysis revealed the presence of L1-Fc in the spinal cord after two weeks of intrathecal infusion. To assess locomotor recovery, each rat was scored weekly for 3 months, using open-field BBB locomotor scores as set forth in Table 6, above. These scores represent behavior ranging from total paralysis (score of 0) to normal locomotion (score of 21). Scores of 0 to 8 signify hip, knee and ankle joint movements without weight support, while a score of 9 indicates standing without stepping. A score of 10 indicates occasional ($\leq$50%) weight-supported steps, while 11 indicates frequent (>50%) to consistent (>95%) stepping with no forelimb-hindlimb coordination. A score of 12 indicates frequent to consistent stepping and occasional coordination. Scores of 10 or higher represent important qualitative improvements over scores of 9 or less, differentiating walking and non-walking rats.

At 11 weeks after injury, the rats were anesthetized with pentobarbital (40-60 mg/kg). Craniotomies were carried out to expose the motor cortex for injections of 1% BDA (Biotinylated dextran amine) solutions. This procedure causes selective anterograde labelling of the corticospinal tracts. At 12 weeks after injury, the rats were anesthetized with pentobarbital (60 mg/kg i.p.) and perfused with 300 ml of 4% formalin at 50 ml/min.

FIG. 34B shows the mean locomotor scores of L1-Fc treated and saline-treated rats. On the day after injury, all rats had 0 BBB scores, indicating complete paralysis of both hindlimbs. Both L1-Fc and saline-treated groups had similar early recovery, reaching a score of about 9 by 4 weeks. However, beyond the 4th week, the scores begin to diverge. Repeated measures ANOVA showed a statistically significant effect of L1-Fc on the locomotor scores, with a mean of 10.83±0.7 compared with 8.86±0.34 in controls ($p<0.01$). A score of 11 signifies an animal that is able to step consistently with no forelimb-hindlimb coordination, while a score of 9 signifies an animal that is able to stand and take an occasional step, a large behavioral difference.

Histological Assessment of L1-Fc and Saline-Treated Spinal Cords

At 3 months after injury, all the rats in both L1-Fc and saline-treated groups showed similarly thin rims of white matter at the injury site. Thin plastic sections stained with toluidine blue were cut from the injury site. At low magnifications, the injury sites appeared to be qualitatively similar in both treatment groups. At higher magnifications, however, the L1-Fc treated rats appeared to have more large unmyelinated or partially myelinated axons than the saline treated rats. Otherwise, the degree of inflammation, the extent of tissue damage, and the myelination of the axons appeared to be very similar.

To assess for the presence of regenerated descending axons, we injected BDA stain into the motor cortex bilaterally, waited a week, and then stained the spinal cords with DAB+nickel. Visual inspection of BDA-labelled fibers revealed heavily labelled bands of corticospinal fibers in the proximal cord, ending approximately one segment above the injury site. Microscopic inspection of coronal sections of the cord revealed visible dark stains localized to the corticospinal tracts at the ventral tip of the dorsal columns. Under dark field microscopy, some stain could be seen in pial membranes in proximal and distal cord. Animals without BDA injections did not show such stains.

Many corticospinal fibers grow across the injury site. Once past the injury site, many of the fibers lost their intense blue stain but were still clearly visualizable on dark-field as gold-colored bundles of axons. In saline-treated rats, the labelled axons tended to be deeper but many crossed the injury site and terminated in the distal cord, usually less than a mm from the contusion center. In L1-Fc treated rats, however, axons were frequently more superficial and penetrated longer distances (>5 mm) into the lumbosacral spinal cord. Quantitative analyses with counts of fibers at different distances from the injury site are being conducted. These data strongly suggest that L1-Fc treatment allows functional regeneration in adult rats after moderate severe spinal cord contusion.

Several conclusions may be drawn from these studies. First, L1-Fc coated poly-lysine surfaces not only allow greater adhesion and survival of neurons but also markedly increases neurite growth, reflected in the length of neurite lengths after 16 hours in culture. Secondly, L1-Fc applied to culture media incubating frozen sections of spinal cords remarkably neutralizes white matter inhibitors that prevent neuronal adhesion and growth. Thirdly, L1 is upregulated in injured spinal cords and is localized on spinal axons, indicating that axons possess L1 receptors in injured spinal cords and should respond to L1. Further, application of L1-Fc significantly improves locomotor recovery in rats after moderately severe spinal cord injury (25 mm weight drop). Finally, preliminary data suggest that at least one long tract, the corticospinal tract, regenerates longer distances into the spinal cord distal to the injury site than saline-treated controls.

These results confirm that a cellular adhesion molecule, particularly L1-Fc, produces functional regeneration in injured adult rat spinal cords. In addition to the differences in locomotor recovery, this observation strongly suggests that the recovery results from regeneration stimulated by the L1-Fc therapy. The functional recovery, unlike recovery that occurs after a neuroprotective therapy, was delayed and did not appear to be statistically significant until 6 weeks after injury. The treated and control groups were almost identical during the first 5 weeks after injury.

The recovery difference is statistically highly significant. Note that the treatment and control groups had only 6 rats per treatment group. Despite such a small number of rats in each group, the results were significant at a p-value of <0.01. These results could not be attributed to differences in injury severity because the injury parameters in the two groups were virtually identical. In addition, the locomotor scores of the rats during the first five weeks after injury were virtually identical, diverging only at the 6th week.

The difference in locomotor scores between L1-Fc treated rats and control untreated rats represents a substantial change in behavior. A BBB score of 9 indicates a rat that is able to do plantar paw placement and support its weight in stance when stationary, or a rat that is stepping with the dorsum of its paws. This is a highly abnormal locomotor behavior that can be readily distinguished from a rat that has a score of 11. Rats with scores of 11 are rats that are taking weight-supported plantar steps with occasional forelimb-hindlimb coordination. Several rats were taking frequent to consistent coordinated plantar stepping. The difference between 9 and 11 represent the difference between rats that were only able to stand and rats that were able to walk, albeit not normally.

The treatment used may not have been fully optimized. We treated the rats only for 2 weeks after injury. We also used a relatively low dose of L1-Fc (150 µg/ml) applied at the rate of 0.5 µliters per hour. The amount of L1 received by the rat, although considerably more than is present in the spinal cord, nevertheless is much less than the 40 µg/ml concentrations that completely neutralizes white matter growth inhibitors in vitro. Higher concentration and longer duration therapies should produce significantly better locomotor recovery.

The tissue culture data also strongly supported the use of L1-Fc as a regenerative treatment. When applied to polylysine surfaces for even short periods, L1-Fc supported growth of neurites with a clear dose-response curve. The presence of 40 µg/ml of L1-Fc completely neutralized the inhibitory effects of white matter on neuronal growth. It also improved adherence and survival of seeded neurons to white matter. This suggests the L1-Fc may play a neuroprotective role as well as a growth promoting and white matter inhibitor neutralizing roles.

Application of L1-Fc was started shortly after injury, and the treatment was discontinued at 2 weeks after injury. Therefore, some recovery may have resulted from neuroprotection. However, two findings argue strongly against this possibility. First, the L1-Fc treated or saline-treated rats had virtually identical locomotor recovery during the first six weeks after injury. If L1-Fc were neuroprotective, one would expect to see earlier divergence of the locomotor scores. Second, the injury site were examined and, at least qualitatively, no significant differences were found between the two groups in white matter sparing.

None of the L1-Fc treated or saline-treated rats became seriously ill or died during the planned 3-month survival period, even though all received daily cyclosporin (CyA) for the 2-week period of intrathecal L1-Fc administration. CyA was used since the rats were receiving a foreign mouse-human chimera protein. Both the L1-Fc and saline-treated rats were immunosuppressed for 2 weeks by CyA. In unpublished experiments a tenfold lower concentration of the immunogenic chick NgCAM (15 µg/ml) was given intrathecally to 6 rats without CyA treatments (data not shown). This treatment did not result in locomotor recovery or evidence of regenerating corticospinal tracts.

The L1 used in this experiment was from mice. Yet, it is effective in stimulating growth of chick dorsal root sensory ganglia and rat corticospinal tract. This strongly argues that this molecule acts across species boundaries and under a variety of conditions. In fact, L1 is believed to act on the NgCAM receptor rather than the L1 receptor in chick, despite substantial differences in the molecular sequence between L1 and NgCAM [Burgoon M P, Grumet M, Mauro V, Edelman G M, Cunningham B A (1991). *Journal of Cell Biology* 112: 1017-29; Grumet M (1992). *Journal of Neuroscience Research* 31: 1-13; Grumet M, Friedlander D R, Edelman G M (1993) *Cell Adhesion & Communication* 1: 177-90; Grumet M, Mauro V, Burgoon M P, Edelman G M, Cunningham B A (1991) *Journal of Cell Biology* 113:1399-412; Reid R A, Hemperly J J (1992) *Journal of Molecular Neuroscience* 3:127-35]. Whether the L1-Fc is acting on FGF receptors, as claimed by Doherty, et al. [Green P J, Walsh F S, Doherty P (1996) *Bioessays* 18: 639-46; Hall H, Walsh F S, Doherty P (1996). *Cell Adhesion & Communication* 3: 441-50; Saffell J L, Williams E J, Doherty P, Walsh F W (1995). *Biochemical Society Transactions* 23: 469-70] is unclear. However, it is of interest that the dose-response curve of mouse L1-Fc is similar to that reported for the human L1-Fc.

L1-Fc was delivered directly to the spinal cord. This avoids any question of L1-Fc penetration across the blood brain barrier. Also, much lower amounts of L1-Fc would be required. The intrathecal catheter was placed one segment distal to the injury site and have examined the Evan's blue dye delivered to this site. The dye was limited to the spinal cord and extended at least 2 cm proximally and involved the entire lumbosacral spinal cord. The weight of the stained portions of the spinal cord is approximately 1 gm, suggesting that the tissue distribution space may be about 1 ml. The binding and clearance of L1-Fc to and from the spinal cord are not known. However, even in the best case, at 150 µg/ml delivered at the rate of 0.5 µl per hour, the spinal cord received less than 75 ng/hour of L1-Fc.

Our experiments with poly-lysine bound L1-Fc suggest that exposure to 20 µg/ml solutions of L1-Fc may be required to stimulate neurite growth. Even if we assumed that the L1-Fc was minimally degraded or cleared from the spinal cord, that L1-Fc bound to tissue at about the same level that it bound to poly-lysine, and the L1-Fc distributed within a ml of tissue around the infusion site, concentrations of L1-Fc in the spinal cord would be unlikely to reach 20-40 µg/ml for at least a week or more after starting infusion. If there were any clearance or degradation of L1-Fc, the accumulation rate is likely to be much slower.

L1-Fc was given for only two weeks after injury. The locomotor recovery of the L1-Fc and saline-treated rats in this experiment began to diverge only after 5 weeks, 3 weeks after the L1-Fc infusion had stopped. This suggests several possibilities. First, L1-Fc may have a very long half-life in the spinal cord. Second, once exposed to L1, axons do not require continued presence of L1-Fc for growth. Third, very low levels of L1-Fc will stimulate axonal growth in the spinal cord. Fourth, much of the axonal growth may have occurred relatively rapidly during the first three weeks but functional reconnection may have taken a long time. Further studies are needed to confirm or rule out these possibilities.

L1-Fc is an attractive regenerative therapy for several reasons. First, both L1 and Fc are naturally present in the body. L1, for example, is abundant in peripheral nerves. Fc is, of course, the constant region of immunoglobulins and is ubiquitously present. If the human forms of the molecules are used, this molecule is unlikely to provoke immune responses. Second, L1 is upregulated in injured spinal cord, perhaps accounting for some of the spontaneous axonal growth in the spinal cord. However, the extent, duration, and distribution of native L1 may not be sufficient to sustain long-distance axonal regeneration. Our experiments indicate that a 2-week intrathecal infusion of exogenous L1-Fc is sufficient to induce and maintain functional recovery in rats. Third, since it is a naturally expressed molecule that participates in normal development of the spinal cord, it is less likely to produce toxic effects or promote tumor formation.

These results indicate that L1 strongly promotes spinal axonal growth and effectively neutralizes neurite growth inhibitors in spinal white matter. The simplest and most straightforward explanation of such results is that L1 simultaneously stimulates axonal L1 receptors that promote growth and reduces sensitivity of growing axons to white matter inhibitors. Although other mechanisms may play a role in vivo, a direct interaction of L1 with axonal L1 receptors is a necessary and sufficient mechanism to account for the axonal growth that we have observed in vitro and in vivo. More important, these data clearly establish the feasibility of using L1-Fc as a practical pharmacological therapy to produce functional regeneration in a spinal cord injury model that closely resembles the human condition.

EXAMPLE 27

The L1 Neural Cell Adhesion Molecule is a Survival Factor for Fetal Dopaminergic Neurons L1 is involved in the activation of different second messenger pathways in different cell types. For example, dorsal root ganglion cells and Schwann cells respond the addition of L1, or antibodies to L1, with increased inositol phosphate turnover and calcium mobilization (see von Bohlen and Halbach et al, 1992), while PC12 cells show a drop in inositol phosphate metabolism (see Schuch et al, 1992). Cerebellar neurons respond to L1 with a marked increase in cAMP levels, in addition to elevated intracellular calcium and IP3 (von Bohlen and Halbach, supra.; Appel et al., 1995).

Parkinsons Disease is characterized by the degeneration of mid-brain dopaminergic neurons. An effective means of improving the survival of dopaminergic neurons is through the elevation of cAMP levels. It has been shown that an increase in cAMP levels protects dopaminergic neurons both in vitro and in vivo from the cytotoxic effects of MPTP, a specific toxin for dopaminergic neurons (Hartikka et al., 1992; Hulley et al, 1995).

Based on this information, the following experiment was conducted to study the effects of L1 or a natural ligand to L1, on the signal transduction events that might mediate an increase in intracellular cAMP and thereby enhance survival of dopaminergic neurons. The details of the experiments follow below.

Methods

Cell culture, dopamine uptake and treatment with $MPP^+$ have been described (Hartikka et al., 1992). Primary cultures containing dopaminergic neurons were prepared from the ventral mesencephalon of 14-day-old fetal rats and plated in 24 well plates. A culture well usually contained $6 \times 10^5$ cells/well, of which 3-5% were dopaminergic. Duplicate cultures were prepared for dopamine uptake or tyrosine hydroxylase staining. Dopamine uptake was measured using tritiated dopamine at concentrations of 50 nM (sp, act. 45 Ci/mmol, New England Nuclear). The survival of dopaminergic neurons in the culture was assayed by counting tyrosine hydroxylase (TH) immunopositive neurons, stained with a monoclonal antibody to TH (Boehringer Mannheim).

The monoclonal L1 antibodies 327 and 557.B6 (referred to as 557) were added to the culture medium on the day of plating at concentrations of 7.5-120 µg/ml and left for 3 days. In addition to treatment of the culture medium with antibodies, they were also substrate coated prior to plating of the cells, as described (Appel et al., 1993). In experiments with $MPP^+$ (active metabolite of methyl-phenyl-tetrahydropyridine, MPTP), antibodies or cAMP-elevating agents were added to the culture medium of 5-day-old cultures, followed by 1 µM $MPP^+$ on day 6 and cells were fixed on day 8 for immunocytochemistry. The PDE type IV inhibitor NQ-A (1-(3-carbomethoxyphenyl)-3-benzyl-quinazoline-2,4-dione) was synthesised at Novartis Ltd, Basel according to a published protocol (Lowe et al., 1991) and forskolin was from Sigma Ltd.

Results

Both immunoglobulin-like domains and fibronectin homologous repeats of the L1 glycoprotein have been shown to promote neurite outgrowth and participate in short-term cell adhesion with varying efficacy (Appel et al, 1993; Holm et al., 1995). Furthermore, a monoclonal antibody (557) reacting with a short peptide connecting the fibronectin type III repeats 2 and 3 is as effective as the purified L1 molecule itself in increasing both intracellular calcium levels and inositol phosphate turnover, and in promoting neurite outgrowth (Appel et al., 1995). The effects of this antibody both as a substrate and as a culture medium additive have been compared on survival of primary mid-brain cultures containing embryonic rat dopaminergic neurons.

Cultures from embryonic rat mid-brain exhibit a dramatic post-plating loss of dopaminergic neurons, with up to 50% of cells dying in the first three days of culture, followed by a more gradual decrease to around 80% cell loss by 13 days after plating (Hartikka et al., 1992). Therefore, in the experiments described here, cultures were treated with potential survival factors at the time of plating and then left for three days. At this point cultures were either fixed for immunocytochemistry or dopamine uptake was performed. The antibody 557 improved tritiated dopamine uptake by dopaminergic neurons (a measure of dopamine metabolism) at concentrations of 60 µg/ml whether used to coat the culture well or when added to the culture medium at the time of plating (not shown). Therefore most subsequent experiments were done using antibodies as culture medium additives and all the results presented here are from this treatment method. A dose response curve was made using concentrations ranging from 7.5-120, μg/ml and dopamine uptake/well increased in a dose-dependent manner, even at 7.5, μg/ml, when a slight increase was observed (FIG. 35). The control monoclonal L1 antibody, 327, which reacts with a conformational epitope on the sixth Ig-like domain of L1 (Appel et al., 1995) had no effect on dopamine uptake in the concentration range 7.5-120, μg/ml (result for 60 μg/ml shown in FIG. 35).

In order to determine whether triggering of L1 at the cell surface might increase dopamine uptake by elevating intracellular cAMP levels, the three day treatment of cells with antibody was combined with exposure to phosphodiesterase inhibitor NQ-A, which blocks the breakdown of cAMP (Lowe et al., 1991). While the phosphodiesterase inhibitor NQ-A caused a slight elevation of dopamine uptake at 0.5 μM concentration as previously reported (FIG. 35; Hulley et al., 1996), this increase in uptake was additive to the effects seen with the 557 antibody, rather then synergistic (FIG. 35). This suggests that the two substances are exerting their effects through separate signal transduction pathways, since an exponential increase in dopamine uptake is seen when forskolin and any PDE-IV inhibitor are combined, both substances acting to elevate cAMP (Hulley et al., 1995).

Dopamine uptake can be elevated in two ways, by an increase in the number of dopaminergic neurons or by an increase in the number of uptake transporter sites per neuron which takes place during differentiation. In order to establish which of these accounted for the L1 antibody-induced elevation of dopamine uptake, duplicate cultures were treated with 557 antibody for three days. Of the duplicate cultures, half were processed for immunocytochemistry using tyrosine hydroxylase antibodies and dopamine uptake measurements were performed on the other half. FIG. 36 shows that the number of tyrosine hydroxylase immunopositive neurons increased with increasing concentrations of L1 antibody, 557 (FIG. 36A), and that this correlated well with dopamine uptake (FIG. 36B). The dopamine uptake per neuron remained unchanged (FIG. 36C). This indicates that the L1-induced increase in dopamine uptake was caused by an increase in the number of surviving cells and not simply by an enhanced differentiation of existing cells or an increase in uptake mechanisms. The control antibody 327 had no significant effect on either cell number or dopamine uptake (not shown).

Dopaminergic neurons can be protected from $MPP^+$-induced neurotoxicity by treating 5 day old cultures with cAMP analogues or forskolin for one day before exposure to $MPP^+$ (Hartikka et al., 1992). A similar result was achieved here using a combination of forskolin and PDE-IV inhibitor NQ-A (FIG. 37A). The number of surviving dopaminergic neurons was assessed on day 8 of culture. When cultures were treated according to the same schedule with 120 μg/ml concentrations of the antibodies 557 and 327, there was no protection from $MPP^+$-induced neurotoxicity (FIG. 37B).

Concentrations of 30 μg/ml and 60, μg/ml 557 antibody were also tested with no protective effect (not shown). In untreated control cultures, there is a relatively slight decrease in dopaminergic cell number between days 5 and 8 of culture (Hartikka at al., 1992), hence the selection of this treatment period.

Discussion

Antibody 557, directed against the junction between repeats 2 and 3 of the fibronectin type III domain of the L1 neural cell adhesion molecule, promotes the survival of fetal dopaminergic neurons either when added acutely to the culture medium or as a coated substrate, as shown by an increase in both dopamine uptake and cell number. This correlates with a previous report that antibody 557 causes a pronounced second messenger response and increased neurite outgrowth in small cerebellar neurons (Appel et al., 1995). There is increasing evidence that ligand binding alone does not automatically cause a cellular response, and that not all domains of L1 are involved in signal transduction (Appel et al., 1995; Holm at al., 1995). The control antibody, 327, is directed against an immunoglobulin-like repeat which is unable to activate signal transduction in cerebellar neurons, and this proved to be true also for dopaminergic neurons.

The neural cell adhesion molecules, L1 and N-CAM, were first shown to influence second messenger systems when triggered with specific antibodies at the surface of PC12 cells (Schuch et al., 1989). These antibodies or the isolated molecules themselves have been further shown to elicit cell type-specific responses that can be modulated by the substrate on which the cells are maintained (von Bohlen und Halbach et al., 1992). Depending on the cell type, treatment with antibodies or CAMs triggers L1 or N-CAM connected pathways, resulting in up- or down-regulation of inositol phosphate turnover, by raising intracellular $Ca^{2+}$ levels, or by an increase or decrease of intracellular pH. Elevation of intracellular cAMP in response to L1 and its antibodies has only been reported in cerebellar neurons (Von Bohlen und Halbach et al., 1992). In dopaminergic neurons it does not seem as if cAMP is responsible for the improved survival observed with L1 triggering, since phosphodiesterase inhibitors do not potentiate this response in an exponential manner. Presumably another, as yet uncharacterised pathway is involved.

There is evidence suggesting that L1 acts not only on L1 receptors but also on the fibroblast growth factor (FGF) receptors. L1 has been shown to signal via the FGF receptor in experiments where the neurite outgrowth response to L1 was completely blocked by specific antibodies for the FGF receptor (Doherty et al., 1995), and in an FGF-receptor independent manner, by activation of src-kinase (Ignelzi et al., 1994). Basic FGF has previously been reported to have beneficial effects on the survival of dopaminergic neurons in vitro and in vivo (Otto and Unsicker, 1990; Date et al., 1993; Chadi et al., 1993). This may be an indirect effect, since when astrocytes are activated with bFGF, they produce a factor or factors which strongly promotes the differentiation of midbrain dopaminergic neurons in culture (Gaul and Lubbert, 1992). Further evidence for an indirect effect comes from a recent report by Hou et al. (1997) which shows that bFGF stimulates glia to produce glutathione, and that glutathione is the central factor by which bFGF protects dopaminergic neurons from 6-hydroxydopamine toxicity. Furthermore, the neuro-protective and neurotrophic effects of bFGF in vitro are abolished by inhibition of cell proliferation, which implicates glia rather than neurons (Knüsel et al., 1990; Engele and Bohn, 1991; Park and Mytilineou, 1992; Hou et al., 1997). It has been found that while bFGF enhances dopamine uptake, it does not improve the survival of dopaminergic neurons in vitro, nor is it able to protect them from $MPP^+$ toxicity under culture conditions where cAMP was strongly protective (Hartikka et al., 1992). This suggests that L1 might not be acting on neuron survival through the same pathway as bFGF on neurite outgrowth promotion, as suggested by Williams et al. (1994), since a clear improvement is seen in the number of surviving dopaminergic neurons upon triggering of L1.

Treatment of mid-brain cultures with the L1 antibody 557, at concentrations which clearly improve cell survival in culture, failed to protect against $MPP^+$ toxicity. This might tie in with our findings that the L1 antibody does not appear to generate a significant cAMP response in combination with a PDE type IV inhibitor (indirectly assessed by measuring cAMP-responsive dopamine uptake). Combined treatment of cultures with PDE-IV inhibitor and L1 antibody caused an additive increase of dopamine uptake, indicating that two separate pathways are being activated. An exponential increase results when PDE-IV inhibitor is combined with forskolin (Hulley et al., 1995), since both substances act on cAMP metabolism, and this combination of substances effectively protects against MPP$^+$ toxicity. While L1 strongly promoted neuronal survival during the plating of primary cultures, it was not able to protect dopaminergic neurons from MPP$^+$ toxicity at later stages in culture at the concentrations tested. However, cultures were only treated with antibody for one day prior to MPP$^+$ exposure, these being the conditions which are known to work with cAMP elevating agents, and it is possible that a longer pretreatment might prove more effective.

The mechanisms by which the L1 antibody 557 promotes the survival of dopaminergic neurons in culture are unclear, but are likely to involve the complex signaling cascades that are emerging for other cell types in the prevention of cell death. Thus, recognition of an appropriate cellular environment appears to be very important for neuronal survival and function, both in the embryonic and adult nervous systems, and cell recognition molecules undoubtedly mediate this process. Accordingly, the role that the agents of the invention and particularly, L1 and its ligands, play in this process and consequently, in Parkinsons Disease, is demonstrated and supported.

EXAMPLE 28

Prevention of Neuronal Cell Death by the Neural Adhesion Molecules L1 and CHL1

In the following experiments the role that L1 and the members of its family play in neuronal protection was further explored, the results of which confirm the disclosure herein that the present agents promote neuronal survival and correspondingly, are capable of preventing apoptosis and necrosis.

Apoptosis, also known as programmed cell death, plays a key role in the normal development of the nervous system. Apoptosis leads to elimination of up to 50% of developing neurons, and is the mechanism responsible for matching neuronal populations to target size (Oppenheim, R. W. (1991). Survival is largely controlled by a limiting supply of target-derived growth factors, but is further influenced by afferent stimulation (Linden, R. (1994)). Accumulating evidence suggests that apoptosis is also involved in pathological neuronal death, which occurs in neurodegenerative disorders such as Alzheimer disease (Bredesen, O. E. (1996)). Therefore, to understand how the brain develops and degenerates, it is clearly important to understand how the survival of neurons is controlled.

Growth and differentiation of many cell types requires attachment to the extracellular matrix (Ruoslahti, et al. (1994)). Recent findings demonstrate that the extracellular matrix also functions as a cell survival factor for many cell types (Raff, M. C. (1992); Re, et al. (1994)).

The neural adhesion molecule L1 is an important mediator of cell interactions during development of the nervous system, and during regeneration and synaptic plasticity in the adult (Martin, K. C., et al, (1996); Fields, et al. (1996); Wong, et al. (1995)). In humans, mutations in the L1 gene can lead to mental retardation, hydrocephalus, spastic paraplegia, and other developmental abnormalities (Wong, et al. (1995); Hortsch, M. (1996)). Disruption of the L1 gene in mice resulted in malformations of the nervous system, including enlarged ventricles and a reduced size of the corticospinal tract (Holm, J., et al. (1996)). These findings confirm that L1 is a crucial player in normal brain development. CHL1 is another member of the L1 family in the mouse (Holm, id). CHL1 exhibits a spatial and temporal pattern of expression overlapping but distinct from that of L1 (R. Hillenbrand, M. Molthagen, D. Montag, and M. Schachner, submitted)

Although much has been learned about the many different factors that act on neurons to influence their survival, the intracellular events that lead to neuronal survival or death are not well characterized. The protein Bcl-2 is a major inhibitor of cell death for many type of cells (Kroemer, G. (1997)), including neurons (reviewed in (Davies, A. M. (1995); Merry, D. E., et al. (1997)). Expression of Bcl-2 is widespread in the developing nervous system, consistent with a role in regulating neuronal survival (Merry, D. E., et al. (1994)). Over expression of the bcl-2 gene can prevent neuronal death in vivo during development and after axotomy (Farlia, P. G., et al. (1995)); in cell culture it is effective after deprivation of growth factor (Farlia, P. G., et al. (1995)) or diverse other insults (Zhong, L.-T., et al (1993); Kane, U. J., et al (1995)). The immediate early gene c-jun is best known for its rapid induction after stimulation (Morgan, J. I., et al (1995)), but longer lasting induction with slower onset has been reported to be associated with apoptosis of sympathetic neurons, both in vitro (Estus, S, et al (1994); Ham, J., et al (1995)) and in vivo (Messina, A., et al (1996)).

The following experiments show that fusion proteins containing the extracellular domain of L1 or CHL1 can promote survival of both cerebellar and hippocampal neurons in culture. This effect is accompanied by an increase in Bcl-2 and a decrease in c-Jun.

Experimental Procedures

Fusion Proteins L1-Fc and CHL1-Fc (L1-Fc and CHL1-Fc, Fusion Proteins Containing the Extracellular Domain of L1 or CHL1, Respectively, Fused to the Fc Portion of Immunoglobulin IgG1; PLL, Poly-L-Lysine; MTT, 3-[4,5-Dimethylthiazol-2-yl]2,5-diphenyltetrazolium Bromide)

L1 cDNA coding for the extracellular domain of mouse L1 from a linker-derived Eco RI site flanking 27 nucleotide upstream of the start codon to a Bbs 1 site cutting at nucleotide 3319 of the mouse L1 sequence (GenBank 5 GenBank Accession Number X12875), was inserted with the aid of a Bbs I-splice donor-BamHI adapter into the vector pLG1 (vector and splice donor sequence described by Simmons (Simmons, D. L. (1993)). For production of stable transformants, an Eco RI-Not I fragment containing the L1 and immunoglobulin Fc coding regions was transferred to a derivative of plasmid pEE14 (Bebbington, C. R. (1991)) in which the BamHI site had been destroyed, giving plasmid pEE14-L1-Fc. The L1 sequences were substituted by CHL1 sequences, from a linker-derived Sal I site flanking nucleotide 129 before the start codon to nucleotide 3328 of the mouse CHL1 sequence (GenBank 5 GenBank Accession Number X94310), to give plasmid pEE14-CHL1-Fc. A similar construct was prepared containing NCAM sequences, from an Eco RI site in a polylinker upstream of nucleotide 42 to an Ava II site at nucleotide 2233 of the sequence (GenBank 5 GenBank Accession Number X15049). The plasmid were introduced into CHOK1 cells and transformants selected as described (Bebbington, C. R. (1991)).

The secreted L1-Fc and CHL1-Fc were purified by affinity chromatography on protein A-Sepharose CL-4B. One liter clarified medium was applied to a 1 ml column, washed first with 0.1 M Tris-HCl (pH 8.0), 0.5 M NaCl, 1 mM EDTA, and then with 25 mM Tris-HCl (pH 6.8). The bound proteins were eluted with 50 mM NaAc (pH4.0) into tubes containing 1.5 M Tris-HCl (pH 8-8). Fusion proteins were concentrated with Centricon YM 100 membranes (Amicon, Inc., Beverly, USA) and dialyzed against PBS. The final products were characterized by Western blotting with monoclonal anti-L1 antibody 324 and with a single-chain monoclonal antibody against CHL1.

Coating of L1-Fc and CHL1-Fc

The tissue culture wells and glass cover slips (1.1 cm diameter) were incubated overnight at 4° C. with 0.01% poly-L-lysine (PLL) and washed three times with distilled water. L1-Fc or CHL1-Fc diluted in Ca/Mg-free Hank's Balanced Salt Solution were applied overnight at 4° C., at the concentrations indicated in the text. The wells and coverslips were washed twice with Hank's and once with seeding medium just before plating cells.

Cell Cultures

Cerebellar granule neurons were prepared from 6-8 day-old mice as described (Keilhauer, G., et al (1985)). The cells were re-suspended and cultured in X1 medium (BME basal medium (Life Technologies) with 1 mg/ml BSA, 2.2 mg/ml NaHCO3, 100 µg/ml transferrin, 10 µg/ml insulin, 4 nM thyroxine 30 nM NaSeO3, 0.027 TIU/ml aprotinin, 5 µU/ml penicillin and 5 µg/ml streptomycin).

Hippocampal neurons were prepared from 18-day rat embryos as described (Lochter, A., et al (1991); Brewer, G. J., et al (1993)). Neurons were re-suspended and plated in serum-free Dulbecco's modified Eagle's medium/Nutrient Mix F12 (Life Technologies, Inc.) supplemented with N2 components, 33 mM D-glucose, I mM pyruvate, 1 mg/ml BSA, and 5 mM Hepes.

Neurite Outgrowth Assay

Cerebellar granule cells and hippocampal neurons were seeded into pro-treated 96-well tissue culture plates at a density of $1 \times 10^4$ cells or $5 \times 10^3$ cells per well, respectively, in 100 µl medium. Soluble fusion proteins were added, when used, 2 hours after seeding the cells, to avoid effects on initial adhesion. After 16-20 hours, the cells were fixed by adding 10 µl of 25% glutaraldehyde, and stained with toluidine blue (2.5% in 1% sodium borate). The lengths of individual neurite were analyzed and quantified with an IBAS image analysis system (Kontron). Only neurites that did not contact other cells and had a length of at least one cell diameter were measured. For each cell measured, the total length of all neurites was determined. In each experiment, 50 cells in each of three wells were analyzed. All data derived from three independent experiments.

Cell Survival Assay

Mitochondrial function was assessed as a measure of cell viability, by measuring the conversion of soluble MTT (3-[4, 5-dimethylthiazol-2-yl]2,5-diphenyltetrazolium bromide) into an insoluble dark blue formazan reaction product, using the procedure of Mosmann (Mosmann, t. (1983)) modified according to the instruction manual for the MTT Cell Proliferation Kit (Boehringer Mannheim). Cerebellar granule cells or hippocampal neurons were seeded in 96-well plates at densities of $1 \times 10^5$ or $5 \times 10^4$ cells/well, respectively. The percentage survival determined by the MTT assay was nearly identical to that determined by trypan blue exclusion staining. Values are expressed as the % of control wells (with PLL only) in each experiment. Viability was also assessed by differential staining of live and dead cells using an assay kit ("LIVE/DEAD® Viability/Cytotoxicity assay Kit™; Molecular Probes, Inc., Eugene, Oreg.) according to the manufacturers instructions. Fragmentation of DNA was analyzed as described (Hockenbery, D., et al (1990); D'Mello, et al (1993); Yang, R. J., et al (1996)).

Analysis of bcl-2 and c-Jun

Cerebellar granule cells were cultured in 100 mm dishes at a density of $7.5 \times 10^6$ cells per dish. At various times in culture, adherent and detached cells were collected, centrifuged, and extracts prepared as described (Yang, R. J., et al (1996)) with modifications. Cell pellets were lysed in 100 µl of cold lysis buffer (150 mM NaCl, 1% Triton X 100, 10 mM Tris-HCl (pH 7.4), 5 mM EDTA) containing a cocktail of protease inhibitors (20 µg/ml of antipain, chymostatin, leupeptin, pepstatina, aprotinin, all from Sigma) for 30 min at 4° C. Insoluble material was removed by centrifugation for 30 min at 14,000× g. For Western blots of BGI-2 protein, 50 µg protein were separated on 12% SDS-PAGE gels and transferred to nitrocellulose membranes (0.2 µm, BA 83, Schleicher & Schuell, Germany). The filters were blocked for 2 hr using 5% skim milk powder (Fluka) in 50 mM Tris-HCl (pH 7.5), 0.15 M NaCl, 0.1% Tween 20) and incubated with polyclonal rabbit antibody against the human Bcl-2 protein (#PC68, Oncogene Science Inc., Cambridge, Mass., USA) overnight at 4° C. in 1 µg/ml concentration. A horseradish peroxidase conjugated anti-rabbit secondary antibody and the enhanced chemiluminescence (ECL) system (Amersham) were used for detection.

Cell extracts for c-Jun western blotting were prepared as described by Ham, et al. (Ham, J., et al (1995)). For Western blots, 20 µg proteins were separated on 10% SDS-PAGE, and blotted onto Hybond-ECL nitrocellulose. The c-Jun was detected with affinity-purified rabbit polyclonal antibody against the peptide T P T P T Q F L C P K N V T D (amino acids, 73 to 87 in the N-terminal region of v-Jun) at concentration of 10 µg/ml (Oncogene Science Inc.) as described by Pfarr et al (Pfarr, C. M., et al (1994)), using a horseradish peroxidase-conjugated anti-rabbit secondary antibody and the ECL detection system.

Cytochemical Staining

Cerebellar granule cells grown on glass coverslips were washed with PBS, fixed for 5 min in 4% paraformaldehyde at room temperature, and washed again with PBS. Cells were stained with Hoechst 33258 (Sigma) at 1 µg/ml in water for 30 min at room temperature. Photomicrographs were obtained using a Zeiss Axiophot microscope.

Results

L1-Fc and CHL1-Fc Stimulate Neurite Outgrowth of Small Cerebellar and Hippocampal Neurons.

Figure 38A:
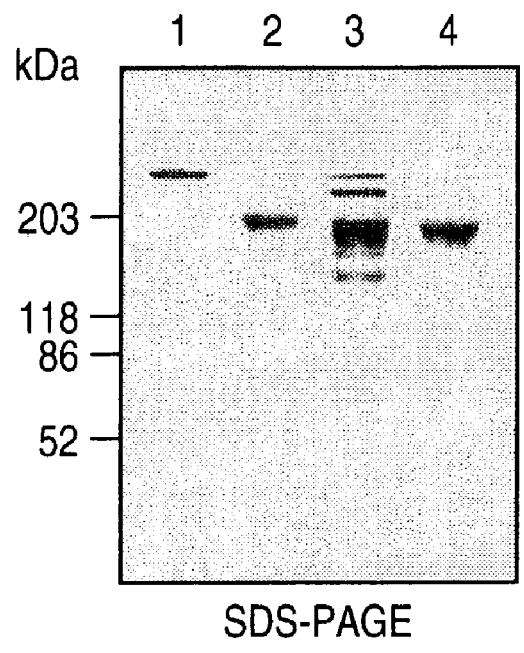
Figure 38B:
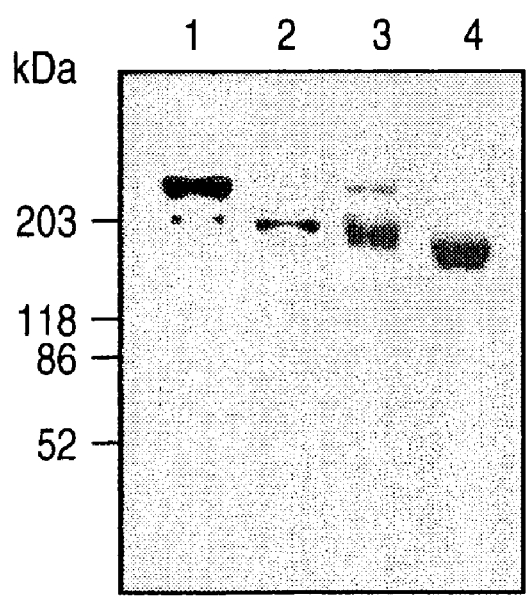

Previous studies have shown that soluble chimeric proteins consisting the extracellular domain of a neural adhesion molecule fused to the Fc part of human immunoglobulin can promote neurite extension from neurons of the central nervous system (Doherty, P., et al (1995); Voikmer, H., et al (1996)). We combined elements of previously used expression plasmid (Simmons, D. L. (1993); Bebbington, C. R. (1991)) in order to achieve high expression of fusion proteins in stably transformed CHO-K1 cells. The fusion proteins comprise the extracellular domains of mouse L1 or CHL1, in conjunction with the Fc part of human immunoglobulin IgG1. After purification of the secreted proteins by affinity chromatography on protein A-Sepharose, L1-Fc gave a single band in SDS-PAGE, corresponding to approximately 400 kDa under non-reducing conditions and 200 kDa under reducing conditions (FIG. 38A, lanes 1 and 2). Affinity purified CHL1-Fc gave several bands under non-reducing conditions and one band corresponding to 190 kDa upon reduction (FIG. 38A, lanes 3 and 4). The molecular weights are consistent with the extracellular domains being glycosylated to a similar extent as in L1 and CHL1 from mouse brain. The L1-Fc and CHL1-Fc were readily detectable by Western blot analysis with the cognate antibodies (FIG. 38B).

Figure 39B:
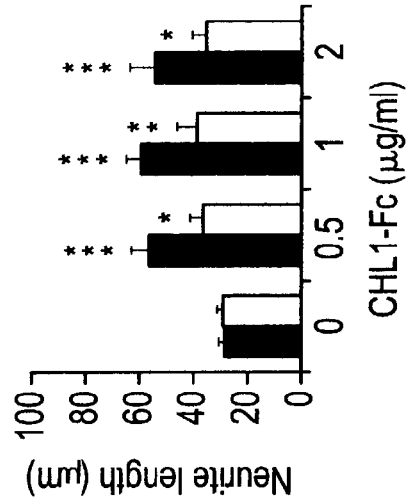
Figure 39D:
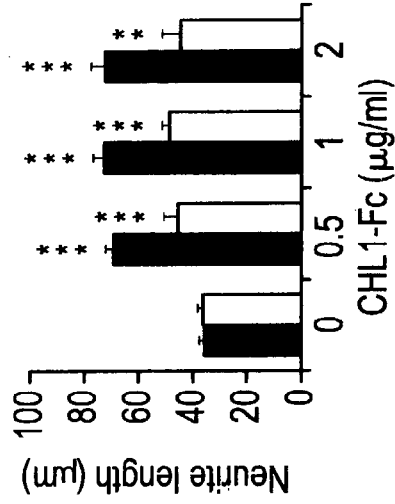
Figure 39A:
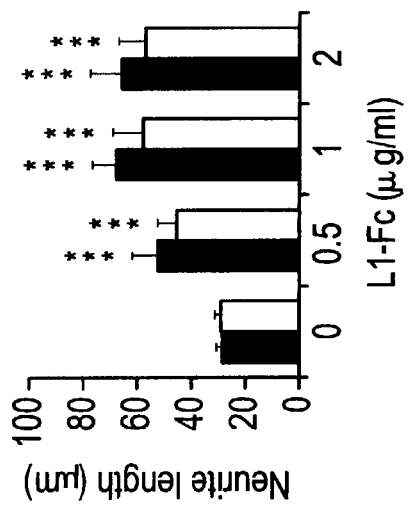
Figure 39C:
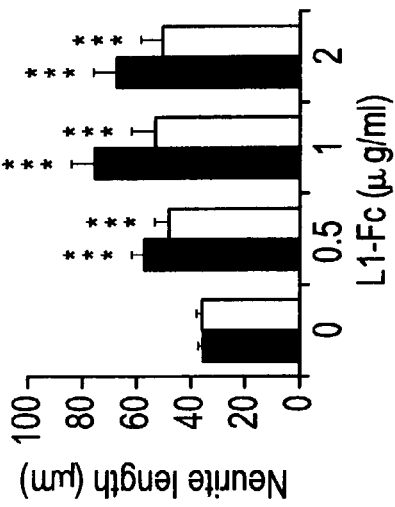

For the neurite outgrowth assay, cerebellar granule cells from 6-to-8-day old mice were prepared and cultured in chemically defined serum-free medium as described by Keilhauer, et al. (Keilhauer, G., et al (1985)). L1-Fc and CHL1-Fc were immobilized on dishes pre-coated with poly-L-lysine (PLL) (defined as substrate-bound form), or directly added to the cultures after cells had attached (soluble form). The average total length of neurites per cell was determined. Compared to PLL alone, both L1-Fc and CHL1-Fc added at 0.5 µg/ml to 2.0 µg/ml stimulated neurite outgrowth up to 2 to 3 fold (FIGS. 39A and B). Both the soluble and substrate-bound forms were active, the latter somewhat more so. The Fc moiety alone has previously been shown to have no effect on neurite outgrowth (Doherty, P., et al (1995); Voikmer, H., et al (1996)). The effect of L1-Fc and CHL1-Fc was also tested with hippocampal neurons isolated from 18-day mt embryos, and, here too, a stimulation was observed (FIGS. 39C and 39D).

Figure 40A:
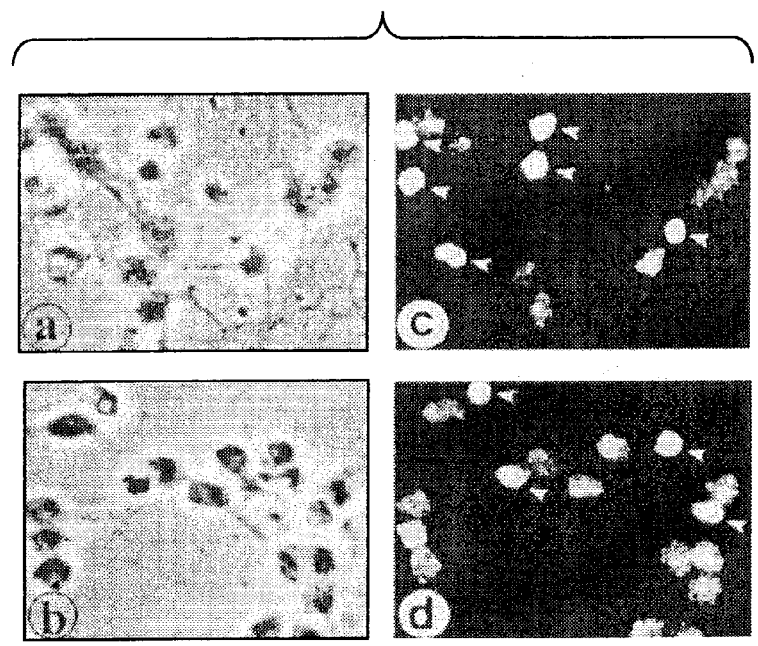
Figure 40B:
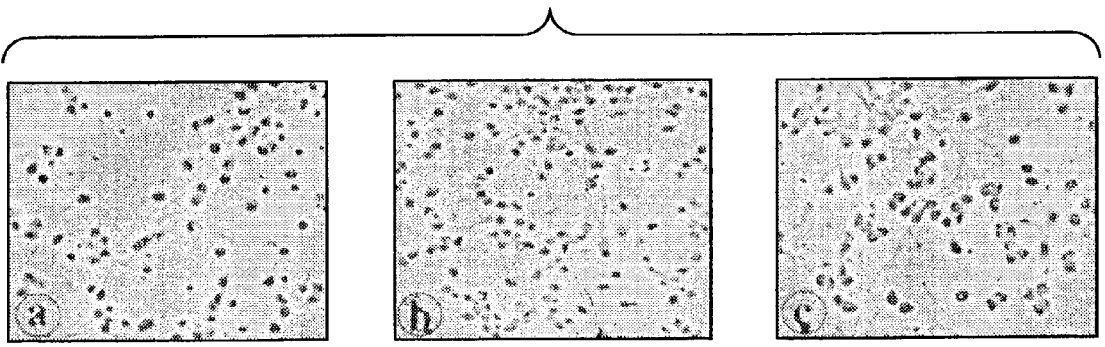

Cerebellar Granule Cells Maintained in Serum-Free Medium Undergo Programmed Cell Death When cerebellar granule cells are cultured in serum-free medium at high densities ($2.5\text{-}3.0\times10^5$ cells/cm$^2$), less than 10% of the seeded cells survive after two weeks. We asked whether the cell death occurring in these cultures could be attributed to apoptosis. Condensation of chromatin and fragmentation of nuclei are typical features of apoptotic cells (Raff, M. C. (1992); Ellis, R., et al (1991)). Upon staining of cerebellar granule cells with the dye Hoechst 33258, nuclear condensation was indeed observed (FIG. 40A). Moreover, DNA was degraded, with cleavage of chromatin into nucleosomal fragments (data not shown). Morphological features of the cerebellar granule cells after 5 days in culture with or without L1-Fc or CHL1-Fc are shown in FIG. 40B. Neurons maintained on PLL alone were often only partially attached and neurite were sometimes fragmented. Treatment with L1-Fc or CHL1-Fc gave denser, generally healthier-looking cultures, with a complex network of neurite.

Promotion of Survival by L1-Fc and CHL1-Fc

Figure 41A:
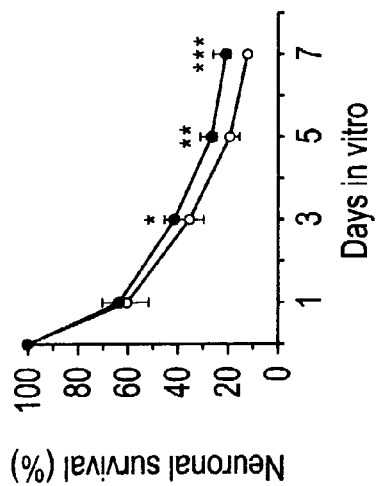
Figure 41B:
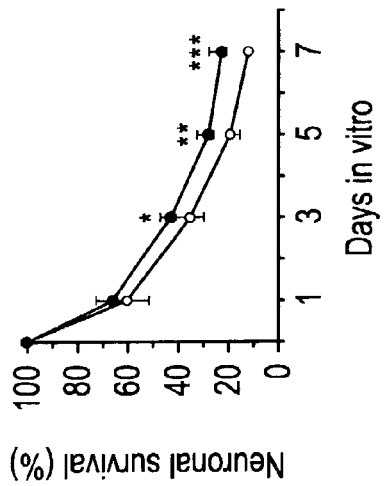
Figure 41C:
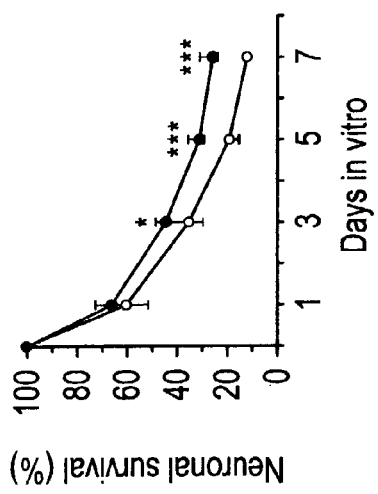
Figure 41D:
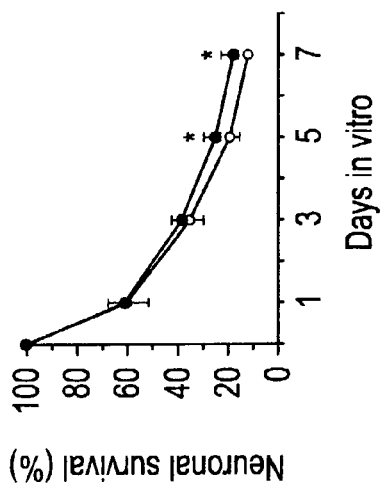
Figure 42C:
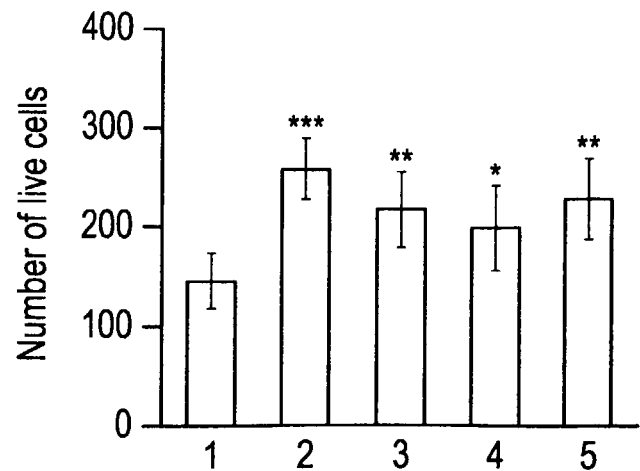

The time course of cell death of cerebellar granule calls was determined in the presence and absence of L1-Fc and CHL1-Fc. When estimated by the MTT method, the fraction of viable cells in untreated cultures gradually dropped by day 7 reaching about 12% of the value at the time of seeding (FIG. 41). L1-Fc offered as a substrate increased survival significantly at all times after 3 days, with about 26% surviving at 7 days (FIG. 41A). L1-Fc in solution was somewhat less effective, giving about 20% survival at 7 days (FIG. 41B). For CHL1-Fc the soluble form was most effective, and could increase survival to about 22% (FIG. 41D) compared to 18% when coated (FIG. 41C). Maximal promotion of survival was achieved at a dose of 1 µg/ml fusion protein, either in soluble or coated form (FIGS. 42A and 42B), and a significant effect was already seen at 0.5 µg/ml. A double staining procedure confirmed the results of the MTT test (FIG. 42C). NCAM-Fc had no effect on survival (not shown).

It was also investigated as to whether L1-Fc and CHL1-Fc could enhance the survival of neurons isolated from embryonic rat hippocampus. About 10% of neurons survived after 2 weeks when seeded at a density of $5\times10^4$ cells/cm$^2$ on PLL and maintained in DMEM/F12 serum-free supplemented medium. Glial cells were less than 2% of all cells after this culture period (not shown). The dose-response curve (FIG. 43) showed that both L1-Fc and CHL1-Fc enhanced survival after 5 days in culture, with a maximal effect 1 µg/ml.

L1-Fc Enhances Bcl-2 Expression but Decreases c-Jun in Cerebellar Granule Cells

Figure 44A:
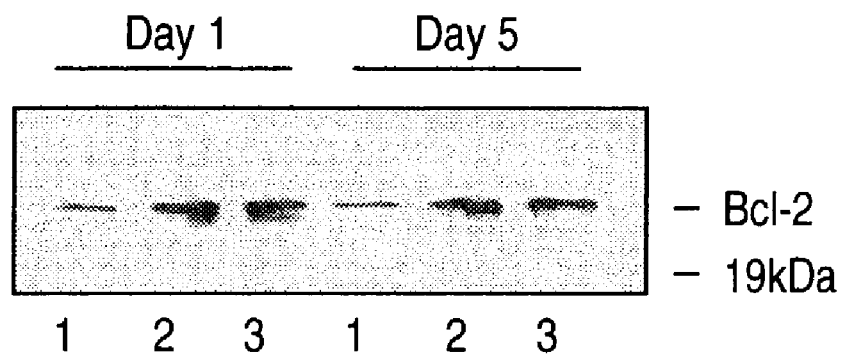
Figure 44B:
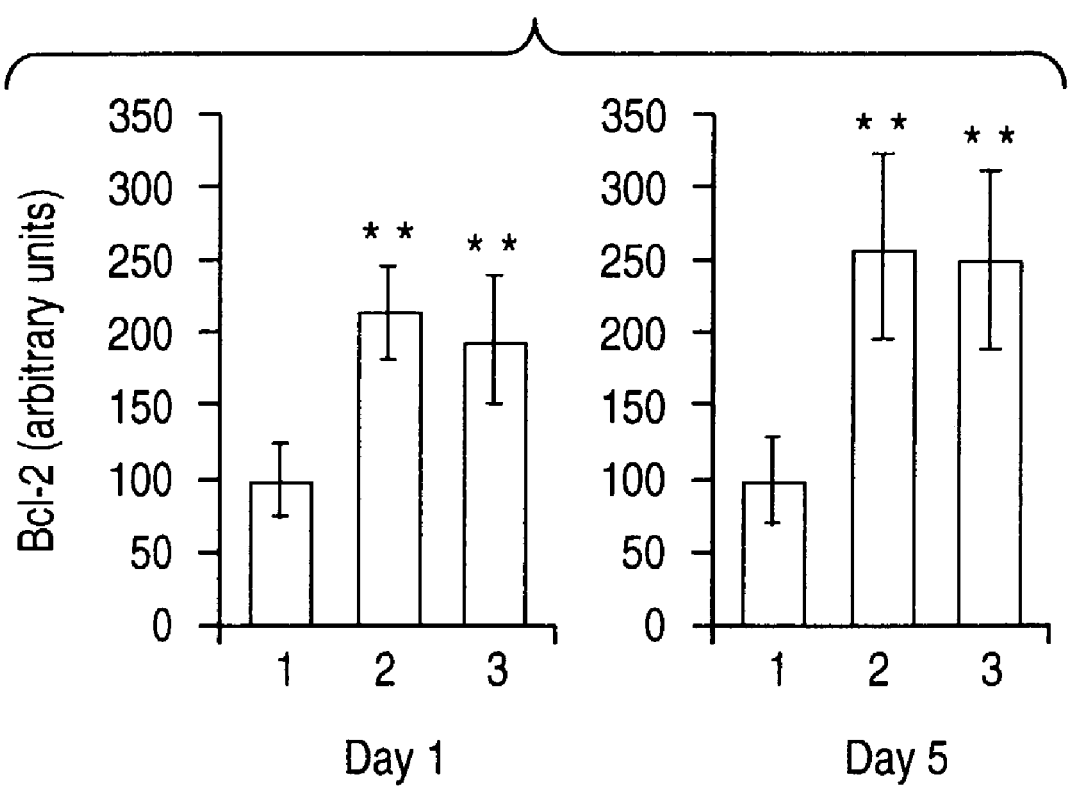

Having established that L1-Fc and CHL1-Fc can increase survival of neurons derived from the central nervous system, the expression of Bcl-2 was examined as it is a biochemical signal that has been shown to inhibit apoptosis (Merry, D. E., et al (1997)). Bcl-2 levels in cerebellar granule cells cultured for 1 or 5 days were assessed by Western blotting. The presence of L1-Fc, in either soluble or substrate-bound form, led to higher levels of Bcl-2 protein (FIG. 44A). Already at day 1 there was a more than 2-fold increase of Bcl-2 protein in treated neurons compared with neurons growing on PLL alone, and the effect was sustained until day 5 (FIG. 44B).

The role of c-Jun was also investigated as it was thought that it might be involved in the signalling of L1 in prevention of neuronal cell death. L1-Fc has no significant effect at day 1. However, treatment with L1-Fc for longer times (5 days) reduced c-Jun to about 50% compared to controls (FIG. 45).

Discussion

In this study, it has been shown that two members of the L1 family, L1 and CHL1, are significant promoters of neurite outgrowth and neuronal survival in cell culture. That L1-Fc stimulates neurite outgrowth was expected from previous work (Doherty, P., et al (1995)). CHL1 has been shown to promote neurite outgrowth when presented by transfected cells (R. Hillenbrand, M. Molthagen, D. Montag, and M. Schachner, submitted), and it is shown here that also the purified extracellular domain has this activity. It is noteworthy that both soluble and substrate-bound forms of L1-Fc and CHL1-Fc promote neurite outgrowth, CHL1 is expressed by neuronal cell types in part different from those expressing L1, and CHL1 is up-regulated in glial cells after a lesion; with CHL1-Fc we now have available to us a reagent to look at the impact of CHL1 on neurite outgrowth from different neuronal populations in vitro and in vivo. L1 and CHL1 not only promote neurite outgrowth, but also exert positive effects on survival of two types of neuronal cell populations in culture, cerebellar granule cells and hippocampal neurons (FIGS. 41-43). Stimulation of L1 by a specific monoclonal antibody (Appel, F., et al (1995)) has been reported to enhance survival of dopaminergic neurons in cultures derived from embryonic mesencephalon of rats (Hulley, P. (1998)). Thus, L1, possibly by homophilic interactions, can enhance survival of at least three types of L1 positive neurons.

The up-regulation of Bcl-2 observed upon treatment with L1-Fc (FIG. 44) may be compared to the over expression achieved by driving the bcl-2 gene with heterologous promoters (Farlia, P. G., et al (1995); Zhong, L. T, et al (1993); Kane, U. J., et al (1995)). Neuronal survival is improved in both cases, supporting the notion that L1 influences neuronal survival at least in part via the antiapoptotic activity of Bcl-2.

High levels of c-Jun protein (Ham, J., et al (1995)) and mRNA (Estus, S., et al (1994)) have been observed in cultured sympathetic neurons deprived of nerve growth factor and undergoing apoptosis, and the accumulation of c-Jun has also been observed in apoptotic sympathetic neurons in vivo (Messina, A., et al (1996)). Apoptosis in the culture system could be blocked by injection of anti-c-Jun antibody (Estus, S., et al (1994)) or expression of a dominant-negative form of c-Jun (Ham, J., et al (1995)), showing that the expression of c-Jun is a necessary for the cell death program. The drop in c-Jun levels produced by treatment with L1-Fc (FIG. 45) may therefore represent another of the mechanisms by which L1 promotes survival.

NCAM-Fc, which was used as a control in our experiments, promoted neurite outgrowth but did not enhance neuronal survival. However, NCAM does promote survival of cultured oligodendrocyte (Gard, A. L., et al (1996)), indicating that different cell types may use different cell adhesion molecules for survival. Interestingly, also the myelin associated glycoprotein (MAG) shares with NCAM its positive effects on survival of oligodendrocyte; mutants doubly deficient for NCAM and MAG show enhanced degeneration of myelin profiles in the peripheral nervous system (Carenini, S., et al (1997)).

The studies of NCAM and MA G mutants, together with the results presented here, demonstrate that morphogenetically active recognition molecules that shape the nervous system during development may have functional roles in supporting survival of neuronal cells at late stages of development and in the adult. Contact between L1 positive cells may promote survival by triggering L1, and anything increasing accumulation of L1 at the cell surface would contribute to this effect. Since the expression of several recognition molecules has been shown to be regulated by neurotrophins (nerve growth factor enhances L1 expressions in neurons and Schwann cells (Seilheimer, B., et al (1987); Mann, D. A., et al (1989); Itoh, K., et al (1995)); transforming growth factor (TGF) β2 increases NCAM expression (Saad, B., et al (1991)), neurotrophins may well exert their actions on neuronal cell survival in part by promoting the synthesis of recognition molecules present at the cell surface and in the extracellular matrix.

Although both L1 and NCAM have signalling pathways in common, including the opening of calcium channels (Williams, E. J., et al (1992); Doherty, P., et al (1991); Walsh, F. S., et al (1992)) and activation of the MAP kinase cascade (Schmid, R.-S., Graff, R. D., Schaller, M., Chen, S., Schachner, M. Hemperly, J. J., and Maness, P. F., submitted and unpublished data) there must also be differences, as shown by the differential effects on cell survival.

The following is an alphabetical list of the references referred to herein. The disclosures of the listed references as well as other publications, patent disclosures or documents recited herein, are all incorporated herein by reference in their entireties.

Adams, M. D., Dubnick, M., Kerlavage, A. R., Moreno, R., Kelley, J. M., Utterback, T. R., Nagle, J. W., fields, C. and Venter, J. C. (1992). Sequence identification of 2375 human brain genes. *Nature.* 355:632-634.

Adams, M. D., Kerlavage, A. R., Fields, C. and Venter, J. C. (1993). 3400 new expressed sequence tags identify diversity of transcripts in human brain. *Nature Genet.* 4:258-267.

Appel, F., Holm, J., Conscience, J. F. and Schachner, M. (1993). Several extracellular domains of the neural cell adhesion molecule L1 are involved in neurite outgrowth and cell body adhesion. *J. Neurosci.* 13:4764-4775.

Appel, F., Holm, J., Conscience, J.-F., von Bohlen und Halbach, F., Faissner, A., James, P. and Schachner, M. (1995). Identification of the border between fibronectin type III homologous repeats 2 and 3 of the neural cell adhesion molecule L1 as a neurite outgrowth promoting and signal transducing domain. *J. Neurobiol.* 28:297-312.

Arquint, M., Roder, J., Chia, L.-S, Down, J., Wilkinson, D., Bayley, H., Braun, P. and Dunn, R. (1987). Molecular cloning and primary structure of myelin-associated glycoprotein. *Proc. Natl. Acad. Sci.* (*USA*) 84:600-604.

Baron, M., Main, A. L., Driscoll, P. C., Mardon, H. J., Boyd, J. and Campbell, I. D. (1992). H-NMR assignment and secondary structure of the cell adhesion type III module of fibronectin. *Biochem.* 31:2068-2073.

Bartheis, D., Santoni, M.-J., Wille, W., Ruppert, C., Chaix, J.-C., Hirsch, M.-R., Fontecilla-Champs, J. C. and Goridis, C. (1987). Isolation and nucleotide sequence of mouse N-CAM cDNA that codes for a Mr 79000 polypeptide without a membrane-spanning region. *EMBO J.* 6:907-914.

Bartsch, S., Bartsch, U., Dörries, U., Faissner, A., Weller, A., Ekblom, P., and Schachner, M. (1992). Expression of tenascin in the developing and adult cerebellar cortex. *J. Neurosci.* 12:736-749.

Berglund, E. O. and Ranscht, B. (1994). Molecular cloning and in situ localization of the human contactin gene (CNTN1) on chromosome 12q11-q12. *Genomics* 21:571-582.

Bieber, A. J., Snow, P. M., Hortsch, M., Patel, N. H., Jacobs, J. R., Traquina, Z. R., Schilling, J. and Goodman, C. S. (1989). *Drosophila* neurogilan: a member of the immunoglobulin superfamily with extensive homology to the vertebrate neural cell adhesion molecule L1. *Cell* 59:447-460.

Bixby, J. L., Lilien, J. and Reichardt, L. F. (1988). Identification of the major proteins that promote neuronal process outgrowth on Schwann cells in vitro. *J. Cell Biol.* 107:353-362.

Bollenson, E. and Schachner, M. (1987). The peripheral myelin glycoprotein Po expresses the L2/NK-1 and L3 carbohydrate structures shared by neural adhesion molecules. *Neurosci. Lett.* 82:77-82.

Bradford, M. M. (1976). A rapid and sensitive method for quantitation of microgram quantities of protein utilizing the principle of protein-dye binding. *Anal. Biochem.* 72:248-254.

Brummendorf, T., Wolff, J. M., Frank, R. and Rathjen, F. G. (1989). Neural cell recognition molecule F11: homology with fibronectin type III and immunoglobulin type C domains. *Neuron* 2:1351-1361.

Brummendorf, T. and Rathjen, F. G. (1993). Axonal glycoproteins with immunoglobulin and fibronectin type III-related domains in vertebrates: structural features, binding activities, and signal transduction. *J. Neurochem.* 61:1207-1219.

Brummendorf, T. and Rathjen, F. G. (1994). Cell adhesion molecules 1: immunoglobulin superfamily. In Sheterline, P., ed. *Protein Profile*, Academic Press, London, 951-1058.

Burgoon, M. P., Grumet, M., Mauro, V., Edelman, G. M. and Cunningham, B. A. (1991). Structure of the chicken neuron-glia cell adhesion molecule Ng-CAM: origin of the polypeptide and relation to the Ig superfamily. *J. Cell Biol.* 112:1017-1029.

Chomczynski, P. and Sacchi, N. (1987). Single-step method of RNA isolation by acidic guanidinium thiocyanate-phenol-chloroform extraction. *Anal. Biochem.* 162:158-159.

Connelly, M. A., Grady, R. C., Mushinski, J. F. and Marcu, K. B. (1994). PANG, a gene encoding a neuronal glycoprotein, is ectropically activated by intracisternal A-type particle long terminal repeats in murine plasmacytomas. *Proc. Natl. Acad. Sci.* (*USA*) 91:1337-1341.

Cunningham, B. A., Hemperley, J. J., Murray, B. A., Prediger, E. A., Brackenbury, R. and Edelman, G. M. (1987). Neural cell adhesion molecule: structure, immunoglobulin-like domains, cell surface modulation, and alternative RNA splicing. *Science* 236:799-806.

Davis, J. Q., McLaughlin, T. and Bennett, V. (1993). Ankyrin-binding proteins related to nervous system cell adhesion molecules: Candidates to provide transmembrane and intracellular connections in adult brain. *J. Cell Biol.* 121: 121-133.

Davis, J. and Bennett, V. (1994). Ankyrin binding activity shared by the neurofascin/L1/NrCAM family of nervous system cell adhesion molecules. *J. Biol. Chem.* 269:27163-27166.

Dodd, J., Morton, S., Karagogeos, D., Yamamoto, M. and Jessell, T. (1988). Spatial regulation of axonal glycoprotein expression on subsets of embryonic spinal neurons. *Neuron* 1:105-116.

Dorries, U., Bartsch, U., Nolte, C., Roth, J. and Schachner, M. (1993). Adaption of a non-radioactive in situ hybridisation method to electron microscopy: Detection of tenaxcin mRNAs in mouse cerebellum with digoxigenin-labelled probes and gold-labelled antibodies. *Histochem.* 99:251-262.

Edelman, G. M. (1970). The covalent structure of a human IgG. XI. Functional implications. *Biochem.* 9:3197-3205.

Edelman, G. M. (1988). Morphoregulatory molecules. Biochem. 27:3533-3543.

Erickson, H. P. (1993). Tenascin-C, tenascin-R, and tenascin-X: A family of talented proteins in search of functions. *Curr. Opin. Cell Biol.* 5:869-876.

Faissner, A., Teplow, D. B., Kubler, D., Keilhauer, G., Kinzel, V. and Schachner, M. (1985). Biosynthesis and membrane topography of the neural cell adhesion molecule L1. *EMBO J.* 4:3105-3113.

Fearon, E. R., Cho, K. R., Nigro, J. M., Kern, S. E., Simons, J. W., Ruppert, J. M., Hamilton, S. R., Preisinger, A. C., Thomas, G., Kinzler, K. W. and Vogelstein, B. (1990). Identification of a chromosome 18q gene that is altered in colorectal cancers. *Science* 247:49-56.

Feisenfeld, D. P., Hynes, M. A., Skolor, K. M., Furley, A. J. and Jessel, T. M. (1994). TAG-1 can mediate homophilic binding, but neurite outgrowth on TAG-1 requires an L1-like molecule and $B_1$ integrins. *Neuron* 12:675-690.

Frei, T., von Bohlen und Halbach, F., Wille, W. and Schachner, M. (1992). Different extracellular domains of the neural cell adhesion molecule (N-CAM) are involved in different functions. *J. Cell Biol.* 118:177-194.

Furley, A. J., Morton, S. B., Manalo, D., Karagogeos, D., Dodd, J. and Jessell, T. M. (1990). The axonal glycoprotein TAG-1 is an immunoglobulin superfamily member with neurite outgrowth-promoting activity. *Cell* 61:157-170.

Gennarini, G., Cibelli, G., Rougon, G., Mattei, M. G. and Goridis, C. (1989). The mouse neuronal cell surface protein F3: A phosphatidylinositol-anchored member of the immunoglobulin superfamily related to chicken contactin. *J. Cell Biol.* 109:775-788.

Gennarini, G., Durbec, P., Bonad, A., Rougon, G. and Gordis, C. (1991). Transfected F3/F11 neuronal cell surface protein mediates intercellular adhesion and promotes neurite outgrowth. *Neuron* 6:595-606.

Glasgow, L. R., Paulson, J. C. and Hill, R. L. (1977). Systematic purification of five glycosidases from *Streptococcus* (*Diplococcus*) *pneumoniae*. *J. Biol. Chem.* 252:8615-8623.

Grumet, M., Hoffman, S., Chuong, C. M. and Edelman, G. M. (1984). Polypeptide components and binding functions of neuron-glia cell adhesion molecules. *Proc. Natl. Acad. Sci. USA* 81:7989-7993.

Grumet, M., Mauro, V., Burgoon, M. P., Edelman, G. M. and Cunningham, B. A. (1991). Structure of a new nervous system glycoprotein, Nr-CAM, and its relationship to subgroups of neural cell adhesion molecules. *J. Cell Biol.* 113:1399-1412.

Guénard, V., Gwynn, L. and Wood, P. (1994). Astrocytes inhibit Schwann cell proliferation and myelination of dorsal root ganglion neurons in vitro. *J. Neurosci.* 14:2980-2992.

Hall, H., Liu, L., Schachner, M. and Schmitz, B. (1993). The L2/HNK-1 carbohydrate mediates adhesion of neural cells to laminin. *Eur. J. Neurosci.* 5:34-42.

Hall, H., Vorherr, T. and Schachner, M. (1995). Characterization of a 21 amino acid peptide sequence of the laminin G2 domain that is involved in HNK-1 carbohydrate binding and cell-adhesion. *Glycobiology* 5:435-441.

Hasler, T. H., Rader, C., Stoeckli, E. T., Zuellig, R. A. and Sonderegger, P. (1993). cDNA cloning, structural features, and eucaryotic expression of human TAG-1/axonin-1. *Eur. J. Biochem.* 211:329-339.

Hein, J. (1990). Unified approach to alignment and phylogenies. *Meth. Enzymol.* 183:628-645.

Heijne von, G. (1986). A new method for predicting sequence cleavage sites. *Nucl. Acids Res.* 14:4683-4690.

Hlavin, M. L. and Lemmon, V. (1991). Molecular structure and functional testing of human L1 CAM: An interspecies comparison. *Genomics* 11:416-423.

Holm, J., Appel, F. and Schachner, M. (1995). Several extracellular domains of the neural cell adhesion molecule L1 are involved in homophilic interactions. *J. Neurosci. Res.* 42:9-20.

Hubbard, S. C. and Ivatt, R. J. (1981). Synthesis and processing of aspargine-linked oligosaccharides. *Annu. Rev. Biochem.* 50:555-583.

Husmann, K., Faissner, A. and Schachner, M. (1992). Tenascin promotes cerebellar granule cell migration and neurite outgrowth by different domains in the fibronectin type-III repeats. *J. Cell Biol.* 116:1475-1486.

Hynes, R. O. (1992). Integrins: Versatility, modulation, and signaling in cell adhesion. *Cell* 68:11-25.

Kanla, G. S., Han, P. L., Kim, Y. T., and Bellen, H. (1993). NEUROMUSCULIN, a *Drosophila* gene expressed in peripheral neuronal precursors and muscles, encodes a cell adhesion molecule. *Neuron.* 11:673-687.

Kayyam, J. F., Roman, J. M., de la Rosa, E. J. Schwarz, U. and Dreyer, W. J. (1992). Bravo/NrCAM is closely related to the cell adhesion molecules L1 and Ng-CAM and has a similar heterodimer structure. *J. Cell Biol.* 118:1259-1270.

Keilhauer, G., Faissner, A., and Schachner, M. (1986). Differential inhibition of neurone-neurone, neurone-astrocyte and astrocyte-astrocyte adhesion by L1, L2, and N-CAM antibodies. *Nature* 316:728-730.

Kluxen, F. W., Bruns, C. and Lubbert, H. (1992). Expression cloning of rat brain somatostatin receptor cDNA. *Proc. Natl. Acad. Soc. (USA)*, 89:4618-4022.

Kluxen, F. W. and Lubbert, H. (1993). Maximal expression of recombinant cDNAs in COS cells for use in expression cloning. *Anal. Biochem.* 208:352-356.

Kornblihtt, A. R., Umezawa, K. Vibe-Pedersen, K. and Baralle, F. E. (1985). Primary structure of human fibronectin: differential splicing may generate at least 10 polypeptide from a single gene. *EMBO J.* 4:1755-1759.

Kozak, M. (1987). At least six nucleotides preceding the AUG initiator codon enhance (translation in mammalian cells. *J. Mol. Biol.* 196:947-950.

Kruse, J., Mailhammer, R., Wernecke, H., Falssner, A., Sommer, I., Goridis, C. and Schachner, M. (1984). Neural cell adhesion molecules and myelin-associated glycoprotein share a common carbohydrate moiety recognized by monoclonal antibodies L2 and HNK-1. *Nature* 311:153-155.

Kunemund, V., Jungawala, F. B., Fischer, G. Chou. D. K. H., Keilhauer, G. and Schachner, M. (1988). The L2/Hnk-1 carbohydrate of neural cell adhesion molecules is involved in cell interactions. *J. Cell Biol.* 106:213-223.

Kyte, J. and Doolittle, R. F. (1982). A simple method for displaying the hydropathic character of a protein. *J. Mol. Biol.* 157:105-132.

Laemmil. U. K. (1970). Cleavage of structural proteins during the assembly of the head of bacteriophage T4. *Nature* 227:680-685.

Laeng. P., Decimo, D., Pettmann, B. Janet. T. and Labourdette. G. (1994). Retinoic acid regulates the development of oligodendrocyte precursor cells in vitro. *J Neurosci. Res.* 39:613-633.

Lai, C., Brow, M. A., Nave. K. A. Noronha. A. B., Quarles, R. H., Bloom, F. E., Milner, R. J. and Sutcliffe, J. G. (1987). Two forms of 18236/myelin-associated glycoprotein, a cell adhesion molecule for postnatal neural development, are produced by alternative splicing. *Proc. Natl. Acad. Sci. (USA).* 84:4337-4341.

Leahy, D. J., Hendrickson, W. A., Aukil, I. and Erickson, H. P. (1992). Structure of a fibronectin type-III domain from tenascin phased by MAD analysis of the selenomethionyl protein. *Science* 258:987-991.

Lemmon, V., Farr, K. L. and Lagenaur, C. (1989). L1-mediated axon growth occurs via a hemophilic binding mechanism. *Neuron* 2:1597-1603.

Lipman, D. J. and Pearson, W. R. (1985). Rapid and sensitive protein similarity searches. *Science* 227:1435-1441.

Main, A. L., Harvey, T. S., Baron, M., Boyd, J. and Campbell, I. D. (1992). The three-dimensional structure of the tenth type III module of fibronectin: an insight into RGD-mediated interactions. *Cell* 71:671-678.

Mark, M. R., Scadden, D. T., Wang, Z., Gu. O. Goddard, A, and Godowski, P. J. (1994). Rse, a novel receptor-type tyrosine kinase with homology to Ax1/Ufo, is expressed at high levels in the brain. *J. Biol. Chem.* 269:10720-10728.

Martini, R. and Schachner, M. (1986). Immunoelectron microscopic localization of neural cell adhesion molecules (L1, N-CAM, and MAG) and their shared carbohydrate epitope and myelin basic protein in developing sciatic nerve. *J. Cell Biol.* 103:2439-2448.

McCarthy, K. D. and De Vellis J. (1980). Preparation of separate astroglial and oligodendroglial cell cultures from rat cerebral tissue. *J. Cell Biol.* B5:890-902.

McGarry, R. C., Helfand, S. L., Quarles, R. H. and Roder, J. C. (1983). Recognition of myelin-associated glycoprotein by the monoclonal antibody HNK-1. *Nature* 306:376-378.

Melton, D. A., Krieg, P. A., Rebagliati, M. A., Maniatis, T., Zinn, K. and Green, M. R. (1984). Efficient in vitro synthesis of biologically active RNA and RNA hybridization probes from plasmids containing a SP6 promoter. *Nucl. Acids Res.* 12:7035-7056.

Miura, M. Kobayasahi, M., Asou, H. and Uyemura, K. (1991). Molecular cloning of cDNA encoding the rat neural cell adhesion molecule L1. Two L1 isoforms in the cytopiesmic region are produced by differential splicing. *FEBS Lett.* 289:91-95.

Moos, M., Tacke, R. Scherer, H., Teplow, D., Fruh. K. and Schachnor, M, (1988). Neural adhesion molecule L1 as a member of the immunoglobulin superfamily with binding domains similar to fibronectin. *Nature* 334:701-703.

Moscoso, L. M. and Sanes, J. R. (1995). Expression of four immunoglobulin superfamily adhesion molecules (L1, Nr-CAM/BRAVO. Neurofascin/ABGP, and N-CAM) in the developing mouse spinal cord. *J. Comp. Neurol.* 352:321-334.

Pesheva, P., Gennarini, G., Goridis, C. and Schachner, M. (1993). The F3/11 cell adhesion molecule mediates the repulsion of neurons by the extracellular matrix glycoprotein J1-160/180. *Neuron* 10:69-82.

Pierceall, W. E., Cho, K. R., Getzenberg, R. H., Roale, M. A., Hedrick, L., Vogelstein, B. and Fearon. E. R. (1994). NIH3T3 cells expressing the deleted in colorectal cancer tumor suppressor gene product stimulate neurite outgrowth in rat PC 12 pheochromocytoma cells. *J. Cell Biol.* 124:1017-1027.

Pierschbacher, M. D. and Ruosiahti, E. (1984). Cell attachment activity of fibronectin can be duplicated by small synthetic fragments of the molecule. *Nature* 309:30-33.

Pisano, A., Redmond, J. W., Williams, K. L. and Gooley, A. A. (1993). Glycosylation sites identified by solid-phase Edman degradation: O-linked glycosylation motifs on human glycophorin A. *Glycobiol.* 3:429-435.

Poltorak, M., Sadoul, R. Kelhauer, G., Landa, C., Faharing, T. and Schachner, M. (1987). The myelin-associated glycoprotein (MAG), a member of the L2/HMNK-1 family of neural cell adhesion molecules, is involved in neuron-oligodandorocyte and oligodendrocyte-oligodendrocyte interaction. *J. Cell Biol.* 105:1893-1899.

Prince, J. T., Alberti, L., Healy, P. A., Nauman, S. J. and Stallcup, W. B. (1991). Molecular cloning of NILE glycoprotein and evidence for its continued expression in mature rat CNS, *J. Neurosci. Res.* 30:567-581.

Pulido, D., Campuzano, S., Kida, T., Modolell, J. and Barbacid, M. (1992). Dtrk, a *Drosophila* gene related to the trk family of neurotrophin receptors, encodes a novel class of neural cell adhesion molecule. *EMBO J.* 111:391-404.

Ranscht, B. (1988). Sequence of contactin, a 130 kD glycoprotein concentrated in areas of interneuronal contact, defines a new member of the immunoglobulin supergene family in the nervous system. *J. Cell Biol.* 107:1561-1573.

Rathjen, F. G. and Schachner, M. (1984). Immunocytological and biochemical characterization of a new neuronal cell surface component (L1 antigen) which is involved in cell adhesion. *EMBO J.* 3:1-10.

Rathjen, F. G. and Jessell, T. M. (1991). Glycoproteins that regulate the growth and guidance of vertebrate axons: Domains and dynamics of the immunoglobulin/fibronectin type III subfamily. *Semin. Neurosci.* 3:297-307.

Ruoslahtl, E. and Pierschbacher, M. D. (1987). New perspectives in cell adhesion: RGD and integrins. *Science* 238:491-497.

Ruoslahtl, E. (1988). Fibronectin and its receptors. *Annu. Rev. Biochem.* 57:375-413.

Rutlshauser, U. (1993). Adhesion molecules of the nervous system. *Curr. Opin. Neurobiol.* 3:709-715.

Sadoul, K., Sadoul, R., Faissner, A. and Schachner, M. (1988). Biochemical characterization of different molecular forms of the neural cell adhesion molecule L1. *J. Neurochem.* 50:510-521.

Salzer, J. L. Holmes, W. P. and Colman, D. R. (1987). The amino acid sequences of the myelin-associated glycoproteins: Homology to the immunoglobulin gene superfamily. *J. Cell Biol.* 104:957-965.

Sambrook, J., Fritsch, E. F. and Maniatis, T. (1989). Molecular cloning: A laboratory manual. Cold Spring Harbor Laboratory, Cold Spring Harbor, N.Y.

Sanger, F. S., Nicklen, S. and Coulson, A. R. (1977). DNA sequencing with chain-terminating inhibitors. *Proc. Natl. Acad. Sci. (USA)* 74:5463-5467.

Schachner, M. (1991). Neural recognition molecules and their influence on cellular functions. In Letoumeau, P. C., Kater, S. B. and Macagno, E. R., eds. *The Nerve Growth Cone*. Raven Press, NY, 237-254.

Schachner, M. (1994). Neural recognition molecules in disease and regeneration. *Curr. Opin. Neurobiol.* 4:726-734.

Schnitzer, J. and Schachner, M. (1981). Expression of Thy-1, H-2, and NS-4 cell surface antigens and tetanus toxin receptors in early postnatal and adult mouse cerebellum. *Neuroimmunol.* 1:429-456.

Seilheimer, B. and Schachner, M. (1988). Studies of adhesion molecules mediating interactions between cells of peripheral nervous system indicate a major role for L1 in mediating sensory neuron growth on Schwann cells in culture. *J. Cell Biol.* 107:341-351.

Sommer, I. and Schachner, M. (1981). Monoclonal antibodies (O1 to O4) to oligodendrocyte surfaces: An immunocytochemical study in the central nervous system. *Dev. Biol.* 83:311-327.

Southern, E. M. (1975). Detection of specific sequences among DNA fragments separated by gel electrophoresis. *J. Mol. Biol.* 98:503.

Staatz, W. D., Fok, K. F., Zutter, M. M., Adams, S. P., Rodriguez, B. A. and Santoro, S. A. (1991). Identification of a tetrapeptide recognition sequence to the $\alpha_2\beta_1$ integrin in collagen. *J. Biol. Chem.* 266:7363-7367.

Streuli, M., Krueger, N. X., Hall, L. R., Schlossman, S. F. and Saito, H. (1988). A new member of the immunoglobulin superfamily that has a cytoplasmic region homologous to the leukocyte common antigen. *J. Exp. Med.* 168:1523-1530.

Studier, F. W. and Moffatt, B. A. (1986). Use of bacteriophage T7 RNA polymerase to direct selective high-level expression of cloned genes. *J. Mol. Biol.* 189:113-130.

Tacke, R., Moos, M., Teplow, D. B., Fruh, K., Scherer, H., Bach, A. and Schachner, M. (1987). Isolation of cDNA clones of the mouse neural cell adhesion molecule L1. *Neurosci. Lett.* 82:89-94.

Taketchi, M. (1991). Cadherin cell adhesion receptors as a morphogenetic regulator. *Science.* 251:449-455.

Tannahill, L., Klein, R. and Schachner, M. (1995). The neurotrophin receptors TrkA and TrkB are inhibitory for neurite outgrowth. *Eur. J. Neurosci.* 6:1424-1428.

Taylor, J., Pesheva, P. and Schachner, M. (1993). Influence of janusin and tenascin on growth cone behavior in vitro. *J. Neurosci. Res.* 35:347-362.

Tongiorgi, E., Bernardt, R. R. and Schachner, M. (1995). Zebrafish neurons express two L1-related molecules during early axonogenesis. *J. Neurosci. Res.* 42:547-561.

Talotra, P. C., Karagogeos, D., Theodorakis, K., Michaelidis, T. M., Modi, W. S., Furley, A. J., Jessell, T. M. and Papamatheakis, J. (1993). Isolation of the cDNA and chromosomal localization of the gene (TAX-1) encoding the human axonal glycoprotein TAG-1. *Genomics* 18:562-567.

Volkmer, H., Hassel, B., Wolff, J. M., Frank, R. and Rathjen, F. G. (1992). Structure of the axonal surface recognition molecule neurofascin and its relationship to a neural subgroup of the immunoglobulin superfamily. *J. Cell Biol.* 118:149-161.

Williams, A. F. and Barclay, A. N. (1988). The immunoglobulin superfamily—domains for cell surface recognition. *Ann. Rev. Immunol.* 6:381-405.

Yoshihara, Y., Kawasaki, M., Tani, A., Tamada, A., Nagata, S., Kagamiyama, H. and Mori, K. (1994). BIG-1: A new TAG-1/F3-related member of the immunoglobulin superfamily with neurite outgrowth-promoting activity. *Neuron* 13:415-426.

Oppenheim, R. W. (1991) *Ann. Rev. Neurosci.* 14:453-501

Linden, R. (1994) *Neuroscience,* 58:671-682

Bredesen, O. E. (1996) *Perspectives Devel. Neurobiol,* 3:101-109

Ruoslahti, E., and Reed, J. C. (1994) *Cell,* 77:477-478

Raff, M. C. (1992) *Nature,* 356:397-400

Re, F., Zanetti, A., Sironi, M., Polentarutti, N., Lanfrancone, L., Dejana, E., and Colotte, F. (1994) *J. Cell Biol.,* 127:537-546

Martin, K. C., and Kandel, E. R. (1996) *Neuron,* 17:567-570

Fields, R. D., and Itoh, K. (1996) *Trends Nourosci.,* 19:473-480

Wong, E. V., Kenwdck, S., Willems, P., and Lommon, V. (1995) *Trends Neurosci.,* 18:168-172

Hortsch, M. (1996) *Neuron,* 17:587-593

Holm, J., Hillenbrand, R., Steuber, V., Bartsch, U., Moos, M., Lijbbert, H., Montag, D., and Schachner, M. (1996) *Eur. J. Neurosci.,* 8:1613-1629

Kroemer, G. (1997) *Nat. Med.,* 3:614-620

Davies, A. M. (1995) *Trends Neurosci.,* 18:355-358

Merry, D. E., and Korsmeyer, S. J. (1997) *Ann. Rev. Neurosci.,* 20:245-267

Merry, D. E., Veis, D. J., Hickey, W. F., and Korsmeyer, S. J. (1994) *Development,* 120:301-311

Farlia, P. G., Dringen, R., Rees, S. M., Kannourakis, G., and Bernard, O. (1995) *Proc. Natl. Acad Sci. U.S.A.,* 92:4397-4401

Zhong, L.-T., Saraflan, T, Kane, D. J., Charles, A. C., Mah, S. P., Edwards, R. H., and Bradesen, D. E. (1993) *Proc. Natl. Acad. Sci. u.s.a.,* 90:4533-4537

Kane, U. J., 6rd, T., Anton, R., and Bradesen, D. E. (1995) *J. Neurosci. Res.,* 40:269-275

Morgan, J. I., and Curran, T. (1995) *Trends Neurosci,* 18:66-7

Estus, S., Zaks, W. J., Freeman, R. S., Gruda, M., Bravo, R., and Johnson, E. M., Jr. (1994) *J. Cell Biol.,* 127:1717-27

Ham, J., Babij, C., Whitfield, J., Pfarr, C. M., Lailemand, D., Yaniv, M., and Rubin, L. L. (1995) *Neuron,* 14:927-939

Messina, A., Jaworowski, A., and Bell, C. (1996) *J. Comp. Neuroi.,* 372:544-550

Simmons, D. L. (1993) in *Cellular interactions in development* (Hartley, D. A., ed), IRL Press, Oxford Bebbington, C. R. (1991) *Methods, a companion to Methods in Enzymology,* 2:136-145

Keilhauer, G., Faissner, A., and Schachner, M. (1985) *Nature,* 316:728-730

Lochter, A., Vaughan, L., Kapiony, A., Prochiantz, A., Schachner, M., and Faissner, A. (1991) *J. Cell Biol.,* 113:1159-1171

Brewer, G. J., Tordcoill, J. R., Evege, E. K., and Price, P. J. (1993) *J. Neurosci. Res.,* 35:567-576

Mosmann, T. (1983) *J. Immunol Meth.,* 65:55-63

Hockenbery, D., Nunez, G., Milliman, C., Schreiber, R. D., and Korsmeyer, S. J. (1990) *Nature,* 348:334-336

D'Mello, S. R., Gaili, C., Ciotti, T., and Calissano, P. (1993) *Proc. Natl. Acad. Sci. U.S.A.,* 90:10989-10993

Yang, R. J., Moss, S. F., Arber, N., Kraiewski, S., Reed, J. C., and Holt, P. R. (1996) *Oncogene,* 12:2605-2609

Pfarr, C. M., Mechta, F., Spyrou, G., Lailemand, D., Cadilo, S., and Yaniv, M. (1994) *Cell,* 176:747-760

Doherty, P., Williams, E., and Walsh, F. S. (1995) *Neuron,* 14:57-66

Voikmer, H., Leuschner, R., Zacharias, U., and Rathjen, F. G. (1996) *J. Cell Biol.,* 135:1059-1069

Ellis, R., Yuan, J., and Horvitz, H. R. (1991) *Ann. Rev. Cell Biol.,* 7:663-698

Appel, F., Holm, J., Conscience, J. F., von Bohlen und Halbach, F., Faissner, A., James, P., and Schachner, M. (1995) *J. Neurobiol.*, 28:297-312

Hulley, P., Schachner, M., and Lübbert, H. (1998) *J. Neurosci. Res.*, (in press).

Schuch, U., Lohse, M. J., and Schachner, M. (1989) *Neuron*, 3:13-20 von Bohlen und Halbach, F., Taylor, J, and Schachner, M. (1992) *Eur. J. Neurosci.*, 4:896-909

Harper, S. J., Bolsover, S. R., Walsh, F. S., and Doherty, P. (1994) *Cell Adhes. Commun.*, 2:441-453

Williams, E. J., Doherty, P., Turner, G., Reid, R. A., Hemperty, J. J., and Walsh, F. S. (1992) *J. Cell Biol.*, 9:853-892

Gard, A. L., Maughon, R. H., and Schachner, M. (1996) *J. Neurosci.*, 46:415-426

Carenini, S., Montag, D., Cremer, H., Schachner, M., and Martini, R. (1997) *Cell Tissue Res.*, 287:3-9

Seilheimer, B., and Schachner, M. (1987) *EMBO J.*, 6:1611-1616

Mann, D. A., Doherty, P., and Walsh, F. S. (1989) *J. Neurochem.*, 53:1581-1588

Itoh, K., Brackenbury, R., and Akeson, R. A. (1995) *J. Nourosci.*, 15:2504-2512

Saad, B., Constam, D. B., Ortmann, R., Moos, M., Fontana, A., and Schachner, M. (1991) *J. Cell Biol.*, 115:473-484

Doherty, P., Ashton, S. V., Moore, S. E., and Walsh, F. S. (1991) *Cell*, 67:21-33

Walsh, F. S., and Doherty, P. (1992) *Cold Spring Harb. Symp. Quant Biol.*, 57:431-440

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A method for promoting neurite outgrowth in vivo in the central nervous system of a mammal comprising administering to said mammal a neurite outgrowth promoting amount of an antibody to a neural cell adhesion molecule L1 or an active fragment of said antibody, wherein said antibody or active fragment thereof is an agonist of L1, is directed against the junction between repeats 2 and 3 of the fibronectin type III domain of L1, and is capable of promoting neurite outgrowth.

2. A method for decreasing axonal cell death in the central nervous system of a mammal comprising administering to said mammal a therapeutically effective amount of an antibody to a neural cell adhesion molecule L1 or an active fragment of said antibody, wherein said antibody or active fragment thereof is an agonist of L1, is directed against the junction between repeats 2 and 3 of the fibronectin type III domain of L1, and is capable of decreasing axonal cell death.

3. A method for promoting neuronal survival in vivo in the central nervous system of a mammal comprising administering to said mammal a neuronal survival promoting amount of an antibody to a neural cell adhesion molecule L1 or an active fragment of said antibody, wherein said antibody or active fragment thereof is an agonist of L1, is directed against the junction between repeats 2 and 3 of the fibronectin type III domain of L1, and is capable of promoting neuronal survival.

* * * * *

SEQUENCE LISTING

<160> NUMBER OF SEQ ID NOS: 15

<210> SEQ ID NO 1
<211> LENGTH: 294
<212> TYPE: DNA
<213> ORGANISM: murine

<400> SEQUENCE: 1

```
cagcgggaag ccgccaacta gaaactccct tggattctca agaggcgctg gacctcgttt      60
ggtcccttt gccccagtga tccagcttta ggagaagttt tcccaagaga aggtaccaga     120
cagatvggat gtcaagaggc ggctcaggtg ttatagactg caggcaatga ttctaccttg     180
ataatccagg cagaccaccg tggatcaaaa attcctggtt tctcccattt cctcagtgaa     240
cagaaagtat tagagaccct ttccagtctt tgcacgttgc ctcctttctg agga           294
```

<210> SEQ ID NO 2
<211> LENGTH: 1209
<212> TYPE: PRT
<213> ORGANISM: murine

<400> SEQUENCE: 2

```
Met Met Glu Leu Pro Leu Cys Gly Arg Gly Leu Ile Leu Ser Leu Ile
1               5                   10                  15

Phe Leu Leu Lys Leu Ser Ala Ala Glu Ile Pro Leu Ser Val Gln
            20                  25                  30

Gln Val Pro Thr Ile Val Lys Gln Ser Tyr Val Gln Val Ala Phe Pro
        35                  40                  45

Phe Asp Glu Tyr Phe Gln Ile Glu Cys Glu Ala Lys Gly Asn Pro Glu
    50                  55                  60

Pro Ile Phe Ser Trp Thr Lys Asp Asp Lys Pro Phe Asp Leu Ser Asp
65                  70                  75                  80

Pro Arg Ile Ile Ala Ala Asn Asn Ser Gly Thr Phe Lys Ile Pro Asn
                85                  90                  95

Glu Gly His Ile Ser His Phe Gln Gly Lys Tyr Arg Cys Phe Ala Ser
            100                 105                 110

Asn Arg Leu Gly Thr Ala Val Ser Glu Glu Ile Glu Phe Ile Val Pro
        115                 120                 125

Gly Val Pro Lys Phe Pro Lys Glu Lys Ile Glu Pro Ile Asp Val Glu
    130                 135                 140
```

-continued

```
Glu Gly Asp Ser Ile Val Leu Pro Cys Asn Pro Pro Lys Gly Leu Pro
145                 150                 155                 160

Pro Leu His Ile Tyr Trp Met Asn Ile Glu Leu His Ile Glu Gln
            165                 170                 175

Asp Glu Arg Val Tyr Met Ser Gln Arg Gly Asp Leu Tyr Phe Ala Asn
            180                 185                 190

Val Glu Glu Asn Asp Ser Arg Asn Asp Tyr Cys Cys Phe Ala Ala Phe
            195                 200                 205

Pro Lys Leu Arg Thr Ile Val Gln Lys Met Pro Met Lys Leu Thr Val
210                 215                 220

Asn Ser Ser Asn Ser Ile Lys Gln Arg Lys Pro Lys Leu Leu Leu Pro
225                 230                 235                 240

Pro Ala Gln Met Gly Ser Leu Ser Ala Lys Thr Val Leu Lys Gly Asp
            245                 250                 255

Thr Leu Leu Leu Glu Cys Phe Ala Glu Gly Leu Pro Thr Pro His Ile
            260                 265                 270

Gln Trp Ser Lys Pro Gly Ser Glu Leu Pro Glu Gly Arg Ala Thr Ile
            275                 280                 285

Glu Val His Glu Lys Thr Leu Lys Ile Glu Asn Ile Ser Tyr Gln Asp
290                 295                 300

Arg Gly Asn Tyr Arg Cys Thr Ala Asn Asn Leu Leu Gly Lys Ala Ser
305                 310                 315                 320

His Asp Phe His Val Thr Val Glu Glu Pro Pro Arg Trp Lys Lys Lys
            325                 330                 335

Pro Gln Ser Ala Val Tyr Ser Thr Gly Ser Ser Gly Ile Leu Leu Cys
            340                 345                 350

Glu Ala Glu Gly Glu Pro Gln Pro Thr Ile Lys Trp Arg Leu Asn Gly
            355                 360                 365

Leu Pro Ile Glu Lys His Pro Phe Pro Gly Asp Phe Met Phe Pro Arg
370                 375                 380

Glu Ile Ser Phe Thr Asn Leu Leu Phe Asn His Thr Gly Val Tyr Gln
385                 390                 395                 400

Cys Glu Ala Ser Asn Ile His Gly Thr Ile Leu Ala Asn Ala Asn Ile
            405                 410                 415

Asp Val Ile Asp Val Ile Pro Leu Ile Lys Thr Lys Asn Glu Glu Asn
            420                 425                 430

Tyr Ala Thr Val Val Gly Tyr Ser Ala Phe Leu His Cys Glu Tyr Phe
            435                 440                 445

Ala Ser Pro Lys Ala Thr Val Val Trp Glu Val Ala Asp Glu Thr His
450                 455                 460

Pro Leu Glu Gly Asp Arg Tyr His Thr His Glu Asn Gly Thr Leu Glu
465                 470                 475                 480

Ile Tyr Arg Thr Thr Glu Glu Asp Ala Gly Ser Tyr Ser Cys Trp Val
            485                 490                 495

Asp Asn Ala Met Gly Lys Ala Val Ile Thr Ala Asn Leu Asp Ile Arg
            500                 505                 510

Asn Ala Thr Lys Leu Arg Val Ser Pro Lys Asn Pro Arg Ile Pro Lys
            515                 520                 525

Ser His Val Leu Glu Leu Tyr Cys Glu Ser Gln Cys Asp Ser His Leu
            530                 535                 540

Lys His Ser Leu Lys Leu Ser Trp Ser Lys Asp Gly Glu Ala Phe Glu
545                 550                 555                 560

Met Asn Gly Thr Glu Asp Gly Arg Ile Val Ile Asp Gly Ala Tyr Leu
```

-continued

```
                565                 570                 575
Thr Ile Ser Asn Ile Thr Ala Glu Asp Gln Gly Val Tyr Ser Cys Ser
                580                 585                 590
Ala Gln Thr Ser Leu Asp Ser Thr Ser Glu Lys Thr Gln Val Thr Val
                595                 600                 605
Leu Gly Val Pro Asp Pro Glu Thr Phe Thr Cys Gln Lys Asp Lys
            610                 615                 620
Asn Arg Ser Val Arg Leu Leu Arg Glu Ala Gly Asp Asp His Asn Ser
625                 630                 635                 640
Lys Ser Ala Ser Thr Ile Val Glu Phe Glu Gly Asn Arg Glu Pro
                645                 650                 655
Gly Lys Trp Glu Glu Leu Thr Arg Val Gln Gly Glu Glu Thr Asp Val
            660                 665                 670
Val Leu Ser Leu Ala Pro Tyr Val Arg Tyr Gln Phe Arg Val Thr Ala
                675                 680                 685
Val Asn Glu Val Gly Arg Ser His Ala Ser Leu Pro Ser Asp His His
            690                 695                 700
Glu Thr Pro Pro Ala Ala Pro Asp Lys Asn Pro Gln Asn Ile Arg Val
705                 710                 715                 720
Gln Ala Ser Gln Pro Lys Glu Met Ile Ile Lys Trp Glu Pro Leu Lys
                725                 730                 735
Ser Met Glu Gln Asn Gly Pro Gly Leu Glu Tyr Lys Val Ser Trp Lys
                740                 745                 750
Pro Gln Gly Ala Pro Glu Glu Trp Glu Glu Ile Val Thr Asn His
            755                 760                 765
Thr Leu Arg Val Met Thr Pro Thr Val Tyr Ala Pro Tyr Asp Val Lys
            770                 775                 780
Val Gln Ala Ile Asn Gln Leu Gly Ser Ser Pro Asp Pro Gln Pro Val
785                 790                 795                 800
Thr Leu Tyr Ser Gly Glu Asp Tyr Pro Ser Thr Ala Pro Val Ile Gln
                805                 810                 815
Arg Val Asp Val Met Asn Ser Thr Leu Val Lys Val Thr Trp Ser Ser
                820                 825                 830
Ile Pro Lys Glu Thr Val His Gly Leu Leu Arg Gly Tyr Gln Ile Asn
            835                 840                 845
Trp Trp Lys Thr Lys Ser Leu Leu Asp Gly Arg Thr His Pro Lys Glu
            850                 855                 860
Val Asn Ile Leu Arg Phe Ser Gly Gln Arg Asn Ser Gly Met Val Pro
865                 870                 875                 880
Ser Leu Asp Pro Phe Ser Glu Phe His Leu Thr Val Leu Ala Tyr Asn
                885                 890                 895
Ser Lys Gly Ala Gly Pro Glu Ser Glu Pro Tyr Ile Phe Gln Thr Pro
            900                 905                 910
Glu Gly Val Pro Glu Gln Pro Ser Phe Leu Lys Val Ile Lys Val Asp
            915                 920                 925
Lys Asp Thr Ala Thr Leu Ser Trp Gly Leu Pro Lys Lys Leu Asn Gly
            930                 935                 940
Asn Leu Thr Gly Tyr Leu Leu Gln Tyr Gln Ile Ile Asn Asp Thr Tyr
945                 950                 955                 960
Glu Leu Gly Glu Leu Asn Glu Ile Asn Val Thr Thr Pro Ser Lys Ser
                965                 970                 975
Ser Trp His Leu Ser Asn Leu Asn Ser Thr Thr Lys Tyr Lys Phe Tyr
            980                 985                 990
```

```
Leu Arg Ala Cys Thr Ser Arg Gly Cys Gly Lys Pro Ile Ser Glu Glu
    995                 1000                1005

Gly Ala Thr Leu Gly Glu Gly Ser Lys Gly Ile Arg Lys Ile Thr Glu
    1010                1015                1020

Gly Val Asn Val Thr Gln Lys Ile His Pro Val Glu Val Leu Val Pro
1025                1030                1035                1040

Gly Ala Glu His Ile Val His Leu Met Thr Lys Asn Trp Gly Asp Asn
                1045                1050                1055

Asp Ser Ile Phe Gln Asp Val Ile Glu Thr Arg Gly Arg Glu Tyr Ala
            1060                1065                1070

Gly Leu Tyr Asp Asp Ile Ser Thr Gln Gly Trp Phe Ile Gly Leu Met
        1075                1080                1085

Cys Ala Ile Ala Leu Leu Thr Leu Ile Leu Leu Thr Ile Cys Phe Val
    1090                1095                1100

Lys Arg Asn Arg Gly Gly Lys Tyr Ser Val Lys Glu Lys Glu Asp Leu
1105                1110                1115                1120

His Pro Asp Pro Glu Val Gln Ser Ala Lys Asp Glu Thr Phe Gly Glu
                1125                1130                1135

Tyr Ser Asp Ser Asp Glu Lys Pro Leu Lys Gly Ser Leu Arg Ser Leu
            1140                1145                1150

Asn Arg Asn Met Gln Pro Thr Glu Ser Ala Asp Ser Leu Val Glu Tyr
        1155                1160                1165

Gly Glu Gly Asp Gln Ser Ile Phe Asn Glu Asp Gly Ser Phe Ile Gly
    1170                1175                1180

Ala Tyr Thr Gly Ala Lys Glu Lys Gly Ser Val Glu Ser Asn Gly Ser
1185                1190                1195                1200

Ser Thr Ala Thr Phe Pro Leu Arg Ala
                1205

<210> SEQ ID NO 3
<211> LENGTH: 515
<212> TYPE: DNA
<213> ORGANISM: murine

<400> SEQUENCE: 3
tgagaacaac acattcaggc accacgggtg gctaagccgg acaaggggag caaggccttt        60
tacacaggag cggaaacgtg tccagaggtt gatattctgc aattttgatg aagaatagca       120
ctgccttcaa agaagggaaa aaatcagatg ccaagaactt cagactgtgt tcatttggtt       180
tgattcaggt gctcaaaatg cagaacacga acaaatcct gtacttagat ccactttgac        240
tgaatccaaa gttcccattt cagatactcc acatctacct ggctctcctg ttcagtgtgt       300
gtgcattgat gttgctaaga tgtgtgggtt tctctctgga tggcacaatt atacttagtt       360
ttgaagaact gttttagtga attcgattca ctacaggata aagattgta agcaagcaag        420 ctggttattt aaaatgtaaa aaggaacatg attgtcttat taaacatccc gtggaatcta       480
aaaaaaaaaa aaaaaaaaa aaaaaaaaa aaaaa                                    515

<210> SEQ ID NO 4
<211> LENGTH: 105
<212> TYPE: PRT
<213> ORGANISM: murine

<400> SEQUENCE: 4

Lys Arg Asn Arg Gly Gly Lys Tyr Ser Val Lys Glu Lys Glu Asp Leu
1               5                   10                  15

His Pro Asp Pro Glu Val Gln Ser Ala Lys Asp Glu Thr Phe Gly Glu
```

```
                    20                  25                  30
Tyr Ser Asp Ser Asp Glu Lys Pro Leu Lys Gly Ser Leu Arg Ser Leu
                35                  40                  45

Asn Arg Asn Met Gln Pro Thr Glu Ser Ala Asp Ser Leu Val Glu Tyr
            50                  55                  60

Gly Glu Gly Asp Gln Ser Ile Phe Asn Glu Asp Gly Ser Phe Ile Gly
65                  70                  75                  80

Ala Tyr Thr Gly Ala Lys Glu Lys Gly Ser Val Glu Ser Asn Gly Ser
                85                  90                  95

Ser Thr Ala Thr Phe Pro Leu Arg Ala
                100                 105

<210> SEQ ID NO 5
<211> LENGTH: 114
<212> TYPE: PRT
<213> ORGANISM: murine

<400> SEQUENCE: 5

Lys Arg Ser Lys Gly Gly Lys Tyr Ser Val Lys Asp Lys Glu Asp Thr
1               5                   10                  15

Gln Val Asp Ser Glu Ala Arg Pro Met Lys Asp Glu Thr Phe Gly Glu
                20                  25                  30

Tyr Arg Ser Leu Glu Ser Asp Asn Glu Glu Lys Ala Phe Gly Ser Ser
                35                  40                  45

Gln Pro Ser Leu Asn Gly Asp Ile Lys Pro Leu Gly Ser Asp Asp Ser
            50                  55                  60

Leu Ala Asp Tyr Gly Gly Ser Val Asp Val Gln Phe Asn Glu Asp Gly
65                  70                  75                  80

Ser Phe Ile Gly Gln Tyr Ser Gly Lys Lys Glu Lys Glu Ala Ala Gly
                85                  90                  95

Gly Asn Asp Ser Ser Gly Ala Ile Ser Pro Ile Asn Pro Ala Val Ala
                100                 105                 110

Leu Glu

<210> SEQ ID NO 6
<211> LENGTH: 114
<212> TYPE: PRT
<213> ORGANISM: murine

<400> SEQUENCE: 6

Arg Arg Asn Lys Gly Gly Lys Tyr Pro Val Lys Glu Lys Glu Asp Ala
1               5                   10                  15

His Ala Asp Pro Glu Leu Gln Pro Met Lys Glu Asp Asp Gly Thr Phe
                20                  25                  30

Gly Glu Tyr Ser Asp Ala Glu Asp His Lys Pro Leu Lys Lys Gly Ser
                35                  40                  45

Arg Thr Pro Ser Asp Arg Thr Val Lys Lys Glu Asp Ser Asp Asp Ser
            50                  55                  60

Leu Val Asp Tyr Gly Glu Gly Val Asn Gly Gln Phe Asn Glu Asp Gly
65                  70                  75                  80

Ser Phe Ile Gly Gln Tyr Ser Gly Lys Lys Glu Lys Glu Pro Ala Glu
                85                  90                  95

Gly Asn Glu Ser Ser Glu Ala Pro Ser Pro Val Asn Ala Met Asn Ser
                100                 105                 110

Phe Val
```

```
<210> SEQ ID NO 7
<211> LENGTH: 111
<212> TYPE: PRT
<213> ORGANISM: murine

<400> SEQUENCE: 7

Lys Arg Ser Lys Gly Gly Lys Tyr Ser Val Lys Asp Lys Glu Asp Thr
1               5                   10                  15
Gln Val Asp Ser Glu Ala Arg Pro Met Lys Asp Glu Thr Phe Gly Glu
            20                  25                  30
Tyr Arg Ser Leu Glu Ser Glu Ala Glu Lys Gly Ser Ala Ser Gly Ser
        35                  40                  45
Gly Ala Gly Ser Gly Val Gly Ser Pro Gly Arg Gly Pro Ala Ala Gly
    50                  55                  60
Ser Glu Asp Ser Leu Ala Gly Tyr Gly Gly Ser Gly Asp Val Gln Phe
65                  70                  75                  80
Asn Glu Asp Gly Ser Phe Ile Gly Gln Tyr Arg Gly Pro Gly Ala Gly
                85                  90                  95
Pro Gly Ser Ser Gly Pro Ala Ser Pro Ala Gly Pro Pro Leu Asp
            100                 105                 110

<210> SEQ ID NO 8
<211> LENGTH: 113
<212> TYPE: PRT
<213> ORGANISM: murine

<400> SEQUENCE: 8

Lys Arg Ser Arg Gly Gly Lys Tyr Pro Val Arg Asp Asn Lys Asp Glu
1               5                   10                  15
His Leu Asn Pro Glu Asp Lys Asn Val Glu Asp Gly Ser Phe Asp Tyr
            20                  25                  30
Arg Ser Leu Glu Ser Asp Glu Asp Asn Lys Pro Leu Pro Asn Ser Gln
        35                  40                  45
Thr Ser Leu Asp Gly Thr Ile Lys Gln Gln Glu Ser Asp Asp Ser Leu
    50                  55                  60
Val Asp Tyr Gly Glu Gly Gly Glu Gly Gln Phe Asn Glu Asp Gly Ser
65                  70                  75                  80
Phe Ile Gly Gln Tyr Thr Val Lys Lys Asp Lys Glu Glu Thr Glu Gly
                85                  90                  95
Asn Glu Ser Ser Glu Ala Thr Ser Pro Val Asn Ala Ile Tyr Ser Leu
            100                 105                 110
Ala

<210> SEQ ID NO 9
<211> LENGTH: 85
<212> TYPE: PRT
<213> ORGANISM: murine

<400> SEQUENCE: 9

Arg Arg Asn Arg Gly Gly Lys Tyr Asp Val His Asp Arg Glu Leu Ala
1               5                   10                  15
Asn Gly Arg Arg Asp Tyr Pro Glu Glu Gly Gly Phe His Glu Tyr Ser
            20                  25                  30
Gln Pro Leu Asp Asn Lys Ser Ala Gly Arg Gln Ser Val Ser Ser Ala
        35                  40                  45
Asn Lys Pro Gly Val Glu Ser Asp Thr Asp Ser Met Ala Glu Tyr Gly
    50                  55                  60
Asp Gly Asp Thr Gly Met Asn Glu Asp Gly Ser Phe Ile Gly Gln Tyr
```

-continued

```
                65                  70                  75                  80
Gly Arg Lys Gly Leu
                85

<210> SEQ ID NO 10
<211> LENGTH: 122
<212> TYPE: PRT
<213> ORGANISM: murine

<400> SEQUENCE: 10

Lys Lys Ser Lys Gly Gly Lys Tyr Ser Val Lys Asp Lys Glu Glu Gly
1               5                   10                  15

Gln Gly Asp Ala Ala Asn Gln Lys Leu Lys Asp Asp Ala Phe Gly Glu
            20                  25                  30

Tyr Arg Ser Leu Glu Ser Asp Met Glu Lys Cys Ser Ile Ser Gln Pro
        35                  40                  45

Ser Gly Cys Glu Ser Lys Arg Ser Ser Asn Asp Ser Leu Ala Asp Tyr
    50                  55                  60

Gly Asp Ser Val Asp Ile Gln Phe Asn Glu Asp Gly Ser Phe Ile Gly
65                  70                  75                  80

Gln Tyr Ser Gly Arg Arg Asp Pro Arg Gly His Asp Ser Ser Gly Ala
                85                  90                  95

Val Ser Pro Val Asn Pro Asn Met Pro Pro Pro Ser His Ser Phe Pro
            100                 105                 110

Thr Ser Val Thr Gly Ile Leu Gly Pro Asn
        115                 120

<210> SEQ ID NO 11
<211> LENGTH: 122
<212> TYPE: PRT
<213> ORGANISM: murine

<400> SEQUENCE: 11

Lys Arg Ser Lys Gly Gly Lys Tyr Ser Val Lys Glu Lys Glu Glu Gly
1               5                   10                  15

Gln Ile Asp Ser Glu Ala Arg Pro Met Asn Asn Glu Ala Phe Gly Glu
            20                  25                  30

Tyr Arg Ser Leu Glu Ser Asp Asn Glu Glu Lys Arg Thr Ala Ser Gln
        35                  40                  45

Pro Ser Leu Cys Glu Asp Ser Lys Leu Cys Thr Asp Asp Gly Leu Asp
    50                  55                  60

Asp Tyr Ala Asn Ser Asn Ser Val Gln Thr Glu Val Ile Met Asp Glu
65                  70                  75                  80

Ser Leu Ala Ser Gln Ser Ser Gly Val Arg Asp Val Pro Asp Ala Phe
                85                  90                  95

Thr Gln Glu Ser Ser Pro Leu Asn Pro Ala Thr Ala Ile Ser His His
            100                 105                 110

Gly Leu Pro Asn Ser Ala Ala Leu Leu Asp
        115                 120

<210> SEQ ID NO 12
<211> LENGTH: 12
<212> TYPE: PRT
<213> ORGANISM: murine
<220> FEATURE:
<221> NAME/KEY: unsure
<222> LOCATION: (1)...(12)
<223> OTHER INFORMATION: Xaa = any amino acid.

<400> SEQUENCE: 12
```

```
Asp Xaa Gly Xaa Xaa Tyr Xaa Cys Xaa Ala Xaa Asn
 1               5                  10
```

```
<210> SEQ ID NO 13
<211> LENGTH: 33
<212> TYPE: PRT
<213> ORGANISM: murine
<220> FEATURE:
<221> NAME/KEY: unsure
<222> LOCATION: (1)...(33)
<223> OTHER INFORMATION: Xaa = any amino acid.

<400> SEQUENCE: 13

Phe Xaa Val Xaa Ala Xaa Asn Xaa Xaa Gly Xaa Xaa Xaa Xaa Xaa
 1               5                  10                  15

Xaa Xaa Ser Xaa Xaa Xaa Xaa Thr Xaa Xaa Ala Xaa Pro Xaa Xaa Xaa
             20                  25                  30

Pro
```

```
<210> SEQ ID NO 14
<211> LENGTH: 9
<212> TYPE: PRT
<213> ORGANISM: murine
<220> FEATURE:
<221> NAME/KEY: unsure
<222> LOCATION: (1)...(9)
<223> OTHER INFORMATION: Xaa = any amino acid.

<400> SEQUENCE: 14

Asn Xaa Xaa Gly Xaa Gly Pro Xaa Ser
 1               5
```

```
<210> SEQ ID NO 15
<211> LENGTH: 15
<212> TYPE: PRT
<213> ORGANISM: murine

<400> SEQUENCE: 15

Thr Pro Thr Pro Thr Gln Phe Leu Cys Pro Lys Asn Val Thr Asp
 1               5                  10                  15
```